US007655688B2

(12) United States Patent
Salvati et al.

(10) Patent No.: US 7,655,688 B2
(45) Date of Patent: Feb. 2, 2010

(54) FUSED CYCLIC SUCCINIMIDE COMPOUNDS AND ANALOGS THEREOF, MODULATORS OF NUCLEAR HORMONE RECEPTOR FUNCTION

(75) Inventors: Mark E. Salvati, Lawrenceville, NJ (US); Ricardo M. Attar, Lawrenceville, NJ (US); Marco M. Gottardis, Princeton, NJ (US); James Aaron Balog, Scotch Plains, NJ (US); Dacia A. Pickering, Lawrenceville, NJ (US); Rogelio L. Martinez, Monmouth Junction, NJ (US); Chongqing Sun, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 821 days.

(21) Appl. No.: 11/311,731

(22) Filed: Dec. 19, 2005

(65) Prior Publication Data
US 2006/0111424 A1    May 25, 2006

Related U.S. Application Data

(63) Continuation of application No. 10/075,870, filed on Feb. 14, 2002, now abandoned.

(60) Provisional application No. 60/271,672, filed on Feb. 27, 2001.

(51) Int. Cl.
A61K 31/40 (2006.01)
A61K 31/47 (2006.01)
A61K 31/34 (2006.01)

(52) U.S. Cl. .............. 514/411; 514/408; 514/410; 514/311; 514/312; 514/314; 514/470; 514/307

(58) Field of Classification Search .............. 514/408, 514/410, 411, 412, 425, 311, 312, 314, 470, 514/307
See application file for complete search history.

(56) References Cited

U.S. PATENT DOCUMENTS

| | | | |
|---|---|---|---|
| 3,215,597 A | 11/1965 | Stevenson |
| 3,261,845 A | 7/1966 | Bockstahler |
| 3,320,270 A | 5/1967 | Grogan et al. |
| 3,343,940 A | 9/1967 | Popoff et al. |
| 3,428,538 A | 2/1969 | Scheiner |
| 3,821,232 A | 6/1974 | Redmore |
| 3,906,102 A | 9/1975 | Tottori et al. |
| 3,923,490 A | 12/1975 | Redmore |
| 3,925,554 A | 12/1975 | Tottori et al. |
| 3,965,264 A | 6/1976 | Redmore |
| 3,997,293 A | 12/1976 | Redmore |
| 3,998,833 A | 12/1976 | Redmore |
| 4,089,650 A | 5/1978 | Redmore |
| 4,092,413 A | 5/1978 | Arth et al. |
| 4,097,578 A | 6/1978 | Perronnet et al. |
| 4,191,775 A | 3/1980 | Glen |
| 4,234,736 A | 11/1980 | Bernauer et al. |
| 4,239,776 A | 12/1980 | Glen et al. |
| 4,397,857 A | 8/1983 | Vincent et al. |
| 4,472,382 A | 9/1984 | Labrie et al. |
| 4,473,393 A | 9/1984 | Nagpal |
| 4,476,184 A | 10/1984 | Lubowitz et al. |
| 4,507,303 A | 3/1985 | Ishizumi et al. |
| 4,533,737 A | 8/1985 | Ryang |
| 4,536,559 A | 8/1985 | Lubowitz et al. |
| 4,543,355 A | 9/1985 | Ishizumi et al. |
| 4,562,255 A | 12/1985 | Freed et al. |
| 4,582,886 A | 4/1986 | Ryang |
| 4,584,364 A | 4/1986 | Lubowitz et al. |
| 4,598,072 A | 7/1986 | Schweikert et al. |
| 4,656,235 A | 4/1987 | Tesoro et al. |
| 4,659,695 A | 4/1987 | Labrie |
| 4,666,885 A | 5/1987 | Labrie |
| 4,673,748 A | 6/1987 | Rock et al. |
| 4,739,075 A | 4/1988 | Odagiri et al. |
| 4,753,957 A | 6/1988 | Chan |
| 4,760,053 A | 7/1988 | Labrie |
| 4,775,660 A | 10/1988 | Labrie et al. |
| 4,775,661 A | 10/1988 | Labrie |
| 4,851,495 A | 7/1989 | Sheppard et al. |
| 4,873,256 A | 10/1989 | Coussediere et al. |
| 4,892,578 A | 1/1990 | Chang et al. |
| 4,892,943 A | 1/1990 | Abou-Gharbia |
| 4,944,791 A | 7/1990 | Schröder et al. |
| 4,980,481 A | 12/1990 | Lubowitz et al. |
| 5,084,472 A | 1/1992 | Moguilewsky et al. |
| 5,093,500 A | 3/1992 | Wang |
| 5,098,888 A | 3/1992 | Vincent et al. |
| 5,104,967 A | 4/1992 | Sheppard et al. |
| 5,112,939 A | 5/1992 | Lubowitz et al. |
| 5,114,612 A | 5/1992 | Benicewicz et al. |
| 5,116,935 A | 5/1992 | Lubowitz et al. |
| 5,151,487 A | 9/1992 | Lubowitz et al. |
| 5,155,206 A | 10/1992 | Lubowitz et al. |
| 5,210,213 A | 5/1993 | Sheppard et al. |

(Continued)

FOREIGN PATENT DOCUMENTS

AU    A-16993/83    1/1984

(Continued)

OTHER PUBLICATIONS

Alekperov, N.A. et al., "Effect of the Nature of the Groups at the Bridging Carbon Atom on the Formation of Endo,Endo- and Endo,Exo-Anhydrides and Imides of the 3,6-Epoxytricyclo[6.2.1.0$^{2,7}$]-undecene Series", Zhurnal Organicheskoi Khimii, vol. 16, No. 4, pp. 675-682 (1980) (English language version).

(Continued)

Primary Examiner—Shengjun Wang
(74) Attorney, Agent, or Firm—Burton Rodney

(57) ABSTRACT

Fused cyclic compounds, methods of using such compounds in the treatment of nuclear hormone receptor-associated conditions such as cancer and immune disorders, and pharmaceutical compositions containing such compounds.

8 Claims, No Drawings

U.S. PATENT DOCUMENTS

| | | | |
|---|---|---|---|
| 5,239,046 A | 8/1993 | Lubowitz et al. |
| 5,367,083 A | 11/1994 | Sheppard et al. |
| 5,399,725 A | 3/1995 | Poss et al. |
| 5,403,666 A | 4/1995 | Lubowitz et al. |
| 5,434,176 A | 7/1995 | Claussner et al. |
| 5,446,120 A | 8/1995 | Lubowitz et al. |
| 5,455,115 A | 10/1995 | Lubowitz et al. |
| 5,463,076 A | 10/1995 | Sheppard et al. |
| 5,482,921 A | 1/1996 | Seckinger et al. |
| 5,512,676 A | 4/1996 | Sheppard et al. |
| 5,516,876 A | 5/1996 | Lubowitz et al. |
| 5,530,089 A | 6/1996 | Sheppard et al. |
| 5,532,372 A | 7/1996 | Saji et al. |
| 5,550,107 A | 8/1996 | Labrie |
| 5,556,983 A | 9/1996 | Claussner et al. |
| 5,573,854 A | 11/1996 | Sheppard et al. |
| 5,587,105 A | 12/1996 | Sheppard et al. |
| 5,589,497 A | 12/1996 | Claussner et al. |
| 5,594,089 A | 1/1997 | Lubowtiz et al. |
| 5,595,985 A | 1/1997 | Labrie |
| 5,610,317 A | 3/1997 | Lubowtiz et al. |
| 5,627,201 A | 5/1997 | Gaillard-Kelly et al. |
| 5,643,855 A | 7/1997 | Kilama |
| 5,645,925 A | 7/1997 | Sheppard et al. |
| 5,693,741 A | 12/1997 | Sheppard et al. |
| 5,714,566 A | 2/1998 | Lubowtiz et al. |
| 5,750,553 A | 5/1998 | Claussner et al. |
| 5,780,583 A | 7/1998 | Lubowitz et al. |
| 5,817,649 A | 10/1998 | Labrie |
| 5,817,744 A | 10/1998 | Sheppard et al. |
| RE35,956 E | 11/1998 | Gaillard-Kelly et al. |
| 5,929,146 A | 7/1999 | Amos et al. |
| 6,017,924 A | 1/2000 | Edwards et al. |
| 6,020,327 A | 2/2000 | Messenger |
| 6,054,487 A | 4/2000 | Sekut et al. |
| 6,071,957 A | 6/2000 | Miller et al. |
| 6,090,837 A | 7/2000 | Lavielle et al. |
| 6,124,460 A | 9/2000 | Tomiyama et al. |
| 6,162,444 A | 12/2000 | Dubois |
| 6,200,573 B1 | 3/2001 | Locke |
| 6,242,611 B1 | 6/2001 | Claussner et al. |
| 6,384,050 B1 | 5/2002 | Takemura et al. |
| 6,448,284 B1 | 9/2002 | Bach et al. |
| 6,482,861 B2 | 11/2002 | Miller et al. |
| 6,573,218 B1 | 6/2003 | Tsukamoto et al. |
| 6,638,933 B2 | 10/2003 | Gerlach et al. |
| 6,642,230 B2 | 11/2003 | Wilde et al. |
| 6,653,320 B2 | 11/2003 | Hayakawa et al. |
| 6,670,386 B2 | 12/2003 | Sun et al. |
| 6,673,810 B2 | 1/2004 | Lam et al. |
| 6,673,927 B2 | 1/2004 | Gordon et al. |
| 6,686,358 B2 | 2/2004 | De Nanteuil et al. |
| 6,686,471 B2 | 2/2004 | Chiu et al. |
| 6,696,464 B2 | 2/2004 | McClure et al. |
| 6,706,750 B1 | 3/2004 | Bentley et al. |
| 6,710,048 B2 | 3/2004 | Kuo et al. |
| 6,720,334 B2 | 4/2004 | Dellaria et al. |
| 6,723,735 B1 | 4/2004 | Hallett et al. |
| 6,750,225 B2 | 6/2004 | Pinto et al. |
| 6,800,625 B2 | 10/2004 | Jiang et al. |
| 6,953,679 B2 | 10/2005 | Salvati et al. |
| 6,960,474 B2 | 11/2005 | Salvati et al. |
| 7,001,911 B2 | 2/2006 | Salvati et al. |
| 2001/0020002 A1 | 9/2001 | Lederman et al. |
| 2003/0181728 A1 | 9/2003 | Salvati et al. |
| 2004/0019063 A1 | 1/2004 | Sun et al. |
| 2004/0077605 A1 | 4/2004 | Salvati et al. |
| 2004/0176324 A1 | 9/2004 | Salvati et al. |
| 2004/0181064 A1 | 9/2004 | Sun et al. |
| 2005/0187273 A1 | 8/2005 | Salvati et al. |
| 2005/0192253 A1 | 9/2005 | Salvati et al. |
| 2005/0272799 A1 | 12/2005 | Salvati et al. |
| 2005/0282813 A1 | 12/2005 | Salvati et al. |
| 2006/0020002 A1 | 1/2006 | Salvati et al. |

FOREIGN PATENT DOCUMENTS

| | | |
|---|---|---|
| CN | 1050877 | 4/1991 |
| DE | 23 65 677 | 5/1982 |
| DE | 32 27 055 | 1/1984 |
| EP | 0 001 813 | 11/1981 |
| EP | 0 051 020 | 8/1984 |
| EP | 0 082 402 | 4/1986 |
| EP | 0 277 476 | 8/1988 |
| EP | 0 091 596 | 9/1991 |
| EP | 0 253 503 | 12/1991 |
| EP | 0 406 119 | 1/1994 |
| EP | 0 436 426 | 6/1994 |
| EP | 0 626 384 | 11/1994 |
| EP | 0 678 507 | 10/1995 |
| EP | 0 494 819 | 7/1996 |
| EP | 1 008 457 | 7/2003 |
| FR | 2 075 751 | 10/1971 |
| FR | 2 329 276 | 5/1977 |
| GB | 1 039 020 | 8/1966 |
| GB | 2 133 006 | 10/1986 |
| GB | 2 290 296 | 12/1995 |
| JP | 51-088631 | 8/1976 |
| JP | 53-086035 | 7/1978 |
| JP | 63-170383 | 7/1988 |
| JP | 64-006258 | 1/1989 |
| JP | 1-125381 | 5/1989 |
| JP | 7-144477 | 6/1995 |
| WO | WO 91/06297 | 5/1991 |
| WO | WO 95/18794 | 7/1995 |
| WO | WO 96/19458 | 6/1996 |
| WO | WO 97/21993 | 6/1997 |
| WO | WO 97/49709 | 12/1997 |
| WO | WO 98/16830 | 4/1998 |
| WO | WO 98/29495 | 7/1998 |
| WO | WO 98/32439 | 7/1998 |
| WO | WO 98/39303 | 9/1998 |
| WO | WO 98/49555 | 11/1998 |
| WO | WO 99/27365 | 6/1999 |
| WO | WO 99/32463 | 7/1999 |
| WO | WO 00/06525 | 2/2000 |
| WO | WO 00/37430 | 6/2000 |
| WO | WO 01/07052 | 2/2001 |
| WO | WO 01/16108 | 3/2001 |
| WO | WO 01/16133 | 3/2001 |
| WO | WO 01/16139 | 3/2001 |
| WO | WO 01/19831 | 3/2001 |
| WO | WO 01/27622 | 4/2001 |
| WO | WO 01/30781 | 5/2001 |
| WO | WO 02/00617 | 1/2002 |
| WO | WO 02/00653 | 1/2002 |
| WO | WO 02/24702 | 3/2002 |
| WO | WO 02/067939 | 9/2002 |
| WO | WO 03/053354 | 7/2003 |
| WO | WO 03/053358 | 7/2003 |
| WO | WO 03/062241 | 7/2003 |

OTHER PUBLICATIONS

Anteunis, M.J.O. et al., "Proof of Delocalization-Stabilization by Sulfur in Enolate Formation During Racemisation of Sulfur Containing Amino Acid Residues", Tetrahedron Letters, vol. 22, No. 32, pp. 3101-3104 (1981).

Avalos, M. et al., "Clay-Catalyzed Solventless Addition Reactions of Furan with α,β-Unsaturated Carbonyl Compounds", Tetrahedron Letters, vol. 39, pp. 9301-9304 (1998).

Ben-Ishai, D. et al., "The Reactions of 5-Methoxyhydantoins with Conjugated Dienes", Tetrahedron, vol. 27, pp. 3119-3127 (1971).

Benítez, A. et al., "Site Selectivity of the Diels-Alder Reactions of 3-[1-(tert-Butyldimethylsilyloxy)vin-1-yl]furan and 3-(Propen-2- yl)furan. Synthesis of 4-Substituted Benzofurans", J. Org. Chem., vol. 61, No. 4, pp. 1487-1492 (1996).

Berson, J.A. et al., "*cis*-Addition in the Bromination of Bicyclic Olefins. The Structure and Stereochemistry of the Dibromides of *exo-cis*-3,6-Endoxo-$\Delta^4$-tetrahydrophthalic Anhydride and *endo-cis*-3,6-Endomethylene-$\Delta^4$-tetrahydrophthalic Anhydride", J. Amer. Chem. Soc., vol. 76, pp. 4060-4069 (1954).

Bockstahler, E.R. et al., "7-Oxabicyclo[2.2.1]heptane-2,3-dicarboximides with Anticonvulsant Activity", J. Med. Chem., vol. 11, pp. 603-606 (1968).

Chemical Abstracts, vol. 54, No. 1480g (1960).

Chemical Abstracts, vol. 57, No. 16561f (1962).

Chemical Abstracts, vol. 65, No. 15325h (1966).

Chemical Abstracts, vol. 65, No. 15326c (1966).

Chemical Abstracts, vol. 68, No. 39458j, p. 3830 (1968).

Chemical Abstracts, vol. 113, No. 40505b, p. 601 (1990).

Chen, C. et al., "Solid Phase Synthesis of 2-Acyl-3,7,8-substituted-5-oxo-2-azabicyclo[2.2.2]octane and Triaza Analogs: Resin Activation/Capture Approach/REACAP Technology", Tetrahedron Letters, vol. 40, pp. 3491-3494 (1999).

Chen, G. et al., "N-Mannich Bases of Norcantharidinimide and Analogs", Chemical Journal of Chinese Universities, vol. 4, No. 2, pp. 201-206 (1983).

Cheng, S. et al., "Synthesis of *N*-substituted, norcantharidinimide and analogues", Huaxue Shiji, vol. 15, No. 1, pp. 1-4 (1993).

Denison, M.S. et al., "Xenobiotic-inducible Transcription of Cytochrome P450 Genes", The Journal of Biological Chemistry, vol. 270, No. 31, pp. 18175-18178 (1995).

Dominianni, S.J. et al., "Some Derivatives of 7-Oxabicyclo[2.2.1]heptane-*exo-cis*-2,3-dicarboxylic Acid", Journal of Medicinal Chemistry, vol. 14, No. 2, p. 175 (1971).

Evans, R.M., "The Steroid and Thyroid Hormone Receptor Superfamily", Science, vol. 240, pp. 889-895 (1988).

Evnin; A.B. et al., "Synthesis and Cycloaddition Reactions of Dehydrohydantoins", J. Org. Chem., vol. 35, No. 9, pp. 3097-3106 (1970).

Fang, Y. et al., "Synthesis of the epoxidised/bromizated derivatives of norcantharidin", Huaxue Tongbao, No. 1, pp. 27-30 (1994).

Fišera, L'. et al., "Stereoselectivity of the Diels-Alder Cycloadditions, Sodium Borohydride Reduction and 1,3-Dipolar Cycloadditions to Furan Derivatives", Chem. Papers, vol. 49, No. 4, pp. 186-191 (1995).

Fuhrmann, U. et al, "Stable Transfection of Androgen Receptor and MMTV-CAT into Mammalian Cells: Inhibition of CAT Expression by Anti-Androgens", J. Steroid Biochem. Molec. Biol., vol. 42, No. 8, pp. 787-793 (1992).

Furr, B.J.A., "The Development of Casodex™ (Bicalutamide): Preclinical Studies", Eur. Urol., vol. 29 (Suppl. 2), pp. 83-95 (1996).

Goldstein, E. et al., "The Reactions of 5-Methoxy-3-phenyl and 5-Methoxy-3-benzylhydantoins with Conjugated Dienes", Tetrahedron Letters, No. 31, pp. 2631-2634 (1969).

Gribble, G.W. et al., "Syntheses and Diels-Alder Cycloaddition Reactions of 4*H*-Furo[3,4-*b*]indoles. A Regiospecific Diels-Alder Synthesis of Ellipticine", J. Org. Chem., vol. 57, No. 22, pp. 5878-5891 (1992).

Gringauz, A., "*o*-Acetoxyphenylacetic Acid, an Aspirin Homolog", J. Med. Chem., vol. 11, pp. 611-612 (1968).

Grogan, C.H. et al., "Bicyclic Imides and Isoindolines", J. Med. Chem., vol. 6, pp. 802-805 (1963).

Grondin, A. et al., "Benzotriazole maleimide as a bifunctional reactant for SERS", J. Chem. Soc., Perkin Trans. 2, pp. 2136-2141 (2001).

Häusler, J. et al., "Hydroxycyclodipeptides by cyclization of pyruvyl amino acids", Chem. Ber., vol. 107, No. 9, pp. 2804-2815 (1974).

Honkanen, R.E., "Cantharidin, another natural toxin that inhibits the activity of serine/threonine protein phosphatases types 1 and 2A", FEBS Letters, vol. 330, No. 3, pp. 283-286 (1993).

Jolivet, J., "Halogen derivatives of norcantharidin and its esters", Compt. Rend., vol. 243, pp. 2085-2086 (1956).

Jolivet, J., "Reaction products of furan and maleic anhydride", Ann. Chim. (Paris), vol. 5, pp. 1165-1217 (1960).

Joshi, B.S. et al., "Synthesis & Anticonvulsant Activity of 7-Oxabicyclo[2.2.1]heptane Derivatives: Part I—N-Alkyl, N-Aryl & N-Heteroaryl Derivatives of 3,6-Epoxyhexahydrophthalimide", Indian Journal of Chemistry, vol. 22B, pp. 131-135 (1983).

Kaplan, F.A. et al., "Annelation of Tricarbonyliron Complexes of Ortho-Disubstituted Annulenes. Synthesis of Tricarbonyliron Complexes of Derivatives of Bicyclo[6.2.0]decapentaene via Wittig Cycloolefination", Journal of the American Chemical Society, vol. 99, No. 2, pp. 513-517 (1977).

Kirby, G.W. et al., "1,4-Elimination Reactions of Chlorohydrin Ethers Derived from an Isoquinoline Reissert Compound", J. Chem. Research (Miniprint), pp. 3089-3097 (1985).

Kirby, G.W. et al., "1,4-Elimination Reactions of Chlorohydrin Ethers derived from an Isoquinoline Reissert Compound", J. Chem. Research (Synop.), p. 273 (1985).

Knaus, E.E. et al., "Diels-Alder Cycloadditions of *N*-Substituted-1,2-Dihydropyridines with 1,2,4-Triazoline-3,5-diones and Maleimides", J. Heterocyclic Chem., vol. 13, pp. 481-486 (1976).

Kobayashi, T. et al., "A Novel Skeletal Rearrangement of 2-Azabicyclo[2.2.1]hept-5-ene-3-carboxylic Acid Derivatives into 2-Oxabicyclo[3.3.0]-oct-7-en-3-ones under Acidic Conditions", Bull. Chem. Soc. Jpn., vol. 65, pp. 61-65 (1992).

Kobayashi, T. et al., "Norbornadiene-Fused Heterocycles: Synthesis and Cycloaddition Reactions of 2-Aryl-4,7-dihydro-4,7-methano-2*H*-isoindoles and 4,7-Dihydro-4,7-methanoisobenzofuran", Bull. Chem. Soc. Jpn., vol. 68, pp. 3269-3275 (1995).

Kobayashi, T. et al., "Novel Imidazoles and Hydantoins Moderately Strained by Incorporation with 2-Azabicyclo[2.2.1]heptane Skeleton", Bull. Chem. Soc. Jpn., vol. 67, No. 11, pp. 3082-3087 (1994).

Kovtunenko, V.A. et al., "1-Ethylthio-2R-isoindoles. An Example of Nonsynchronous Addition in the Diels-Alder Reaction", Khimiya Geterotsiklicheskikh Soedinenii, No. 9, pp. 978-983 (1984) (English language version).

Kovtunenko, V.A. et al., "Criteria for determining the configuration of Diels-Alder adducts in the reaction of N-methylisoindole with maleimide derivatives", Ukr. Khim. Zh. (Russ. Ed.), vol. 49, No. 12, pp. 1287-1293 (1983).

Kovtunenko, V.A. et al., "Criteria for Establishment of Three-Dimensional Structures of Diels-Alder Adducts in the Isoindole Series. 2. Reaction of 1,2-Disubstituted Isoindoles with Maleinimide Derivatives", Khimiya Geterotsiklicheskikh Soedinenii, No. 2, pp. 161-172 (1990) (English language version).

Kovtunenko, V.A. et al., "Initial erythro-9R-1,2,3,4-tetrahydronaphthalene-1,4-imino-2,3-dicarbonic acids", Ukr. Khim. Zh. (Russ. Ed.), vol. 58, No. 11, pp. 1035-1041 (1992).

Kovtunenko, V.A. et al., "Nonsynchronous cycloaddition in the 1-(dimethylamino)-2R-isoindole system", Ukr. Khim. Zh. (Russ. Ed.), vol. 54, No. 11, pp. 1186-1190 (1988).

Kovtunenko, V.A. et al., "Reaction of 2-methyl-1-phenylisoindole with maleimide derivatives", Ukr. Khim. Zh. (Russ. Ed.), vol. 58, No. 7, pp. 588-592 (1992).

Kovtunenko, V.A. et al., "Reaction of N-arylisoindoles with maleimide derivatives", Ukr. Khim. Zh. (Russ. Ed.), vol. 54, No. 2, pp. 186-190 (1988).

Kovtunenko, V.A. et al., "Structure of products of the addition of maleimide derivatives to 1-(dimethylamino)-2-arylisoindoles", Ukr. Khim. Zh. (Russ. Ed.), vol. 57, No. 1, pp. 71-77 (1991).

Kovtunenko, V.A. et al., "The Diels-Alder reaction of 2-aryl-1-methylisoindoles with N-R-maleimides", Ukr. Khim. Zh. (Russ. Ed.), vol. 55, No. 1, pp. 64-69 (1989).

Kreher, R. et al., "5-Pivaloyl-2H-isoindol. An isolable and crystallizable o-quinoid hetarene", Angew. Chem., vol. 94, No. 8, pp. 634-635 (1982).

Kreher, R.P. et al., "1,3-Dimethoxy-2-methyl-2H-isoindole, a reactive o-quinoid hetarene with donor substituents in the 5-membered ring", Chem.-Ztg., vol. 110, No. 10, pp. 363-367 (1986).

Kreher, R.P. et al., "An economical preparation method for 2H-isoindoles", Angew. Chem., vol. 96, No. 7, pp. 507-508 (1984).

Kreher, R.P. et al., "Reactions of 2-alkyl-2H-isoindoles with maleic imides", Chem. Ber., vol. 123, No. 2, pp. 381-390 (1990).

Kreher, R.P. et al., "Reactions of 2-alkyl-4,5,6,7-R″-2H-isoindoles (R″=tetramethyl, tetrachloro) with activated C:C dienophiles", Chem. Ber., vol. 125, No. 1, pp. 183-189 (1992).

Kreher, R.P. et al., "Reactions of 2H-isoindole with maleic imides: a simple procedure for the preparation of 7-azabicyclo[2.2.1]heptenes", Chem. Ber., vol. 121, No. 5, pp. 927-934 (1988).

Kreher, R.P. et al., "Simple preparations of 2H-isoindole", Chem.-Ztg., vol. 111, No. 12, pp. 349-356 (1987).

Kreher, R.P. et al., "Substituted 1-alkoxy-2-methyl-2H-isoindoles. Reactive o-quinonoid hetarenes with unsymmetrical molecular structure", Chem.-Ztg., vol. 112, No. 11, pp. 335-342 (1988).

Krow, G.R. et al., "Diels-Alder Cycloadditions of Diene-Substituted N-Ethoxycarbonyl-2-methyl-1,2-dihydropyridines with N-Phenylmaleimide", J. Heterocyclic Chem., vol. 22, pp. 131-135 (1985).

Krow, G.R. et al., "Heterodienophiles—V: A Stereochemical Study of Aldimine-Diene Cycloadditions", Tetrahedron, vol. 30, pp. 2977-2981 (1974).

Krow, G.R. et al., "Reexamination of Stereochemical Issues Concerning 2-Phenyl-1,2-dihydropyridine-Maleimide Cycloadditions", J. Org. Chem., vol. 47, No. 11, pp. 1989-1993 (1982).

Kucharczyk, N. et al., "Tetrapeptide Tachykinin Antagonists: Synthesis and Modulation of the Physicochemical and Pharmacological Properties of a New Series of Partially Cyclic Analogs", J. Med. Chem., vol. 36, No. 11, pp. 1645-1661 (1993).

Kwart, H. et al., "Isomerism and Adduct Stability in the Diels-Alder Reaction. I. The Adducts of Furan and Maleimide", J. Amer. Chem. Soc., vol. 74, pp. 3094-3097 (1952).

Lee, B.H. et al., "Functionalization of Marcfortine A at C12 and C17 by Treatment with Metallic Oxidizing Agents", Tetrahedron Letters, vol. 37, No. 34, pp. 6053-6056 (1996).

Li, Q. et al., "Gas chromatographic analysis of norcantharidin and related compounds using derivitization to imides", Journal of Pharmaceutical & Biomedical Analysis, vol. 7, No. 12, pp. 1635-1639 (1989).

Lin, J.-H. et al., "An Inhibitory Effect of Cantharidin on Testosterone Production from Dispersed Rat Leydig Cells", Journal of Natural Toxins, vol. 4, No. 2, pp. 147-153 (1995).

Lin, P.-Y. et al., "A Simple Procedure for Preparation of N-Thiazolyl and N-Thiadiazolylcantharidinimides and Evaluation of Their Cytotoxicities against Human Hepatocellular Carconima Cells", Bioorganic Chemistry, vol. 28, pp. 266-272 (2000).

Lin, P.-Y. et al., "Synthesis of Novel N-Pyridylcantharidinimides by Using High Pressure", Journal of the Chinese Chemical Society, vol. 48, No. 1, pp. 49-53 (2001).

Liu, J. et al. "A Study on Antitumor Chemotherapeutic Agents—Synthesis of Cantharidine Derivatives", Acta Pharmaceutica Sinica, vol. 15, No. 5, pp. 271-277 (1980).

Liu, J.-Y. et al., "Studies on Antitumor Chemotherapeutic Agents. II. Synthesis of Cantharidine Derivatives and Analogues", Acta Pharmaceutica Sinica, vol. 18, No. 10, pp. 752-759 (1983).

Liu, X.-H. et al., "Effects of Norcantharidin, a Protein Phosphatase Type-2A Inhibitor, on the Growth of Normal and Malignant Haemopoietic Cells", European Journal of Cancer, vol. 31A, No. 6, pp. 953-963 (1995).

Lyle, R.E. et al., "Sodium Borohydride Reduction of Sterically Hindered Pyridinium Salts", J. Org. Chem., vol. 39, No. 25, pp. 3708-3711 (1974).

Maruyama, K. et al., "Photochemistry of Aliphatic Imides. Synthesis of Azetidine-2,4-diones via Photochemical Isomerization of Succinimides and N-Formyl-N-methyl α,β-Unsaturated Amides", J. Org. Chem., vol. 46, No. 1, pp. 27-34 (1981).

Matias, P.M. et al., "Structural Evidence for Ligand Specificity in the Binding Domain of the Human Androgen Receptor: Implications for Pathogenic Gene Mutations", The Journal of Biological Chemistry, vol. 275, No. 34, pp. 26164-26171 (2000).

Mauger, A.B. et al., "N-Methylated Dioxopiperazines", J. Chem. Soc., Perkin Trans. I, pp. 2146-2148 (1972).

Mauger, A.B., "Degradation of Peptides to Diketopiperazines: Application of Pyrolysis-Gas Chromatography to Sequence Determination in Actinomycins", Journal of the Chemical Society, D. Chemical Communications, pp. 39-40 (1971).

Mel'nikow, N.N. et al., "Some Derivatives of 4,5-Dichloro-3,6-endoxohexahydrophthalic Acid", Zh. Obshch. Khim., vol. 29, pp. 949-952 (1959) (English language version).

Mel'nikow, N.N. et al., "Synthesis of Some 3,6-Endoxohexahydrophthalic Acid Derivatives", Zh. Obshch. Khim., vol. 26, pp. 227-232 (1956) (English language version).

Mikhailyuchenko, N.G. et al., "Polyfural(aryl)alkanes and Their Derivatives. 9. Polyfuryl(aryl)methanes in the Diels-Alder Reaction", Khimiya Geterotsiklicheskikh Soedinenii, No. 6, pp. 642-649 (1993) (English language version).

Mishiev, R.D. et al., "Diels-Alder synthesis based on furan and its adducts", Vses. Nauchn. Konf. Khim. Tekhnol. Furanovykh Soedin. (Tezisy Dokl.) 3rd, Sumgait. Filial, Inst. Neftekhim. Protsessov, Sumgait, USSR, Stradyn, Ya. P., ed., pp. 142-143 (1978).

Mueller, R.H. et al., "Diastereoselective Reaction of a Grignard Reagent with Chiral Imides: A Practical Preparation of a Key Intermediate in the Synthesis of Ifetroban Sodium", Organic Process Research & Development, vol. 1, No. 1, pp. 14-19 (1997).

Munoz, B. et al., "Resin Activation Capture Technology: Libraries from Stabilized Acyl-Pyridinium on Solid Support", Biotechnology and Bioengineering (Combinatorial Chemistry), vol. 71, No. 1, pp. 78-84 (2000).

Negro-Vilar, A., "Selective Androgen Receptor Modulators (SARMs): A Novel Approach to Androgen Therapy for the New Millenium", The Journal of Clinical Endocrinology & Metabolism, vol. 84, No. 10, pp. 3459-3462 (1999).

Padwa, A. et al., "Cyclic Carbonyl Ylide Formation from the Rhodium (II) Acetate Catalyzed Reaction of 1-Diazoalkanediones", Tetrahedron Letters, vol. 30, No. 3, pp. 301-304 (1989).

Pons, J.-F. et al., "A Constrained Diketopiperazine as a New Scaffold for the Synthesis of Peptidomimetics", Eur. J. Org. Chem., pp. 853-859 (1998).

Pons, J.-F. et al., "New RGD amphiphilic cyclic peptide and new RGD-mimetic constrained diketopiperazines", Pept. Proc. Am. Pept. Symp., 15th, Meeting Date 1997, Université Montpellier II, Montpellier, France, Tam, J.P., ed., pp. 176-177 (1999).

Reid, P. et al., "Antiandrogens in prostate cancer", Investigational New Drugs, vol. 17, pp. 271-284 (1999).

Remuzon, P. et al., "Fluoronaphthyridines as Antibacterial Agents. 6. Synthesis and Structure-Activity Relationships of New Chiral 7-(1-, 3-, 4-, and 6-Methyl-2,5-diazabicyclo[2.2.1]heptan-2-yl)naphthyridine Analogues of 7[(1R,4R)-2,5-Diazabicyclo[2.2.1]heptan-2-yl]-1-(1,1-dimethylethyl)-6-fluoro-1,4-dihydro-4-oxo-1,8-naphthyridine-3-carboxylic Acid. Influence of the Configuration on Blood Pressure in Dogs. A Quinolone-Class Effect", J. Med. Chem., vol. 35, No. 15, pp. 2989-2909 (1992).

Reyniers, F.S. et al., "Solution Conformation of Cyclic Dipeptides of Pipecolic and Thiapipecolic Acid Combined with Glycine and Sarcosine", Bull. Soc. Chim. Belg., vol. 94, No. 6, pp. 413-419 (1985).

Rosen, T. et al., "Design, Synthesis, and Properties of (4S)-7-(4-Amino-2-substituted-pyrrolidin-1-yl)quinolone-3-carboxylic Acids", J. Med. Chem., vol. 31, No. 8, pp. 1598-1611 (1988).

Sack, J.S. et al., "Crystallographic structures of the ligand-binding domains of the androgen receptor and its T877A mutant complexed with the natural agonist dihydrotestosterone", Proc. Natl. Acad. Sci. USA, vol. 98, No. 9, pp. 4904-4909 (2001).

Salakhov, M.S. et al., "Stereochemistry of the Adducts of Some Polychlorocyclopentadienes with the Anhydride and N-Phenylimide of 3,6-Epoxy-4-cyclohexene-1,2-dicarboxylic Acid", Zhurnal Organicheskoi Khimii, vol. 14, No. 6, pp. 1116-1118 (1978) (English language version).

Salakhov, M.S. et al., "Synthesis and some conversions of diene adducts of 5,5-di(substituted-oxy)tetrachlorocyclopentadienes with 3,6-endo-oxa-4-cyclohexene-1,2-dicarboxylic anhydride and -N-phenylimide", Azerb. Khim. Zh., No. 3, pp. 53-57 (1978).

Schrooten, R. et al., "A Comparative Study of the Aggregation, Rotational Side-Chain Isomerism and Side-Chain/Side-Chain Interactions in the Cyclic Dipeptides", Bull. Soc. Chim. Belg., vol. 89, No. 8, pp. 615-628 (1980).

SciFinder Search Results (Aug. 16, 2000).

SciFinder Search Results, Registry No. 10487-45-3 (Aug. 16, 2000).

SciFinder Search Results, Registry No. 99542-17-3 (Jun. 20, 2001).

SciFinder Search Results, Registry No. 107919-15-3.

SciFinder Search Results, Registry No. 146797-53-7 (Sep. 11, 2000).

Search Report "A" (SciFinder, Jun. 23, 2000).

Search Report "B" (SciFinder, Jun. 5, 2001).
Search Report "C" (SciFinder, Jun. 20, 2001).
Search Report "D" (SciFinder, Jun. 20, 2001).
Search Report "E" (SciFinder, Jun. 20, 2001).
Search Report "F" (SciFinder, Aug. 16, 2000).
Search Report "G" (SciFinder, Aug. 22, 2000).
Search Report "H" (SciFinder, Sep. 12, 2000).
Search Report "I".
Search Report "J" (Jul. 20, 2000).
Search Report "K" (SciFinder, Sep. 11, 2000).
Search Report "L" (SciFinder, Sep. 11, 2000).
Search Report "M" (SciFinder, Sep. 11, 2000).
Search Report "N" (SciFinder, Sep. 11, 2000).
Search Report "O" (SciFinder, Sep. 11, 2000).
Search Report "P" (SciFinder, Sep. 11, 2000).
Search Report "Q" (SciFinder, Sep. 11, 2000).
Search Report "R" (SciFinder, Sep. 11, 2000).
Search Report "S" (SciFinder, Sep. 11, 2000).
Search Report "T" (SciFinder, Sep. 11, 2000).
Search Report "U" (SciFinder, Sep. 11, 2000).
Search Report "V" (SciFinder, Sep. 11, 2000).
Search Report "W".
Search Report "X".
Search Report "Y" (SciFinder, Sep. 11, 2000).
Search Report "Z".
Search Report "AA".
Search Report "BB" (SciFinder, Sep. 11, 2000).
Shalati, M.D. et al., "Attempted Polymerization of Substituted Pipecolic Acid NCA's: Dimerization and Mechanism", Journal of Polymer Science: Polymer Chemistry Edition, vol. 22, pp. 107-120 (1984).
Srivastav, K.K. et al., "Configurational assignment of Diels-Alder adduct of N-carboethoxy 1,2-dihydropyridine-maleimide by DNMR spectroscopy", Natl. Acad. Sci. Letters, vol. 19, No. 1 & 2, pp. 16-18 (1996).
Srivastava, A. et al., "Diels-Alder adduct of 2-methyl furan and N-phenyl maleimides: Configurational assignment through conformational analysis about N-C (phenyl) bond", Natl. Acad. Sci. Letters, vol. 15, No. 2, pp. 41-44 (1992).
Tanaka, K. et al., "Diastereoselective Synthesis of (2R,3R,5R)- and (2S,3S,5S)-3-Hydroxy-5-methyl-2-pyrrolidinecarboxylic Acid as a Component of Actinomycin $Z_1$", Tetrahedron, vol. 54, pp. 10029-10042 (1998).
Térouanne, B. et al., "A stable prostatic bioluminescent cell line to investigate androgen and antiandrogen effects", Molecular and Cellular Endocrinology, vol. 160, pp. 39-49 (2000).
Tosunyan, D.É. et al., "2-Benzopyrylium Salts. 44. Formation of 4-Acyl-3,4-dihydroisoquinolinium Salts from the Reaction of 2-Benzopyrylium Salts with Azomethines and the Cycloaddition of Maleimides to the Product of Their Deprotonation, the 2,3-Dihydroisoquinolines", Khimiya Geterotsiklicheskikh Soedinenii, No. 11, pp. 1249-1254 (1992) (English language version).
Tsuchiya, T. et al., "Photochemistry—IX: Formation of Cyclopropenyl Ketones and Furans from Pyridazine N-Oxides by Irradiation", Tetrahedron, vol. 29, pp. 2747-2751 (1973).
Van Poucke, M. et al., "The Crystal Structure of (3R,6S)-3-Benzyl-4-methyl-1,4-diaza-bicyclo[4.4.0]decan-2,5-dione", Bull. Soc. Chim. Belg., vol. 91, No. 3, pp. 213-218 (1982).
Verbruggen, M. et al., "(3R,6R)-3,4-Dimethyl-1,4-diazabicyclo[4.4.0]decane-2,5-dione", Acta Cryst., vol. C49, pp. 1113-1116 (1993).

Vičar, J. et al., "Amino Acids and Peptides. CIX. Synthesis and Infrared Spectroscopy of 2,5-Piperazinediones Derived from Proline and Pipecolic Acid", Collection Czechoslov. Chem. Commun., vol. 37, pp. 4060-4071 (1972).
Vičar, J. et al., "Amino Acids and Peptides. CXIV. Proton Magnetic Resonance Studies of Cyclodipeptides Containing Pipecolic Acid, Proline and/or 2-Azetidine-carboxylic Acid", Collection Czechoslov. Chem. Commun., vol. 38, pp. 1940-1956 (1973).
Vincent, M. et al., "Synthesis and Conformational Studies of Zabicipril (S 9650-3), a Potent Inhibitor of Angiotensin Converting Enzyme", Tetrahedron Letters, vol. 33, No. 48, pp. 7369-7372 (1992).
Waller, C.L. et al., "Three-Dimensional Quantitative Structure-Activity Relationships for Androgen Receptor Ligands", Toxicology and Applied Pharmacology, vol. 137, pp. 219-227 (1996).
Walter, C.J. et al., "Free-Energy Profile for a Host-Accelerated Diels-Alder Reaction: The Sources of exo Selectivity", Angew. Chem. Intl. Ed. Engl., vol. 34, No. 2, pp. 217-219 (1995).
Walter, G. et al., "Protein serine/threonine phosphatases and cell transformation", Biochimica et Biophysica Acta, vol. 1155, pp. 207-226 (1993).
Walter, W.G., "Antitumor Imide Derivatives of 7-Oxabicyclo[2.2.1]heptane-2,3-dimethyl-2,3-dicarboxylic Acid", Journal of Pharmaceutical Sciences, vol. 78, No. 1, pp. 66-67 (1989).
Wang, G.-S., "Medical Uses of Mylabris in Ancient China and Recent Studies", Journal of Ethnopharmacology, vol. 26, pp. 147-162 (1989).
Ward, D.E. et al., "Diels-Alder Reactions of 2H-Thiopyrans", Tetrahedron Letters, vol. 31, No. 6, pp. 845-848 (1990).
Warrener, R.N. et al., "The Debromination Route to Norbornadienomaleimides and 7-Oxanorbornadienomaleimides: Study of Cycloaddition Specificities with Cyclic Dienes", Tetrahedron Letters, vol. 36, No. 42, pp. 7753-7756 (1995).
Wijnberg, B.P. et al., "Olefin Cyclisations of Hindered α-Acyliminium Ions", Tetrahedron, vol. 38, No. 1, pp. 209-217 (1982).
Xu, B., "Pharmacology of some natural products of China", Trends in Pharmacological Sciences, pp. 271-272 (1981).
Yarbrough, W.G. et al., "A Single Base Mutation in the Androgen Receptor Gene Causes Androgen Insensitivity in the Testicular Feminized Rat", The Journal of Biological Chemistry, vol. 265, No. 15, pp. 8893-8900 (1990).
Yur'ev, Y.K. et al., Synthesis of N-(Trichloromethylmercapto)imide Derivatives of 3,6-Endoxohexahydrophthalic Acid, Zhurnal Obshchei Khimii, vol. 30, No. 3, pp. 869-872 (1960) (English language version).
Zawadowski, T. et al., "Synthesis of New N-Substituted Derivatives of Exo-7-Oxabicyclo[2.2.1]hept-5-ene-2,3-dicarboxylic Acid Imide and of Exo-7-Oxabicyclo[2.2.1]heptane-2,3-dicarboxylic Acid Imide", Roczniki Chemii, Ann. Soc. Chim. Polonorum, vol. 51, pp. 557-560 (1977).
Zhang, S., "A Study on Antitumor Chemotherapeutic Agents—Synthesis of N-Cantharidine Derivatives", Acta Pharmaceutica Sinica, vol. 16, No. 10, pp. 784-786 (1981).
Zhou, Q. et al., "Comparison of the Sensitivity of Murine Hemopoietic and $P_{388}$ Leukemic Stem Cells to Five Antitumor Drugs", Acta Pharmaceutica Sinica, vol. 18, No. 10, pp. 725-730 (1983).

FUSED CYCLIC SUCCINIMIDE COMPOUNDS AND ANALOGS THEREOF, MODULATORS OF NUCLEAR HORMONE RECEPTOR FUNCTION

CROSS-REFERENCE TO RELATED APPLICATION

This application is a continuation of U.S. application Ser. No. 10/075,870, filed Feb. 14, 2002 now abandoned, which claims the benefit of U.S. Provisional Application No. 60/271,672, filed Feb. 27, 2001, which is incorporated herein by reference in its entirety.

FIELD OF THE INVENTION

The present invention relates to fused cyclic compounds, to methods of using such compounds in the treatment of nuclear hormone receptor-associated conditions such as cancer, and to pharmaceutical compositions containing such compounds.

BACKGROUND OF THE INVENTION

Nuclear hormone receptors (NHR's) constitute a large super-family of ligand-dependent and sequence-specific transcription factors. Members of this family influence transcription either directly, through specific binding to the promoter target genes (Evans, in *Science* 240: 889-895 (1988)), or indirectly, via protein-protein interactions with other transcription factors (Jonat et al., *Cell* 62: 1189-1204 (1990), Schuele et al., *Cell* 62: 1217-1226 (1990), and Yang-Yen et al., *Cell* 62: 1205-1215 (1990)). The nuclear hormone receptor super-family (also known in the art as the "steroid/thyroid hormone receptor super-family") includes receptors for a variety of hydrophobic ligands, including cortisol, aldosterone, estrogen, progesterone, testosterone, vitamin D3, thyroid hormone and retinoic acid (Evans, 1988, supra). In addition to these conventional nuclear hormone receptors, the super-family contains a number of proteins that have no known ligands, termed orphan nuclear hormone receptors (Mangelsdorf et al., *Cell* 83: 835-839 (1995), O'Malley et al., *Mol. Endocrinol.* 10: 1293 (1996), Enmark et al., *Mol. Endocrinol.* 10, 1293-1307 (1996) and Giguere, *Endocrin. Rev.* 20, 689-725 (1999)). The conventional nuclear hormone receptors are generally transactivators in the presence of ligand, and can either be active repressors or transcriptionally inert in the absence of ligand. Some of the orphan receptors behave as if they are transcriptionally inert in the absence of ligand. Others, however, behave as either constitutive activators or repressors. These orphan nuclear hormone receptors are either under the control of ubiquitous ligands that have not been identified, or do not need to bind ligand to exert these activities.

In common with other transcription factors, the nuclear hormone receptors have a modular structure, being comprised of three distinct domains: an N-terminal domain of variable size containing a transcriptional activation function AF-1, a highly conserved DNA binding domain and a moderately conserved ligand-binding domain. The ligand-binding domain is not only responsible for binding the specific ligand but also contains a transcriptional activation function called AF-2 and a dimerisation domain (Wurtz et al., *Nature Struc. Biol.* 3, 87-94 (1996), Parker et al., *Nature Struc. Biol.* 3, 113-115 (1996) and Kumar et al., *Steroids* 64, 310-319 (1999)). Although the overall protein sequence of these receptors can vary significantly, all share both a common structural arrangement indicative of divergence from an ancestral archetype, and substantial homology (especially, sequence identity) at the ligand-binding domain.

The steroid binding nuclear hormone receptors (SB-NHR's) comprise a sub-family of nuclear hormone receptors. These receptors are related in that they share a stronger sequence homology to one another, particularly in the ligand binding domain (LBD), than to the other members of the NHR super-family (Evans, 1988, supra) and they all utilize steroid based ligands. Some examples of this sub-family of NHR's are the androgen receptor (AR), the estrogen receptor (ER), the progesterone receptor (PR), the glucocorticoid receptor (GR), the mineralocorticoid receptor (MR), the aldosterone receptor (ALDR) and the steroid and xenobiotic receptor (SXR) (Evans et al., WO 99/35246). Based on the strong sequence homology in the LBD, several orphan receptors may also be members of the SB-NHR sub-family.

Consistent with the high sequence homology found in the LBD for each of the SB-NHR's, the natural ligands for each is derived from a common steroid core. Examples of some of the steroid based ligands utilized by members of the SB-NHR's include cortisol, aldosterone, estrogen, progesterone, testosterone and dihydrotestosterone. Specificity of a particular steroid based ligand for one SB-NHR versus another is obtained by differential substitution about the steroid core. High affinity binding to a particular SB-NHR, coupled with high level specificity for that particular SB-NHR, can be achieved with only minor structural changes about the steroid core (e.g., Waller et al., *Toxicol. Appl. Pharmacol.* 137, 219-227 (1996) and Mekenyan et al., *Environ. Sci. Technol.* 31, 3702-3711 (1997), binding affinity for progesterone towards the androgen receptor as compared to testosterone).

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic agonist of the PR, which is utilized as a birth control agent (Vegeto et al., *Cell* 69: 703-713 (1992)), and Flutamide is an example of an antagonist of the AR, which is utilized for the treatment of prostate cancer (Neri et al, *Endo.* 91, 427-437 (1972)). Tamoxifen is an example of a tissues specific modulator of the ER function, that is used in the treatment of breast cancer (Smigel, *J. Natl. Cancer Inst.* 90, 647-648 (1998)). Tamoxifen can function as an antagonist of the ER in breast tissue while acting as an agonist of the ER in bone (Grese et al., *Proc. Natl. Acad. Sci. USA* 94, 14105-14110 (1997)). Because of the tissue selective effects seen for Tamoxifen, this agent and agents like it are referred to as "partial-agonist" or partial-antagonist". In addition to synthetically derived non-endogenous ligands, non-endogenous ligands for NHR's can be obtained from food sources (Regal et al., *Proc. Soc. Exp. Biol. Med.* 223, 372-378 (2000) and Hempstock et al., *J. Med. Food* 2, 267-269 (1999)). The flavanoid phytoestrogens are an example of an unnatural ligand for SB-NHR's that are readily obtained from a food source such as soy (Quella et al., *J. Clin. Oncol.* 18, 1068-1074 (2000) and Banz et al., *J. Med. Food* 2, 271-273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's or through directed approaches using the available crystal structures of a variety of NHR ligand binding domains (Bourguet et al., *Nature* 375, 377-382 (1995), Brzozowski, et al., *Nature* 389, 753-758 (1997), Shiau et al., *Cell* 95, 927-937 (1998) and Tanenbaum et al., *Proc. Natl. Acad. Sci. USA* 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in *J. Med. Chem.*, 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

The compounds of the present invention comprise a core which serves as a steroid mimic, and are useful as modulators of the function of steroid binding nuclear hormone receptors, as well as other NHR as described following.

SUMMARY OF THE INVENTION

The present invention provides fused cyclic compounds of the following formula I and salts thereof, which compounds are especially useful as modulators of nuclear hormone receptor function:

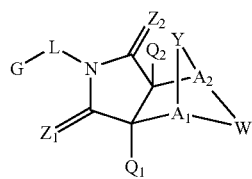
(I)

As used in formula I, and throughout the specification, the symbols have the following meanings unless otherwise indicated, and are, for each occurrence, independently selected:

G is a cycloalkenyl, aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC=O$, $R^1C=O-O-$, $R^1C=O$, $R^1C=S$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, oxo, $(R^1)(R^{1'})P=O$, or $(R^{1'})(NHR^1)P=O$;

$Z_1$ is O, S, NH, or $NR^6$;

$Z_2$ is O, S, NH, or $NR^6$; and (i) Y is J—J'—J" where J is $(CR^7R^{7'})n$ and n=0-3, J' is a bond, C=O, $CR^7R^{7'}$, $C=CR^8R^{8'}$, $R^2P=O$, $R^2P=S$, $R^2OP=O$, $R^2NHP=O$, $OP=OR^2$, $C=NR^7$, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0-3, where Y is not a bond;

W is $CR^7R^{7'}-CR^7R^{7'}$, $CR^8=CR^{8'}$, $CR^7R^{7'}-C=O$, cycloalkyl or substituted cycloalkyl, cycloalkenyl or substituted cycloalkenyl, or aryl or substituted aryl;

$A_1$ is $CR^7$ or N; and $A_2$ is $CR^7$ or N; or alternatively (ii) Y is absent;

W is $CR^7R^{7'}-CR^7R^{7'}$, $CR^8=CR^{8'}$, $CR^7R^{7'}-C=O$, cycloalkyl or substituted cycloalkyl, cycloalkenyl or substituted cycloalkenyl, heterocyclo or substituted heterocyclo, or aryl or substituted aryl;

$A_1$ is $CR^7R^{7'}$ or $NR^7$; and $A_2$ is $CR^7R^{7'}$ or $NR^7$; or alternatively (iii) Y is absent; and $A_1$, $A_2$ and W together are $-NR^7-N=N-$; and $Q_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

$Q_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

L is a bond, $(CR^7R^{7'})n$, NH, $NR^5$, $NH(CR^7R^{7'})n$, or $NR^5(CR^7R^{7'})n$, where n=0-3;

$R^1$ and $R^{1'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, $NR^1R^2$, thiol, alkylthio or substituted alkylthio;

$R^4$ is H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R$^1$C=O, R$^1$NHC=O, SO$_2$OR$^1$, or SO$_2$NR$^1$R$^{1'}$;

R$^5$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R$^1$C=O, R$^1$NHC=O, SO$_2$R$^1$, SO$_2$OR$^1$, or SO$_2$NR$^1$R$^{1'}$;

R$^6$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR$^1$, R$^1$C=O, R$^1$NHC=O, SO$_2$R$^1$, SO$_2$OR$^1$, or SO$_2$NR$^1$R$^{1'}$;

R$^7$ and R$^{7'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, hydroxylamine, hydroxylamide, amino, NHR$^4$, NR$^2$R$^5$, NOR$^1$, thiol, alkylthio or substituted alkylthio, R$^1$C=O, R$^1$OC=O, R$^1$C=O—O—, R$^1$NHC=O, SO$_2$R$^1$, SOR$^1$, PO$_3$R$^1$R$^{1'}$, R$^1$R$^{1'}$NC=O, C=OSR$^1$, SO$_2$R$^1$, SO$_2$OR$^1$, or SO$_2$NR$^1$R$^{1'}$; and R$^8$ and R$^{8'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, OR$^1$, amino, NHR$^4$, NR$^2$R$^5$, NOR$^1$, alkylthio or substituted alkylthio, C=OSR$^1$, R$^1$OC=O, R$^1$C=O, R$^1$NHC=O, R$^1$R$^{1'}$NC=O, SO$_2$OR$^1$, S=OR$^1$, SO$_2$R$^1$, PO$_3$R$^1$R$^{1'}$, or SO$_2$NR$^1$R$^{1'}$.

Compounds within formula I are novel; preferred such compounds are described further in the Examples herein.

The compounds of formula I and salts thereof comprise a core which can serve as a steroid mimic (and do not require the presence of a steroid-type (e.g., cyclopentanoperhydrophenanthrene analog) structure).

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substituents forming, in the latter case, groups such as a perfluoroalkyl group or an alkyl group bearing Cl$_3$ or CF$_3$), alkoxy, alkylthio, hydroxy, carboxy (i.e., —COOH), alkoxycarbonyl, alkylcarbonyloxy, CN, amino (i.e., —NH$_2$), alkylamino, dialkylamino, carbamoyl or substituted carbomoyl, carbamate or substituted carbamate, urea or substituted urea, amidinyl or substituted amidinyl, thiol (i.e., —SH), aryl, heterocycle, cycloalkyl, heterocycloalkyl, —S-aryl, —S-heterocycle, —S—O-aryl, —S=O-heterocycle, arylalkyl-O—, —S(O)$_2$-aryl, —S(O)$_2$-heterocycle, —NHS(O)$_2$-aryl, —NHS(O)$_2$-heterocycle, —NHS(O)$_2$NH-aryl, —NHS(O)$_2$NH-heterocycle, —P(O)$_2$-aryl, —P(O)$_2$-heterocycle, —NHP(O)$_2$-aryl, —NHP(O)$_2$-heterocycle, —NHP(O)$_2$NH-aryl, —NHP(O)$_2$NH-heterocycle, —O-aryl, —O-heterocycle, —NH-aryl, —NH-heterocycle, —NHC=O-aryl, —NHC=O-alkyl, —NHC=O-heterocycle, —OC=O-aryl, —OC=O-heterocycle, —NHC=ONH-aryl, —NHC=ONH-heterocycle, —OC=OO-alkyl, —OC=OO-aryl, —OC=OO-heterocycle, —OC=ONH-aryl, —OC=ONH-heterocycle, —NHC=OO-aryl, —NHC=OO-heterocycle, —NHC=OO-alkyl, —C=ONH-aryl, —C=ONH-heterocycle, —C=OO-aryl, —C=OO-heterocycle, —N(alkyl)S(O)$_2$-aryl, —N(alkyl)S(O)$_2$-heterocycle, —N(alkyl)S(O)$_2$NH-aryl, —N(alkyl)S(O)$_2$NH-heterocycle, —N(alkyl)P(O)$_2$-aryl, —N(alkyl)P(O)$_2$-heterocycle, —N(alkyl)P(O)$_2$NH-aryl, —N(alkyl)P(O)$_2$NH-heterocycle, —N(alkyl)-aryl, —N(alkyl)-heterocycle, —N(alkyl)C=O-aryl, —N(alkyl)C=O-heterocycle, —N(alkyl)C=ONH-aryl, —N(alkyl)C=ONH-heterocycle, —OC=ON(alkyl)-aryl, —OC=ON(alkyl)-heterocycle, —N(alkyl)C=OO-aryl, —N(alkyl)C=OO-heterocycle, —C=ON(alkyl)-aryl, —C=ON(alkyl)-heterocycle, —NHS(O)$_2$N(alkyl)-aryl, —NHS(O)$_2$N(alkyl)-heterocycle, —NHP(O)$_2$N(alkyl)-aryl, NHP(O)$_2$N(alkyl)-heterocycle, —NHC=ON(alkyl)-aryl, —NHC=ON(alkyl)-heterocycle, —N(alkyl)S(O)$_2$N(alkyl)-aryl, —N(alkyl)S(O)$_2$N(alkyl)-heterocycle, —N(alkyl)P(O)$_2$N(alkyl)-aryl, —N(alkyl)P(O)$_2$N(alkyl)-heterocycle, —N(alkyl)C=ON(alkyl)-aryl, and —N(alkyl)C=ON(alkyl)-heterocycle. In the aforementioned exemplary substitutents, in each instance, groups such as "alkyl", "aryl" and "heterocycle" can themselves be optionally substituted; for example, "alkyl" in the group "NCH=OO-alkyl" recited above can be optionally substituted so that both "NHC=OO-alkyl" and "NHC=OO-substituted alkyl" are exemplary substitutents.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkenyl or substituted cycloalkenyl.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkyl or substituted cycloalkyl, or aryl or substituted aryl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl", "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1, 2, 3, 4 or 5 substituents, at any point of attachment. Exemplary substituents include, but are not limited to, nitro, cycloalkyl or substituted cycloalkyl, cycloalkenyl or substituted cycloalkenyl, cyano, alkyl-S(O)$_m$—(m=0, 1 or 2), alkyl or substituted alkyl, as well as those groups recited above as exemplary alkyl substituents and as previously mentioned as preferred aryl substituents in the definition for G. Exemplary substituents also include fused cyclic substituents, such as heterocyclo or cycloalkenyl, or substituted heterocyclo or cycloalkenyl, groups (e.g., thereby forming a fluoroenyl, tetrahydronapthalenyl, or dihydroindenyl group).

"Carbamoyl" refers to the group —CONH— which is bonded on one end to the remainder of the molecule and on the other to hydrogen or an organic moiety (such as alkyl, substituted alkyl, aryl, substituted aryl, heterocycle, alkylcarbonyl, hydroxyl and substituted nitrogen). "Carbamate" refers to the group —O—CO—NH— which is bonded on one end to the remainder of the molecule and on the other to hydrogen or an organic moiety (such as those listed above). "Urea" refers to the group —NH—CO—NH— which is bonded on one end to the remainder of the molecule and on the other to hydrogen or an organic moiety (such as those listed above). "Amidinyl" refers to the group —C(=NH)(NH$_2$). "Substituted carbamoyl," "substituted carbamate," "substituted urea" and "substituted amidinyl" refer to carbamoyl, carbamate, urea or amidinyl groups as described above in which one more of the hydrogen groups are replaced by an organic moiety (such as those listed above).

The terms "heterocycle", heterocyclic" and "heterocyclo" refer to fully saturated, or partially or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl-S(O)$_m$—(m=0, 1 or 2), alkyl or substituted alkyl, as well as those groups recited above as exemplary alkyl substituents, and as previously mentioned as preferred heterocyclo substituents in the definition for G.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The terms "hydroxylamine" and "hydroxylamide" refer to the groups OH—NH— and OH—NH—CO—, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

When a term such as "(CRR)n" is used, it denotes an optionally substituted alkyl chain existing between the two fragments to which it is bonded, the length of which chain is defined by the range described for the term n. An example of this is n=0-3, implying from zero to three (CRR) units existing between the two fragments, which are attached to the primary and terminal (CRR) units. In the situation where the term n is set to zero (n=0) then a bond exists between the two fragments attached to (CRR).

Unless otherwise indicated, any heteroatom with unsatisfied valences is assumed to have hydrogen atoms sufficient to satisfy the valences.

Divalent groups, such as those in the definition of W (e.g., $CR^7R^{7'}$—C=O), may be bonded in either direction to the remainder of the molecule (e.g,

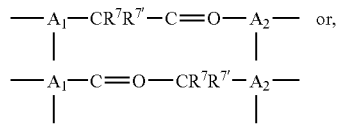

for the aforementioned group within the definition of W).

Carboxylate anion refers to a negatively charged group —COO⁻.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings. In certain cases, for example, the exo or endo conformation can be preferred for the fused ring system bonded to G-L in formula I. As can be appreciated, the preferred configuration can be a function of the particular compound and its preferred activity. Separation of configurational isomers can be achieved by any suitable method, such as column chromatography.

Throughout the specifications, groups and substituents thereof may be chosen to provide stable moieties and compounds.

Embodiments indicated herein as exemplary or preferred are intended to be illustrative and not limiting.

METHODS OF PREPARATION

The compounds of the present invention may be prepared by methods such as those illustrated in the following Schemes I to IV. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques. See the following which describe other methods which may be employed in the preparation of compounds of the present invention: Li, et al., *Eur. J. Org. Chem.* 9, 1841-1850 (1998); Li, Y-Q, *Synlett.* 5, 461-464 (1996); Thiemann, et al., *Bull. Chem. Soc. Jpn.* 67, 1886-1893 (1994); Tsuge et al., *Heterocycles* 14, 423-428 (1980); Ward et al., *Can J. Chem.* 75, 681-693 (1997); Ward et al., *Can J. Chem.* 69, 1487-1497 (1991); Ward et al., *Tetrahedron Lett.* 31, 845-848 (1990); Fleming et al., *J. Org. Chem.* 44, 2280-2282 (1979); Jankowski et al., *J. Organomet. Chem.* 595, 109-113 (2000); Keglevich et al., *J. Organomet. Chem.* 579, 182-189 (1999); Keglevich et al., *J. Organomet. Chem.* 570, 49-539 (1998); Jankowski et al., *Hetroat. Chem.* 7, 369-374 (1996); Jankowski et al., *J. Am. Chem. Soc.* 113, 7011-7017 (1991); Quin et al., *Tetrahedron Lett.* 31, 6473-6476 (1990); Quin et al., *J. Org. Chem.* 59, 120-129 (1994); Quin et al., *J. Org. Chem.* 58, 6212-6216 (1993); Quin et al., *Phosphorous, Sulfur Silicon Relat. Elem.* 63, 349-362 (1991); Quin et al., *Hetroat. Chem.* 2, 359-367 (1991); Hussong et al., *Phosphorus Sulfur.* 25, 201-212 (1985); Quin et al, *J. Org. Chem.* 51, 3341-3347 (1986); Myers et al., *J. Am. Chem. Soc.* 114, 5684-5692 (1992); Myers et al., *J. Am. Chem. Soc.* 113, 6682-6683 (1991); Shen et al., U.S. Pat. No. 5,817,679; Cordone et al., *J. Am. Chem. Soc.* 111, 5969-5970 (1989); Jung et al., *J. Chem. Soc. Commun.* 630-632 (1984); Lay et al., *J. Am. Chem. Soc.* 104, 7658-7659 (1982); Gonzalez et al., *J. Am. Chem. Soc.* 117, 3405-3421 (1995); Kreher et al., *Chem Ber.* 125, 183-189 (1992); Simig et al., *Synlett.* 7, 425-426 (1990); Sha et al., *J. Org. Chem.* 55, 2446-2450 (1990); Drew et al., *J. Chem. Soc., Perkin Trans.* 17, 1277-1284 (1985); Kreher et al., *Anorg. Chem., Org Chem.* 31B, 599-604 (1976); Avalos et al., *Tetrahedron Lett.* 39, 9301-9304 (1998); Gousse et al., *Macromolecules* 31, 314-321 (1998); Mikhailyuchenko et al., *Khim. Geterotsikl. Soedin.* 6, 751-758 (1993); Lubowitz et al., U.S. Pat. No. 4,476,184; Padwa et al., *J. Org. Chem.* 61, 3706-3714 (1996); Schlessinger et al., *J. Org. Chem.* 59, 3246-3247 (1994); Buchmeiser et al., WO Publication No. 9827423; Tanabe et al., Japanese Patent Document JP 07144477; Mochizucki et al., Japanese Patent Document JP 63170383; Hosoda et al., Japanese Patent Document JP 62053963; Onaka et al., Japanese Patent Document JP 62053964; Kato et al., Japanese Patent Document JP 53086035; Kato et al., Japanese Patent Document JP 51088631; Tottori et al., Japanese Patent Document JP 49124225; Augustin et al., German Patent Document DD101271; Title et al., French Patent Document FR 2031538; Gousse et al., *Polym. Int.* 48, 723-731 (1999); Padwa et al., *J. Org. Chem.* 62, 4088-4096 (1997); Theurillat-Moritz et al., *Tetrahedron: Asymmetry* 7, 3163-3168 (1996); Mathews et al., *J. Carbohydr. Chem.* 14, 287-97 (1995); Srivastava et al., *Natl. Acad. Sci. Lett. (India)* 15, 41-44 (1992); Mayorga et al., *Rev. Cubana Quim.* 4, 1-6 (1988); Kondoli et al., *J. Chem. Res., Synop.* 3, 76 (1987); Primelles et al., *Cent. Azucar* 7-14 (1985); Solov'eva et al., *Khim. Geterotsikl. Soedin.* 5, 613-15 (1984); Liu et al., *Yaoxue Xuebao* 18, 752-759 (1983); Joshi et al., *Indian J. Chem, Sect. B.* 22B, 131-135 (1983); Amos et al., WO Publication No. 9829495; Odagiri et al., U.S. Pat. No. 4,670,536; Gallucci et al., European Patent Document EP 355435; Redmore, D. U.S. Pat. No. 3,821,232; Nakano et al., *Heterocycles* 35, 37-40 (1993); Tomisawa et al., *Chem. Pharm. Bull.* 36, 1692-1697 (1988); Krow et al., *J. Heterocycl. Chem.* 22, 131-135 (1985); Krow et al., *J. Org. Chem.* 47, 1989-1993 (1982); Liu et al., *Yaoxue Xuebao* 18, 752-759 (1983); Nishikawa et al., *Yaoxue Xuebao* JP 01061457; and/or Rice et al., *J. Med. Chem.* 11, 183-185 (1968).

All documents cited in the present specification, such as those cited in this "Methods of Preparation" as well as other sections herein, are incorporated herein by reference in their entirety. Reference to any document herein is not to be construed as an admission that such document is prior art.

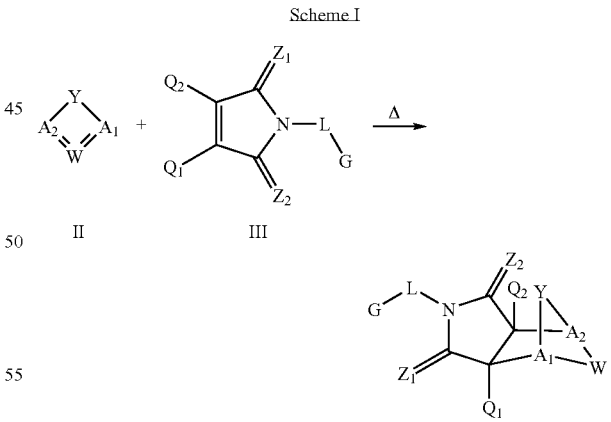

As illustrated in Scheme I, a diene of formula II can be reacted with a dienophile of formula III, under conditions readily selected by one skilled in the art (such as by the addition of heat ("Δ")), to obtain a compound of formula IV, which is a compound of formula I. An intermediate diene of formula II can be obtained from commercial sources or readily made by one skilled in the art, for example, in accordance with the following literature documents and the references found therein: Hofman et al., *J. Agric. Food Chem.* 45, 898-906 (1997); Baciocchi et al., *J. Chem. Soc., Perkin Trans. 2* 8, 821-824 (1975); Wu et al., *J. Heterocycles* 38, 1507-1518 (1994); Yin et al., *Tetrahedron Lett.* 38, 5953-5954 (1997); Mic'ovic' et al., *Tetrahedron* 20, 2279-2287 (1964); Gorbunova et al., *J. Org. Chem.* 35, 1557-1566 (1999); Rassu et al., *Chem. Soc. Rev.* 29, 109-118 (2000); Kaberdin et al., *Russ. Chem. Rev.* 68, 765-779 (1999); Barluenga et al., *Aldrichimica Acta* 32, 4-15 (1999); Bogdanowicz-Szwed et al., *Pol. Wiad. Chem.* 52, 821-842 (1998); Casiraghi et al., *Adv. Asymmetric Synth.* 3, 113-189 (1998); and/or Baeckvall et al., *Chem. Rev.* 98, 2291-2312 (1998). An intermediate dieneophile of formula III can be obtained from commercial sources or readily made by one skilled in the art, for example, in accordance with the following literature references and the references found therein: Deshpande et al., *Heterocycles* 51, 2159-2162 (1999); Seijas et al., *J. Chem. Res., Synop.* 7, 420-421 (1999); Langer et al., *Eur. J. Org. Chem.* 7, 1467-1470 (1998); Kita et al., Japanese Patent Document JP 09194458; Lopez-Alvarado et al., *J. Org. Chem.* 61, 5865-5870 (1996); Condon et al., U.S. Pat. No. 5,523,277; Sasakihara et al., Japanese Patent Document JP 04290868; Igarashi et al., Japanese Patent Document JP 04149173; Aoyama et al., Japanese Patent Document JP 04134063; Aoyama et al., Japanese Patent Document JP 04134062; Pastor et al., *J. Org. Chem.* 53, 5776-5779 (1988); and/or Takahashi et al., *Chem. Lett.* 6, 1229-1232 (1987).

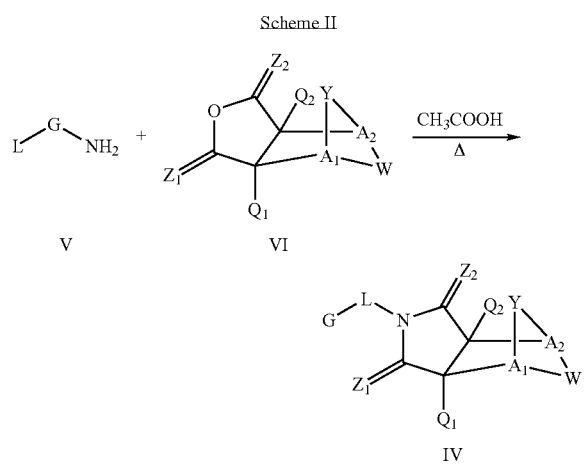

As illustrated in Scheme II, compounds of formula I can be obtained by reaction of a primary amine of formula V with a substituted anhydride-like intermediate of formula VI, for example, in a solvent such as acetic acid with or without heating, to yield a compound of formula IV, which is a compound of formula I. Primary amines of formula V can be obtained from commercial sources or readily synthesized by one skilled in the art. Anhydride-like agents of formula VI can be obtained from commercial sources or readily synthesized by one skilled in the art. The documents listed following describe exemplary approaches for the synthesis of intermediates of formula VI as well as synthetic approaches which can be applied to the synthesis of compounds of formula IV (all incorporated herein by reference in their entirety): Kohler, E. P.; Tishler, M.; Potter, H.; Thompson, H. T. *J. Am. Chem. Soc.* 1939, 1057-1061; Yur'ev, Y. K.; Zefirov, N. S. *J. Gen. Chem. U.S.S.R. (Engl. Transl.)* 1961, 31, 772-5; Norman G. Gaylord U.S. Pat. No. 3,995,099; Schueler, P. E.; Rhodes, Y. E. *J. Org. Chem.* 1974, 39, 2063-9; Ishitobi, H.; Tanida, H; Tsuji, T. *Bull. Chem. Soc. Japan* 1971, 44, 2993-3000; Stájer, G.; Virág, M.; Szabó, A. E.; Bernáth, G.; Sohár, P.; Sillanpää, R. *Acta. Chem. Scand.* 1996, 50, 922-30; Hart, H.; Ghosh, T. *Tetrahedron Lett.* 1988, 29, 881-884; Kato, M.; Yamamoto, S.; Yoshihara, T.; Furuichi, K; Miwa, T. *Chem. Lett.* 1987, 1823-1826; Kottwitz, J.; Vorbrüggen, H. *Synthesis* 1995, 636-637; Creary, X. *J. Org. Chem.* 1975, 40, 3326-3331; Alder, K.; Ache, H.-J.; Flock, F. H. *Chem. Ber.* 1960, 93, 1888-1895; Toder, B. H.; Branca, S. J.; Dieter, R. K.; Smith, A. B. III *Synth. Commun.* 1975, 5, 435-439; Sprague, P. W.; Heikes, J. E.; Gougoutas, J. Z.; Malley, M. F.; Harris, D. N.; and/or Greenberg, R. *J. Med. Chem.* 1985, 28, 1580-1590.

The aforementioned approach(es) can be applied in a combinatorial fashion, for example, by utilizing a multi-well reaction block such as is described in Waldemar Ruediger, Wen-Jeng Li, John W., Allen Jr., and Harold N. Weller III, U.S. Pat. No. 5,961,925, Apparatus for Synthesis of Multiple Organic Compounds With Pinch Valve Block (incorporated herein by reference in its entirety). By utilizing the above-mentioned multi-well reaction block, one can, for example, perform multiples of 96 reactions at a time. Solvent can then be removed from the reaction tubes without removal from the reaction block and the crude products can be precipitated using a base such as sodium bicarbonate. The precipitates can be collected by filtration of the reaction block and then the desired products can be transferred directly to 96 well plates for screening. In this fashion, a large array of compounds of formula I can be synthesized, and tests conducted as desired by an automated approach.

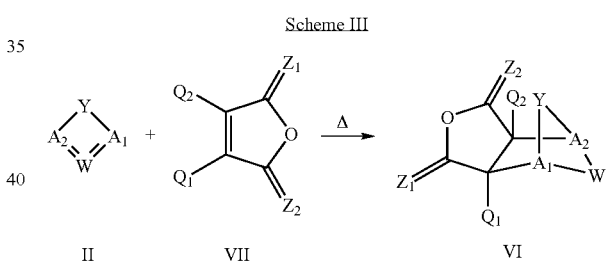

Scheme III describes a method for preparing an intermediate compound of formula VI which can be used to synthesize a compound of formula I, as described in Scheme II. As described in Scheme III, a diene of formula II can be reacted with a dieneophile of formula VII to yield the intermediate of formula VI. The methods applied to obtain such a transformation are analogous to those described in Scheme I.

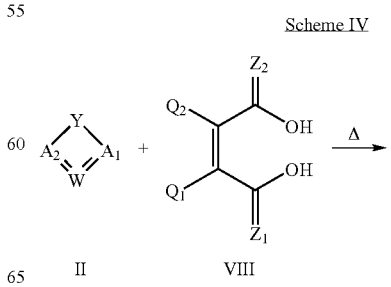

-continued

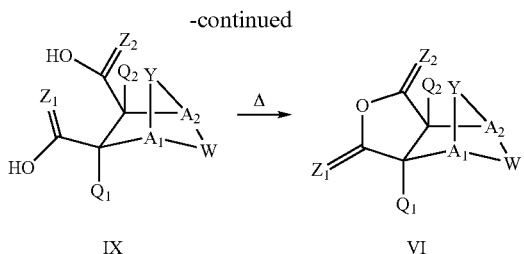

IX    VI

Scheme IV describes a method for preparing an intermediate compound of formula VI which can be used to synthesize a compound of formula I, as described in Scheme II. As shown in Scheme IV, a diene of formula II can be reacted with a dieneophile of formula VIII to yield the intermediate of formula IX. The intermediate of formula IX can be dehydrated to an anhydride-like intermediate of formula VI. Dehydration of the bis-acid intermediate of formula IX to can be achieved by a variety of methods, such as those known to one skilled in the art and described in the following documents and the references embodied therein: Sprague et al., *J. Med. Chem.* 28, 1580-1590 (1985); and/or Retemi et al., *J. Org. Chem.* 61, 6296-6301 (1996).

Preferred Compounds

A preferred subgenus of the compounds of the present invention includes compounds of the formula I or salts thereof wherein one or more, preferably all, of the following substituents are as defined below:

G is a cycloalkenyl, an aryl (preferably phenyl or naphthyl), or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC=O$, $R^1C=O—O—$, $R^1C=O$, $R^1C=S$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, oxo, $(R^1)(R^{1'})P=O$, or $(R^{1'})(NHR^1)P=O$;

$Z_1$ is O or S;

$Z_2$ is O or S; and (i) Y is $—(CR^7R^{7'})_n$ and n=1-3, $C=CR^8R^{8'}$, $C=O$, cycloalkyl or substituted cycloalkyl, cycloalkenyl or substituted cycloalkenyl, or aryl or substituted aryl;

W is $CR^7R^{7'}—CR^7R^{7'}$, $CR^8=CR^{8'}$, $CR^7R^{7'}—C=O$, cycloalkyl or substituted cycloalkyl, or aryl or substituted aryl;

$A_1$ is $CR^7$; and $A_2$ is $CR^7$; or alternatively, (ii) Y is absent;

W is $CR^7R^{7'}—CR^7R^{7'}$ or $CR^8=CR^{8'}$;

$A_1$ is $CR^7$; and $A_2$ is $CR^7$; or alternatively, (iii) Y is absent; and $A_1$, $A_2$ and W together are $—NR^7—N=N—$; and $Q_1$ is H, alkyl or substituted alkyl;

$Q_2$ is H, alkyl or substituted alky; and

L is a bond, NH or $NR^5$.

USE AND UTILITY

The compounds of the present invention modulate the function of nuclear hormone receptors (NHR), and include compounds which are, for example, agonists, partial agonists, antagonists or partial antagonists of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHR's, the Orphan receptors or other NHR'S. Selective modulation of one such NHR relative to others within the NHR family is preferred. "Modulation" includes, for example, activation (e.g., agonist activity) or inhibition (e.g., antagonist activity).

The present compounds are thus useful in the treatment of NHR-associated conditions. A "NHR-associated condition", as used herein, denotes a condition or disorder which can be treated by modulating the function of a NHR in a subject, wherein treatment comprises prevention, partial alleviation or cure of the condition or disorder. Modulation may occur locally, for example, within certain tissues of the subject, or more extensively throughout a subject being treated for such a condition disorder.

The compounds of the present invention are useful for the treatment of a variety of conditions and disorders including, but not limited to, those described following:

Compounds of formula I can be applied as agonists, partial agonists, antagonists, or partial antagonists of the estrogen receptor, preferably selectively to that receptor, in an array of medical conditions which involve modulation of the estrogen receptor pathway. Applications of said compounds include but are not limited to: osteoporosis, hot flushes, vaginal dryness, prostate cancer, breast cancer, endometrial cancer, cancers expressing the estrogen receptor such as the aforementioned cancers and others, contraception, pregnancy termination, menopause, amennoreahea, and dysmennoreahea.

Compounds of formula I can be applied as agonists, partial agonists, antagonists or partial antagonists of the progesterone receptor, preferably selectively to that receptor, in an array of medical conditions which involve modulation of the progesterone receptor pathway. Applications of said compounds include but are not limited to: breast cancer, other cancers containing the progesterone receptor, endometriosis, cachexia, contraception, menopause, cyclesynchrony, meniginoma, dysmennoreahea, fibroids, pregnancy termination, labor induction and osteoporosis.

Compounds of formula I can be applied as agonists, partial agonists, antagonists or partial antagonists of the glucocorticoid receptor, preferably selectively to that receptor, in an array of medical conditions which involve modulation of the glucocorticoid receptor pathway. Applications of said compounds include but are not limited to: inflammatory diseases, autoimmune diseases, prostate cancer, breast cancer, Alzheimer's disease, psychotic disorders, drug dependence, non-insulin dependent Diabetes Mellitus, and as dopamine receptor blocking agents or otherwise as agents for the treatment of dopamine receptor mediated disorders. Glucocorticoid receptor AP-1 ("GR AP-1") inhibitors (which compounds can, for example, avoid side effects connected with GR agonists) can be used as anti-inflammatory and immunosuppressive agents, for example, to treat a wide variety of inflammatory and autoimmune diseases. These diseases include without limitation: rheumatoid arthritis, osteoarthritis, inflammatory bowel disease, asthma, chronic obstructive pulmonary disease, prevention of transplant rejection, multiple sclerosis, and psoriasis, among others. GR AP-1 inhibitors of the present invention can be employed together with known GR AP-1 inhibitors, such as the steroid prednisone (which is used to treat the above diseases).

Compounds of formula I can be applied as agonists, partial agonists, antagonists or partial antagonists of the mineralocorticoid receptor, preferably selectively to that receptor, in an array of medical conditions which involve modulation of the mineralocorticoid receptor pathway. Applications of said compounds include but are not limited to: drug withdrawal syndrome and inflammatory diseases.

Compounds of formula I can be applied as agonists, partial agonists, antagonists or partial antagonists of the aldosterone receptor, preferably selectively to that receptor, in an array of medical conditions which involve modulation of the aldosterone receptor pathway. One application of said compounds includes but is not limited to: congestive heart failure.

Compounds of formula I can be applied as agonists, partial agonists, antagonists or partial antagonists of the androgen receptor, preferably selectively to that receptor, in an array of medical conditions which involve modulation of the androgen receptor pathway. Applications of said compounds include but are not limited to: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers, modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers.

Compounds of formula I can be applied as (preferably, selective) antagonists of the mutated androgen receptor, for example, found in many tumor lines. Examples of such mutants are those found in representative prostate tumor cell lines such as LNCap, (T877A mutation, Biophys. Acta, 187, 1052 (1990)), PCa2b, (L701H & T877A mutations, J. Urol., 162, 2192 (1999)) and CWR22, (H874Y mutation, Mol. Endo., 11, 450 (1997)). Applications of said compounds include but are not limited to: adenomas and neoplasies of the prostate, breast cancer and endometrial cancer.

Compounds of formula I can be applied as agonists, partial agonists, antagonists or partial antagonists of the steroid and xenobiotic receptor, preferably selectively to that receptor, in an array of medical conditions which involve modulation of the steroid and xenobiotic receptor pathway. Applications of said compounds include but are not limited to: treatment of disregulation of cholesterol homeostasis, attenuation of metabolism of pharmaceutical agents by co-administration of an agent (compound of the present invention) which modulates the P450 regulator effects of SXR.

Along with the aforementioned NHR, there also exist a number of NHR for which the activating or deactivating ligands may not be characterized. These proteins are classified as NHR due to strong sequence homology to other NHR, and are known as the Orphan receptors. Because the Orphan receptors demonstrate strong sequence homology to other NHR, compounds of formula I include those which serve as modulators of the function of the Orphan NHR. Orphan receptors which are modulated by NHR modulators such as compounds within the scope of formula I are exemplified, but not limited to, those listed in Table 1. Exemplary therapeutic applications of modulators of said Orphan receptors are also listed in Table 1, but are not limited to the examples therein.

TABLE 1

Exemplary Orphan nuclear hormone receptors, form (M = monomeric, D = heterodimeric, H = homodimeric), tissue expression and target therapeutic applications. (CNS = central nervous system)

| Receptor | Form | Tissue Expression | Target Therapeutic Application |
|---|---|---|---|
| NURR1 | M/D | Dopaminergic Neurons | Parkinson's Disease |
| RZRβ | M | Brain (Pituitary), Muscle | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| NGFI-Bβ | M/D | Brain | CNS Disorders |
| COUP-Tfα | H | Brain | CNS Disorders |
| COUP-TFβ | H | Brain | CNS Disorders |
| COUP-TFγ | H | Brain | CNS Disorders |
| Nur77 | H | Brain, Thymus, Adrenals | CNS Disorders |
| Rev-ErbAα | H | Muscle, Brain (Ubiquitous) | Obesity |
| HNF4α | H | Liver, Kidney, Intestine | Diabetes |
| SF-1 | M | Gonads, Pituitary | Metabolic Disorders |
| LXRα, β | D | Kidney (Ubiquitous) | Metabolic Disorders |
| GCNF | M/H | Testes, Ovary | Infertility |
| ERRα, β | M | Placenta, Bone | Infertility, Osteoporosis |
| FXR | D | Liver, Kidney | Metabolic Disorders |
| CARα | H | Liver, Kidney | Metabolic Disorders |
| PXR | H | Liver, Intestine | Metabolic Disorders |

The present invention thus provides methods for the treatment of NHR-associated conditions, comprising the step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating a NHR-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders.

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosupressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

As mentioned above, the compounds of the present invention can be employed alone or in combination with each other and/or other suitable therapeutic agents useful in the treatment of NHR-associated conditions.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tarnoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR modulators (including, but not limited to, those of present invention) such as AR modulators, ER modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

The compounds of the present invention may be employed adjuvant to surgery.

Another application of the present compounds is in combination with antibody therapy such as but not limited to antibody therapy against PSCA. An additional application is in concert with vaccine/immune modulating agents for the treatment of cancer.

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a NHR modulator. Preferred are those compounds with an activity greater than 20 μm for binding or transactivation in any of these assays. Various compounds of the present invention were determined to have AR modulator activity utilizing the transactivation assay, and standard AR binding assays as described following.

Transactivation Assays:

AR Specific Assay:

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.*, 271 (12): 7043-51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions-5322 and -3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA 453 cells were collected in media containing 10% charcoal stripped FBS. Each cell suspension was distributed into two Gene Pulser Cuvetts (Bio-Rad) which then received 8 μg of the reporter construct, and electoporated using a Bio-Rad Gene Pulser at 210 volts and 960 μFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from 10-10 to 10-5 M (sample). Duplicates were used for each sample. The compound dilutions were performed on a Biomek 2000 laboratory workstation. After 48 hours, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay:

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM –0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_1$ values were determined by application of the Cheng-Prusoff equation to the $IC_{50}$ values, where:

$$K_1 = \frac{IC_{50}}{(1 + (^3H\text{-}DHT)/K_d \text{ for } ^3H\text{-}DHT)}.$$

After correcting for non-specific binding, $IC_{50}$ values were determined. The $IC_{50}$ is defined as the concentration of competing ligand needed to reduce specific binding by 50%. The Kds for [$^3$H]-DHT for MDA 453 and LNCaP were 0.7 and 0.2 mM respectively.

Human Prostate Cell Proliferation Assay:

Compounds of the present invention were tested ("test compounds") on the proliferation of human prostate cancer cell lines. For that, MDA PCa2b cells, a cell line derived from the metastasis of a patient that failed castration, Navone et al., *Clin. Cancer Res.*, 3, 2493-500 (1997), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/ average$_{sample}$−average$_{blank}$])

Data was plotted and the concentration of compound that inhibited 50% of the [$^3$H]-Thymidine incorporation was quantified ($IC_{50}$).

C2C12 Mouse Myoblast Transactivation Assay:

Two functional transactivation assays were developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which stably expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. *The Journal of Biological Chemisty* 272, 8227-8235, (1997). It was developed by random mutagenesis of an AR/GR consensus enhancer sequence.

ARTA Stable 1:
1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, and 800 µg/ml Geneticin (Gibco BRL, Cat. No.: 10131-035).
2. 48 hours later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEMem media (Gibco BRL, Cat. No.: 31985-070). To this, 0.5 µl/well Plus reagent is added. This mixture is incubated for 15 minutes at room temperature. In a separate vessel, 0.385 µl/well LipofectAMINE reagent is diluted with 5 µl/well Opti-MEM. The DNA mixture is then combined with the LipofectAMINE mixture and incubated for an additional 15 minutes at room temperature. During this time, the media from the cells is removed and replaced with 60 l/well of Opti-MEM. To this is added 10 µl/well of the DNA/LipofectAMINE transfection mixture. The cells are incubated for 4 hours.
3. The transfection mixture is removed from the cells and replaced with 90 µl of media as in #1 above.
4. 10 µl/well of appropriate drug dilution is placed in each well.
5. 24 hours later, the Steady-Glo™ Luciferase Assay System is used to detect activity according to the manufacturer's instructions (Promega, Cat. No.: E2520).

ARTA Stable 2
1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, 800 µg/ml Geneticin (Gibco BRL, Cat. No.: 10131-035) and 800 µg/ml Hygromycin β (Gibco BRL, Cat. No.: 10687-010).
2. 48 hours later, the media on the cells is removed and replaced with 90 µl fresh. 10 µl/well of appropriate drug dilution is placed in each well.
3. 24 hours later, the Steady-Glo™ Luciferase Assay System is used to detect activity according to the manufacturer's instructions (Promega, Cat. No.: E2520).

Proliferation Assays

Murine Breast Cell Proliferation Assay:
The ability of compounds of the present invention ("test compounds") to modulate the function of the AR was determined by testing said compounds in a proliferation assay using the androgen responsive murine breast cell line derived from the Shionogi tumor, Hiraoka et al., *Cancer Res.,* 47, 6560-6564 (1987). Stable AR dependent clones of the parental Shionogi line were established by passing tumor fragments under the general procedures originally described in Tetuo, et. al., *Cancer Research* 25, 1168-1175 (1965). From the above procedure, one stable line, SC114, was isolated, characterized and utilized for the testing of example compounds. SC114 cells were incubated with or without the test compounds for 72 hours and the amount of [3H]-thymidine incorporated into DNA was quantified as a surrogate endpoint to assess the number of cells and therefore the proliferation rate as described in Suzuki et. al, *J. Steroid Biochem. Mol. Biol.* 37, 559-567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1; 1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi of [3H]-Thymidine (Amersham) was added per well and incubated for another 2 hr followed by tripsinization, and harvesting of the cells onto GF/B filters. Micro-scint PS were added to the filters before counting them on a Beckman TopCount.

For the antagonist mode, the % Inhibition was calculated as:

$$\% \text{ Inhibition} = 100 \times (1 - [\text{average}_{sample} - \text{average}_{blank} / \text{average}_{control} - \text{average}_{blank}])$$

Data was plotted and the concentration of compound that inhibited 50% of the [$^3$H]-Thymidine incorporation was quantified ($IC_{50}$).

For the agonist mode % Control was referred as the effect of the tested compound compared to the maximal effect observed with the natural hormone, in this case DHT, and was calculated as:

$$\% \text{ Control} = 100 \times (\text{average}_{sample} - \text{average}_{blank}) / (\text{average}_{control} - \text{average}_{blank})$$

Data was plotted and the concentration of compound that inhibited 50% of the [$^3$H]-Thymidine incorporation was quantified ($EC_{50}$).

In Vitro Assay to Measure GR Induced AP-1 Transrepression:
The AP-1 assay is a cell based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/ml geneticin. Cells are plated the day before the assay at approximately 40000 cells/well. On assay day, the media is removed by aspiration and 20 µl assay buffer (RPMI without phenol red+10% FCS (charcoal-treated)+Pen/Strep) is added to each well. At this point either 20 µl assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 µl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of $\leq 10$ µM typically suppresses activity by 65%. Test compounds which demonstrate an inhibition of PMA induction of 50% or greater at a concentration of test compound of $\leq 10$ µM are deemed active.

Wet Prostate Weight Assay AR Antagonist Assay:

The activity of compounds of the present invention as AR antagonists was investigated in an immature male rat model, a standard, recognized test of antiandrogen activity of a given compound, as described in L. G. Hershberger et al., *Proc. Soc. Expt. Biol. Med.,* 83, 175 (1953); P. C. Walsh and R. F. Gittes, "Inhibition of extratesticular stimuli to prostate growth in the castrated rat by antiandrogens", *Endocrinology,* 86, 624 (1970); and B. J. Furr et al., "ICI 176,334: A novel nonsteroid, peripherally selective antiandrogen", *J. Endocrinol.,* 113, R7-9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. Clin. Invest. Med., 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. By E. Knobil and J. D. Neill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawely) were castrated under metofane ansestesia. Five days after surgery these castrated rats (60-70 g, 23-25 day-old) were dosed for 3 days. Animals were dosed sub-cutaneously (s.c.) 1 mg/kg with Testosterone Proprionate (TP) in arachis oil vehicle and anti-androgen test compounds (compounds of the present invention) were dosed orally by gavage (p.o.) in dissolved/suspensions of 80% PEG 400 and 20% Tween 80 (PEGTW). Animals were dosed (v/w) at 0.5 ml of vehicle/100 g body weight. Experimental groups were as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 3-day treatment, the animals were sacrificed, and the ventral prostate weighed. To compare data from different experiments, the sexual organs weights were first standardized as mg per 100 g of body weight, and the increase in organ weight induced by TP was considered as the maximum increase (100%). ANOVA followed by one-tailed Student or Fischer's exact test was used for statistical analysis.

The gain and loss of sexual organ weight reflect the changes of the cell number (DNA content) and cell mass (protein content), depending upon the serum androgen concentration. See Y. Okuda et al., *J. Urol.,* 145, 188-191 (1991), the disclosure of which is herein incorporated by reference. Therefore, measurement of organ wet weight is sufficient to indicate the bioactivity Qf androgens and androgen antagonist. In immature castrated rats, replacement of exogenous androgens increases seminal vesicles (SV) and the ventral prostate (VP) in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10-30-fold higher potency than free T.

In this immature castrated rat model, a known AR antagonist (Casodex) was also administered simultaneously with 0.1 mg of TP ($ED_{80}$), inhibiting the testosterone-mediated increase in the weights of the VP and SV in a dose dependent manner. The antagonist effects were similar when dosing orally or subcutaneously. Compounds of the invention also exhibited AR antagonist activity by suppressing the testosterone-mediated increase in the weights of VP and SV.

Levator Ani & Wet Prostate Weight Assay AR Agonist Assay:

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.,* 83, 175 (1953); B. L. Beyler et al, "Methods for evaluating anabolic and catabolic agents in laboratory animals", *J. Amer. Med. Women's Ass.,* 23, 708 (1968); H. Fukuda et al., "Investigations of the levator ani muscle as an anabolic steroid assay", *Nago Dai. Yak Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized, M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.—Soc. Ital. Biol. Sper.* 42, 1596 (1966); Z. Gori et al., "Testosterone hypertrophy of levator ani muscle of castrated rats. II. Electron-microscopic observations" *Boll.—Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7-14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10-30-fold higher potency than free T.

MDA PCa2b Human Prostate Zenograft Assay:

In Vivo Antitumor Testing: MDA-PCa-2b human prostate tumors were maintained in Balb/c nu/nu nude mice. Tumors were propagated as subcutaneous transplants in adult male nude mice (4-6 weeks old) using tumor fragments obtained from donor mice. Tumor passage occurred every 5-6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100-200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight=(length×width2)÷2.

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

$$TVDT = \text{Median time (days) for control tumors to reach target size} - \text{Median time (days) for control tumors to reach half the target size s And, Log cell kill} = (T-C) \div (3.32 \times TVDT).$$

Statistical evaluations of data were performed using Gehan's generalized Wilcoxon test.

Dunning Prostate Tumor:

Dunning R3327H prostate tumor is a spontaneously derived, well differentiated androgen responsive adenocarcinoma of the prostate (Smolev J K, Heston W D, Scott W W, and Coffey D S, *Cancer Treat Rep.* 61, 273-287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin. Oncol.*, 119, 669-674 (1993), Furr B. J. A. *Euro. URL.* 18 (suppl. 3), 2-9 (1990), Shain S. A. and Huot R I. *J. Steriod Biochem.* 31, 711-718 (1988)).

At the beginning of the study, the Dunning tumor pieces (about 4×4 mm) are transplanted subcutaneously to the flank of mature male Copenhagen rats (6-7 weeks old, Harlan-Sprague Dawley, Indianapolis, Md.). About 6 weeks after the implantation, the animals with tumors of measurable size (about 80-120 $mm^2$) are randomized into treatment groups (8-10 rats/group) and the treatments are initiated. One group of the rats are castrated to serve as the negative control of tumor growth. Animals are treated daily with compounds of the current invention, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St Louis, Mo.). Typical therapeutic experiments would include three groups of three escalating doses for each standard or test compound (in a range of 300-3 mg/kg).

Tumors in the vehicle (control) group reach a size of 1500 to 2500 $mm^3$, whereas the castrated animal group typically shows tumor stasis over the 14 weeks of observation. Animals treated orally with 20 mg/kg of bicalutamide or flutamide would be expected to show a 40% reduction in tumor volumes compared to control after 14 weeks of treatment. The size of tumors are measured weekly by vernier caliper (Froboz, Switzerland), taking perpendicular measurements of length and width. Tumor volumes are measured in $mm^3$ using the formula: Length×Width×Height=Volume. Statistical differences between treatment groups and control are evaluated using multiple ANOVA analysis followed by one tail nonparametric Student t test.

Mature Rat Prostate Weight Assay:

The activity of compounds of the present invention were investigated in a mature male rat model, which is a variation of the Levator ani & wet prostate weight assay described above. The above in vivo assays are recognized assays for determining the anabolic effects in muscle and sustaining effects in sex organs for a given compound, as described in L. G. Hershberger et al., 83 Proc. Soc. Expt. Biol. Med., 175 (1953); B. L. Beyler et al, "Methods for evaluating anabolic and catabolic agents in laboratory animals", 23 J. Amer. Med. Women's Ass., 708 (1968); H. Fukuda et al., "Investigations of the levator ani muscle as an anabolic steroid assay", 14 Nago Dai. Yak. Ken. Nem. 84 (1966) the disclosures of which are herein incorporated by reference. The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et. al. 16 Clin. Invest. Med., 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues, M. C. Luke and D. S. Coffey, "The Physiology of Reproduction" ed. By E. Knobil and J. D. Neill, 1, 1435-1487 (1994). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalmic region. Testosterone levels in the blood serve to inhibit the secretion of LHRH and subsequently reduce levels of LH and ultimately the levels of circulating testosterone levels. By measuring blood levels of LH as they are effected by compounds of the present invention ("test compounds"), it is possible to determine the level of agonist or antagonist activity of said compounds at the hypothalamic axis of this endocrine cycle.

Matched sets of Harlan Sprague-Dawely rats (40-42 days old, 180-220 g), were dosed orally by gavage (p.o.) with the test compounds in dissolved/suspensions of 80% PEG 400 and 20% Tween 20 (PEGTW) for 14 days. Two control groups, one intact and one castrated were dose orally only with the PEGTW vehicle. Animals were dosed (v/w) at 0.5 ml of vehicle/100 g body weight. Experimental groups were as follows:

1. Intact vehicle (p.o., PEGTW, QD)

2. Control vehicle (p.o., PEGTW, QD)

3. Bicalutamide (Casodex, a recognized antiandrogen, as a reference compound) or a compound of the present invention, p.o. in PEGTW QD. (in a range of doses). At the end of the 14-day treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) is quantitatively determined with the Biotrak [125 I] kit (Amersham Pharmacia Biotek), following the manufacturer directions. The assay is based on the competition by the LH present in the serum of the binding of [$^{125}$ I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration, see Y. Okuda et al., J. Urol., 145, 188-191 (1991), the disclosure of which in herein incorporated by reference. Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vessicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

CWR22 Human Prostate Zenograft Assay:

In Vivo Antitumor Testing: CWR22 human prostate tumors were maintained in Balb/c nu/nu nude mice. Tumors were propagated as subcutaneous transplants in adult male nude mice (4-6 weeks old) using tumor fragments obtained from donor mice. Tumor passage occurred every 5-6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100-200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight=(length× width2)÷2.

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size And, Log cell kill=$(T-C) \div (3.32 \times TVDT)$ Statistical evaluations of data were performed using Gehan's generalized Wilcoxon test.

The following Examples illustrate embodiments of the present invention, and are not intended to limit the scope of the claims.

ABBREVIATIONS

The following abbreviations are used herein:
4-DMAP=4-dimethylaminopyridine
DMF=dimethylformamide
EtOAc=ethyl acetate
Me=methyl
RT=retention time
TFA=trifluoroacetic acid
THF=tetrahydrofuran
TLC=thin layer chromatography
pTSA=para-toluenesulfonic acid
□=heat
t-Bu=tert-butyl
TMSOTf=trimethylsilyl trifluoromethane sulfonate
TEA=triethylamine
n-BuLi=n-butyllithium
rt=room temperature
LC=liquid chromatography
Ph=phenyl
Et=ethyl
DMS=dimethylsulfate
MS=molecular sieves
MS(ES)=Electro-Spray Mass Spectrometry
mCPBA=m-chloroperoxybenzoic acid
sat=saturated
Ac=acetyl
h=hours
HMPA=hexamethylphosphoramide
Lawesson's Reagent=2,4-bis(4-methoxyphenyl)-1,3,2,4-dithiadiphosphetane-2,4-disulfide
Freshyl cracked cyclopentadiene=monomer of cyclopentadiene generated by Diels-Alder dimer product
AIBN=2,2'-azobis(2-methylpropionitrile)
aq=aqueous
QD=dosed once a day
PMA=Phrobal-12-myristate-13 acetate

EXAMPLE 1

(3aα,4β,8β,8aα)-4,5,6,7,8,8a-Hexahydro-2-[3-(trifluoromethyl)phenyl]-4,8-ethenocyclohepta[c]pyrrole-1,3(2H,3aH)-dione (1B)

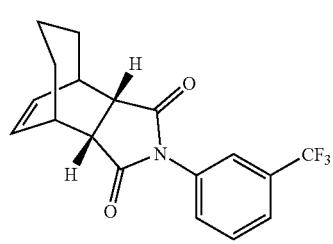

A. (3aα,4β,8β,8aα)-4,5,6,7,8,8a-Hexahydro-4,8-etheno-1H-cyclohepta[c]furan-1,3(3aH)-dione (1A)

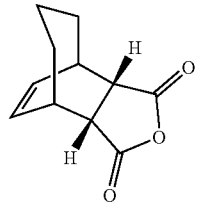

Compound 1A was made in accordance with the procedure described in Kohler, et. al., *J. Am. Chem. Soc.* 1057-1061 (1939). A solution of cycloheptadiene (5 g, 53.1 mmol, 1 eq) and maleic anhydride (5.73 g, 58.4 mmol, 1.1 eq) in xylenes (300 mL) was heated to reflux overnight. The solution was concentrated via distillation and hexanes were added until the solution became cloudy. The resulting brown precipitate (~1 g) was removed by filtration and the filtrate were placed in a freezer. The white solid which crystallized from the filtrate was isolated by filtration and dried under vacuum to give 5 g of compound 1A which required no further purification.

B. (3aα,4β,8β,8aα)-4,5,6,7,8,8a-Hexahydro-2-[3-(trifluoromethyl)phenyl]-4,8-ethenocyclohepta[c]pyrrole-1,3(2H,3aH)-dione (1B)

Compound 1A (100 mg, 0.520 mmol, 1.2 eq) was combined with 3-(trifluoromethyl)aniline (0.054 mL, 0.434 mmol, 1 eq) in acetic acid (2 mL) and heated at 115° C. overnight. After the reaction was allowed to cool to rt, water was added, and the resulting precipitate was isolated by filtration. The material was washed sequentially with aqueous $K_2CO_3$ and water and then dried in a vacuum oven to provide 114.2 mg (78.4%) of compound 1B as a tan crystalline solid. HPLC: 98% at 1.82 min (retention time) (YMC S5 Turbo-Pack Pro column 4.6×33 mm, 10-90% aqueous methanol over 2 minutes containing 0.1% $CF_3CO_2H$, 4 mL/min, monitoring at 220 nm), MS (ES): m/z 336.2 [M+H]$^+$.

EXAMPLE 2

(3aα,4β,8β,8aα)-4,5,6,7,8,8a-Hexahydro-2-[3-(trifluoromethyl)phenyl]-4,8-ethanocyclohepta[c]pyrrole-1,3(2H,3aH)-dione (2B)

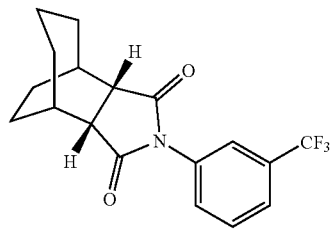

A. (3aα,4β,8β,8aα)-4,5,6,7,8,8a-Hexahydro-4,8-ethano-1H-cyclohepta[c]furan-1,3(3aH)-dione (2A)

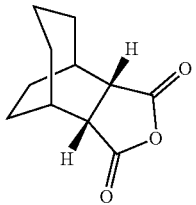

A solution of compound 1A (1 g, 5.20 mmol) and 10% Pd/C (~20 mg) in EtOAc was shaken under $H_2$ at 40 psi overnight. The reaction solution was filtered through a pad of celite eluting with EtOAc and concentrated to give 0.86 g of compound 2A as a white powder.

B. (3aα,4β,8β,8aα)-4,5,6,7,8,8a-Hexahydro-2-[3-(trifluoromethyl)phenyl]-4,8-ethanocyclohepta[c]pyrrole-1,3(2H,3aH)-dione (2B)

Compound 2A (2.37 g, 12.2 mmol, 1.2 eq) was combined with (trifluoromethyl)aniline (1.27 mL, 10.2 mmol, 1.0 eq) in AcOH (45 mL) and heated at 115° C. overnight. After the reaction mixture was cooled to room temperature, the resulting precipitate was collected, washed with MeOH and dried to give 2.7 g (78.6%) of compound 2B as a white crystalline solid. HPLC: 99% at 3.61 min (retention time) (YMC S5 ODS column 4.6×50 mm eluting with 10-90% aqueous methanol over 4 minutes containing 0.1% TFA, 4 mL/min, monitoring at 220 nm), MS (ES): m/z 338.4 $[M+H]^+$.

EXAMPLE 3

(3aα,4β,7β,7aα)-3a,4,7,7a-Tetrahydro-2-(1-naphthalenyl)-4,7-methano-1H-isoindole-1,3(2H)-dione (3B)

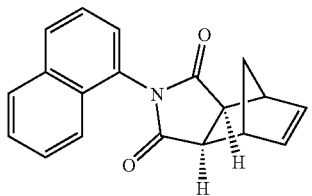

A. cis-5-Norbornene-exo-2,3-dicarboxylic anhydride (3A)

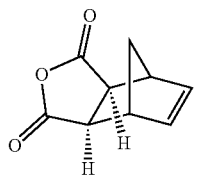

Compound 3A was made in accordance with the procedure described in Norman et. al., U.S. Pat. No. 3,995,099. cis-5-Norbornene-endo-2,3-dicarboxylic anhydride (4 g) was heated for 4 hours at 220° C. The resulting solid was recrystallized 4× from benzene to give 0.63 g of compound 3A (>99:1 exo by $^1$H NMR) as light brown crystals.

B. (3aα,4β,7β,7aα)-3a,4,7,7a-Tetrahydro-2-(1-naphthalenyl)-4,7-methano-1H-isoindole-1,3(2H)-dione (3B)

Compound 3A (100 mg, 0.609 mmol, 1.1 eq) was combined with 1-aminonaphthalene (79 mg, 0.554 mmol, 1 eq) in acetic acid (2 mL) and heated at 115° C. overnight. After the reaction was allowed to cool to rt, water was added, and the resulting precipitate was isolated by filtration. The material was washed sequentially with aqueous $K_2CO_3$ and water. Treatment with charcoal to remove colored impurities, followed by drying under vacuum provided 103.2 mg (64.7%) of compound 3B as an off-white powder. HPLC: 95% at 1.54 min (retention time) (YMC S5 TurboPack Pro column 4.6×33 mm, 10-90% aqueous methanol over 2 minutes containing 0.1% $CF_3CO_2H$, 4 mL/min, monitoring at 220 nm), MS (ES): m/z 290.0 $[M+H]^+$.

EXAMPLE 4

(3aα,4β,7β,7aα)-Hexahydro-2-[3-(trifluoromethyl)phenyl]-4,7-methano-1H-isoindole-1,3(2H)-dione (4B)

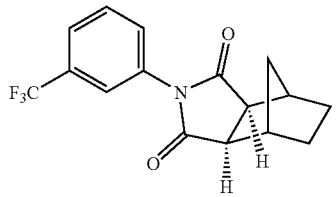

A. (3aα,4β,7β,7aα)-Hexahydro-4,7-methanobenzofuran-1,3-dione (4A)

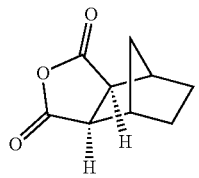

A solution of compound 3A (434 mg, 2.64 mmol) and 10% Pd/C (~10 mg) in EtOAc was stirred under $H_2$ balloon overnight. The reaction mixture was filtered through celite eluting with EtOAc, concentrated under reduced pressure to give 429 mg of compound 4A as an off-white powder.

B. (3aα,4β,7β,7aα)-Hexahydro-2-[3-(trifluoromethyl)phenyl]-4,7-methano-1H-isoindole-1,3(2H)-dione (4B)

Compound 4A (1.8 g, 10.84 mmol, 1.0 eq) was combined with 3-(trifluoromethyl)aniline (1.49 mL, 11.93 mmol, 1.1 eq) in AcOH (40 mL) and heated at 115° C. overnight. After the reaction mixture was cooled to room temperature, the resulting precipitate was collected, washed with MeOH and recrystallized from $CH_2Cl_2$/hexanes to give 2.17 g (64.8%) of compound 4B as a white crystalline solid. HPLC: 99% at 3.23 min (retention time) (YMC S5 ODS column 4.6×50 mm eluting with 10-90% aqueous methanol over 4 minutes containing 0.1% TFA, 4 mL/min, monitoring at 220 nm), MS (ES): m/z 310.2 $[M+H]^+$.

EXAMPLE 5

(3aα,4β,4aα,5aα,6β,6aα)-4,4a,5,5a,6,6a-Hexahydro-2-[3-(trifluoromethyl)phenyl]-4,6-ethenocycloprop[f]isoindole-1,3(2H,3aH)-dione (5B)

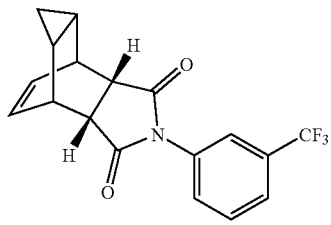

A. (3aα,4β,4aα,5aα,6β,6aα)-4,4a,5,5a,6,6a-Hexahydro-4,6-etheno-1H-cycloprop[f]isobenzofuran-1,3(3aH)-dione (5A)

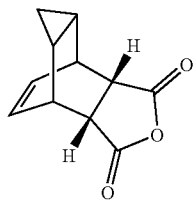

Compound 5A was made in accordance with the procedure described in Schueler et. al., *J. Org. Chem.* 39, 2063-2069 (1974). A solution of cycloheptatriene (6.1 mL, 58.79 mmol, 1.1 eq) and maleic anhydride (5.1 g, 53.44 mmol, 1.0 eq) in xylenes (20 mL) was heated to reflux for 90 hours. The reaction mixture was placed in the freezer, and the resulting precipitate was filtered, washed with xylenes and dried to give 4.10 g compound 5A as a white crystalline solid.

B. (3aα,4β,4aα,5aα,6β,6aα)-4,4a,5,5a,6,6a-Hexahydro-2-[3-(trifluoromethyl)phenyl]-4,6-ethenocycloprop[f]isoindole-1,3(2H,3aH)-dione (5B)

Compound 5A (100 mg, 0.526 mmol, 1.2 eq) was combined with 3-(trifluoromethyl)aniline (0.055 mL, 0.438 mmol, 1 eq) in acetic acid (2 mL) and heated at 115° C. overnight. After the reaction was allowed to cool to rt, water was added, and the resulting precipitate was isolated by filtration. The material was washed sequentially with aqueous $K_2CO_3$ and water and then dried in a vacuum oven to provide 145.5 mg (99%) of compound 5B as an off-white crystalline solid. HPLC: 99% at 1.74 min (retention time) (YMC S5 TurboPack Pro column 4.6×33 mm, 10-90% aqueous methanol over 2 minutes containing 0.1% $CF_3CO_2H$, 4 mL/min, monitoring at 220 nm), MS (ES): m/z 334.0 $[M+H]^+$.

EXAMPLE 6

(3aα,4β,4aα,5aα,6β,6aα)-2-(4-Bromo-3-methylphenyl)-4,4a,5,5a,6,6a-hexahydro-4,6-ethanocycloprop[f]isoindole-1,3(2H,3aH)-dione (6B)

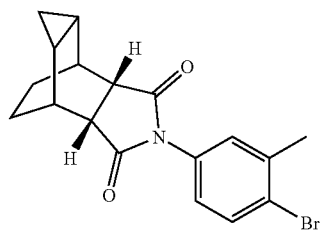

A. (3aα,4β,4aα,5aα,6β,6aα)-Hexahydro-4,6-ethano-1H-cycloprop[f]isobenzofuran-1,3(3aH)-dione (6A)

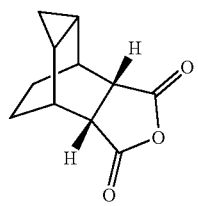

Compound 6A was made in accordance with the procedure described in Ishitobi et al, *Bull. Chem. Soc. Japan* 44, 2993-3000 (1971). A solution of compound 5A (10 g, 52.58 mmol) and 10% Pd/C (0.6 g) in 15:1 acetic acid:acetic anhydride (176 mL) was stirred under $H_2$ balloon until starting material was consumed (~1 h). The reaction mixture was filtered through celite, eluting with EtOAc and concentrated under reduced pressure. The resulting oil was triturated with hexanes and the solid was recrystallized from toluene/hexanes to give 8 g compound 6A as a white crystalline solid.

B. (3aα,4β,4aα,5aα,6β,6aα)-2-(4-Bromo-3-methylphenyl)-4,4a,5,5a,6,6a-hexahydro-4,6-ethanocycloprop[f]isoindole-1,3(2H,3aH)-dione (6B)

Compound 6A (1.92 g, 10 mmol, 1.0 eq) was combined with 4-bromo-3-methylaniline (2.05 g, 11 mmol, 1.1 eq) in AcOH (40 mL) and heated at 115° C. overnight. After the reaction mixture was cooled to room temperature, the resulting precipitate was collected, washed with MeOH and dried to give 3.2 g (88.9%) of compound 6B as a white crystalline solid. HPLC: 99% at 3.52 min (retention time) (YMC S5 ODS column 4.6×50 mm eluting with 10-90% aqueous methanol over 4 minutes containing 0.1% TFA, 4 mL/min, monitoring at 220 nm), MS (ES): m/z 360.0 & 362.0 $[M+H]^+$.

EXAMPLE 7

(3aα,4α,5α,7α,7aα)-2-(4-Bromo-3-methylphenyl) hexahydro-5-phenyl-4,7-methano-1H-isoindole-1,3 (2H)-dione (7C)

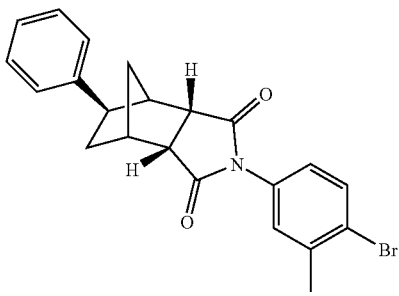

A. (2-endo, 3-endo, 5-exo)-5-Phenylbicyclo[2.2.1] heptane-2,3-dicarboxylic acid (7A)

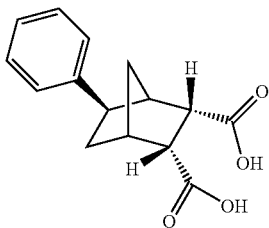

Compound 7A was made in accordance with the procedure described in Stájer et. al., *Acta. Chem. Scand.* 50, 922-30 (1996). To a suspension of aluminum trichloride (11.5 g, 86.0 mmol, 2.4 eq) in benzene (20 mL) was added cis-norbornene-endo-2,3-dicarboxylic acid (6.53 g). After stirring for 30 min, the reaction mixture was heated to 50° C. for 2 hours. The cooled reaction mixture was poured onto ice (170 mL) and conc. HCl (17 mL) and the resulting precipitate was filtered, washed with cold $H_2O$ and dried. Recrystallization of the solid from glacial acetic acid gave 7.73 g of compound 7A as a white solid, which was taken on without further purification.

B. (3aα,4α,5α,7α,7aα)-Hexahydro-5-phenyl-4,7-methanoisobenzofuran-1,3-dione (7B)

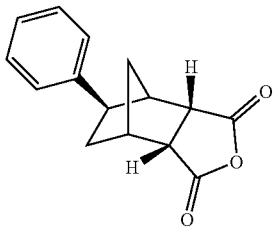

A solution of compound 7A (7.7 g, 29.6 mmol) in $Ac_2O$ (30 mL) was heated to reflux for 3 hours. The solvent was removed under reduced pressure and the residue was purified by column chromatography on silica gel, eluting with 50% EtOAc/hexanes, to give 5.2 g of compound 7B as a tan viscous oil, which solidified on standing.

C. (3aα,4α,5α,7α,7aα)-2-(4-Bromo-3-methylphenyl)hexahydro-5-phenyl-4,7-methano-1H-isoindole-1,3(2H)-dione (7C)

Compound 7B (1 g, 4.13 mmol, 1 eq) was combined with 4-bromo-3-methylaniline (768 mg, 4.13 mmol, 1 eq) in acetic acid (20 mL) and heated at 115° C. overnight. After the reaction was allowed to cool to rt, water was added and the reaction was extracted with $CH_2Cl_2$. The organic extracts were washed with aqueous $NaHCO_3$, dried over $MgSO_4$, concentrated in vacuo, and purified by flash chromatography on silica gel eluting with a gradient of 25-50% ethyl acetate in hexanes to provide 1.6 g (95%) of compound 7C as a light yellow crystalline solid. HPLC: 99% at 3.96 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 410.0 & 412.0 $[M+H]^+$.

EXAMPLE 8

(3aα,4α,7α,7aα)-2-(1,2-Dihydro-4-methyl-2-oxo-7-quinolinyl)-3a,4,7,7a-tetrahydro-5-phenyl-4,7-methano-1H-isoindole-1,3(2H)-dione (8C)

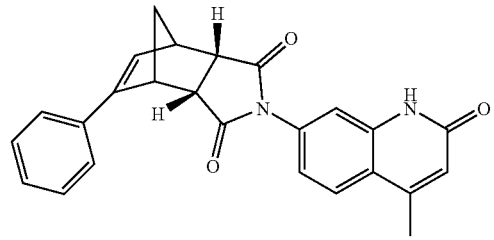

A. 2-Phenyl-2-cyclopenten-1-ol (8A)

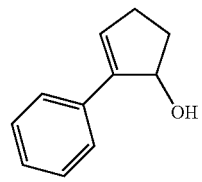

Compound 8A was made in accordance with the procedure described in Hart, et. al., *Tetrahedron Lett.* 29, 881-884 (1988). To a solution of 1-phenylcyclopentene (5 g, 34.67 mmol, 1 eq) in t-BuOH (87 mL) was added selenium dioxide (4.2 g, 38.14 mmol, 1.1 eq). After stirring overnight, the reaction mixture was filtered through celite and concentrated under reduced pressure. The crude material was purified by flash chromatography on silica gel eluting with 25% EtOAc/hexanes to give 2.6 g of compound 8A.

B. (3aα,4α,7α,7aα)-3a,4,7,7a-Tetrahydro-5-phenyl-4,7-methanoisobenzofuran-1,3-dione (8B)

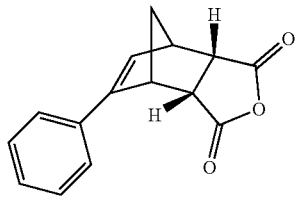

A mixture of compound 8A (1.3 g, 8.11 mmol, 1 eq), maleic anhydride (796 mg, 8.11 mmol, 1 eq) and CuSO$_4$ (2.6 g, 16.23 mmol, 2 eq) in benzene (50 mL) was heated to reflux overnight. The cooled reaction solution was poured into H$_2$O and the resulting mixture was extracted with EtOAc (3×), dried over MgSO$_4$ and purified by flash chromatography on silica gel eluting with 25% EtOAc/Hexanes to give 1.13 g of compound 8B as a light tan powder.

C. (3aα,4α,7α,7aα)-2-(1,2-Dihydro-4-methyl-2-oxo-7-quinolinyl)-3a,4,7,7a-tetrahydro-5-phenyl-4,7-methano-1H-isoindole-1,3(2H)-dione (8C)

Compound 8B (60 mg, 0.25 mmol, 1.0 eq) was combined with 7-amino-4-methyl-2(1H)-quinoline (47.9 mg, 0.27 mmol, 1.1 eq) in AcOH (1.5 mL) and heated at 115° C. overnight. The reaction mixture was concentrated under reduced pressure. Purification by flash chromatography on SiO$_2$ eluting with a gradient of 0% to 10% methanol/EtOAc followed by recrystallization from AcOH/H$_2$O gave 31.4 mg (32%) of compound 8C as a light tan solid. HPLC: 95% at 3.14 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 397.0 [M+H]$^+$.

EXAMPLE 9

(3aα,4α,5β,7α,7aβ)-2-(3,5-Dichlorophenyl)hexahydro-5-phenyl-4,7-methano-1H-isoindole-1,3(2H)-dione (9B)

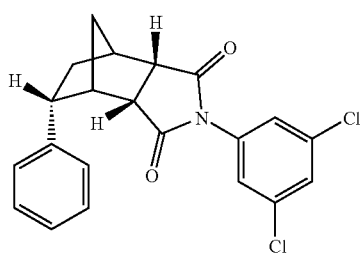

A. (3aα,4α,5α,7α,7aα)-hexahydro-5-phenyl-4,7-methanoisobenzofuran-1,3-dione (9A)

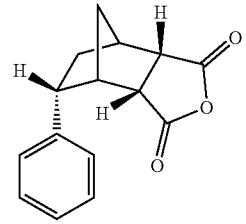

Compound 8B (0.66 g, 2.75 mmol) was reduced with 10% Pd/C in EtOAc (14 mL) under H$_2$ at 50 psi. When the pressure on gauge remained constant, the reaction mixture was filtered through celite and concentrated under reduced pressure to give 0.61 g compound 9A as a yellow oil.

B. (3aα,4α,5β,7α,7aα)-2-(3,5-Dichlorophenyl)hexahydro-5-phenyl-4,7-methano-1H-isoindole-1,3(2H)-dione (9B)

Compound 9A (50 mg, 0.21 mmol, 1.2 eq) was combined with 3,5-dichloroaniline (28 mg, 0.17 mmol, 1 eq) in acetic acid (1 mL) and heated at 121° C. overnight. The reaction was concentrated in vacuo and purified by flash chromatography on silica gel eluting with 5% ethyl acetate in CH$_2$Cl$_2$ to provide 11.2 mg (17.1%) of compound 9B as a beige solid. HPLC: 90% at 3.87 min (retention time) (YMC ODSA S5 C18 column 4.6×50 mm, 10-90% aqueous methanol over 4 minutes containing 0.1% CF$_3$CO$_2$H, 4 mL/min, monitoring at 220 nm), MS (ES): m/z 386.0 & 388.0 [M+H]$^+$.

EXAMPLE 10

(3aα,4α,4aβ,5aβ,6α,6aα)-2-(3,5-Dichlorophenyl)-4,4a,5,5a,6,6a-hexahydro-4,6-methanocycloprop[f]isoindole-1,3(2H,3aH)-dione (10B)

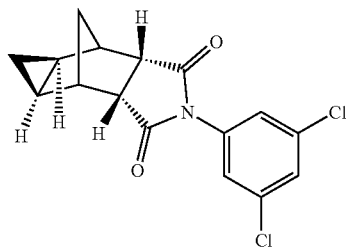

A. (3aα,4α,4aβ,5aαβ,6α,6aα)-4,4a,5,5a,6,6a-Hexahydro-4,6-methano-1H-cycloprop[f]isobenzofuran-1,3(3aH)-dione (10A)

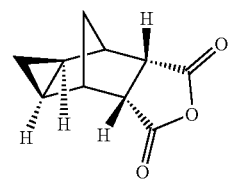

Compound 10A was made in accordance with the procedure described in Kato, et. al., *Synthesis,* 636-637 (1995), Creary, et. al., *J. Org. Chem.* 40, 3326-3331 (1975) and Fieser & Fieser coll. vol. 1, pg. 192. A mixture of 40% aq. KOH (23 mL) and Et$_2$O (75 mL) was cooled to 0° C. N-Methyl-N'-nitro-N-nitrosoguanidine (7.5 g) was added portionwise to the mixture and stirred for 5 min. The Et$_2$O layer was separated and added dropwise to a stirred solution of cis-5-norbornene-endo-2,3-dicarboxylic anhydride (3 g, 18.3 mmol) and Pd(OAc)$_2$ (30 mg) in Et$_2$O (60 mL) at 0° C. The reaction mixture was allowed to warm to rt overnight, filtered and concentrated. Recrystallization from CH$_2$Cl$_2$/hexanes gave 1.42 g of compound 10A as a light yellow crystalline solid.

B. (3aα,4α,4aβ,5aβ,6α,6aα)-2-(3,5-Dichlorophenyl)-4,4a,5,5a,6,6a-hexahydro-4,6-methanocycloprop[f]isoindole-1,3(2H,3aH)-dione (10B)

Compound 10A (1.42 g, 7.98 mmol, 1.0 eq) was combined with 3,5-dichloroaniline (1.55 g, 9.57 mmol, 1.2 eq) in AcOH (30 mL) and heated at 115° C. overnight. After the reaction mixture was cooled to room temperature, the resulting precipitate was collected, washed with MeOH and dried. Purification by flash chromatography on SiO$_2$ eluting with CH$_2$Cl$_2$ gave 1.63 g (63.5%) of compound 10B as a white crystalline solid. HPLC: 99% at 3.48 min (retention time) (YMC ODSA S5 C18 column 4.6×50 mm, 10-90% aqueous methanol over 4 minutes containing 0.1% CF$_3$CO$_2$H, 4 mL/min, monitoring at 220 nm), MS (ES): m/z 322.0 & 324.0 [M+H]$^+$.

EXAMPLE 11

(3aα,4β,4aα,5aα,6β,6aα)-4,4a,5,5a,6,6a-Hexahydro-2-(4-nitro-1-naphthalenyl)-4,6-methanocycloprop[f]isoindole-1,3(2H,3aH)-dione (11B)

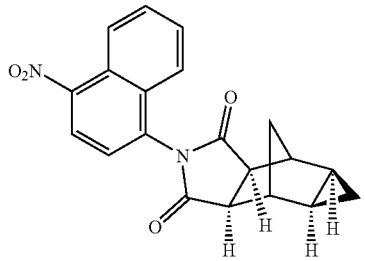

A. (3aα,4β,4aα,5aα,6β,6aα)-4,4a,5,5a,6,6a-Hexahydro-4,6-methano-1H-cycloprop[f]isobenzofuran-1,3 (3aH)-dione (11A)

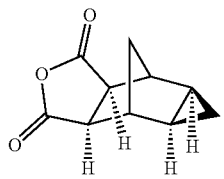

Compound 11A was made in accordance with the procedure described in Kato, et. al., *Chem. Lett.* 1823-1826 (1987), Kottwitz, et. al., *Synthesis* 636-637 (1995). Creary, et. al., *J. Org. Chem.* 40, 3326-3331 (1975) and Fieser & Fieser vol. 1, pg. 192. A mixture of 40% aq. KOH (11 mL) and Et$_2$O (40 mL) was cooled to 0° C. N-Methyl-N'-nitro-N-nitrosoguanidine (3.6 g) was added portionwise to the mixture and stirred for 5 mins. The Et$_2$O layer was separated and added dropwise to a stirred solution of compound 4A (1 g, 6.09 mmol) and Pd(OAc)$_2$ (15 mg) in Et$_2$O (30 mL) and THF (10 mL) at 0° C. The reaction mixture was allowed to warm to room temperature overnight, filtered and concentrated. Recrystallization from CH$_2$Cl$_2$/hexanes gave 0.75 g of compound 11A as a white crystalline solid.

B. (3aα,4β,4aα,5aα,6β,6aα)-4,4a,5,5a,6,6a-Hexahydro-2-(4-nitro-1-naphthalenyl)-4,6-methanocycloprop[f]isoindole-1,3(2H1,3aH)-dione (11B)

Compound 11A (100 mg, 0.561 mmol, 1.2 eq) was combined with 1-amino-4-nitronaphthalene (88.0 mg, 0.468 mmol, 1.0 eq) in AcOH (2 mL) and heated at 115° C. overnight. After the reaction mixture was cooled to room temperature, the resulting precipitate was collected, washed with H$_2$O and dried to give 138.4 mg (85%) of compound 11B as a dark brown crystalline solid. HPLC: 99% at 3.19 & 3.29 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 349.2 [M+H]$^+$.

EXAMPLE 12

(3aα,4'α,7'α,7a'α)-3a',4',7',7a'-Tetrahydro-2'-[3-(trifluoromethyl)phenyl]spiro[cyclopropane-1,8'-[4,7]methano[1H]isoindole]-1',3'(2'H)-dione (12B)

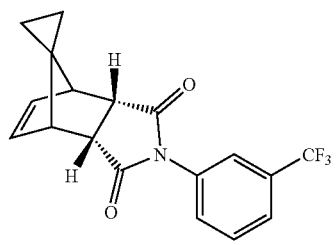

A. (3aα,4'α,7'α,7a'α)-3a',4',7',7a'-Tetrahydrospiro[cyclopropane-1,8'-[4,7]methanoisobenzofuran]-1',3'-dione (12A)

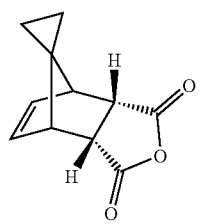

Compound 12A was made in accordance with the procedure described in Alder, et. al., *Chem. Ber.* 93, 1888-1895 (1960). To a stirred solution of maleic anhydride (3.92 g, 39.9 mmol, 1 eq) in Et$_2$O (40 mL) at 0° C. was added spiro[2.4]hepta-4,6-diene (4 mL, 39.9 mmol, 1 eq) dropwise. After stirring for 1 day, the reaction mixture was concentrated and the resulting precipitate was filtered to give 2.5 g compound 12A as a white powder.

B. (3a'α, 4'α,7'α,7a'α)-3a',4',7',7a'-Tetrahydro-2'-[3-(trifluoromethyl)phenyl]spiro[cyclopropane-1,8'-[4,7]methano[1H]isoindole]-1',3'(2'H)-dione (12B)

Compound 12A (100 mg, 0.526 mmol, 1.2 eq) was combined with 3-(trifluoromethyl)aniline (0.055 mL, 0.438 mmol, 1 eq) in acetic acid (2 mL) and heated at 115° C. overnight. After the reaction was allowed to cool to rt, water was added, and the resulting precipitate was isolated by filtration. The material was washed sequentially with aqueous K$_2$CO$_3$ and water and then dried in a vacuum oven to provide 139.4 mg (95.5%) of compound 12B as a brownish-gray powder. HPLC: 95% at 3.29 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 334.0 [M+H]$^+$.

EXAMPLE 13

(3aα,4α,7α,7aα)-2-(4-Bromo-3-methylphenyl)tetrahydro-4,7-methano-1H-isoindole-1,3,5(2H,4H)-trione (13C)

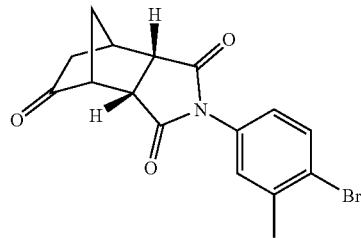

A. (1,4-Cyclopentadien-1-yloxy)-(1,1-dimethylethyl)dimethylsilane (13A)

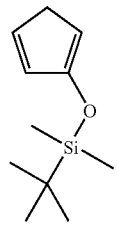

Cyclopentenone (2.5 mL, 29.8 mmol) was dissolved in methylene chloride (300 mL) followed by addition of TEA (6.23 mL, 44.7 mmol) and cooling to 0° C. TMSOTf (5.40 mL) was then added dropwise over 5 minutes. The reaction was slowly warmed to 25° C. and after 1.5 h, the reaction was filtered to remove the TEA salt. The solvent was removed in vacuo and compound 13A was taken on crude.

B. 1-(4-Bromo-3-methylphenyl)-1H-pyrrole-2,5-dione (13B)

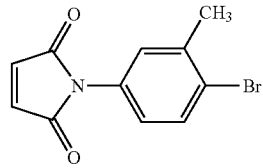

4-Bromo-3-methylaniline (1.55 g, 8.33 mmol) and maleic anhydride (0.898 g, 9.16 mmol) were dissolved in acetic acid (10 mL) and heated at 115° C. for 12 h. The reaction was then cooled to 25° C. and the acetic acid was removed in vacuo. The resulting residue was suspended in 5% K$_2$CO$_3$ (100 mL), stirred for 25 minutes followed by filtering and rinsing with water. The material was then dried in vacuo to give compound 13B as a light brown solid (1.65 g). HPLC: 100% at 2.96 min (retention time) (YMC S5 ODS column 4.6×50 mm eluting with 10-90% aqueous methanol over 4 minutes containing 0.1% TFA, 4 mL/min, monitoring at 220 nm).

C. (3aα,4α,7α,7aα)-2-(4-Bromo-3-methylphenyl)tetrahydro-4,7-methano-1H-isoindole-1,3,5(2H,4H)-trione (13C)

Compound 13A (0.35 g, 2.26 mmol) was added to a suspension of compound 13B (0.250 g, 0.94 mmol) in toluene (5.0 mL). The reaction was heated at 105° C. for 5 h and then cooled to 25° C. The reaction was diluted with methylene chloride/TFA (20:1, 10 mL) and stirred for 1 h. The TFA was neutralized by addition of sat NaHCO$_3$. This was then extracted with methylene chloride (3×40 mL). The combined organics were dried over anhydrous Na$_2$SO$_4$. The crude material was purified by flash chromatography on SiO$_2$ eluting with 5% EtOAc/methylene chloride to give 0.173 g of compound 13C as a white powder. HPLC: 100% at 3.093 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 365.0 [M+NH$_4$]$^+$.

EXAMPLE 14

(3aα,4α,7α,7aα)-2-(4-Bromo-3-methylphenyl)tetrahydro-4,7-ethano-1H-isoindole-1,3,5(2H,4H)-trione (14)

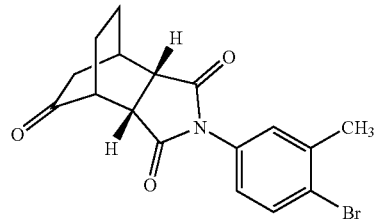

2-(trimethylsilyloxy)cyclohexadiene (Aldrich) (0.132 mL, 0.703 mmol) and compound 13B (0.075 g, 0.234 mmol) were heated in toluene (1.0 mL) at 110° C. for 3 h. MeOH/HCl (4:1) 5 mL was then added and the reaction was stirred at rt for 1 h. The reaction was then diluted with methylene chloride and washed with sat NaHCO₃. The organics were then dried over anhydrous Na₂SO₄. The crude material was purified by preparative TLC eluting with 5% EtOAc in methylene chloride to give 0.057 g of compound 14 as a white solid. HPLC: 96% at 3.367 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 362.04 [M+H]⁺.

EXAMPLE 15

(3aα,4α,7α,7aα)-2-(4-Bromo-3-methylphenyl)tetrahydro-4,7-ethano-1H-isoindole-1,3,5(2H,4H)-trione (15B)

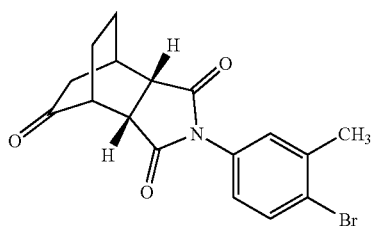

A. (3aα,4α,7π,7aα)-3a,4,7,7a-Tetrahydro-5-[(trimethylsilyl)oxy]-4,7-ethanoisobenzofuran-1,3-dione (15A)

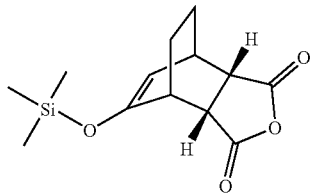

2-(trimethylsilyloxy)cyclohexadiene (Aldrich) (1.91 mL, 10.2 mmol) and maleic anhydride (1.00 g, 10.2 mmol) were heated in toluene (20 mL) at 110° C. for 3 h. The reaction was then cooled to rt and the toluene removed in vacuo, to yield compound 15A (2.5 g) as a yellow viscous oil of >90% purity by NMR. This material was taken on without further purification.

B. (3aα,4α,7α,7aα)-2-(4-Bromo-3-methylphenyl) tetrahydro-4,7-ethano-1H-isoindole-1,3,5(2H,4H)-trione (15B)

Compound 15A (0.200 g, 0.752 mmol) and 3-methyl-4-bromoaniline (0.122 g, 0.752 mmol) were heated in AcOH (2.0 mL) for 14 h at 115° C. After cooling to rt, the reaction was poured into cold sat K₂CO₃ and stirred vigorously for 0.5 h. The mixture was then filtered and rinsed with water. The resulting tan solid was dried in vacuo giving 0.204 g of compound 15B. HPLC: 96% at 3.367 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 362.04 [M+H]⁺.

EXAMPLE 16

(3aα,4α,7α,7aα)-3a,4,7,7a-Tetrahydro-2-(4-nitro-1-naphthalenyl)-3a-methyl-4,7-methano-1H-isoindole-1,3(2H)-dione (16B)

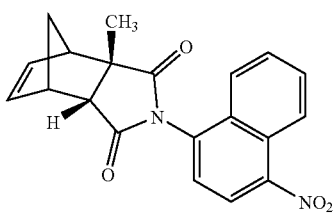

A. 3-Methyl-1-(4-nitro-1-naphthalenyl)-1H-pyrrole-2,5-dione (16A)

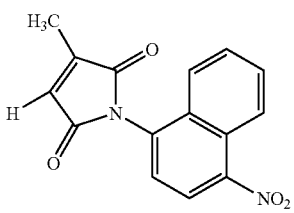

4-nitro-1-naphthalamine (2.00 g, 10.63 mmol) and citraconic anhydride (1.05 mL, 11.69 mmol) were dissolved in acetic acid (10 mL) and heated to 115° C. for 14 h. The reaction was then cooled to 25° C. and transferred to cold sat K₂CO₃ with vigorous stirring. After 15 min, the solution was filtered, rinsed with water and dried under vacuum to yield 3.63 g of compound 16A as a yellow solid. This material was taken on to the next step without further purification.

B. (3aα,4α,7α,7aα)-3a,4,7,7a-Tetrahydro-2-(4-nitro-1-naphthalenyl)-3a-methyl-4,7-methano-1H-isoindole-1,3(2H)-dione (16B)

Compound 16A (1.80 g, 6.38 mmol) and freshly cracked cyclopentadiene (1.68 g, 25.5 mmol) were dissolved in dichloroethane (10 mL) and stirred at 25° C. for 16 h. After 4 h, additional cyclopentadiene (1.68 mL, 25.5 mmol) was added. After 16 h, the volatiles were removed in vacuo and the resulting residue was purified by flash chromatography on SiO₂ eluting with 20%-0% hexanes/methylene chloride. This yielded 2.01 g of compound 16B as a pale yellow solid. HPLC: 100% at 3.093 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 366.2 [M+NH₄]⁺.

EXAMPLE 17

(3aα,4α,7α,7aα)-2-(3,5-Dichlorophenyl)hexahydro-8-(1-methylethylidene)-4,7-methano-1H-isoindole-1,3(2H)-dione (17B)

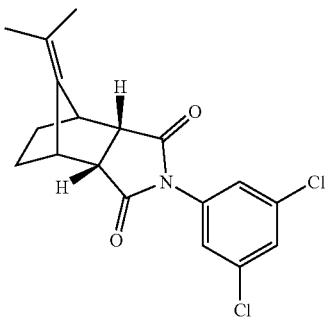

A. (3aα,4α,7α,7aα)-Hexahydro-8-(1-methylethylidene)-4,7-methanoisobenzofuran-1,3-dione (17A)

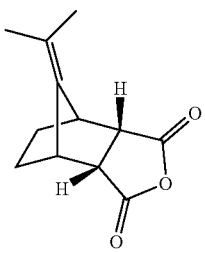

Compound 17A was synthesized as described in L. R. Corwin; D. M. McDaniel; R. J. Bushby and J. A. Berson *J. Amer. Chem. Soc.* 102, 276-287 (1980). Both the endo and exo isomers of the anhydride were isolated.

B. (3aα,4α,7α,7aα)-2-(3,5-Dichlorophenyl)hexahydro-8-(1-methylethylidene)-4,7-methano-1H-isoindole-1,3(2H)-dione (17B)

Compound 17A (endo isomer, 0.900 g, 4.37 mmol) and 3,5-dichloroaniline (0.644 g, 3.97 mmol) were dissolved in AcOH and then heated at 115° C. for 14 h. The reaction was allowed to cool to 25° C. and then the AcOH was removed in vacuo. The resulting slurry was added to cold sat $K_2CO_3$ and stirred vigorously for 15 min. The suspension was then filtered and rinsed with water. The crude product was purified by flash chromatography on $SiO_2$ eluting with 20% hexanes/methylene chloride affording 1.14 g of compound 17B as a white solid. HPLC: 88% at 4.527 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 367.1 [M+H]$^+$.

EXAMPLE 18

(3aα,4α,7α,7aα)-2-(3,5-Dichlorophenyl)hexahydro-8,8-dihydroxy-4,7-methano-1H-isoindole-1,3(2H)-dione (18)

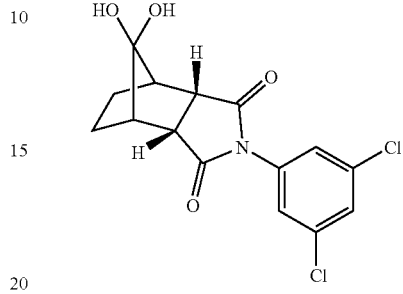

Compound 17B (1.20 g, 3.43 mmol) was dissolved in $CCl_4$ (50 mL) and methylene chloride (5 mL) and cooled to −25° C. $O_3$ was then bubbled through the reaction until a blue color persisted (~10 min). DMS (2.47 mL, 34.4 mmol) was then added and the reaction warmed to 25° C. After 12 h, a white precipitate formed and was filtered, rinsing with $CCl_4$ and dried to yield 1.01 g of compound 18 which was 95% pure by $H^1$ NMR spectroscopy and not stable to LC conditions employed. MS (ES): m/z 340.0 [M−H]$^-$.

EXAMPLE 19

(3aα,4α,7α,7aα)-2-[4-Bromo-3-(trifluoromethyl)phenyl]-8,8-diethoxy-3a,4,7,7a-tetrahydro-4,7-methano-1H-isoindole-1,3(2H)-dione (19B)

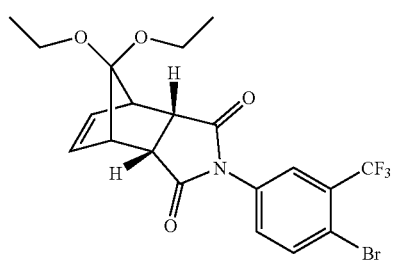

A. 5,5-Diethoxy-1,3-cyclopentadiene (19A)

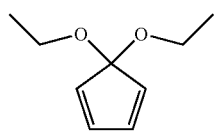

Compound 19A was synthesized as described in P. E. Eaton, R. A. Hudson *J. Amer. Chem. Soc.* 87, 2769-2770 (1965).

B. (3aα,4α,7α,7aα)-2-[4-Bromo-3-(trifluoromethyl) phenyl]-8,8-diethoxy-3a,4,7,7a-tetrahydro-4,7-methano-1H-isoindole-1,3(2H)-dione (19B)

Freshly prepared compound 19A (6.32 mmol) was added to 1-[4-bromo-3-(trifluoromethyl)phenyl]-1H-pyrrole-2,5-dione (0.400 g, 1.25 mmol, as prepared in Example 13B) in Et$_2$O (50 mL) at 25° C. After 10 h, the reaction was concentrated in vacuo and purified by flash chromatography eluting with 20%-10% hexanes/methylene chloride to give 0.501 g of compound 19B as a white foam. HPLC: 100% at 4.203 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 497.4 [M+Na]$^+$.

EXAMPLE 20

(3aα,4α,7α,7aα)-2-[4-Bromo-3-(trifluoromethyl) phenyl]-3a,4,7,7a-tetrahydro-4,7-methano-1H-isoindole-1,3,8(2H)-trione (20)

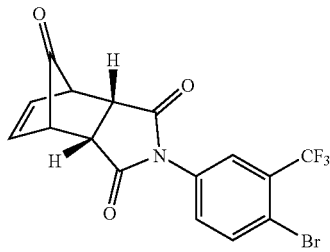

Compound 19B (0.025 g, 0.052 mmol) in acetone (1.0 mL) and pTSA.H$_2$O (0.005 g) was added and the reaction was heated to reflux for 12 h. The volatiles were then removed in vacuo and the residue purified by preparative TLC eluting with 2.5% EtOAc/methylene chloride giving the compound 20 (0.021 g) as a pale yellow solid. Not stable to LC conditions employed, purity (95%) determined by H$^1$ NMR spectroscopy. MS (DCI): m/z 399.7 [M+H]$^+$.

EXAMPLE 21

(3aα,4α,7α,7aα)-Tetrahydro-4,7-dimethyl-2-[3-(trifluoromethyl)phenyl]-4,7-methano-1H-isoindole-1,3,5(2H,4H)-trione (21C)

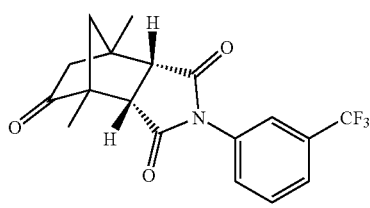

A. 3,5-Dimethyl-2-cyclopenten-1-one (21A)

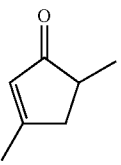

Compound 21A was made in accordance with the procedure described in Toder, et. al., *Synth. Commun.* 5, 435-439 (1975). To a stirred solution of diisopropylamine (17 mL, 121.2 mmol, 1 eq) in THF (300 mL) at 0° C. under N$_2$ was added 2.5 M n-BuLi (53.3 mL, 133.3 mmol, 1.1 eq). The reaction mixture was cooled to −78° C. and HMPA (21 mL, 121.2 mmol, 1 eq) was added. After 30 min, 3-methyl-2-cyclopenten-1-one (12 mL, 121.2 mmol, 1 eq) was added, then 30 min later, methyl iodide (8.3 mL, 133.3 mmol, 1.1 eq) was added. The reaction mixture was stirred for a further 60 min at −78° C., warmed to room temperature, quenched with sat. NH$_4$Cl, extracted with Et$_2$O (3×), dried over MgSO$_4$ and concentrated under reduced pressure. The crude product was distilled at atmospheric pressure and the fraction that came over between 165-178° C. was collected to give 10.5 g of compound 21A as a light yellow oil.

B. (3aα,4α,7α,7aα)-Tetrahydro-4,7-dimethyl-4,7-methanoisobenzofuran-1,3,5(4H)-trione

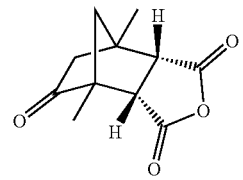

Compound 21A (3.4 g, 30.87 mmol, 1 eq) and maleic anhydride (3.0 g, 30.87 mmol, 1 eq) were heated together at 100° C. in a sealed tube for 10 h. The resulting dark brown paste was triturated with hexanes containing a small portion of EtOAc. A portion of the paste dissolved and a precipitate eventually fell from the solution. The precipitate was isolated by filtration to give a light brown powder. Crude compound 21B was taken on without further purification.

C. (3aα,4α,7α,7aα)-Tetrahydro-4,7-dimethyl-2-[3-(trifluoromethyl)phenyl]-4,7-methano-1H-isoindole-1,3,5(2H,4H)-trione (21C)

A solution of 21B (154 mg, 0.74 mmol, 1.2 eq) and 3-(trifluoromethyl)aniline (0.077 mL, 0.616 mmol, 1 eq) in AcOH (3 mL) was heated 115° C. for 5 h. After cooling to rt, H$_2$O was added. The resulting precipitate was collected and washed with H$_2$O (1×) with aq. NaHCO$_3$ (1×) and with H$_2$O (3×) and dried to give 157.3 mg (73%) of 21C as a tan powder. HPLC: 95% at 2.75 min (retention time) (YMC S5 ODS 4.6×50 mm, 10-90% aqueous methanol over 4 minutes containing 0.2% phosphoric acid, monitoring at 220 nm), MS (ES): m/z 352.0 [M+H]⁺.

EXAMPLE 22

(3aα,4α,7α,7aα)-2-(4-Bromo-3-methylphenyl)-1,2,3,4,7,7a-hexahydro-1,3-dioxo-4,7-methano-3aH-isoindole-3a-acetic acid (22B)

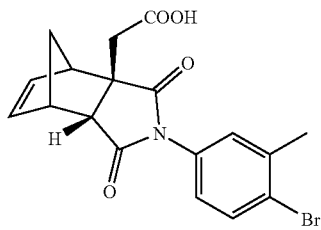

A. (3aα,4α,7α,7aα)-1,4,7,7a-Tetrahydro-1,3-dioxo-4,7-methanoisobenzofuran-3a(3H)-acetic acid (22A)

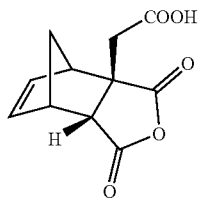

Cis-1,2,3-propenetricarboxylic acid anhydride (5.00 g, 32.1 mmol) was suspended in dichloroethane (30 mL) and freshly cracked cyclopentadiene (4.23 g, 64.2 mmol) was added. The mixture was then heated at 80° C. for 24 h, becoming homogenous after 3 h. Upon cooling to 25° C., the product precipitated out of solution and was filtered rinsing with 1:1 hexanes/methylene chloride. After drying in vacuo, 6.9 g of compound 22A was isolated as a white powder. NMR spectroscopy showed only the endo isomer was isolated.

B. (3aα,4α,7α,7aα)-2-(4-Bromo-3-methylphenyl)-1,2,3,4,7,7a-hexahydro-1,3-dioxo-4,7-methano-3aH-isoindole-3a-acetic acid (22B)

Compound 22A (1.00 g, 4.50 mmol) and 4-bromo-3-methylaniline (0.754 g, 4.05 mmol) were dissolved in AcOH (10 mL) and heated to 112° C. for 14 h. After cooling to 25° C., the AcOH was removed in vacuo and the resulting residue transferred to cold sat K₂CO₃. The resulting precipitate was isolated by filtration and rinsed with water. The crude solid was purified by preparative reverse phase HPLC (10-90% aqueous methanol) to give 0.787 g of compound 22B as a white foam. HPLC: 100% at 2.943 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 391.17 [M+H]⁺.

EXAMPLE 23

(3aα,4α,7α,7aα)-2-(4-Bromo-3-methylphenyl)-1,2,3,4,7,7a-hexahydro-1,3-dioxo-4,7-methano-3aH-isoindole-3a-acetic acid, methyl ester (23)

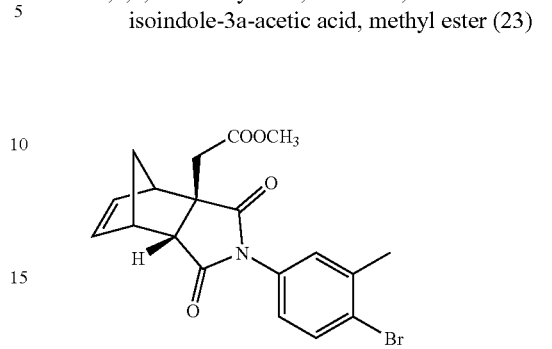

Compound 22B (0.020 g, 0.051 mmol) was dissolved in MeOH (2.0 mL) and H₂SO₄ (1 drop) was added. The mixture was then heated at 64° C. for 2 h. After cooling to 25° C., the reaction was poured into sat NaHCO₃. This mixture was extracted with methylene chloride (3×10 mL) and the combined organics were dried over anhydrous Na₂SO₄. Removal of the volatiles gave 0.018 g of compound 23 as a white solid. No purification was necessary. HPLC: 95% at 3.187 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 405.3 [M+H]⁺.

EXAMPLE 24

(3aα,4α,7α,7aα)-2-(4-Bromo-3-methylphenyl)-1,2,3,4,7,7a-hexahydro-1,3-dioxo-N-phenyl-4,7-methano-3aH-isoindole-3a-acetamide (24)

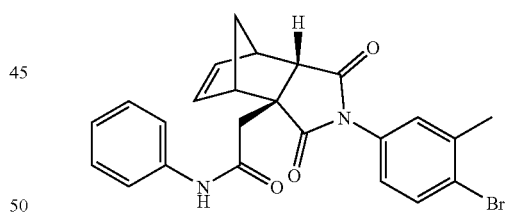

Compound 22B (0.100 g, 0.256 mmol) was dissolved in methylene chloride (1.5 mL). TEA (0.060 mL, 0.435 mmol) and then 2,6-benzoyl chloride (0.037 mL, 0.256 mmol) were added. The reaction was then stirred at 25° C. for 16 h. Benzylamine (0.023 mL, 0.256 mmol) was then added followed by 4-DMAP (cat). After 3 h, the volatiles were removed in vacuo and the resulting residue was purified by preparative reverse phase HPLC (YMC S5 ODS 30×250 mm column, 25 ml/min, 0-100% in 30 mins) to give 0.010 g of compound 24 as a white solid. HPLC: 100% at 3.597 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 464.15 [M+H]⁺.

EXAMPLE 25

(3aα,4α,7α,7aα)-3a,4,7,7a-Tetrahydro-2-(2-methyl-7-quinazolinyl)-4,7-methano-1H-isoindole-1,3(2H)-dione (25D)

A. 2-Methyl-7-nitroquinazoline (25A)

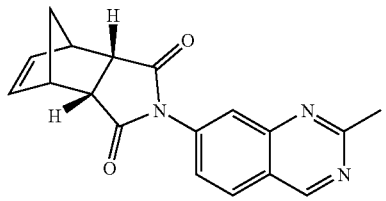

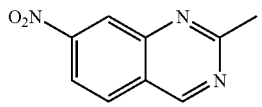

2-Fluoro-4-nitrobenzaldehyde (1.00 g, 5.92 mmol) and acetamidine hydrochloride (0.783 g, 8.28 mmol) were added to a suspension of activated 4 Å MS (1.2 g) in acetonitrile (60 mL). $K_2CO_3$ (1.14 g, 8.28 mmol) was then added and the reaction was heated to reflux for 4 h. The reaction was then cooled to 25° C. and filtered through celite rinsing with $CH_2Cl_2$. The crude product was purified by flash chromatography on silica eluting with 0-10% acetone in $CH_2Cl_2$ to give 0.386 g of compound 25A as a yellow solid.

B. 7-Amino-2-methylquinazoline (25B)

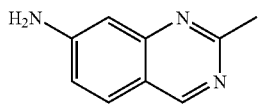

Compound 25A (0.400 g, 2.12 mmol) was dissolved in EtOAc (20 mL) and Pd/C (10% Pd, 0.045 g) was added. Hydrogen was then introduced to the flask with a balloon. After 6 h, the reaction was filtered through celite rinsing with EtOAc. Concentration in vacuo gave compound 25B as a yellow solid (0.311 g). This was taken on without purification to subsequent reactions.

C. (endo, endo)-3-[[2-Methyl-7-quinazolinyl)amino]carbonyl]bicyclo[2.2.1]hept-5-ene-2-carboxylic acid (25C)

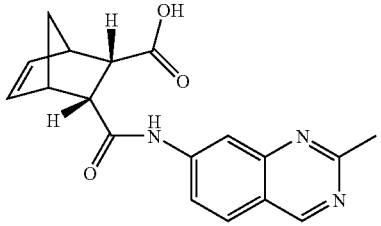

Compound 25B (0.100 g, 0.629 mmol) and cis-5-norbornene-endo-2,3-dicarboxylic anhydride (0.132 g, 0.818 mmol) were suspended in THF (3.0 mL) and heated to reflux for 3 h. The mixture became homogenous upon initial heating and then a yellow precipitate formed as the reaction progressed. After cooling to 25° C., the mixture was filtered and rinsed with THF to yield 0.088 g of compound 25C. This material was carried to the next step without further purification.

D. (3aα,4α,7α,7aα)-3a,4,7,7a-Tetrahydro-2-(2-methyl-7-quinazolinyl)-4,7-methano-1H-isoindole-1,3(2H)-dione (25D)

Compound 25C (0.051 g) was suspended in $Ac_2O$ (1.0 mL) and heated to 140° C. for 1.5 h. After cooling to 25° C., the solution was poured into cold sat $K_2CO_3$ and stirred to 0.5 h. The solution was then filtered, rinsed with water and the isolated solid was dried under vacuum to yield 0.029 g of compound 25D as yellow powder. The compound was not stable to LC conditions employed, purity (95%) was determined by $H^1$ NMR spectroscopy. MS (ES): m/z 306.2 $[M+H]^+$.

EXAMPLE 26

(3aα,4α,7α,7aα)-2-(2-Amino-4,5-dichlorophenyl)-3a,4,7,7a-tetrahydro-4,7-methano-1H-isoindole-1,3(2H)-dione (26)

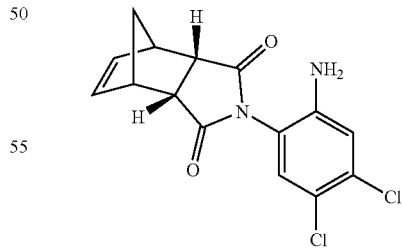

1,2-Diamino-4,5-dichlorobenzene (1.00 g, 5.65 mmol) and cis-5-norbornene-endo-2,3-dicarboxylic anhydride (1.02 g, 6.21 mmol) were dissolved in THF (5.0 mL) and heated to 85° C. in a sealed tube for 3 h. After cooling to 25° C. the volatiles were removed in vacuo and the resulting brown residue was diluted with absolute ethanol and cooled to −20° C. After 2 h, the product crashed out and was filtered rinsing with cold ethanol. The brown colored solid was recrystallized from absolute ethanol to give 1.39 g of compound 26 as a white solid. HPLC: 99% at 4.190 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 324.10 [M+H]$^+$.

EXAMPLE 27

(3aα,4α,7α,7aα)-N-[4,5-Dichloro-2-(1,3,3a,4,7,7a-hexahydro-1,3-dioxo-4,7-methano-2H-isoindol-2-yl)phenyl]benzamide (27)

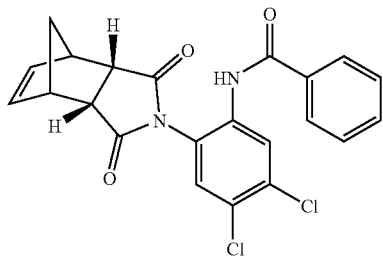

Compound 26 (0.050 g, 0.155 mmol) was dissolved in methylene chloride (3.0 mL) and pyridine (0.038 mL, 0.465 mmol) and 4-DMAP (~5 mg) were added. The mixture was cooled to 0° C. and benzoyl chloride (0.022 mL, 0.186 mmol) was added. The reaction was warmed to 25° C. and after 2 h, the volatiles were removed in vacuo. The resulting residue was purified by preparative TLC eluting with 7% EtOAc/methylene chloride to afford 0.066 g of compound 27 as a white solid. HPLC: 100% at 3.850 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 428.08 [M+H]$^+$.

EXAMPLE 28

(3aα,4β,5α,6α,7β,7aα)-2-(4-Bromo-3-methylphenyl)hexahydro-5,6-dihydroxy 4,7-etheno-1H-isoindole-1,3(2H)-dione (28)

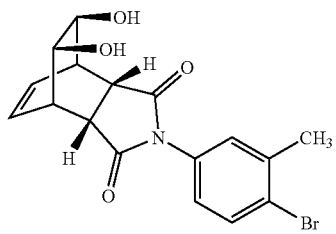

Compound 13B (0.045 g, 0.17 mmol) and cis-1,2-dihydrocatechol (0.057 g, 0.51 mmol) were dissolved in toluene (1.0 mL) and heated to 100° C. for 3 days. The crude reaction mixture was purified by preparative silica gel TLC to yield 41 mg (66% yield) of compound 28 as a white solid. Compound 28 was crystallized from 1:1 acetone/hexane to yield crystals adequate for structural determination. HPLC: 66% at 2.77 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 378.01 [M]$^+$.

EXAMPLE 29

(3aα,4β,4aα,6aα,7β,7aα)-2-(3,4-Dichlorophenyl)-3a,4,4a,6a,7,7a-hexahydro-4,7-etheno-1H-cyclobut[f]isoindole-1,3(2H)-dione (29)

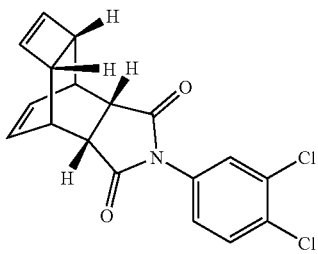

3,5-Dichloroaniline (0.027 g, 0.165 mmol) and 10-oxatetracyclo-(6.3.0.2,7.0.3,6)trideca-4,12-diene-9,11-dione (0.040 g, 0.197 mmol, Aldrich Chemicals) was dissolved in acetic acid (1.0 mL) and was heated to 112° C. for 12 hours. The solution was allowed to cool to room temperature for 4.5 hours and the resulting precipitate was isolated by filtration, washed with acetic acid followed by hexane and then dried under vacuum to yield 54 mg of compound 29 as a white solid. Compound 29 was crystallized from 1:1 methylene chloride/methanol to yield crystals adequate for structural determination. HPLC: 66% at 2.77 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 346.04 [M+H]$^+$.

EXAMPLE 30

(3aα,4α,7α,7aα)-2-(1,1-Dioxido-2H-naphth[1,8-cd]isothiazol-5-yl)-3a,4,7,7a-tetrahydro-4,7-methano-1H-isoindole-1,3(2H)-dione (30)

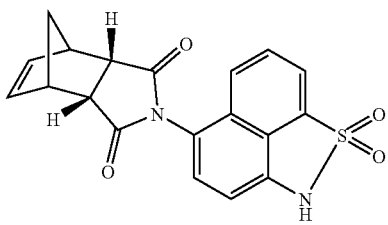

cis-5-Norbornene-endo-2,3-dicarboxylic anhydride (26 mg, 0.16 mmol, 1.2 eq) was combined with 5-amino-1,8-naphthosultam (25 mg, 0.13 mmol, 1.0 eq, synthesized as described in EP-350403 and Hammouda, et al., *J. Heterocycl. Chem.* 21, 337-339 (1984)) in acetic acid (0.6 mL) and heated at 115° C. overnight. The solvent was removed under reduced pressure and the residue was purified by Prep HPLC to give 21% yield of compound 30 as a brown solid. HPLC: 97% at 2.18 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 365.1 [M+H]+

EXAMPLE 31

(3aα,4β,7β,7aα)-2-(3,5-Dichlorophenyl)hexahydro-8-(1-methylethylidene)-4,7-methano-1H-isoindole-1,3(2H)-dione (31B)

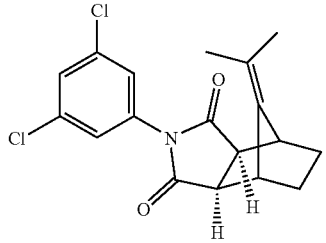

A. (3α,4β,7β,7aα)-Hexahydro-8-(1-methylethylidene)-4,7-methanoisobenzofuran-1,3-dione (31A)

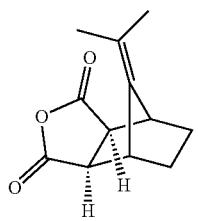

Compound 31A was synthesized as described in L. R. Corwin; D. M. McDaniel; R. J. Bushby and J. A. Berson *J. Amer. Chem. Soc.* 102, 276-287 (1980). Both the endo and exo isomers of the anhydride were isolated.

B. (3aα,4β,7β,7aα)-2-(3,5-Dichlorophenyl)hexahydro-8-(1-methylethylidene)-4,7-methano-1H-isoindole-1,3(2H)-dione (31B)

Compound 31A (exo isomer, 0.386 g, 1.87 mmol) and 3,5-dichloroaniline (0.276 g, 1.70 mmol) were dissolved in AcOH (4.0 mL) and then heated at 115° C. for 14 h. The reaction was allowed to cool to 25° C. and then the AcOH was removed in vacuo. The resulting slurry was added to cold sat K₂CO₃ and stirred vigorously for 15 min. The suspension was then filtered and rinsed with water. The crude product was purified by flash chromatography on SiO₂ eluting with 20% hexanes/methylene chloride affording 0.598 g of compound 31B as a white solid. HPLC: 100% at 3.950 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 367.1 [M+]+.

EXAMPLE 32

(3aα,4β,7β,7aα)-2-(3,5-Dichlorophenyl)hexahydro-8,8-dihydroxy-4,7-methano-1H-isoindole-1,3(2H)-dione (32)

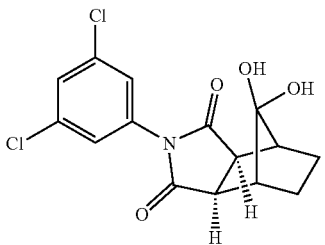

Compound 31B (0.250 g, 0.72 mmol) was dissolved in CCl₄ (10 mL) and methylene chloride (1 mL) and cooled to −25° C. O3 was then bubbled through the reaction until a blue color persisted (~10 min). DMS (0.53 mL, 7.20 mmol) was then added and the reaction warmed to 25° C. After 12 h, a white precipitate formed and was filtered, rinsing with CCl₄ and dried to yield 0.193 g of compound 32 (95% pure by H¹ NMR spectroscopy, not stable to LC conditions). MS (ES): m/z 340.0 [M−H]−. The exo diastereomer was confirmed by determination of the X-ray crystal structure.

EXAMPLE 33

(3aα,4α,7α,7aα)-3a,4,7,7a-Tetrahydro-3a-methyl-2-(4-nitro-1-naphthalenyl)-4,7-ethano-1H-isoindole-1,3(2H)-dione (33)

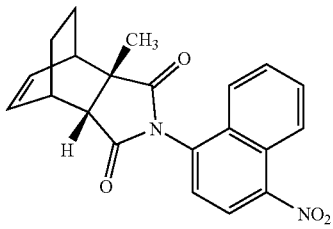

Compound 16A (0.250 g, 0.88 mmol) and 1,3-cyclohexadiene (0.142 g, 1.77 mmol) were dissolved in toluene (2.0 mL). The mixture was then heated to 125° C. in a sealed tube for 20 h. The solution was then cooled to 25° C. and the toluene removed in vacuo. The resulting residue was purified by flash chromatography on SiO₂ eluting with 30%-10%-0% hexane in CH₂Cl₂ to give 0.121 g of compound 33 as a yellow solid. HPLC: 100% at 2.99 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 363.0 [M+H]+.

EXAMPLE 34

(3aα,4β,5β,7β,7aα)-Hexahydro-5-methyl-2-[3-(trifluoromethyl)phenyl]-4,7-ethano-1H-isoindole-1,3(2H)-dione (34B) & (3aα,4β,4aα,5aα,6β,6aα)-4,4a,5,5a,6,6a-Hexahydro-2-[3-(trifluoromethyl)phenyl]-4,6-ethanocycloprop[f]isoindole-1,3(2H,3aH)-dione (34B')

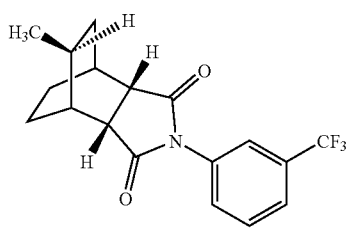

34B

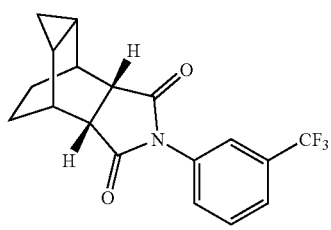

34B'

A. (3aα,4β,5β,7β,7aα)-Hexahydro-5-methyl-4,7-ethanoisobenzofuran-1,3-dione (34A) & (3aα,4β,4aα,5aα,6β,6aα)-Hexahydro-4,6-etheno-1H-cycloprop[f]isobenzofuran-1,3(3aH)-dione (6A)

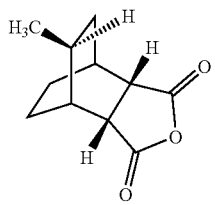

34A

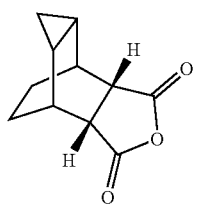

6A

To a solution of compound 5A (33.5 g, 176 mol) in 200 ml of acetone was added Pd/C (10% Pd, 2.00 g). The mixture was put under a hydrogen balloon for 4 h with stirring. The solution was filtered through celite, evaporated under vacuum and then taken up in 250 ml of ethyl acetate. To this solution was added Pd/C (10% Pd, 1.87 g) and the mixture was stirred under a hydrogen balloon for 21 h. The solution was filtered through celite and the filtrate was evaporated under vacuum. The resulting white solid was recrystallized twice with a 50/50 mixture of $CH_2Cl_2$/hexane and followed by a recrystallization with 100% ethyl acetate to yield 3.2 g of a final white solid which was a 1:10 mixture of compounds 34A & 6A.

B. (3aα,4β,5β,7β,7aα)-Hexahydro-5-methyl-2-[3-(trifluoromethyl)phenyl]-4,7-ethano-1H-isoindole-1,3(2H)-dione (34B) & (3aα,4β,4aα,5aα,6β,6aα)-4,4a,5,5a,6,6a-Hexahydro-2-[3-(trifluoromethyl)phenyl]-4,6-ethanocycloprop[f]isoindole-1,3(2H,3aH)-dione (34B')

A solution of compounds 34A & 6A (1:10, 2.3 g, 12.09 mmol, 1.2 eq) and 3-(trifluoromethyl)aniline (1.26 mL, 10.08 mmol, 1 eq) in AcOH (60 mL) was heated at 115° C. overnight. The reaction mixture was concentrated under reduced pressure and the residue was recrystallized from $CH_2Cl_2$/hexanes to give 2.67 g (79%) of compounds 34B & 34B' in a 1:10 ratio by $^1$H NMR. Separation by preparative HPLC 45 min (YMC S10 ODS SH-365-10, 10-90% aqueous $CH_3CN$ over 75 minutes, 4 mL/min, monitoring at 220 nm) gave 211 mg of compound 34B as an off-white crystalline solid and 2.07 g of compound 34B' as a white crystalline solid. Compound 34B: HPLC: 99% at 3.63 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 338.1 $[M+H]^+$. Compound 34B': HPLC 99% at 3.47 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 336.2$[M+H]^+$.

EXAMPLE 35

(3aα,4α,7α,7aα)-2-[(3,4-Dichlorophenyl)amino]-3a,4,7,7a-tetrahydro-4,7-methano-1H-isoindole-1,3(2H)-dione (35)

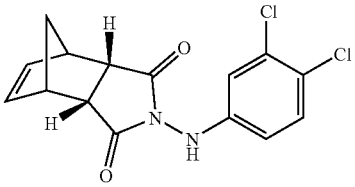

3,4-Dichlorophenylhydrazine hydrochloride (213.5 mg, 1.0 mmol) and cis-5-norbornene-endo-2,3-dicarboxylic anhydride (164.2 mg, 1.0 mmol) were combined in ethanol (20 mL). To this solution was added 324 mg (1.0 mmol) of sodium ethoxide (21 wt. % solution in denatured ethyl alcohol). The reaction mixture was refluxed for 5 h. The reaction was allowed to cool to rt, and the resulting precipitate was collected by filtration, washed with water and ethanol and dried in vacuo to give 236 mg of compound 35 (73%) as an off-white solid. HPLC: 98% at 3.090 min (retention time) (YMC S5 ODS column 4.6×50 mm, 10-90% aqueous methanol over 4 minutes containing 0.1% trifluoroacetic acid, 4 mL/min, monitoring at 220 nm), MS (ESI): m/z 321.0 & 323.0 [M–H]⁻.

EXAMPLE 36

(3aα,4α,7α,7aα)-2-[(3,4-Dichlorophenyl)methylamino]-3a,4,7,7a-tetrahydro-4,7-methano-1H-isoindole-1,3(2H)-dione (36)

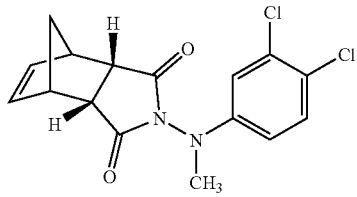

To a solution of compound 35 (130 mg, 0.40 mmol) in 10 ml of THF was added sodium hydride (32 mg, 0.80 mmol, 60% dispersion in mineral oil), followed by iodomethane (114 mg, 0.80 mmol). The reaction mixture was stirred at rt for 2 h, and quenched by addition of sat NH₄Cl. The reaction mixture was extracted with dichloromethane (3×50 ml) and the combined organic extracts were washed with brine, dried over sodium sulfate and concentrated. Flash chromatography (silica, dichloromethane) provided compound 36, (67 mg, 50%), as a white solid. HPLC: 100% at 3.323 min (retention time) (YMC S5 ODS column 4.6×50 mm, 10-90% aqueous methanol over 4 minutes containing 0.1% trifluoroacetic acid, 4 mL/min, monitoring at 220 nm), MS (ES): m/z 391.12 [M+MeOH+Na]⁺.

EXAMPLE 37

(3aα,4α,7α,7aα)-2-(1H-Benzotriazol-1-yl)hexahydro-4,7-methano-1H-isoindole-1,3(2H)-dione (37)

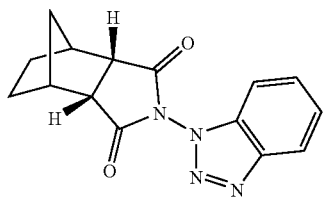

Compound 50A (116.8 mg, 0.703 mmol, 1.0 eq) was combined with 1-aminobenzotriazole (94.3 mg, 0.703 mmol, 1.0 eq) in AcOH (2 mL) and heated at 115° C. overnight. After the reaction mixture was cooled to room temperature, the reaction solution was concentrated under reduced pressure and the resulting solid was washed with MeOH and dried over MgSO₄ to give 124 mg (61%) of compound 37 as a brown solid. HPLC 99% at 2.47 min (YMC S5 ODS column 4.6×50 mm, 10-90% aqueous methanol over 4 minutes containing 0.2% phosphoric acid, 4 mL/min, monitoring at 220 nm), MS (ES): m/z 283.21 [M+H]⁺

EXAMPLE 38

(3aα,4α,7α,7aα)-2,3,3a,4,7,7a-Hexahydro-3-thioxo-2-[3-(trifluoromethyl)phenyl]-4,7-methano-1H-isoindol-1-one (38B)

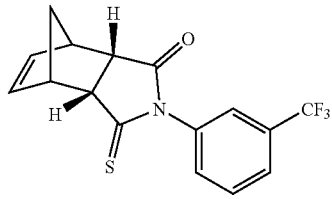

A. (3aα,4α,7α,7aα)-3a,4,7,7a-Tetrahydro-2-[3-(trifluoromethyl)phenyl]-4,7-methano-1H-isoindole-1,3 (2H)-dione (38A)

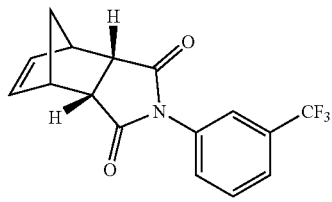

cis-5-Norbornene-endo-2,3-dicarboxylic anhydride (2.0 g, 12.2 mmol, 1.2 eq) was combined with 3-(trifluoromethyl) aniline (1.3 mL, 10.2 mmol, 1 eq) in acetic acid (80 mL) and heated at 115° C. overnight. After the reaction was allowed to cool to rt, water was added, and the resulting precipitate was isolated by filtration. The material was washed sequentially with aqueous K₂CO₃ and water and then dried. Recrystallization from CH₂Cl₂/hexanes gave 2.01 g (63%) of compound 38A as a white crystalline solid. HPLC: 99% at 1.67 min (Phenom-Prime S5 C18 column 4.6×30 mm, 10-90% aqueous methanol over 2 minutes containing 0.1% TFA, 4 mL/min, monitoring at 220 nm). MS (ES): m/z 340.15 [M+MeOH]⁺

B. (3aα,4α,7α,7aα)-2,3,3a,4,7,7a-Hexahydro-3-thioxo-2-[3-(trifluoromethyl)phenyl]-4,7-methano-1H-isoindol-1-one (38B)

A solution of compound 38A (191 mg, 0.622 mmol, 1 eq) and Lawesson's Reagent (126 mg, 0.311 mmol, 0.5 eq) in toluene was heated to reflux for 12 h. The reaction mixture was concentrated under reduced pressure and purified by flash chromatography eluting with CHCl₃ to give compound 38B (31.6 mg, 16%) as a yellow solid. HPLC: 95% at 3.50 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 323.8 [M+H]⁺

EXAMPLE 39

(3aα,4α,7α,7aα)-2-(Benzo[b]thiophen-3-yl)hexahydro-4,7-methano-1H-isoindole-1,3(2H)-dione (39B)

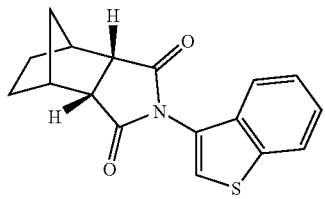

A. 3-Aminobenzo[b]thiophene (39A)

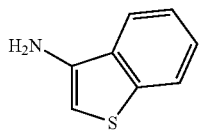

A solution of methyl-3-aminobenzothiophene-2-carboxylate (1 g, 4.83 mmol, 1 eq) in 1-methyl-2-pyrrolidinone (8 mL) and piperazine (2.08 g, 24.13 mmol, 5 eq) was stirred at 130° C. overnight. Ice was added, and the mixture was extracted with EtOAc. The organic extracts were washed twice with water, dried, and concentrated in vacuo. The crude material was purified by flash chromatography on silica gel eluting with 33% ethyl acetate in hexanes to provide 600 mg (83%) of compound 39A as a yellow oil. HPLC: 98% at 1.043 min (retention time) (YMC S5 ODS 4.6×50 mm, 10-90% aqueous methanol over 4 minutes containing 0.2% phosphoric acid, monitoring at 220 nm).

B. (3aα,4α,7α,7aα)-2-(Benzo[b]thiophen-3-yl)hexahydro-4,7-methano-1H-isoindole-1,3(2H)-dione (39B)

Compound 50A (200 mg, 1.2 mmol, 1.0 eq) was combined with compound 39A (197 mg, 1.33 mmol, 1.1 eq) in acetic acid (4 mL) and heated at 110° C. overnight. After the reaction was allowed to cool to rt, water was added, and the resulting precipitate was isolated by filtration. The material was washed with methanol and then dried under vacuum to provide 160 mg (44.9%) of compound 39B as a brown solid. HPLC: 98% at 2.92 min (retention time) (YMC S5 ODS 4.6×50 mm, 10-90% aqueous methanol over 4 minutes containing 0.2% phosphoric acid, monitoring at 220 nm), MS (ES): m/z 298.32 [M+H]$^+$.

EXAMPLE 40

(3aα,4α,7α,7aα)-Hexahydro-2-(1-oxidobenzo[b]thiophen-3-yl)-4,7-methano-1H-isoindole-1,3(2H)-dione (40)

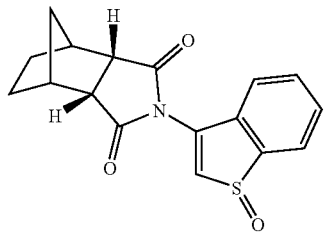

A solution of compound 39B (20 mg, 0.067 mmol, 1 eq) and TFA (0.12 ml) in CH$_2$Cl$_2$ was stirred for 5 minutes. A 30% aqueous solution of H$_2$O$_2$ (0.008 ml, 0.067 mmol, 1 eq) was added and the resulting mixture was stirred at room temperature and monitored by HPLC. After 4 hours, a solution of saturated aqueous NaHCO$_3$ was added and the resulting mixture was extracted with CH$_2$Cl$_2$. The organic layer was concentrated under reduced pressure and the residue was purified by column chromatography on silica gel, eluting with 10% EtOAc/CH$_2$Cl$_2$, to give 15 mg (71%) of compound 40 as a light yellow solid. HPLC: 99% at 2.24 min (retention time) (YMC S5 ODS 4.6×50 mm, 10-90% aqueous methanol over 4 minutes containing 0.2% phosphoric acid, monitoring at 220 nm), MS (ES): m/z 346.15 [M+H]$^+$.

EXAMPLE 41

(3aα,4α,7α,7aα)-2-(1,1-Dioxidobenzo[b]thiophen-3-yl)hexahydro-4,7-methano-1H-isoindole-1,3(2H)-dione (41)

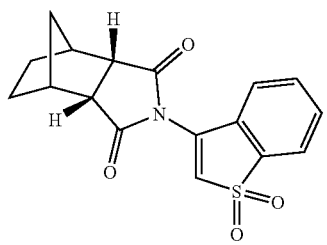

mCPBA (60% mixture, 48.8 mg, 0.283 mmol, 2.4 eq) was added to a solution of compound 39B (35 mg, 0.118 mmol, 1 eq) in CH$_2$Cl$_2$ (3 mL) and the mixture was stirred at room temperature overnight. Additional mCPBA (20 mg, 0.116 mmol, 1 eq) was added and the mixture was stirred for 4 more hours to drive the reaction to completion. The solvent was removed under reduced pressure and the residue was purified by column chromatography on silica gel, eluting with 4% EtOAc/CH$_2$Cl$_2$. The resulting solid was washed with methanol to remove a small amount of impurity and dried under vacuum to give 25 mg (64.4%) of compound 41 as a light yellow solid. HPLC: 99% at 2.39 min (retention time) (YMC S5 ODS 4.6×50 mm, 10-90% aqueous methanol over 4 minutes containing 0.2% phosphoric acid, monitoring at 220 nm), MS (ES): m/z 347.0 [M+NH$_4$]$^+$.

EXAMPLE 42

(3aα,4α,7α,7aα)-Hexahydro-2-[6-(methylthio)-5-nitro-8-quinolinyl]-4,7-methano-1H-isoindole-1,3(2H)-dione (42)

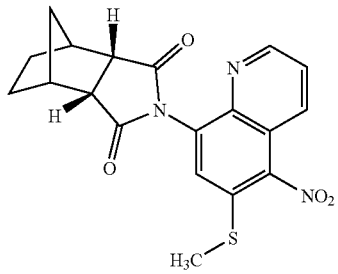

Compound 50A (100 mg, 0.602 mmol, 1.0 eq) was combined with 8-amino-6-(methylthio)-5-nitroquinoline (141 mg, 0.602 mmol, 1.0 eq) in acetic acid (3 mL) and heated at 115° C. overnight. The reaction mixture was added to aqueous NaHCO$_3$ and extracted with CH$_2$Cl$_2$ (3×). The combined organic layers were washed with H$_2$O (1×), dried over MgSO$_4$ and concentrated under reduced pressure. The resulting solid was recrystallized from CH$_2$Cl$_2$/hexanes to give compound 42 as a yellow crystalline solid in 56.5% yield. HPLC: 97% at 3.05 & 3.18 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 384.30 [M+H]$^+$

EXAMPLE 43

(3aα,4α,5α,7α,7aα)-Hexahydro-5-mercapto-2-(4-nitro-1-naphthalenyl)-4,7-methano-1H-isoindole-1,3(2H)-dione (43B)

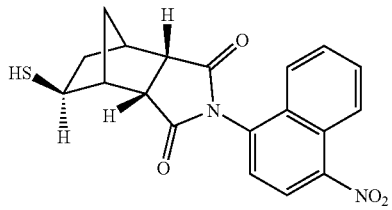

A. (3aα,4α,5α,7α,7aα)-Hexahydro-5-mercapto-4,7-methanoisobenzofuran-1,3-dione (43A)

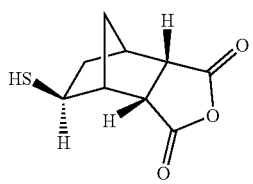

Compound 43A was made in accordance with the procedure described in Haché, et. al., *Tetrahedron Lett.* 35, 1837-1840 (1994). A solution of cis-5-norbornene-endo-2,3-dicarboxylic anhydride (1 g, 6.09 mmol, 1 eq), triphenylsilanethiol (2 g, 6.94 mmol, 1.14 eq) and AIBN (1 g, 6.09 mmol, 1 eq) in benzene (6 mL) was heated to reflux for 15 h. After cooling to rt, TFA (2.35 mL, 30.46 mmol, 5 eq) was added and the mixture was stirred for 30 min. Concentration under reduced pressure and purification by flash chromatography eluting with 25% EtOAc/hexanes gave 300 mg of impure compound 43A which was used directly in the next step.

B. (3aα,4α,5α,7α,7aα)-Hexahydro-5-mercapto-2-(4-nitro-1-naphthalenyl)-4,7-methano-1H-isoindole-1,3(2H)-dione (43B)

Compound 43A (76 mg, 0.383 mmol, 1.0 eq) was combined with 4-nitro-1-naphthalamine (54 mg, 0.289 mmol, 0.75 eq) in acetic acid (2 mL) and heated at 115° C. overnight. After the reaction was allowed to cool to rt, water was added, and the resulting precipitate was isolated by filtration. The material was washed sequentially with aqueous K$_2$CO$_3$ and water and then dried to give material that was 72% pure. Purification by prep HPLC: 10.10 min (YMC ODS 20×100 mm, 10-90% aqueous methanol over 20 minutes containing 0.1% TFA, 20 mL/min, monitoring at 220 nm) gave 14.2 mg (10%) of compound 43B (forms disulfide over time). HPLC: 80% (+12% disulfide) at 3.02 & 3.15 min (YMC S5 ODS column 4.6×50 mm, 10-90% aqueous methanol over 4 minutes containing 0.2% phosphoric acid, 4 mL/min, monitoring at 220 nm), MS (ES): m/z 300.31 [M+H]$^+$

EXAMPLE 44

(3aα,4α,7α,7aα)-3a,4,7,7a-Tetrahydro-2-[3-methoxy-4-(5-oxazolyl)phenyl]-4,7-methano-1H-isoindole-1,3(2H)-dione (44)

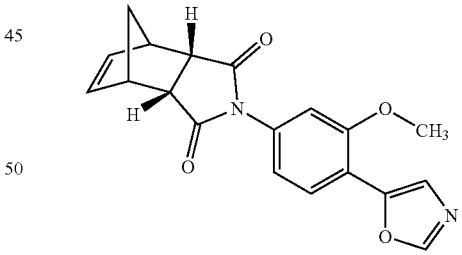

3-Methoxy-4-(oxazol-5-yl)phenylamine (51 mg, 0.27 mmol, prepared as described in WO 00/25780) and cis-5-norbornene-endo-2,3-dicarboxylic anhydride (44 mg, 0.27 mmol) were combined in acetic acid (2 mL) and heated at 110° C. for 1 hr. After the reaction was allowed to cool to rt, the acetic acid was removed under reduced pressure. The residue was washed with methanol to give 90 mg (72%) of compound 44 as a light brown solid. HPLC: 98% at 2.583 min (retention time) (YMC S5 ODS column 4.6×50 mm, 10-90% aqueous methanol over 4 minutes containing 0.1% trifluoroacetic acid, 4 mL/min, monitoring at 220 nm), MS (ES): m/z 337.31 [M+H]$^+$.

EXAMPLE 45

(3aα,4α,7α,7aα)-Hexahydro-2-[3-methoxy-4-(1H-1,2,4-triazol-1-yl)phenyl]-4,7-methano-1H-isoindole-1,3(2H)-dione (45)

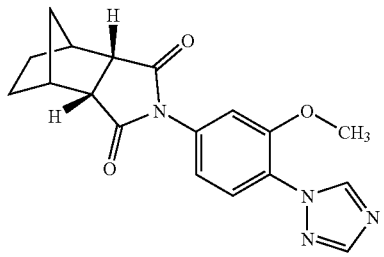

Compound 50A (26 mg, 0.16 mmol, 1.2 eq) was combined with 3-methoxy-4-(1H-1,2,4-triazol-1-yl)-benzenamine (25 mg, 0.13 mmol, 1.0 eq, synthesized as described in WO-0025780) in acetic acid (0.6 mL) and heated at 115° C. overnight. The solvent was removed under reduced pressure and the residue was purified by column chromatography on silica gel, eluting with 70% EtOAc/CH$_2$Cl$_2$, to give 30.9 mg (70%) of compound 45 as a white solid. HPLC: 99% at 2.41 min (retention time) (YMC S5 ODS 4.6×50 mm, 10-90% aqueous methanol over 4 minutes containing 0.2% H$_3$PO$_4$, monitoring at 220 nm), MS (ES): m/z 339.17 [M+H]$^+$.

EXAMPLE 46

(3aα,4α,7α,7aα)-2-(2,3-Dihydro-2-oxo-6-benzothiazolyl)-3a,4,7,7a-tetrahydro-4,7-methano-1H-isoindole-1,3(2H)-dione (46B)

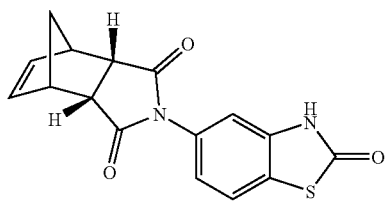

A. 6-Amino-2-benzothiazolinone (46A)

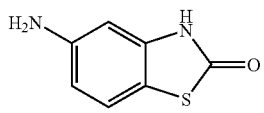

A solution of 6-nitro-2-benzothiazolinone (98 mg, 0.50 mmol) in 20 ml of EtOAc with 10% Pd/C (~20 mg) was stirred under H$_2$ balloon for 4 h. The reaction mixture was filtered through celite eluting with EtOAc, concentrated under reduced pressure to give 80 mg of 6-amino-2-benzothiazolinone.

B. (3aα,4α,7α,7aα)-2-(2,3-Dihydro-2-oxo-6-benzothiazolyl)-3a,4,7,7a-tetrahydro-4,7-methano-1H-isoindole-1,3(2H)-dione (46B)

Compound 46A (80 mg, 0.48 mmol) and cis-5-norbornene-endo-2,3-dicarboxylic anhydride (82 mg, 0.50 mmol) were combined in acetic acid (2 mL) and heated at 110° C. for 5 h. After the reaction was allowed to cool to rt, the acetic acid was removed under vacuum. The residue was washed with methanol to give 96 mg (64%) of compound 46B as a white solid. HPLC: 100% at 2.133 min (retention time) (YMC S5 ODS column 4.6×50 mm, 10-90% aqueous methanol over 4 minutes containing 0.1% trifluoroacetic acid, 4 mL/min, monitoring at 220 nm), MS (ES): m/z 313.04 [M+H]$^+$.

EXAMPLE 47

(3aα,4α,7α,7aα)-2-(2,3-Dihydro-3-methyl-2-oxo-6-benzothiazolyl)-3a,4,7,7a-tetrahydro-4,7-methano-1H-isoindole-1,3(2H)-dione (47)

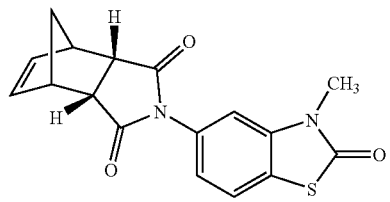

To a solution of compound 46B (50 mg, 0.16 mmol) in 5 ml of DMF was added potassium carbonate (221 mg, 1.6 mmol) and iodomethane (45 mg, 0.32 mmol). The mixture was stirred at rt for 4 hr and then quenched by adding water. The reaction mixture was extracted with dichloromethane (3×25 ml). The combined organic extracts were washed with brine, dried over sodium sulfate and concentrated. Flash chromatography (silica, 1% methanol/dichloromethane) provided compound 47 as a white solid (45 mg, 87%). HPLC: 100% at 2.613 min (retention time) (YMC S5 ODS column 4.6×50 mm, 10-90% aqueous methanol over 4 minutes containing 0.1% trifluoroacetic acid, 4 mL/min, monitoring at 220 nm), MS (ES): m/z 327.04 [M+H]$^+$.

EXAMPLE 48

(3aα,4α,7α,7aα)-2-(1,3-Dihydro-3-oxo-6-isobenzofuranyl)-3a,4,7,7a-tetrahydro-4,7-methano-1H-isoindole-1,3(2H)-dione (48C)

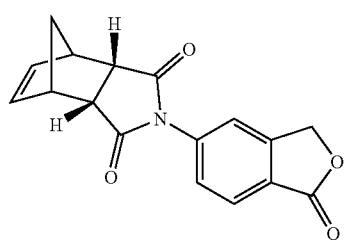

A. 5-nitro & 6-nitrophthalides (48A)

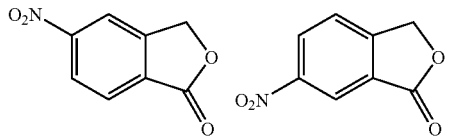

Compound 48A (5-nitro- and 6-nitrophthalides) were made in accordance with the procedure described in Watanabe et. al., *Chem. Pharm Bull.* 26 (2), 530-538 (1978). To a suspension of 4-nitrophthalimide (3 g, 15.6 mmol) in 60 ml of 90% methanol was added NaBH$_4$ (900 mg, 23.8 mmol). The mixture was stirred at rt for 2 h and then quenched by addition of 30 ml of 10% HCl. The aqueous layer was extracted with dichloromethane (3×100 ml). The combined organic extracts were washed with brine, dried over sodium sulfate and concentrated. Flash chromatography (silica, dichloromethane) provided compound 48A as a white solid (840 mg, 30%) with a ratio 1:2, favoring the 6-nitrophthalide isomer. HPLC: 100% at 1.507 min (retention time) (YMC S5 ODS column 4.6×50 mm, 10-90% aqueous methanol over 4 minutes containing 0.1% trifluoroacetic acid, 4 mL/min, monitoring at 220 nm).

B. 5-Amino, 6-aminophthalides (48B)

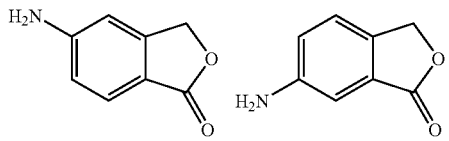

Compound 48A (5-nitro- and 6-nitrophthalides, 810 mg, 4.50 mmol) was taken up in a mixture of 10 ml of acetic acid and 10 ml of ethyl acetate. To this mixture was added 10% Pd/C (162 mg, 20% by weight) and the reaction was stirred under H$_2$ (balloon) for 16 hr. The reaction mixture was filtered through celite eluting with EtOAc and concentrated under reduced pressure to give compound 48B (5-amino- and 6-aminophthalides, 1:2 ratio). The crude mixture was taken on without further purification.

C. (3aα,4α,7α,7aα)-2-(1,3-Dihydro-3-oxo-6-isobenzofuranyl)-3a,4,7,7a-tetrahydro-4,7-methano-1H-isoindole-1,3(2H)-dione (48C)

Compound 48B (crude mixture, 1:2 ratio of 5-amino- and 6-aminophthalide) and cis-5-norbornene-endo-2,3-dicarboxylic anhydride (886 mg, 5.4 mmol) were combined in acetic acid (10 mL) and heated at 110° C. for 5 h. After the reaction was allowed to cool to rt, the acetic acid was removed under reduced pressure. The residue was purified by flash chromatography (silica gel, dichloromethane) and preparative HPLC to give compound 48C (118 mg) as a white solid. HPLC: 98% at 2.213 min (retention time) (YMC S5 ODS column 4.6×50 mm, 10-90% aqueous methanol over 4 minutes containing 0.1% trifluoroacetic acid, 4 mL/min, monitoring at 220 nm), MS (ES): m/z 296.01 [M+H]$^+$.

EXAMPLE 49

(3aα,4α,7α,7aα-2-(1,2-Benzisoxazol-3-yl)-3a,4,7,7a-tetrahydro-4,7-methano-1H-isoindole-1,3(2H)-dione (49)

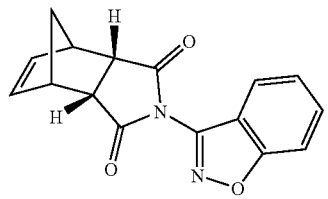

3-Amino-1,2-benzisoxazole (47 mg, 0.54 mmol, prepared as described in Shutske et. al., *J. Heterocycl. Chem.* 26, 1293-1298 (1989)) and cis-5-norbornene-endo-2,3-dicarboxylic anhydride (69 mg mg, 0.42 mmol) were combined in acetic acid (1 mL) and heated at 110° C. for 20 h. After the reaction was allowed to cool to rt, the acetic acid was removed under reduced pressure. To the resulting gum was added 5 ml of saturated NaHCO$_3$ and 10 ml of CH$_2$Cl$_2$ and the mixture was stirred at rt for 30 minutes. The organic layer was isolated, dried over MgSO$_4$ and dried under vacuum. The residue was purified by flash chromatography (silica, 0.5% MeOH in CH$_2$Cl$_2$) to give compound 49 (50 mg, 51%) as a white solid. HPLC: 98% at 2.54 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 303.08 [M+Na]$^+$.

EXAMPLE 50

(3aα,4α,7α,7aα)-2-(1,6-Dihydro-1-methyl-6-oxo-3-pyridinyl)hexahydro-4,7-methano-1H-isoindole-1,3(2H)-dione (50D)

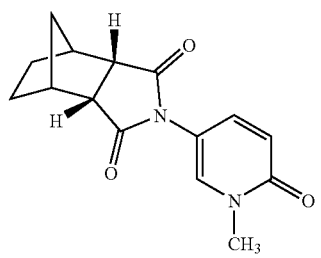

A. cis-Norbornane-endo-2,3-dicarboxylic anhydride (50A)

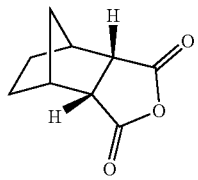

A solution of cis-5-norbornene-endo-2,3-dicarboxylic anhydride (5 g, 31.4 mmol) and 10% Pd/C (~100 mg) in a mixture of EtOAc and EtOH was shaken under H$_2$ at 55 psi for 3 h. The reaction solution was filtered through a pad of celite eluting with EtOAc and concentrated to give 10 g of compound 50A as a white powder.

B. 1-Methyl-5-nitro-2(1H)-pyridinone (50B)

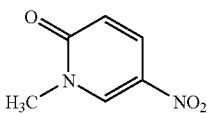

To a solution of 2-hydroxy-5-nitropyridine (600 mg, 4.28 mmol, 1 eq) in DMF (5 mL) was added cesium carbonate (1.67 g, 5.16 mmol, 1.2 eq), followed by methyl iodide (0.4 mL, 6.42 mmol, 1.5 eq). After stirring overnight, the reaction mixture was quenched with water and extracted with ethyl ether (5×20 mL). The ether was dried over Na$_2$SO$_4$ and concentrated under reduced pressure. The crude material was column chromatographed, eluting with 50% EtOAc/hexanes to give 450 mg of compound 50B.

C. 5-Amino-1-methyl-2(1H)-pyridinone (50C)

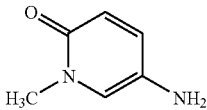

A solution of compound 50B (200 mg, 1.298 mmol) and 10% Pd/C (~5 mg) in MeOH and AcOH was stirred under H$_2$ at 1 atmosphere for 30 minutes. The reaction solution was filtered through a pad of celite eluting with MeOH. The MeOH was removed under reduced pressure to give compound 50C.

D. (3aα,4α,7α,7aα)-2-(1,6-Dihydro-1-methyl-6-oxo-3-pyridinyl)hexahydro-4,7-methano-1H-isoindole-1,3(2H)-dione (50D)

Compound 50C in AcOH was combined with compound 50A (209 mg, 1.298 mmol, 1 eq) in acetic acid (4 mL) and heated at 165° C. for 6 h. The acetic acid was distilled off and the material was washed with aqueous K$_2$CO$_3$ and water. The crude material was column chromatographed, eluting with 50% EtOAc/hexanes to give 260 mg of compound 50D as a white solid. HPLC: 99% at 1.62 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 273.0 [M+H]$^+$.

EXAMPLE 51

(3aα,4α,7α,7aα)-2-(3-Fluoro-4-methylphenyl)tetrahydro-4,7-ethano-1H-isoindole-1,3,5(2H,4H)-trione (51)

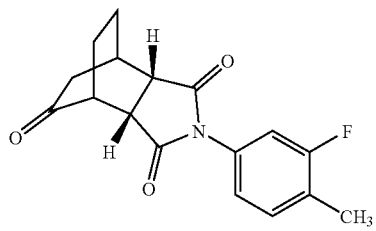

The below procedure describes a general approach for the production of solution phase combinatorial libraries of compounds of formula I. The general procedure described can be extrapolated from the processes described above in Step B of Example 1 ("1B"), Step B of Example 2 ("2B"), and Step C of Example 7 ("7C") where anhydride-like intermediates such as compounds 6A or 15A or commercially available anhydrides such as 1,2-cyclohexanedicarboxylic anhydride, endo-bicyclo(2.2.2)-5-octene-2,3-dicarbo anhydride or cis-5-norbornene-endo-2,3-dicarboxylic anhydride can replace the intermediate compounds 1A, 2A, or 7B. Other anhydride-like intermediates which can be used in replacement of compounds 1A, 2A, or 7B are, but are not limited to, compounds 3A, 4A, 5A, 8B, 9A, 10A, 11A, 12A, 15A, 17A, 22A, 31A, 34A, 43A, and 50A.

The specific procedure shown describes in detail the synthesis of a library of compounds derived from the reaction of the intermediate compound 15A with an array of substituted aniline intermediates. In this Example, specific data is given on one example compound from this library; data on other compounds so obtained is provided in the following Tables. This general procedure can be modified by one skilled in the art to accommodate the synthesis of an array of compounds derived from related anhydride and aniline intermediates.

4-Methyl-3-fluoroaniline (0.010 g, 0.08 mmols) was dissolved in acetic acid (0.400 mL) and transferred to a 1.5 mL conical vial with a septa cap. Stock solutions of an additional 95 amines were prepared as described above. To each of the above vials was added 0.4 mL (0.12 mmol) of a stock solution of compound 15A in acetic acid. The vials were then sealed and heated at 110° C. for 10 h. Upon cooling to 25° C., the solutions were transferred by robot to filter tubes with a medium pore frit. Nitrogen was then blown into the tubes to remove the acetic acid. A 1.0 mL portion of methylene chloride and 0.5 g of silica gel were then added to the tubes and they were shaken for 30 minutes. The tubes were drained into pre-tared custom microtubes. A 1.5 mL portion of 10% ethyl acetate in methylene chloride was then added to the filter tubes and they were again shaken for 15 minutes and drained as before. Each tube was assayed for product purity (analytical LC) and identity (LC-MS). The tubes were then concentrated in vacuo and weighed for yields. The tube containing the reaction of 4-methyl-3-fluoroaniline and compound 15A, yielded 0.0161 g of compound 51 as a white solid. HPLC: 85% at 2.43 min (retention time) (YMC S5 ODS column 4.6×50 mm eluting with 10-90% aqueous methanol over 4 minutes containing 0.1% TFA, 4 mL/min, monitoring at 220 nm), MS (ES): m/z 302.23 [M+H]+. Of the remaining 95 additional reactions run, a total of 80 final compounds were obtained in >70% purity and >5 mg yield. Several samples needed further purification which was performed by short SiO2 column eluting with methylene chloride/acetone.

EXAMPLES 52 TO 182

Additional compounds of the formula I were prepared by procedures analogous to those described above. The compounds of Example 52 to 182 have the following structure:

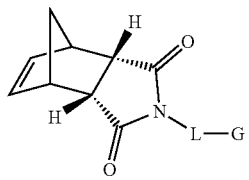

where —L—G, the compound name, retention time, molecular mass (provided for certain compounds in the "Retention Time" column), and the procedure employed, are set forth in Table 1.

The chromatography techniques used to determine the compound retention times of Table 1 are as follows:

LCMS=YMC S5 ODS column, 4.6×50 mm eluting with 10-90% MeOH/H2O over 4 minutes containing 0.1% TFA; 4 mL/min, monitoring at 220 nm.

LCMS*=YMC S5 ODS column, 4.6×50 mm eluting with 10-90% MeOH/H2O over 2 minutes containing 0.1% TFA; 4 mL/min, monitoring at 220 nm.

LC=YMC S5 ODS column 4.6×50 mm eluting with 10-90% MeOH/H2O over 4 minutes containing 0.2% phosphoric acid, 4 mL/min, monitoring at 220 nm.

The molecular mass of the compounds listed in Table 1, where provided, were determined by MS (ES) by the formula m/z.

TABLE 1

| Ex. No. | —L—G | Compound Name | Retention Time Min. | Procedure of Example |
|---|---|---|---|---|
| 52 | | (3aα,4α,7α,7aα)-2-(2-Fluorenyl)-3a,4,7,7a-tetrahydro-4,7-methano-1H-isoindole-1,3(2H)-dione. | 3.26 LC | 51 |
| 53 | | (3aα,4α,7α,7aα)-2-(1H-Benzotriazol-5-yl)-3a,4,7,7a-tetrahydro-4,7-methano-1H-isoindole-1,3(2H)-dione. | 1.82 LC | 51 |
| 54 | | (3aα,4α,7α,7aα)-2-[3-Chloro-4-(4-morpholinyl)phenyl]-3a,4,7,7a-tetrahydro-4,7-methano-1H-isoindole-1,3(2H)-dione. | 2.82 LC | 51 |
| 55 | | (3aα,4α,7α,7aα)-2-(2,3-Dihydro-1H-inden-5-yl)-3a,4,7,7a-tetrahydro-4,7-methano-1H-isoindole-1,3(2H)-dione. | 3.50 LC | 51 |
| 56 | | (3aα,4α,7α,7aα)-2-(4-Bromo-1-naphthalenyl)-3a,4,7,7a-tetrahydro-4,7-methano-1H-isoindole-1,3(2H)-dione. | 3.25 LCMS | 51 |
| 57 | | (3aα,4α,7α,7aα)-2-(4-Chloro-1-naphthalenyl)-3a,4,7,7a-tetrahydro-4,7-methano-1H-isoindole-1,3(2H)-dione. | 3.11 LC | 51 |

TABLE 1-continued

| Ex. No. | —L—G | Compound Name | Retention Time Min. | Procedure of Example |
|---|---|---|---|---|
| 58 | (naphthalene with OH) | (3aα,4α,7α,7aα)-3a,4,7,7a-Tetrahydro-2-(7-hydroxy-1-naphthalenyl)-4,7-methano-1H-isoindole-1,3(2H)-dione. | 2.04 & 2.40 LC | 51 |
| 59 | (4-nitronaphthalene) | (3aα,4α,7α,7aα)-3a,4,7,7a-Tetrahydro-2-(4-nitro-1-naphthalenyl)-4,7-methano-1H-isoindole-1,3(2H)-dione. | 2.77 & 2.86 LC | 51 |
| 60 | (indole) | (3aα,4α,7α,7aα)-3a,4,7,7a-Tetrahydro-2-(1H-indol-5-yl)-4,7-methano-1H-isoindole-1,3(2H)-dione. | 2.20 LC | 51 |
| 61 | (indazole) | (3aα,4α,7α,7aα)-3a,4,7,7a-Tetrahydro-2-(1H-indazol-6-yl)-4,7-methano-1H-isoindole-1,3(2H)-dione. | 2.08 LC | 51 |
| 62 | (benzodioxole) | (3aα,4α,7α,7aα)-2-(1,3-Benzodioxol-5-yl)-3a,4,7,7a-tetrahydro-4,7-methano-1H-isoindole-1,3(2H)-dione. | 2.33 LC | 51 |
| 63 | (4-amino-3-trifluoromethylphenyl) | (3aα,4α,7α,7aα)-2-[4-Amino-3-(trifluoromethyl)phenyl]-3a,4,7,7a-tetrahydro-4,7-methano-1H-isoindole-1,3(2H)-dione. |  | 51 |
| 64 | (2-methylquinoline) | (3aα,4α,7α,7aα)-3a,4,7,7a-Tetrahydro-2-(2-methyl-4-quinolinyl)-4,7-methano-1H-isoindole-1,3(2H)-dione. | 0.913 LC | 51 |
| 65 | (8-quinolinyl) | (3aα,4α,7α,7aα)-3a,4,7,7a-Tetrahydro-2-(8-quinolinyl)-4,7-methano-1H-isoindole-1,3(2H)-dione. | 1.98 LC | 51 |
| 66 | (benzodioxin) | (3aα,4α,7α,7aα)-2-(2,3-Dihydro-1,4-benzodioxin-6-yl)-3a,4,7,7a-tetrahydro-4,7-methano-1H-isoindole-1,3(2H)-dione. | 2.27 LC | 51 |

TABLE 1-continued

| Ex. No. | —L—G | Compound Name | Retention Time Min. | Procedure of Example |
|---|---|---|---|---|
| 67 | [structure: 4,7-dimethylcoumarin] | (3aα,4α,7α,7aα)-3a,4,7,7a-Tetrahydro-2-(4-methyl-2-oxo-2H-1-benzopyran-7-yl)-4,7-methano-1H-isoindole-1,3(2H)-dione. | 2.37 LC | 51 |
| 68 | [structure: 5-isoquinolinyl] | (3aα,4α,7α,7aα)-3a,4,7,7a-Tetrahydro-2-(5-isoquinolinyl)-4,7-methano-1H-isoindole-1,3(2H)-dione. | 1.49 LCMS | 51 |
| 69 | [structure: 2,5-dimethoxy-4-nitrophenyl] | (3aα,4α,7α,7aα)-2-(2,5-Dimethoxy-4-nitrophenyl)-3a,4,7,7a-tetrahydro-4,7-methano-1H-isoindole-1,3(2H)-dione. | 2.39 LC | 51 |
| 70 | [structure: 2,3,5,6-tetrafluoro-4-cyanophenyl] | (3aα,4α,7α,7aα)-2,3,5,6-Tetrafluoro-4-(1,3,3a,4,7,7a-hexahydro-1,3-dioxo-4,7-methano-2H-isoindol-2-yl)benzonitrile. | | 51 |
| 71 | [structure: 2,4,5-trifluorophenyl] | (3aα,4α,7α,7aα)-3a,4,7,7a-Tetrahydro-2-(2,4,5-trifluorophenyl)-4,7-methano-1H-isoindole-1,3(2H)-dione. | 2.77 LC | 51 |
| 72 | [structure: 2,4,5-trichlorophenyl] | (3aα,4α,7α,7aα)-3a,4,7,7a-Tetrahydro-2-(2,4,5-trichlorophenyl)-4,7-methano-1H-isoindole-1,3(2H)-dione. | | 51 |
| 73 | [structure: 3,4-difluorophenyl] | (3aα,4α,7α,7aα)-2-(3,4-Difluorophenyl)-3a,4,7,7a-tetrahydro-4,7-methano-1H-isoindole-1,3(2H)-dione. | 2.66 LC | 51 |
| 74 | [structure: 2,3-dihydro-1H-indol-6-yl] | (3aα,4α,7α,7aα)-2-(2,3-Dihydro-1H-indol-6-yl)-3a,4,7,7a-tetrahydro-4,7-methano-1H-isoindole-1,3(2H)-dione. | | 51 |

TABLE 1-continued

| Ex. No. | —L—G | Compound Name | Retention Time Min. | Procedure of Example |
|---|---|---|---|---|
| 75 | 3-chloro-4-fluorophenyl group | (3aα,4α,7α,7aα)-2-(3-Chloro-4-fluorophenyl)-3a,4,7,7a-tetrahydro-4,7-methano-1H-isoindole-1,3(2H)-dione. | 2.12 LCMS | 51 |
| 76 | 3,4-dichlorophenyl group | (3aα,4α,7α,7aα)-2-(3,4-Dichlorophenyl)-3a,4,7,7a-tetrahydro-4,7-methano-1H-isoindole-1,3(2H)-dione. | 3.27 LC | 51 |
| 77 | 3,4,5-trichlorophenyl group | (3aα,4α,7α,7aα)-3a,4,7,7a-Tetrahydro-2-(3,4,5-trichlorophenyl)-4,7-methano-1H-isoindole-1,3(2H)-dione. |  | 51 |
| 78 | 3-chloro-4-methoxyphenyl group | (3aα,4α,7α,7aα)-2-(3-Chloro-4-methoxyphenyl)-3a,4,7,7a-tetrahydro-4,7-methano-1H-isoindole-1,3(2H)-dione. | 2.75 LC | 51 |
| 79 | 3-chloro-4-methylphenyl group | (3aα,4α,7α,7aα)-2-(3-Chloro-4-methylphenyl)-3a,4,7,7a-tetrahydro-4,7-methano-1H-isoindole-1,3(2H)-dione. | 2.68 LC | 51 |
| 80 | 2-methyl-1-naphthalenyl group | (3aα,4α,7α,7aα)-3a,4,7,7a-Tetrahydro-2-(2-methyl-1-naphthalenyl)-4,7-methano-1H-isoindole-1,3(2H)-dione. | 2.91 LC | 51 |
| 81 | 4-chloro-3-methylphenyl group | (3aα,4α,7α,7aα)-2-(4-Chloro-3-methylphenyl)-3a,4,7,7a-tetrahydro-4,7-methano-1H-isoindole-1,3(2H)-dione. | 2.81 LC | 51 |
| 82 | 3,4-dimethylphenyl group | (3aα,4α,7α,7aα)-2-(3,4-Dimethylphenyl)-3a,4,7,7a-tetrahydro-4,7-methano-1H-isoindole-1,3(2H)-dione. | 2.86 LC | 51 |
| 83 | 4-bromo-3-(trifluoromethyl)phenyl group | (3aα,4α,7α,7aα)-2-[4-Bromo-3-(trifluoromethyl)phenyl]-3a,4,7,7a-tetrahydro-4,7-methano-1H-isoindole-1,3(2H)-dione. | 3.38 LCMS | 51 |

TABLE 1-continued

| Ex. No. | —L—G | Compound Name | Retention Time Min. | Procedure of Example |
|---|---|---|---|---|
| 84 | 4-Br, 3-CH₃ phenyl | (3aα,4α,7α,7aα)-2-(4-Bromo-3-methylphenyl)-3a,4,7,7a-tetrahydro-4,7-methano-1H-isoindole-1,3(2H)-dione. | 3.21 LC | 51 |
| 85 | 4-F, 3-NO₂ phenyl | (3aα,4α,7α,7aα)-2-(4-Fluoro-3-nitrophenyl)-3a,4,7,7a-tetrahydro-4,7-methano-1H-isoindole-1,3(2H)-dione. | 2.62 LC | 51 |
| 86 | 4-F, 3-CF₃ phenyl | (3aα,4α,7α,7aα)-2-[4-Fluoro-3-(trifluoromethyl)phenyl]-3a,4,7,7a-tetrahydro-4,7-methano-1H-isoindole-1,3(2H)-dione. | 2.89 LC | 51 |
| 87 | 4-Cl, 3-NO₂ phenyl | (3aα,4α,7α,7aα)-2-(4-Chloro-3-nitrophenyl)-3a,4,7,7a-tetrahydro-4,7-methano-1H-isoindole-1,3(2H)-dione. | 2.96 LC | 51 |
| 88 | 4-Cl, 3-CF₃ phenyl | (3aα,4α,7α,7aα)-2-[4-Chloro-3-(trifluoromethyl)phenyl]-3a,4,7,7a-tetrahydro-4,7-methano-1H-isoindole-1,3(2H)-dione. |  | 51 |
| 89 | 2-OCH₃, 4-Cl, 5-CH₃ phenyl | (3aα,4α,7α,7aα)-2-(4-Chloro-2-methoxy-5-methylphenyl)-3a,4,7,7a-tetrahydro-4,7-methano-1H-isoindole-1,3(2H)-dione. | 3.05 LC | 51 |
| 90 | 3,5-diCl, 4-OH phenyl | (3aα,4α,7α,7aα)-2-(3,5-Dichloro-4-hydroxyphenyl)-3a,4,7,7a-tetrahydro-4,7-methano-1H-isoindole-1,3(2H)-dione. | 2.98 LC | 51 |
| 91 | 4-OH, 3-NO₂ phenyl | (3aα,4α,7α,7aα)-3a,4,7,7a-Tetrahydro-2-(4-hydroxy-3-nitrophenyl)-4,7-methano-1H-isoindole-1,3(2H)-dione. | 2.56 LC | 51 |
| 92 | 4-NH₂, 3-NO₂ phenyl | (3aα,4α,7α,7aα)-2-(4-Amino-3-nitrophenyl)-3a,4,7,7a-tetrahydro-4,7-methano-1H-isoindole-1,3(2H)-dione. | 2.37 LC | 51 |

TABLE 1-continued

| Ex. No. | —L—G | Compound Name | Retention Time Min. | Procedure of Example |
|---|---|---|---|---|
| 93 | | (3aα,4α,7α,7aα)-2,2'-(2,3,5,6-Tetramethyl-1,4-phenylene)bis[3a,4,7,7a-tetrahydro-4,7-methano-1H-isoindole-1,3(2H)-dione]. | 2.19 LC | 51 |
| 94 | | (3aα,4α,7α,7aα)-3a,4,7,7a-Tetrahydro-2-(4-methyl-3-nitrophenyl)-4,7-methano-1H-isoindole-1,3(2H)-dione. | 2.80 LC | 51 |
| 95 | | (3aα,4α,7α,7aα)-3a,4,7,7a-Tetrahydro-2-(3,4,5-trimethoxyphenyl)-4,7-methano-1H-isoindole-1,3(2H)-dione. | 2.33 LC | 51 |
| 96 | | (3aα,4α,7α,7aα)-2-(3,4-Dimethoxyphenyl)-3a,4,7,7a-tetrahydro-4,7-methano-1H-isoindole-1,3(2H)-dione. | | 51 |
| 97 | | (3aα,4α,7α,7aα)-3a,4,7,7a-Tetrahydro-2-(3-hydroxy-4-methoxyphenyl)-4,7-methano-1H-isoindole-1,3(2H)-dione. | 2.00 LC | 51 |
| 98 | | (3aα,4α,7α,7aα)-2-(5-Chloro-2-hydroxy-4-nitrophenyl)-3a,4,7,7a-tetrahydro-4,7-methano-1H-isoindole-1,3(2H)-dione. | 1.94 LC | 51 |
| 99 | | (3aα,4α,7α,7aα)-3a,4,7,7a-Tetrahydro-2-(2-methoxy-3-dibenzofuranyl)-4,7-methano-1H-isoindole-1,3(2H)-dione. | 2.78 LC | 51 |
| 100 | | (3aα,4α,7α,7aα)-3a,4,7,7a-Tetrahydro-2-(2,3,4-trifluorophenyl)-4,7-methano-1H-isoindole-1,3(2H)-dione. | | 51 |

TABLE 1-continued

| Ex. No. | —L—G | Compound Name | Retention Time Min. | Procedure of Example |
|---|---|---|---|---|
| 101 | | (3aα,4α,7α,7aα)-2-(2,3-Dihydro-2-methyl-1,3-dioxo-1H-isoindol-5-yl)-3a,4,7,7a-tetrahydro-4,7-methano-1H-isoindole-1,3(2H)-dione. | | 51 |
| 102 | | (3aα,4α,7α,7aα)-2-(4-Bromo-2,3,5,6-tetrafluorophenyl)-3a,4,7,7a-tetrahydro-4,7-methano-1H-isoindole-1,3(2H)-dione. | 2.43 LC | 51 |
| 103 | | (3aα,4α,7α,7aα)-2-[2,5-Dichloro-4-(1H-pyrrol-1-yl)phenyl]-3a,4,7,7a-tetrahydro-4,7-methano-1H-isoindole-1,3(2H)-dione. | | 51 |
| 104 | | (3aα,4α,7α,7aα)-2-[3-[(Diethylamino)methyl]-4-hydroxyphenyl]-3a,4,7,7a-tetrahydro-4,7-methano-1H-isoindole-1,3(2H)-dione. | 3.42 LC | 51 |
| 105 | | (3aα,4α,7α,7aα)-2-(6-Benzothiazolyl)-3a,4,7,7a-tetrahydro-4,7-methano-1H-isoindole-1,3(2H)-dione. | 1.44 LC | 51 |
| 106 | | (3aα,4α,7α,7aα)-4-(1,3,3a,4,7,7a-Hexahydro-1,3-dioxo-4,7-methano-2H-isoindol-2-yl)-2-methoxybenzenecarboxylic acid, methyl ester. | 2.23 LC | 51 |
| 107 | | (3aα,4α,7α,7aα)-3a,4,7,7a-Tetrahydro-2-(2-oxo-2H-1-benzopyran-6-yl)-4,7-methano-1H-isoindole-1,3(2H)-dione. | 2.49 LC | 51 |
| 108 | | (3aα,4α,7α,7aα)-3a,4,7,7a-Tetrahydro-2-(2-methyl-8-quinolinyl)-4,7-methano-1H-isoindole-1,3(2H)-dione. | 2.21 LC | 51 |

TABLE 1-continued

| Ex. No. | —L—G | Compound Name | Retention Time Min. | Procedure of Example |
|---|---|---|---|---|
| 109 | | (3aα,4α,7α,7aα)-3a,4,7,7a-Tetrahydro-2-(2,3,5,6-tetramethyl-4-nitrophenyl)-4,7-methano-1H-isoindole-1,3(2H)-dione. | | 51 |
| 110 | | (3aα,4α,7α,7aα)-3a,4,7,7a-Tetrahydro-2-(2,4,5-trimethylphenyl)-4,7-methano-1H-isoindole-1,3(2H)-dione. | 3.10 LC | 51 |
| 111 | | (3aα,4α,7α,7aα)-2-(4-Fluoro-3-methylphenyl)-3a,4,7,7a-tetrahydro-4,7-methano-1H-isoindole-1,3(2H)-dione. | | 51 |
| 112 | | (3aα,4α,7α,7aα)-3a,4,7,7a-Tetrahydro-2-(3-methoxy-4-methylphenyl)-4,7-methano-1H-isoindole-1,3(2H)-dione. | | 51 |
| 113 | | (3aα,4α,7α,7aα)-N-Ethyl-5-(1,3,3a,4,7,7a-hexahydro-1,3-dioxo-4,7-methano-2H-isoindol-2-yl)-2-methyl-N-phenylbenzenesulfonamide | 2.75 LC | 51 |
| 114 | | (3aα,4α,7α,7aα)-6-(1,3,3a,4,7,7a-Hexahydro-1,3-dioxo-4,7-methano-2H-isoindol-2-yl)-2,4-dimethyl-3-pyridinecarbonitrile. | | 51 |
| 115 | | (3aα,4α,7α,7aα)-2-(3-Dibenzofuranyl)-3a,4,7,7a-tetrahydro-4,7-methano-1H-isoindole-1,3(2H)-dione. | 3.21 LC | 51 |

TABLE 1-continued

| Ex. No. | —L—G | Compound Name | Retention Time Min. | Procedure of Example |
|---|---|---|---|---|
| 116 | | (3aα,4α,7α,7aα)-3a,4,7,7a-Tetrahydro-2-(2'-hydroxy[1,1':3',1''-terphenyl]-5'-yl)-4,7-methano-1H-isoindole-1,3(2H)-dione. | | 51 |
| 117 | | (3aα,4α,7α,7aα)-2-(1,3-Dihydro-2,2-dioxidobenzo[c]thiophen-5-yl)-3a,4,7,7a-tetrahydro-4,7-methano-1H-isoindole-1,3(2H)-dione. | 3.31 LC | 51 |
| 118 | | (3aα,4α,7α,7aα)-3a,4,7,7a-Tetrahydro-2-(2,2,3,3-tetrafluoro-2,3-dihydro-1,4-benzodioxin-6-yl)-4,7-methano-1H-isoindole-1,3(2H)-dione. | 2.16 LC | 51 |
| 119 | | (3aα,4α,7α,7aα)-2-(4-Amino-2,3,5,6-tetrafluorophenyl)-3a,4,7,7a-tetrahydro-4,7-methano-1H-isoindole-1,3(2H)-dione. | 1.82 LC | 51 |
| 120 | | (3aα,4α,7α,7aα)-N-[2-Chloro-6-fluoro-4-(1,3,3a,4,7,7a-hexahydro-1,3-dioxo-4,7-methano-2H-isoindol-2-yl)phenyl]acetamide. | 1.94 & 2.03 LC | 51 |
| 121 | | (3aα,4α,7α,7aα)-4-(1,3,3a,4,7,7a-Hexahydro-1,3-dioxo-4,7-methano-2H-isoindol-2-yl)-2-(trifluoromethyl)-benzonitrile. | 3.04 LC | 51 |
| 122 | | (3aα,4α,7α,7aα)-2-Fluoro-5-(1,3,3a,4,7,7a-hexahydro-1,3-dioxo-4,7-methano-2H-isoindol-2-yl)benzonitrile. | | 51 |
| 123 | | (3aα,4α,7α,7aα)-3a,4,7,7a-Tetrahydro-2-[3-(trifluoromethyl)phenyl]-4,7-methano-1H-isoindole-1,3(2H)-dione. | 3.04 LC | 25D or 38A |

TABLE 1-continued

| Ex. No. | —L—G | Compound Name | Retention Time Min. | Procedure of Example |
|---|---|---|---|---|
| 124 | (structure: 2-ethoxy-8-methyl-4-(trifluoromethyl)quinolin-7-yl) | (3aα,4α,7α,7aα)-2-[2-Ethoxy-8-methyl-4-(trifluoromethyl)-7-quinolinyl]-3a,4,7,7a-tetrahydro-4,7-methano-1H-isoindole-1,3(2H)-dione. | 417.0 [M + H]⁺ | 25D or 38A |
| 125 | (structure: 1,2-dihydro-8-methyl-2-oxo-4-(trifluoromethyl)quinolin-7-yl) | (3aα,4α,7α,7aα)-2-[1,2-Dihydro-8-methyl-2-oxo-4-(trifluoromethyl)-7-quinolinyl]-3a,4,7,7a-tetrahydro-4,7-methano-1H-isoindole-1,3(2H)-dione. | 389.0 [M + H]⁺ | 25D or 38A |
| 126 | (structure: 9-ethyl-9H-carbazol-2-yl) | (3aα,4α,7α,7aα)-2-(9-Ethyl-9H-carbazol-2-yl)-3a,4,7,7a-tetrahydro-4,7-methano-1H-isoindole-1,3(2H)-dione. | 7.25 LCMS 357.0 [M + H]⁺ | 25D or 38A |
| 127 | (structure: 4-(1-piperidinyl)phenyl) | (3aα,4α,7α,7aα)-3a,4,7,7a-Tetrahydro-2-[4-(1-piperidinyl)phenyl]-4,7-methano-1H-isoindole-1,3(2H)-dione. | 3.66 LCMS 323.0 [M + H]⁺ | 25D or 38A |
| 128 | (structure: 4-(4-morpholinyl)phenyl) | (3aα,4α,7α,7aα)-3a,4,7,7a-Tetrahydro-2-[4-(4-morpholinyl)phenyl]-4,7-methano-1H-isoindole-1,3(2H)-dione. | 4.89 LCMS 325.0 [M + H]⁺ | 25D or 38A |
| 129 | (structure: 7-quinolinyl) | (3aα,4α,7α,7aα)-3a,4,7,7a-Tetrahydro-2-(7-quinolinyl)-4,7-methano-1H-isoindole-1,3(2H)-dione. | 3.47 LCMS 291.0 [M + H]⁺ | 25D or 38A |
| 130 | (structure: 3-chlorophenyl) | (3aα,4α,7α,7aα)-2-(3-Chlorophenyl)-3a,4,7,7a-tetrahydro-4,7-methano-1H-isoindole-1,3(2H)-dione. | 2.84 LC | 25D or 38A |
| 131 | (structure: 2-naphthalenyl) | (3aα,4α,7α,7aα)-3a,4,7,7a-Tetrahydro-2-(2-naphthalenyl)-4,7-methano-1H-isoindole-1,3(2H)-dione. | 3.48 LC | 25D or 38A |

TABLE 1-continued

| Ex. No. | —L—G | Compound Name | Retention Time Min. | Procedure of Example |
|---|---|---|---|---|
| 132 | | (3aα,4α,7α,7aα)-3a,4,7,7a-Tetrahydro-2-(1,2,3,4-tetrahydro-2-oxo-7-quinolinyl)-4,7-methano-1H-isoindole-1,3(2H)-dione. | 2.69 LCMS 309.0 [M + H]$^+$ | 25D or 38A |
| 133 | | (3aα,4α,7α,7aα)-2-[3-(1,3,3a,4,7,7a-Hexahydro-1,3-dioxo-4,7-methano-2H-isoindol-2-yl)-2-methylphenoxyl]-2-methylpropanoic acid, ethyl ester. | 6.82 & 6.93 LCMS 384.0 [M + H]$^+$ | 25D or 38A |
| 134 | | (3aα,4α,7α,7aα)-3a,4,7,7a-Tetrahydro-2-[4-(4-methyl-1-piperazinyl)phenyl]-4,7-methano-1H-isoindole-1,3(2H)-dione. | 2.13 LCMS 338.0 [M + H]$^+$ | 25D or 38A |
| 135 | | (3aα,4α,7α,7aα)-2-[4-(Diethylamino)-1-naphthalenyl]-3a,4,7,7a-tetrahydro-4,7-methano-1H-isoindole-1,3(2H)-dione. | 4.37 & 4.85 LCMS 361.0 [M + H]$^+$ | 25D or 38A |
| 136 | | (3aα,4α,7α,7aα)-3a,4,7,7a-Tetrahydro-2-(8-hydroxy-5-quinolinyl)-4,7-methano-1H-isoindole-1,3(2H)-dione. | 2.80 LC 307.2 [M + H]$^+$ | 25D or 38A |
| 137 | | (3aα,4α,7α,7aα)-3a,4,7,7a-Tetrahydro-2-(4-nitrophenyl)-4,7-methano-1H-isoindole-1,3(2H)-dione. | 3.07 LC | 25D or 38A |
| 138 | | (3aα,4α,7α,7aα)-3a,4,7,7a-Tetrahydro-2-[2-(4-morpholinyl)-5-(trifluoromethyl)phenyl]-4,7-methano-1H-isoindole-1,3(2H)-dione. | 3.65 LC 393.2 [M + H]$^+$ | 25D or 38A |
| 139 | | (3aα,4α,7α,7aα)-2-(3,5-Dichlorophenyl)-3a,4,7,7a-tetrahydro-4,7-methano-1H-isoindole-1,3(2H)-dione. | 3.95 LC | 25D or 38A |

TABLE 1-continued

| Ex. No. | —L—G | Compound Name | Retention Time Min. | Procedure of Example |
|---|---|---|---|---|
| 140 | (structure: 2-fluoro-3-chloro-methylphenyl) | (3aα,4α,7α,7aα)-2-(3-Chloro-4-fluorophenyl)-3a,4,7,7a-tetrahydro-4,7-methano-1H-isoindole-1,3(2H)-dione. | 3.01 LC | 25D or 38A |
| 141 | (structure: 4-fluoro-methylphenyl) | (3aα,4α,7α,7aα)-2-(4-Fluorophenyl)-3a,4,7,7a-tetrahydro-4,7-methano-1H-isoindole-1,3(2H)-dione. | | 25D or 38A |
| 142 | (structure: 4-(1,2,3-thiadiazol-4-yl)phenyl) | (3aα,4α,7α,7aα)-3a,4,7,7a-Tetrahydro-2-[4-(1,2,3-thiadiazol-4-yl)phenyl]-4,7-methano-1H-isoindole-1,3(2H)-dione. | | 25D or 38A |
| 143 | (structure: 2-methyl-4-trifluoromethyl-acetamidophenyl) | (3aα,4α,7α,7aα)-N-[2-(1,3,3a,4,7,7a-Hexahydro-1,3-dioxo-4,7-methano-2H-isoindol-2-yl)-4-(trifluoromethyl)phenyl]acetamide. | 3.34 LC | 25D or 38A |
| 144 | (structure: 3-trifluoromethyl-5-acetamidophenyl) | (3aα,4α,7α,7aα)-N-[5-(1,3,3a,4,7,7a-Hexahydro-1,3-dioxo-4,7-methano-2H-isoindol-2-yl)-3-(trifluoromethyl)phenyl]acetamide. | 3.34 LCMS | 25D or 38A |
| 145 | (structure: 3-amino-5-trifluoromethylphenyl) | (3aα,4α,7α,7aα)-2-[3-Amino-5-(trifluoromethyl)phenyl]-3a,4,7,7a-tetrahydro-4,7-methano-1H-isoindole-1,3(2H)-dione. | 2.70 LC 323.1 [M + H]⁺ | 25D or 38A |
| 146 | (structure: 2-oxo-4-trifluoromethyl-7-quinolinyl) | (3aα,4α,7α,7aα)-2-[1,2-Dihydro-2-oxo-4-(trifluoromethyl)-7-quinolinyl]-3a,4,7,7a-tetrahydro-4,7-methano-1H-isoindole-1,3(2H)-dione. | 3.55 LC 375.2 [M + H]⁺ | 25D or 38A |
| 147 | (structure: 5-methylthio-8-acetamidoquinolinyl) | (3aα,4α,7α,7aα)-N-[5-(1,3,3a,4,7,7a-Hexahydro-1,3-dioxo-4,7-methano-2H-isoindol-2-yl)-6-(methylthio)-8-quinolinyl]acetamide. | 3.17 LC 394.2 [M + H]⁺ | 25D or 38A |

TABLE 1-continued

| Ex. No. | —L—G | Compound Name | Retention Time Min. | Procedure of Example |
|---|---|---|---|---|
| 148 | | (3aα,4α,7α,7aα)-2-[5-Ethoxy-2-(methoxymethyl)-4-(4-morpholinyl)phenyl]-3a,4,7,7a-tetrahydro-4,7-methano-1H-isoindole-1,3(2H)-dione. | 3.25 LC 413.2 [M + H]⁺ | 25D or 38A |
| 149 | | (3aα,4α,7α,7aα)-2-[(1R)-1-(1-naphthalenyl)ethyl]-3a,4,7,7a-tetrahydro-4,7-methano-1H-isoindole-1,3(2H)-dione. | 3.57 LCMS 318.1 [M + H]⁺ | 25D or 38A |
| 150 | | (3aα,4α,7α,7aα)-2-[(1S)-1-(1-naphthalenyl)ethyl]-3a,4,7,7a-tetrahydro-4,7-methano-1H-isoindole-1,3(2H)-dione. | 3.55 LCMS 318.2 [M + H]⁺ | 25D or 38A |
| 151 | | (3aα,4α,7α,7aα)-4-Fluoro-N-[3-(1,3,3a,4,7,7a-hexahydro-1,3-dioxo-4,7-methano-2H-isoindol-2-yl)-5-(trifluoromethyl)phenyl]benzenesulfonamide. | 3.78 LC 481.1 [M + H]⁺ | 25D or 38A |
| 152 | | (3aα,4α,7α,7aα)-3a,4,7,7a-Tetrahydro-2-[7-(trifluoromethyl)-4-quinolinyl]-4,7-methano-1H-isoindole-1,3(2H)-dione. | 3.00 LCMS | 25D or 38A |
| 153 | | (3aα,4α,7α,7aα)-3a,4,7,7a-Tetrahydro-2-[8-(trifluoromethyl)-4-quinolinyl]-4,7-methano-1H-isoindole-1,3(2H)-dione. | 2.73 LCMS | 25D or 38A |
| 154 | | (3aα,4α,7α,7aα)-2-(3,4-Dimethyl-5-isoxazolyl)-3a,4,7,7a-tetrahydro-4,7-methano-1H-isoindole-1,3(2H)-dione. | 2.06 LCMS | 25D or 38A |
| 155 | | (3aα,4α,7α,7aα)-3a,4,7,7a-tetrahydro-2-(1-naphthalenyl)-4,7-methano-1H-isoindole-1,3(2H)-dione. | 2.99 LCMS | 25D or 38A |

TABLE 1-continued

| Ex. No. | —L—G | Compound Name | Retention Time Min. | Procedure of Example |
|---|---|---|---|---|
| 156 | (naphthalene with CN) | (3aα,4α,7α,7aα)-4-(1,3,3a,4,7,7a-Hexahydro-1,3-dioxo-4,7-methano-2H-isoindol-2-yl)-1-naphthalenecarbonitrile. | 2.66 & 2.79 LCMS | 25D or 38A |
| 157 | (benzothiophene with CO2CH3) | (3aα,4α,7α,7aα)-3-(1,3,3a,4,7,7a-Hexahydro-1,3-dioxo-4,7-methano-2H-isoindol-2-yl)benzo[b]thiophene-2-carboxylic acid, methyl ester. | 2.99 LC 354.0 [M + H]⁺ | 25D or 38A |
| 158 | (isoquinoline with NO2) | (3aα,4α,7α,7aα)-3a,4,7,7a-Tetrahydro-2-(5-nitro-8-isoquinolinyl)-4,7-methano-1H-isoindole-1,3(2H)-dione, trifluoroacetate (1:1). | 2.46 LC 336.0 [M + H]⁺ | 25D or 38A |
| 159 | (naphthalene with NH2) | (3aα,4α,7α,7aα)-2-(4-Amino-1-naphthalenyl)-3a,4,7,7a-tetrahydro-4,7-methano-1H-isoindole-1,3(2H)-dione. | 1.96 & 2.30 LCMS | 25D or 38A |
| 160 | (naphthalene with OH) | (3aα,4α,7α,7aα)-3a,4,7,7a-Tetrahydro-2-(4-hydroxy-1-naphthalenyl)-4,7-methano-1H-isoindole-1,3(2H)-dione. | 2.22 & 2.49 LCMS | 25D or 38A |
| 161 | (phenyl with CH3) | (3aα,4α,7α,7aα)-3a,4,7,7a-Tetrahydro-2-(3-methylphenyl)-4,7-methano-1H-isoindole-1,3(2H)-dione. | 2.53 LC | 25D or 38A |
| 162 | (phenyl with Br) | (3aα,4α,7α,7aα)-2-(4-Bromophenyl)-3a,4,7,7a-tetrahydro-4,7-methano-1H-isoindole-1,3(2H)-dione. | 2.89 LCMS | 25D or 38A |
| 163 | (phenyl with CN) | (3aα,4α,7α,7aα)-4-(1,3,3a,4,7,7a-Hexahydro-1,3-dioxo-4,7-methano-2H-isoindol-2-yl)benzonitrile. | 2.34 LC | 25D or 38A |
| 164 | (naphthalene with NHC(O)CH3) | (3aα,4α,7α,7aα)-N-[4-(1,3,3a,4,7,7a-Hexahydro-1,3-dioxo-isoindol-2-yl)-1-naphthalenyl]acetamide. | 2.04 & 2.26 LC | 25D or 38A |

TABLE 1-continued

| Ex. No. | —L—G | Compound Name | Retention Time Min. | Procedure of Example |
|---|---|---|---|---|
| 165 | | (3aα,4α,7α,7aα)-N-[4-(1,3,3a,4,7,7a-Hexahydro-1,3-dioxo-4,7-methano-2H-isoindol-2-yl)-1-naphthalenyl] methanesulfonamide. | 2.15 & 2.33 LC | 25D or 38A |
| 166 | | (3aα,4α,7α,7aα)-2-(5-Bromo-8-isoquinolinyl)-3a,4,7,7a-tetrahydro-4,7-methano-1H-isoindole-1,3(2H)-dione. | 2.60 LC 370.0 [M + H]$^+$ | 25D or 38A |
| 167 | | (3aα,4α,7α,7aα)-2-(7,8-Dichloro-5-quinolinyl)-3a,4,7,7a-tetrahydro-4,7-methano-1H-isoindole-1,3(2H)-dione. | 2.76 & 3.06 LC 359.0 [M + H]$^+$ | 25D or 38A |
| 168 | | (3aα,4α,7α,7aα)-3a,4,7,7a-Tetrahydro-2-(3-methyl-4-nitrophenyl)-4,7-methano-1H-isoindole-1,3(2H)-dione. | 2.75 LCMS | 25D or 38A |
| 169 | | (3aα,4α,7α,7aα)-N-[4-(1,3,3a,4,7,7a-Hexahydro-1,3-dioxo-4,7-methano-2H-isoindol-2-yl)-1-naphthalenyl]-N'-methylurea. | 2.07 & 2.25 LC | 25D or 38A |
| 170 | | (3aα,4α,7α,7aα)-4-(1,3,3a,4,7,7a-Hexahydro-1,3-dioxo-4,7-methano-2H-isoindol-2-yl)-2-methoxy-1-naphthalenecarbonitrile. | 2.82 LC | 25D or 38A |
| 171 | | (3aα,4α,7α,7aα)-2-(6-Bromo-1,2-benzisoxazol-3-yl)-3a,4,7,7a-tetrahydro-4,7-methano-1H-isoindole-1,3(2H)-dione. | 3.19 LCMS 349.0 [M + H]$^+$ | 25D or 38A |
| 172 | | (3aα,4α,7α,7aα)-2-(5-Bromo-1,2-benzisoxazol-3-yl)-3a,4,7,7a-tetrahydro-4,7-methano-1H-isoindole-1,3(2H)-dione. | 3.12 LCMS 359.0 [M + H]$^+$ | 25D or 38A |
| 173 | | (3aα,4α,7α,7aα)-2-(4-Fluoro-1H-indazol-3-yl)-3a,4,7,7a-tetrahydro-4,7-methano-1H-isoindole-1,3(2H)-dione. | 2.42 LCMS 298.3 [M + H]$^+$ | 25D or 38A |

TABLE 1-continued

| Ex. No. | —L—G | Compound Name | Retention Time Min. | Procedure of Example |
|---|---|---|---|---|
| 174 | | (3aα,4α,7α,7aα)-2-(6-Chloro-1H-indazol-3-yl)-3a,4,7,7a-tetrahydro-4,7-methano-1H-isoindole-1,3(2H)-dione. | 2.84 LCMS 313.0 [M + H]$^+$ | 25D or 38A |
| 175 | | (3aα,4α,7α,7aα)-3a,4,7,7a-Tetrahydro-2-(5-nitro-1,2-benzisoxazol-3-yl)-4,7-methano-1H-isoindole-1,3(2H)-dione. | 2.79 LC | 25D or 38A |
| 176 | | (3aα,4α,7α,7aα)-3-(1,3,3a,4,7,7a-Hexahydro-1,3-dioxo-4,7-methano-2H-isoindol-2-yl)-2-benzofurancarboxylic acid, methyl ester. | 2.91 LCMS 337.0 [M + H]$^+$ | 25D or 38A |
| 177 | | (3aα,4α,7α,7aα)-2-(3-Benzofuranyl)-3a,4,7,7a-tetrahydro-4,7-methano-1H-isoindole-1,3(2H)-dione. | 2.80 LCMS 279.0 [M + H]$^+$ | 25D or 38A |
| 178 | | (3aα,4α,7α,7aα)-2-(4-Chlorophenyl)-3a,4,7,7a-tetrahydro-4,7-methano-1H-isoindole-1,3(2H)-dione. | 2.76 LC | 25D or 38A |
| 179 | | (3aα,4α,7α,7aα)-Hexahydro-2-[3-methoxy-4-(1H-1,2,4-triazol-1-yl)phenyl]-4,7-methano-1H-isoindole-1,3(2H)-dione. | 2.41 LC | 25D or 38A |
| 180 | | (3aα,4α,7α,7aα)-2-(2,3-Dihydro-2-oxo-6-benzothiazolyl)-3a,4,7,7a-tetrahydro-4,7-methano-1H-isoindole-1,3(2H)-dione. | 2.13 LC | 25D or 38A |
| 181 | | (3aα,4α,7α,7aα)-2-(2,3-Dihydro-3-methyl-2-oxo-6-benzothiazolyl)-3a,4,7,7a-tetrahydro-4,7-methano-1H-isoindole-1,3(2H)-dione. | 2.61 LC | 25D or 38A |
| 182 | | (3aα,4α,7α,7aα)-2-(2,3-Dihydro-1-methyl-2-oxo-1H-indol-5-yl)-3a,4,7,7a-tetrahydro-4,7-methano-1H-isoindole-1,3(2H)-dione. | 2.68 LC | 25D or 38A |

EXAMPLES 183 TO 271

Additional compounds of the formula I were prepared by procedures analogous to those described above. The compounds of Examples 183 to 271 have the following structure:

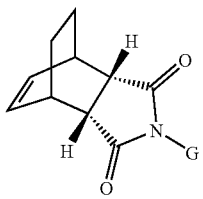

where G, the compound name, retention time, and the procedure employed, are set forth in Table 2 (L is a bond for the compounds of Table 2).

The chromatography techniques used to determine the compound retention times of Table 2 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

LCMS*=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 2, where provided, were determined by MS (ES) by the formula m/z.

TABLE 2

| Ex. No. | —L—G | Compound Name | Retention Time Min. | Procedure of Example |
|---|---|---|---|---|
| 183 | | (3aα,4α,7α,7aα)-2-(2-Fluorenyl)-3a,4,7,7a-tetrahydro-4,7-ethano-1H-isoindole-1,3(2H)-dione. | 3.48 LCMS | 51 |
| 184 | | (3aα,4α,7α,7aα)-2-(1H-Benzotriazol-5-yl)-3a,4,7,7a-tetrahydro-4,7-ethano-1H-isoindole-1,3(2H)-dione. | 1.52 LCMS | 51 |
| 185 | | (3aα,4α,7α,7aα)-2-[3-Chloro-4-(4-morpholinyl)phenyl]-3a,4,7,7a-tetrahydro-4,7-ethano-1H-isoindole-1,3(2H)-dione. | 2.88 LCMS | 51 |
| 186 | | (3aα,4α,7α,7aα)-2-(2,3-Dihydro-1H-inden-5-yl)-3a,4,7,7a-tetrahydro-4,7-ethano-1H-isoindole-1,3(2H)-dione. | 2.98 LCMS | 51 |
| 187 | | (3aα,4α,7α,7aα)-2-(4-Bromo-1-naphthalenyl)-3a,4,7,7a-tetrahydro-4,7-ethano-1H-isoindole-1,3(2H)-dione. | 3.19 LCMS | 51 |
| 188 | | (3aα,4α,7α,7aα)-2-(4-Chloro-1-naphthalenyl)-3a,4,7,7a-tetrahydro-4,7-ethano-1H-isoindole-1,3(2H)-dione. | 3.21 LCMS | 51 |

TABLE 2-continued

| Ex. No. | —L—G | Compound Name | Retention Time Min. | Procedure of Example |
|---|---|---|---|---|
| 189 | (naphthalene with H₂N) | (3aα,4α,7α,7aα)-2-(5-Amino-1-naphthalenyl)-3a,4,7,7a-tetrahydro-4,7-ethano-1H-isoindole-1,3(2H)-dione. | 1.07 LCMS | 51 |
| 190 | (naphthalene with OH) | (3aα,4α,7α,7aα)-3a,4,7,7a-Tetrahydro-2-(7-hydroxy-1-naphthalenyl)-4,7-ethano-1H-isoindole-1,3(2H)-dione. | 1.57 LCMS | 51 |
| 191 | (naphthalene with O₂N) | (3aα,4α,7α,7aα)-3a,4,7,7a-Tetrahydro-2-(4-nitro-1-naphthalenyl)-4,7-ethano-1H-isoindole-1,3(2H)-dione. | 2.76 LCMS | 51 |
| 192 | (indole) | (3aα,4α,7α,7aα)-3a,4,7,7a-Tetrahydro-2-(1H-indol-5-yl)-4,7-ethano-1H-isoindole-1,3(2H)-dione. | 1.93 LCMS | 51 |
| 193 | (indazole) | (3aα,4α,7α,7aα)-3a,4,7,7a-Tetrahydro-2-(1H-indazol-6-yl)-4,7-ethano-1H-isoindole-1,3(2H)-dione. | 1.79 LCMS | 51 |
| 194 | (benzodioxole) | (3aα,4α,7α,7aα)-2-(1,3-Benzodioxol-5-yl)-3a,4,7,7a-tetrahydro-4,7-ethano-1H-isoindole-1,3(2H)-dione. | 2.02 LCMS | 51 |
| 195 | (phenyl with H₂N and CF₃) | (3aα,4α,7α,7aα)-2-[4-Amino-3-(trifluoromethyl)phenyl]-3a,4,7,7a-tetrahydro-4,7-ethano-1H-isoindole-1,3(2H)-dione. | 2.36 LCMS | 51 |
| 196 | (phenyl with I and Cl) | (3aα,4α,7α,7aα)-2-(3-Chloro-4-iodophenyl)-3a,4,7,7a-tetrahydro-4,7-ethano-1H-isoindole-1,3(2H)-dione. | 3.46 LCMS | 51 |
| 197 | (quinoline) | (3aα,4α,7α,7aα)-3a,4,7,7a-Tetrahydro-2-(8-quinolinyl)-4,7-ethano-1H-isoindole-1,3(2H)-dione. | 1.72 LCMS | 51 |

TABLE 2-continued

| Ex. No. | —L—G | Compound Name | Retention Time Min. | Procedure of Example |
|---|---|---|---|---|
| 198 | | (3aα,4α,7α,7aα)-2-(1,4-Benzodioxin-6-yl)-3a,4,7,7a-tetrahydro-4,7-ethano-1H-isoindole-1,3(2H)-dione. | 2.11 LCMS | 51 |
| 199 | | (3aα,4α,7α,7aα)-3a,4,7,7a-Tetrahydro-2-[2-oxo-4-(trifluoromethyl)-2H-1-benzopyran-7-yl]-4,7-ethano-1H-isoindole-1,3(2H)-dione. | 3.14 LCMS | 51 |
| 200 | | (3aα,4α,7α,7aα)-3a,4,7,7a-Tetrahydro-2-(4-methyl-2-oxo-2H-1-benzopyran-7-yl)-4,7-ethano-1H-isoindole-1,3(2H)-dione. | 2.24 LCMS | 51 |
| 201 | | (3aα,4α,7α,7aα)-3a,4,7,7a-Tetrahydro-2-(5-isoquinolinyl)-4,7-ethano-1H-isoindole-1,3(2H)-dione. | 0.56 LCMS | 51 |
| 202 | | (3aα,4α,7α,7aα)-2-(2,5-Dimethoxy-4-nitrophenyl)-3a,4,7,7a-tetrahydro-4,7-ethano-1H-isoindole-1,3(2H)-dione. | 2.21 LCMS | 51 |
| 203 | | (3aα,4α,7α,7aα)-3a,4,7,7a-Tetrahydro-2-(2,4,5-trifluorophenyl)-4,7-ethano-1H-isoindole-1,3(2H)-dione. | 2.56 LCMS | 51 |
| 204 | | (3aα,4α,7α,7aα)-3a,4,7,7a-Tetrahydro-2-(2,4,5-trichlorophenyl)-4,7-ethano-1H-isoindole-1,3(2H)-dione. | 3.45 LCMS | 51 |
| 205 | | (3aα,4α,7α,7aα)-2-(2-Amino-4,5-dichlorophenyl)-3a,4,7,7a-tetrahydro-4,7-ethano-1H-isoindole-1,3(2H)-dione. | 2.79 LCMS | 51 |

TABLE 2-continued

| Ex. No. | —L—G | Compound Name | Retention Time Min. | Procedure of Example |
|---|---|---|---|---|
| 206 | (3,4-difluorophenyl) | (3aα,4α,7α,7aα)-2-(3,4-Difluorophenyl)-3a,4,7,7a-tetrahydro-4,7-ethano-1H-isoindole-1,3(2H)-dione. | 2.57 LCMS | 51 |
| 207 | (6-methyl-1-acetylindoline) | (3aα,4α,7α,7aα)-1-Acetyl-6-(1,3,3a,4,7,7a-hexahydro-1,3-dioxo-4,7-ethano-2H-isoindol-2-yl)-2,3-dihydro-1H-indole. | 1.82 LCMS | 51 |
| 208 | (3-chloro-4-fluorophenyl) | (3aα,4α,7α,7aα)-(3-Chloro-4-fluorophenyl)-3a,4,7,7a-tetrahydro-4,7-ethano-1H-isoindole-1,3(2H)-dione. | 2.89 LCMS | 51 |
| 209 | (3,4-dichlorophenyl) | (3aα,4α,7α,7aα)-2-(3,4-Dichlorophenyl)-3a,4,7,7a-tetrahydro-4,7-ethano-1H-isoindole-1,3(2H)-dione. | 3.31 LCMS | 51 |
| 210 | (3,4,5-trichlorophenyl) | (3aα,4α,7α,7aα)-3a,4,7,7a-Tetrahydro-2-(3,4,5-trichlorophenyl)-4,7-ethano-1H-isoindole-1,3(2H)-dione. | 3.92 LCMS | 51 |
| 211 | (3-chloro-4-methoxyphenyl) | (3aα,4α,7α,7aα)-2-(3-Chloro-4-methoxyphenyl)-3a,4,7,7a-tetrahydro-4,7-ethano-1H-isoindole-1,3(2H)-dione. | 2.6 LCMS | 51 |
| 212 | (3-chloro-4-methylphenyl) | (3aα,4α,7α,7aα)-2-(3-Chloro-4-methylphenyl)-3a,4,7,7a-tetrahydro-4,7-ethano-1H-isoindole-1,3(2H)-dione. | 3.1 LCMS | 51 |
| 213 | (2-methyl-1-naphthalenyl) | (3aα,4α,7α,7aα)-3a,4,7,7a-Tetrahydro-2-(2-methyl-1-naphthalenyl)-4,7-ethano-1H-isoindole-1,3(2H)-dione. | 2.78 LCMS | 51 |
| 214 | (4-chloro-3-methylphenyl) | (3aα,4α,7α,7aα)-2-(4-Chloro-3-methylphenyl)-3a,4,7,7a-tetrahydro-4,7-ethano-1H-isoindole-1,3(2H)-dione. | 3.09 LCMS | 51 |

TABLE 2-continued

| Ex. No. | —L—G | Compound Name | Retention Time Min. | Procedure of Example |
|---|---|---|---|---|
| 215 | (2,4-dimethylphenyl group, H₃C at 2-position, CH₃ at 4-position) | (3aα,4α,7α,7aα)-2-(3,4-Dimethylphenyl)-3a,4,7,7a-tetrahydro-4,7-ethano-1H-isoindole-1,3(2H)-dione. | 2.74 LCMS | 51 |
| 216 | (phenyl with Br at 2-position, CF₃ at 3-position) | (3aα,4α,7α,7aα)-2-[4-Bromo-3-(trifluoromethyl)phenyl]-3a,4,7,7a-tetrahydro-4,7-ethano-1H-isoindole-1,3(2H)-dione. | 3.53 LCMS | 51 |
| 217 | (phenyl with Br and CH₃) | (3aα,4α,7α,7aα)-2-(4-Bromo-3-methylphenyl)-3a,4,7,7a-tetrahydro-4,7-ethano-1H-isoindole-1,3(2H)-dione. | 3.2 LCMS | 51 |
| 218 | (phenyl with F and NO₂) | (3aα,4α,7α,7aα)-2-(4-Fluoro-3-nitrophenyl)-3a,4,7,7a-tetrahydro-4,7-ethano-1H-isoindole-1,3(2H)-dione. | 2.44 LCMS | 51 |
| 219 | (phenyl with F and CF₃) | (3aα,4α,7α,7aα)-2-[4-Fluoro-3-(trifluoromethyl)phenyl]-3a,4,7,7a-tetrahydro-4,7-ethano-1H-isoindole-1,3(2H)-dione. | 3.15 LCMS | 51 |
| 220 | (phenyl with Cl and NO₂) | (3aα,4α,7α,7aα)-2-(4-Chloro-3-nitrophenyl)-3a,4,7,7a-tetrahydro-4,7-ethano-1H-isoindole-1,3(2H)-dione. | 2.87 LCMS | 51 |
| 221 | (phenyl with Cl and CF₃) | (3aα,4α,7α,7aα)-2-[4-Chloro-3-(trifluoromethyl)phenyl]-3a,4,7,7a-tetrahydro-4,7-ethano-1H-isoindole-1,3(2H)-dione. | 3.5 LCMS | 51 |
| 222 | (phenyl with OCH₃, Cl, CH₃) | (3aα,4α,7α,7aα)-2-(4-Chloro-2-methoxy-5-methylphenyl)-3a,4,7,7a-tetrahydro-4,7-ethano-1H-isoindole-1,3(2H)-dione. | 2.91 LCMS | 51 |
| 223 | (phenyl with Cl, HO, Cl) | (3aα,4α,7α,7aα)-2-(3,5-Dichloro-4-hydroxyphenyl)-3a,4,7,7a-tetrahydro-4,7-ethano-1H-isoindole-1,3(2H)-dione. | 2.48 LCMS | 51 |

TABLE 2-continued

| Ex. No. | —L—G | Compound Name | Retention Time Min. | Procedure of Example |
|---|---|---|---|---|
| 224 | 2-nitro-4-substituted phenol (O₂N, HO) | (3aα,4α,7α,7aα)-3a,4,7,7a-Tetrahydro-2-(4-hydroxy-3-nitrophenyl)-4,7-ethano-1H-isoindole-1,3(2H)-dione. | 2.2 LCMS | 51 |
| 225 | 2-nitro-4-substituted aniline (O₂N, H₂N) | (3aα,4α,7α,7aα)-2-(4-Amino-3-nitrophenyl)-3a,4,7,7a-tetrahydro-4,7-ethano-1H-isoindole-1,3(2H)-dione. | 1.9 LCMS | 51 |
| 226 | 4-amino-2,3,5,6-tetramethylphenyl (H₃C, CH₃, H₂N, CH₃, CH₃) | (3aα,4α,7α,7aα)-2-(4-Amino-2,3,5,6-tetramethylphenyl)-3a,4,7,7a-tetrahydro-4,7-ethano-1H-isoindole-1,3(2H)-dione. | 1.3 LCMS | 51 |
| 227 | 4-methyl-3-nitrophenyl (O₂N, H₃C) | (3aα,4α,7α,7aα)-3a,4,7,7a-Tetrahydro-2-(4-methyl-3-nitrophenyl)-4,7-ethano-1H-isoindole-1,3(2H)-dione. | 2.65 LCMS | 51 |
| 228 | 3,4,5-trimethoxyphenyl (H₃CO, H₃CO, OCH₃) | (3aα,4α,7α,7aα)-3a,4,7,7a-Tetrahydro-2-(3,4,5-trimethoxyphenyl)-4,7-ethano-1H-isoindole-1,3(2H)-dione. | 2.01 LCMS | 51 |
| 229 | 3,4-dimethoxyphenyl (H₃CO, H₃CO) | (3aα,4α,7α,7aα)-2-(3,4-Dimethoxyphenyl)-3a,4,7,7a-tetrahydro-4,7-ethano-1H-isoindole-1,3(2H)-dione. | 1.83 LCMS | 51 |
| 230 | 3-hydroxy-4-methoxyphenyl (HO, H₃CO) | (3aα,4α,7α,7aα)-3a,4,7,7a-Tetrahydro-2-(3-hydroxy-4-methoxyphenyl)-4,7-ethano-1H-isoindole-1,3(2H)-dione. | 1.54 LCMS | 51 |
| 231 | phthalazinedione (HN, HN, O, O) | (3aα,4α,7α,7aα)-6-(1,3,3a,4,7,7a-Hexahydro-1,3-dioxo-4,7-ethano-2H-isoindol-2-yl)-1,4(2H,3H)-phthalazinedione. | 1.68 LCMS | 51 |
| 232 | 4-methyl-5-nitro-2-pyridinyl (H₃C, O₂N, N) | (3aα,4α,7α,7aα)-3a,4,7,7a-Tetrahydro-2-(4-methyl-5-nitro-2-pyridinyl)-4,7-ethano-1H-isoindole-1,3(2H)-dione. | 1.99 LCMS | 51 |

TABLE 2-continued

| Ex. No. | —L—G | Compound Name | Retention Time Min. | Procedure of Example |
|---|---|---|---|---|
| 233 | | (3aα,4α,7α,7aα)-2-Chloro-4-(1,3,3a,4,7,7a-hexahydro-1,3-dioxo-4,7-ethano-2H-isoindol-2-yl)-α-phenylbenzeneacetonitrile. | 3.44 LCMS | 51 |
| 234 | | (3aα,4α,7α,7aα)-3a,4,7,7a-Tetrahydro-2-(2-methoxy-3-dibenzofuranyl)-4,7-ethano-1H-isoindole-1,3(2H)-dione. | 3.34 LCMS | 51 |
| 235 | | (3aα,4α,7α,7aα)-3a,4,7,7a-Tetrahydro-2-(2,3,4-trifluorophenyl)-4,7-ethano-1H-isoindole-1,3(2H)-dione. | 2.82 LCMS | 51 |
| 236 | | (3aα,4α,7α,7aα)-2-(2,3-Dihydro-2-methyl-1,3-dioxo-1H-isoindol-5-yl)-3a,4,7,7a-tetrahydro-4,7-ethano-1H-isoindole-1,3(2H)-dione. | 2.24 LCMS | 51 |
| 237 | | (3aα,4α,7α,7aα)-2-[2,5-Dichloro-4-(1H-pyrrol-1-yl)phenyl]-3a,4,7,7a-tetrahydro-4,7-ethano-1H-isoindole-1,3(2H)-dione. | 3.61 LCMS | 51 |
| 238 | | (3aα,4α,7α,7aα)-2-[3-[(Diethylamino)methyl]-4-hydroxyphenyl]-3a,4,7,7a-tetrahydro-4,7-ethano-1H-isoindole-1,3(2H)-dione. | 0.8 LCMS | 51 |
| 239 | | (3aα,4α,7α,7aα)-3a,4,7,7a-Tetrahydro-2-[4-(methoxymethyl)-2-oxo-2H-1-benzopyran-7-yl]-4,7-ethano-1H-isoindole-1,3(2H)-dione. | 2.34 LCMS | 51 |

TABLE 2-continued

| Ex. No. | —L—G | Compound Name | Retention Time Min. | Procedure of Example |
|---|---|---|---|---|
| 240 | (benzothiazol-6-yl) | (3aα,4α,7α,7aα)-2-(6-Benzothiazolyl)-3a,4,7,7a-tetrahydro-4,7-ethano-1H-isoindole-1,3(2H)-dione. | 2.04 LCMS | 51 |
| 241 | 4-methoxycarbonyl-3-methoxyphenyl (H3COOC, OCH3) | (3aα,4α,7α,7aα)-4-(1,3,3a,4,7,7a-Hexahydro-1,3-dioxo-4,7-ethano-2H-isoindol-2-yl)-2-methoxybenzoic acid, methyl ester. | 2.32 LCMS | 51 |
| 242 | 4-cyano-3-methylphenyl (NC, H3C) | (3aα,4α,7α,7aα)-5-(1,3,3a,4,7,7a-Hexahydro-1,3-dioxo-4,7-ethano-2H-isoindol-2-yl)-2-methylbenzonitrile. | 2.38 LCMS | 51 |
| 243 | 2-oxo-2H-1-benzopyran-6-yl | (3aα,4α,7α,7aα)-3a,4,7,7a-Tetrahydro-2-(2-oxo-2H-1-benzopyran-6-yl)-4,7-ethano-1H-isoindole-1,3(2H)-dione. | 1.93 LCMS | 51 |
| 244 | 2-methyl-8-quinolinyl | (3aα,4α,7α,7aα)-3a,4,7,7a-Tetrahydro-2-(2-methyl-8-quinolinyl)-4,7-ethano-1H-isoindole-1,3(2H)-dione. | 1.45 LCMS | 51 |
| 245 | 2,3,5,6-tetramethyl-4-nitrophenyl | (3aα,4α,7α,7aα)-3a,4,7,7a-Tetrahydro-2-(2,3,5,6-tetramethyl-4-nitrophenyl)-4,7-ethano-1H-isoindole-1,3(2H)-dione. | 3.16 LCMS | 51 |
| 246 | 2,4,5-trimethylphenyl | (3aα,4α,7α,7aα)-3a,4,7,7a-Tetrahydro-2-(2,4,5-trimethylphenyl)-4,7-ethano-1H-isoindole-1,3(2H)-dione. | 2.92 LCMS | 51 |
| 247 | 4-fluoro-3-methylphenyl | (3aα,4α,7α,7aα)-2-(4-Fluoro-3-methylphenyl)-3a,4,7,7a-tetrahydro-4,7-ethano-1H-isoindole-1,3(2H)-dione. | 2.62 LCMS | 51 |
| 248 | 3-methoxy-4-methylphenyl | (3aα,4α,7α,7aα)-3a,4,7,7a-Tetrahydro-2-(3-methoxy-4-methylphenyl)-4,7-ethano-1H-isoindole-1,3(2H)-dione. | 2.67 LCMS | 51 |

TABLE 2-continued

| Ex. No. | —L—G | Compound Name | Retention Time Min. | Procedure of Example |
|---|---|---|---|---|
| 249 | | (3aα,4α,7α,7aα)-N-Ethyl-5-(1,3,3a,4,7,7a-hexahydro-1,3-dioxo-4,7-ethano-2H-isoindol-2-yl)-2-methyl-N-phenylbenzenesulfonamide. | 3.35 LCMS | 51 |
| 250 | | (3aα,4α,7α,7aα)-2,6-Dibromo-4-(1,3,3a,4,7,7a-hexahydro-1,3-dioxo-4,7-ethano-2H-isoindol-2-yl)benzenesulfonamide. | 3.15 LCMS | 51 |
| 251 | | (3aα,4α,8α,8aα)-2-(2,3-Dimethyl-1H-indol-5-yl)-3a,4,7,7a-tetrahydro-4,7-ethano-1H-isoindole-1,3(2H)-dione. | 2.59 LCMS | 51 |
| 252 | | (3aα,4α,7α,7aα)-2-(3-Dibenzofuranyl)-3a,4,7,7a-tetrahydro-4,7-ethano-1H-isoindole-1,3(2H)-dione. | 3.52 LCMS | 51 |
| 253 | | (3aα,4α,7α,7aα)-3a,4,7,7a-Tetrahydro-2-(2'-hydroxy[1,1':3',1''-terphenyl]-5'-yl)-4,7-ethano-1H-isoindole-1,3(2H)-dione. | 3.51 LCMS | 51 |
| 254 | | (3aα,4α,7α,7aα)-3a,4,7,7a-Tetrahydro-2-(5,6,7,8-tetrahydro-3-hydroxy-2-naphthalenyl)-4,7-ethano-1H-isoindole-1,3(2H)-dione. | 2.86 LCMS | 51 |
| 255 | | (3aα,4α,7α,7aα)-2-(1,3-Dihydro-2,2-dioxidobenzo[c]thiophen-5-yl)hexahydro-4,7-ethano-1H-isoindole-1,3(2H)-dione. | 1.39 LCMS | 51 |

TABLE 2-continued

| Ex. No. | —L—G | Compound Name | Retention Time Min. | Procedure of Example |
|---|---|---|---|---|
| 256 | (structure: 2,5-dimethyl-4-hydroxyphenyl) | (3aα,4α,7α,7aα)-3a,4,7,7a-Tetrahydro-2-(2-hydroxy-4,5-dimethylphenyl)-4,7-ethano-1H-isoindole-1,3(2H)-dione. | 2.3 LCMS | 51 |
| 257 | (structure: 2,2,3,3-tetrafluoro-benzodioxin) | (3aα,4α,7α,7aα)-3a,4,7,7a-Tetrahydro-2-(2,2,3,3-tetrafluoro-2,3-dihydro-1,4-benzodioxin-6-yl)-4,7-ethano-1H-isoindole-1,3(2H)-dione. | 3.63 LCMS | 51 |
| 258 | (structure: 1H-indazol-5-yl) | (3aα,4α,7α,7aα)-3a,4,7,7a-Tetrahydro-2-(1H-indazol-5-yl)-4,7-ethano-1H-isoindole-1,3(2H)-dione. | 1.61 LCMS | 51 |
| 259 | (structure: 4-amino-2,3,5,6-tetrafluorophenyl) | (3aα,4α,7α,7aα)-2-(4-Amino-2,3,5,6-tetrafluorophenyl)-3a,4,7,7a-tetrahydro-4,7-ethano-1H-isoindole-1,3(2H)-dione. | 2.36 LCMS | 51 |
| 260 | (structure: 4-bromo-3-chlorophenyl) | (3aα,4α,7α,7aα)-2-(4-Bromo-3-chlorophenyl)-3a,4,7,7a-tetrahydro-4,7-ethano-1H-isoindole-1,3(2H)-dione. | 3.39 LCMS | 51 |
| 261 | (structure: 5-hydroxy-1-naphthalenyl) | (3aα,4α,7α,7aα)-3a,4,7,7a-Tetrahydro-2-(5-hydroxy-1-naphthalenyl)-4,7-ethano-1H-isoindole-1,3(2H)-dione. | 1.87 LCMS | 51 |
| 262 | (structure: N-acetyl-2-chloro-6-fluoro-4-phenyl) | (3aα,4α,7α,7aα)-N-[2-Chloro-6-fluoro-4-(1,3,3a,4,7,7a-hexahydro-1,3-dioxo-4,7-ethano-2H-isoindol-2-yl)phenyl]acetamide. | 1.39 LCMS | 51 |
| 263 | (structure: 4-cyano-3-trifluoromethylphenyl) | (3aα,4α,7α,7aα)-4-(1,3,3a,4,7,7a-Hexahydro-1,3-dioxo-4,7-ethano-2H-isoindol-2-yl)-2-(trifluoromethyl)benzonitrile. | 3.03 LCMS | 51 |

TABLE 2-continued

| Ex. No. | —L—G | Compound Name | Retention Time Min. | Procedure of Example |
|---|---|---|---|---|
| 264 | | (3aα,4α,7α,7aα)-5-(1,3,3a,4,7,7a-Hexahydro-1,3-dioxo-4,7-ethano-2H-isoindol-2-yl)-2-(4-morpholinyl)benzoic acid, methyl ester. | 2.23 LCMS | 51 |
| 265 | | (3aα,4α,7α,7aα)-2-Fluoro-5-(1,3,3a,4,7,7a-hexahydro-1,3-dioxo-4,7-ethano-2H-isoindol-2-yl)benzonitrile. | 2.23 LCMS | 51 |
| 266 | | (3aα,4α,7α,7aα)-2-(4-Bromophenyl)-3a,4,7,7a-tetrahydro-4,7-ethano-1H-isoindole-1,3(2H)-dione. | 5.96 LC | 33 |
| 267 | | (3aα,4α,7α,7aα)-3a,4,7,7a-Tetrahydro-2-(2-naphthalenyl)-4,7-ethano-1H-isoindole 1,3(2H)-dione. | 7.04 LC | 33 |
| 268 | | (3aα,4α,7α,7aα)-3a,4,7,7a-Tetrahydro-2-[3-(trifluoromethyl)phenyl]-4,7-ethano-1H-isoindole-1,3(2H)-dione. | 3.81 LC | 33 |
| 269 | | (3aα,4α,7α,7aα)-3a,4,7,7a-Tetrahydro-2-(4-nitrophenyl)-4,7-ethano-1H-isoindole-1,3(2H)-dione. | 3.46 LC | 33 |
| 270 | | (3aα,4α,8α,8aα)-2-(9-Ethyl-9H-carbazol-3-yl)-3a,4,7,7a-tetrahydro-4,7-ethano-1H-isoindole-1,3(2H)-dione. | 4.16 LC | 33 |
| 271 | | (3aα,4α,8α,8aα)-2-[1,2-Dihydro-8-methyl-2-oxo-4-(trifluoromethyl)-7-quinolinyl]-3a,4,7,7a-tetrahydro-4,7-ethano-1H-isoindole-1,3(2H)-dione. | 3.60 & 3.97 LC | 33 |

EXAMPLES 272 TO 366

Additional compounds of the formula I were prepared by procedures analogous to those described above. The compounds of Examples 272 to 366 have the following structure:

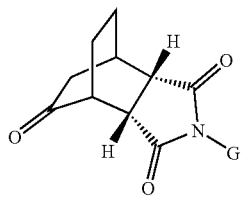

where G, the compound name, retention time, and the procedure employed are set forth in Table 3 (L is a bond for the compounds of Table 3).

The chromatography techniques used to determine the compound retention times of Table 3 are as follows:

LCMS=YMC S5 ODS column, 4.6×50 mm eluting with 10-90% MeOH/$H_2O$ over 4 minutes containing 0.1% TFA; 4 mL/min, monitoring at 220 nm.

LCMS*=YMC S5 ODS column, 4.6×50 mm eluting with 10-90% MeOH/$H_2O$ over 2 minutes containing 0.1% TFA; 4 mL/min, monitoring at 220 nm.

LC=YMC S5 ODS column 4.6×50 mm eluting with 10-90% MeOH/$H_2O$ over 4 minutes containing 0.2% phosphoric acid, 4 mL/min, monitoring at 220 nm.

The molecular mass of the compounds listed in Table 3, where provided, were determined by MS (ES) by the formula m/z.

TABLE 3

| Ex. No. | —L—G | Compound Name | Retention Time Min. | Procedure of Example |
|---|---|---|---|---|
| 272 | 3,5-bis(trifluoromethyl)phenyl | (3aα,4α,7a,7aα)-2-[3,5-Bis(trifluoromethyl)phenyl]-tetrahydro-4,7-ethano-1H-isoindole-1,3,5(2H,4H)-trione. | 3.29 LCMS | 51 |
| 273 | 1,2,3,4-tetrahydronaphthalen-1-yl | (3aα,4α,7α,7aα)-Tetrahydro-2-(1,2,3,4-tetrahydro-1-naphthalenyl)-4,7-ethano-1H-isoindole-1,3,5(2H,4H)-trione. | 2.88 LCMS | 51 |
| 274 | 2,3-dihydro-1H-inden-5-yl | (3aα,4α,7α,7aα)-2-(2,3-Dihydro-1H-inden-5-yl)tetrahydro-4,7-ethano-1H-isoindole-1,3,5(2H,4H)-trione. | 2.63 LCMS | 51 |
| 275 | 4-cyano-1-naphthyl | (3aα,4α,7a,7aα)-4-(Octahydro-1,3,5-trioxo-4,7-ethano-2H-isoindol-2-yl)-1-naphthalenecarbonitrile. | 2.47 LCMS | 51 |
| 276 | 4-chloro-1-naphthyl | (3aα,4a,7α,7aα)-2-(4-Chloro-1-naphthalenyl)-tetrahydro-4,7-ethano-1H-isoindole-1,3,5(2H,4H)-trione. | 3.02 LCMS | 51 |
| 277 | 4-nitro-1-naphthyl | (3aα,4α,7α,7aα)-Tetrahydro-2-(4-nitro-1-naphthalenyl)-4,7-ethano-1H-isoindole-1,3,5(2H,4H)-trione. | 2.64 LCMS | 51 |

TABLE 3-continued

| Ex. No. | —L—G | Compound Name | Retention Time Min. | Procedure of Example |
|---|---|---|---|---|
| 278 | | (3aα,4α,7α,7aα)-Tetrahydro-2-(2-naphthalenyl)-4,7-ethano-1H-isoindole-1,3,5(2H,4H)-trione. | 2.65 LCMS | 51 |
| 279 | | (3aα,4α,7α,7aα)-Tetrahydro-2-(5-quinolinyl)-4,7-ethano-1H-isoindole-1,3,5(2H,4H)-trione. | 1.29 LCMS | 51 |
| 280 | | (3aα,4α,7α,7aα)-Tetrahydro-2-(6-quinolinyl)-4,7-ethano-1H-isoindole-1,3,5(2H,4H)-trione. | 1.12 LCMS | 51 |
| 281 | | (3aα,4α,7α,7aα)-Tetrahydro-2-(4-methyl-2-oxo-2H-1-benzopyran-7-yl)-4,7-ethano-1H-isoindole-1,3,5(2H,4H)-trione. | 2.11 LCMS | 51 |
| 282 | | (3aα,4α,7α,7aα)-Tetrahydro-2-(5-isoquinolinyl)-4,7-ethano-1H-isoindole-1,3,5(2H,4H)-trione. | 1.04 LCMS | 51 |
| 283 | | (3aα,4α,7α,7aα)-2-(3,5-Dinitrophenyl)tetrahydro-4,7-ethano-1H-isoindole-1,3,5(2H,4H)-trione. | 2.37 LCMS | 51 |
| 284 | | (3aα,4α,7α,7aα)-2-(2,5-Dibromophenyl)tetrahydro-4,7-ethano-1H-isoindole-1,3,5(2H,4H)-trione. | 2.58 LCMS | 51 |
| 285 | | (3aα,4α,7α,7aα)-Tetrahydro-2-(2,4,5-trifluorophenyl)-4,7-ethano-1H-isoindole-1,3,5(2H,4H)-trione. | 2.24 LCMS | 51 |

| Ex. No. | —L—G | Compound Name | Retention Time Min. | Procedure of Example |
|---|---|---|---|---|
| 286 | 4-CF₃, 2-Me, 1-F phenyl | (3aα,4α,7α,7aα)-2-[2-Fluoro-5-(trifluoromethyl)phenyl]tetrahydro-4,7-ethano-1H-isoindole-1,3,5(2H,4H)-trione. | 2.62 LCMS | 51 |
| 287 | 4-CH₃, 2-Me, 1-F phenyl | (3aα,4α,7α,7aα)-2-(2-Fluoro-5-methylphenyl)-tetrahydro-4,7-ethano-1H-isoindole-1,3,5(2H,4H)-trione. | 2.18 LCMS | 51 |
| 288 | 2,4,5-trichlorophenyl | (3aα,4α,7α,7aα)-Tetrahydro-2-(2,4,5-trichlorophenyl)-4,7-ethano-1H-isoindole-1,3,5(2H,4H)-trione. | 3.02 LCMS | 51 |
| 289 | 2-Cl, 4-NO₂ phenyl | (3aα,4α,7α,7aα)-2-(2-Chloro-4-nitrophenyl)tetrahydro-4,7-ethano-1H-isoindole-1,3,5(2H,4H)-trione. | 2.42 LCMS | 51 |
| 290 | 2-Cl, 5-CF₃ phenyl | (3aα,4α,7α,7aα)-2-[2-Chloro-5-(trifluoromethyl)-phenyl]tetrahydro-4,7-ethano-1H-isoindole-1,3,5(2H,4H)-trione. | 2.67 LCMS | 51 |
| 291 | 3-fluorophenyl | (3aα,4α,7α,7aα)-2-(3-Fluorophenyl)tetrahydro-4,7-ethano-1H-isoindole-1,3,5(2H,4H)-trione. | 2.02 LCMS | 51 |
| 292 | 3,4-difluorophenyl | (3aα,4α,7α,7aα)-2-(3,4-Difluorophenyl)tetrahydro-4,7-ethano-1H-isoindole-1,3,5(2H,4H)-trione. | 2.26 LCMS | 51 |
| 293 | 3,5-difluorophenyl | (3aα,4α,7α,7aα)-2-(3,5-Difluorophenyl)tetrahydro-4,7-ethano-1H-isoindole-1,3,5(2H,4H)-trione. | 2.30 LCMS | 51 |

TABLE 3-continued

| Ex. No. | —L—G | Compound Name | Retention Time Min. | Procedure of Example |
|---|---|---|---|---|
| 294 | 3-Cl-phenyl | (3aα,4α,7α,7aα)-2-(3-Chlorophenyl)tetrahydro-4,7-ethano-1H-isoindole-1,3,5(2H,4H)-trione. | 2.38 LCMS | 51 |
| 295 | 3-Cl-4-F-phenyl | (3aα,4α,7α,7aα)-2-(3-Chloro-4-fluorophenyl)tetrahydro-4,7-ethano-1H-isoindole-1,3,5(2H,4H)-trione. | 2.56 LCMS | 51 |
| 296 | 3,4-diCl-phenyl | (3aα,4α,7α,7aα)-2-(3,4-Dichlorophenyl)tetrahydro-4,7-ethano-1H-isoindole-1,3,5(2H,4H)-trone. | 2.89 LCMS | 51 |
| 297 | 3,4,5-triCl-phenyl | (3aα,4α,7α,7aα)-Tetrahydro-2-(3,4,5-trichlorophenyl)-4,7-ethano-1H-isoindole-1,3,5(2H,4H)-trione. | 3.37 LCMS | 51 |
| 298 | 3-Cl-4-Me-phenyl | (3aα,4α,7α,7aα)-2-(3-Chloro-4-methylphenyl)tetrahydro-4,7-ethano-1H-isoindole-1,3,5(2H,4H)-trione. | 2.72 LCMS | 51 |
| 299 | 3-I-phenyl | (3aα,4α,7α,7aα)-Tetrahydro-2-(3-iodophenyl)-4,7-ethano-1H-isoindole-1,3,5(2H,4H)-trione. | 2.58 LCMS | 51 |
| 300 | 3-NO₂-phenyl | (3aα,4α,7α,7aα)-Tetrahydro-2-(3-nitrophenyl)-4,7-ethano-1H-isoindole-1,3,5(2H,4H)-trione. | 2.06 LCMS | 51 |
| 301 | 3-acetylphenyl | (3aα,4α,7α,7aα)-2-(3-Acetylphenyl)tetrahydro-4,7-ethano-1H-isoindole-1,3,5(2H,4H)-trione. | 1.86 LCMS | 51 |
| 302 | 3-CF₃-phenyl | (3aα,4α,7α,7aα)-Tetrahydro-2-[3-(trifluoromethyl)phenyl]-4,7-ethano-1H-isoindole-1,3,5(2H,4H)-trione. | 2.62 LCMS | 51 |

TABLE 3-continued

| Ex. No. | —L—G | Compound Name | Retention Time Min. | Procedure of Example |
|---|---|---|---|---|
| 303 | 2,4-dimethylphenyl group | (3aα,4α,7α,7aα)-2-(3,4-Dimethylphenyl)tetrahydro-4,7-ethano-1H-isoindole-1,3,5(2H,4H)-trione. | 2.46 LCMS | 51 |
| 304 | 3,5-dimethylphenyl group | (3aα,4α,7α,7aα)-2-(3,5-Dimethylphenyl)tetrahydro-4,7-ethano-1H-isoindole-1,3,5(2H,4H)-trione. | 2.49 LCMS | 51 |
| 305 | 3-ethylphenyl group | (3aα,4α,7α,7aα)-2-(3-Ethylphenyl)tetrahydro-4,7-ethano-1H-isoindole-1,3,5(2H,4H)-trione. | 2.50 LCMS | 51 |
| 306 | 4-bromophenyl group | (3aα,4α,7α,7aα)-2-(4-Bromophenyl)tetrahydro-4,7-ethano-1H-isoindole-1,3,5(2H,4H)-trione. | 2.53 LCMS | 51 |
| 307 | 4-fluoro-3-nitrophenyl group | (3aα,4α,7α,7aα)-2-(4-Fluoro-3-nitrophenyl)-tetrahydro-4,7-ethano-1H-isoindole-1,3,5(2H,4H)-trione. | 2.16 LCMS | 51 |
| 308 | 4-fluoro-3-trifluoromethylphenyl group | (3aα,4α,7α,7aα)-2-[4-Fluoro-3-(trifluoro-methyl)phenyl]tetrahydro-4,7-ethano-1H-isoindole-1,3,5(2H,4H)-trione. | 2.80 LCMS | 51 |
| 309 | 4-chloro-3-nitrophenyl group | (3aα,4α,7α,7aα)-2-(4-Chloro-3-nitrophenyl)-tetrahydro-4,7-ethano-1H-isoindole-1,3,5(2H,4H)-trione. | 2.55 LCMS | 51 |
| 310 | 4-iodophenyl group | (3aα,4α,7α,7aα)-Tetrahydro-2-(4-iodophenyl)-4,7-ethano-1H-isoindole-1,3,5(2H,4H)-trione. | 2.67 LCMS | 51 |
| 311 | 4-nitrophenyl group | (3aα,4α,7α,7aα)-Tetrahydro-2-(4-nitrophenyl)-4,7-ethano-1H-isoindole-1,3,5(2H,4H)-trione. | 2.12 LCMS | 51 |
| 312 | 4-isopropylphenyl group | (3aα,4α,7α,7aα)-Tetrahydro-2-[4-(1-methylethyl)phenyl]-4,7-ethano-1H-isoindole-1,3,5(2H,4H)-trione. | 2.86 LCMS | 51 |

TABLE 3-continued

| Ex. No. | —L—G | Compound Name | Retention Time Min. | Procedure of Example |
|---|---|---|---|---|
| 313 | | (3aα,4α,7α,7aα)-Tetrahydro-2-(4-methyl-3-nitrophenyl)-4,7-ethano-1H-isoindole-1,3,5(2H,4H)-trione. | 2.34 LCMS | 51 |
| 314 | | (3aα,4α,7α,7aα)-4-(Octahydro-1,3,5-trioxo-4,7-ethano-2H-isoindol-2-yl)benzeneacetonitrile. | 1.68 LCMS | 51 |
| 315 | | (3aα,4α,7α,7aα)-2-(4-Ethylphenyl)tetrahydro-4,7-ethano-1H-isoindole-1,3,5(2H,4H)-trione. | 2.55 LCMS | 51 |
| 316 | | (3aα,4α,7α,7aα)-2-[4-[2-(Acetyloxy)ethyl]phenyl]tetrahydro-4,7-ethano-1H-isoindole-1,3,5(2H,4H)-trione. | 2.25 LCMS | 51 |
| 317 | | (3aα,4α,7α,7aα)-Tetrahydro-2-(4-propylphenyl)-4,7-ethano-1H-isoindole-1,3,5(2H,4H)-trione. | 2.91 LCMS | 51 |
| 318 | | (3aα,4α,7α,7aα)-Tetrahydro-2-(2,3,4-trifluorophenyl)-4,7-ethano-1H-isoindole-1,3,5(2H,4H)-trione. | 2.41 LCMS | 51 |
| 319 | | (3aα,4α,7α,7aα)-2-(4-Bromo-2,6-difluorophenyl)tetrahydro-4,7-ethano-1H-isoindole-1,3,5(2H,4H)-trione. | 2.64 LCMS | 51 |
| 320 | | (3aα,4α,7α,7aα)-Tetrahydro-2-[4-nitro-3-(trifluoromethyl)phenyl]-4,7-ethano-1H-isoindole-1,3,5(2H,4H)-trione. | 2.81 LCMS | 51 |
| 321 | | (3aα,4α,7α,7aα)-2-(6-Benzothiazolyl)tetrahydro-4,7-ethano-1H-isoindole-1,3,5(2H,4H)-trione. | 1.87 LCMS | 51 |

TABLE 3-continued

| Ex. No. | —L—G | Compound Name | Retention Time Min. | Procedure of Example |
|---|---|---|---|---|
| 322 | | (3aα,4α,7α,7aα)-Tetrahydro-2-(2-methyl-8-quinolinyl)-4,7-ethano-1H-isoindole-1,3,5(2H,4H)-trione. | 2.01 LCMS | 51 |
| 323 | | (3aα,4α,7α,7aα)-2-(4-Fluoro-3-methylphenyl)-tetrahydro-4,7-ethano-1H-isoindole-1,3,5(2H,4H)-trione. | 2.37 LCMS | 51 |
| 324 | | (3aα,4α,7α,7aα)-2-(1,3-Dihydro-3-oxo-5-isobenzo-furanyl)tetrahydro-4,7-ethano-1H-isoindole-1,3,5(2H,4H)-trione. | 1.57 LCMS | 51 |
| 325 | | (3aα,4α,7α,7aα)-N-[2-Nitro-4-(octahydro-1,3,5-trioxo-4,7-ethano-2H-isoindol-2-yl)phenyl]acetamide. | 1.87 LCMS | 51 |
| 326 | | (3aα,4α,7α,7aα)-2-(2-Ethyl-5-nitrophenyl)-tetrahydro-4,7-ethano-1H-isoindole-1,3,5(2H,4H)-trione. | 2.47 LCMS | 51 |
| 327 | | (3aα,4α,7α,7aα)-Tetrahydro-2-(2-methyl-5-benzofuranyl)-4,7-ethano-1H-isoindole-1,3,5(2H,4H)-trione. | 2.50 LCMS | 51 |
| 328 | | (3aα,4α,7α,7aα)-Tetrahydro-2-(1H-indazol-5-yl)-4,7-ethano-1H-isoindole-1,3,5(2H,4H)-trione. | 1.58 LCMS | 51 |
| 329 | | (3aα,4α,7α,7aα)-2-(4-Bromo-3-chlorophenyl)-tetrahydro-4,7-ethano-1H-isoindole-1,3,5(2H,4H)-trione. | 2.95 LCMS | 51 |
| 330 | | (3aα,4α,7α,7aα)-Tetrahydro-2-[3-(trifluoro-methoxy)phenyl]-4,7-ethano-1H-isoindole-1,3,5(2H,4H)-trione. | 4.36 LCMS | 51 |

TABLE 3-continued

| Ex. No. | —L—G | Compound Name | Retention Time Min. | Procedure of Example |
|---|---|---|---|---|
| 331 | | (3aα,4α,7α,7aα)-4-(Octahydro-1,3,5-trioxo-4,7-ethano-2H-isoindol-2-yl)-2-(trifluoromethyl)-benzonitrile. | 2.60 LCMS | 51 |
| 332 | | (3aα,4α,7α,7aα)-Tetrahydro-2-[2-(methyl-sulfonyl)-4-nitrophenyl]-4,7-ethano-1H-isoindole 1,3,5(2H,4H)-trione. | 1.64 LCMS | 51 |
| 333 | | (3aα,4α,7α,7aα)-2-(3,5-Dibromophenyl)tetrahydro-4,7-ethano-1H-isoindole-1,3,5(2H,4H)-trione. | 3.12 LCMS | 51 |
| 334 | | (3aα,4α,7α,7aα)-Tetrahydro-2-(3-iodo-4-methylphenyl)-4,7-ethano-1H-isoindole-1,3,5(2H,4H)-trione. | 2.86 LCMS | 51 |
| 335 | | (3aα,4α,7α,7aα)-2-(3-Chloro-4-iodophenyl)-tetrahydro-4,7-ethano-1H-isoindole-1,3,5(2H,4H)-trione. | 2.99 LCMS | 51 |
| 336 | | (3aα,4α,7α,7aα)-Tetrahydro-2-(2-methyl-6-quinolinyl)-4,7-ethano-1H-isoindole-1,3,5(2H,4H)-trione. | 1.10 LCMS | 51 |
| 337 | | (3aα,4α,7α,7aα)-Tetrahydro-2-[2-(methylthio)-5-(trifluoromethyl)phenyl]-4,7-ethano-1H-isoindole-1,3,5(2H,4H)-trione. | 2.58 LCMS | 51 |
| 338 | | (3aα,4α,7α,7aα)-2-(4-Bromo-2,6-diethylphenyl)-tetrahydro-4,7-ethano-1H-isoindole-1,3,5(2H,4H)-trione. | 3.35 LCMS | 51 |

TABLE 3-continued

| Ex. No. | —L—G | Compound Name | Retention Time Min. | Procedure of Example |
|---|---|---|---|---|
| 339 | | (3aα,4α,7α,7aα)-Tetrahydro-2-[4-(trifluoromethyl)phenyl]-4,7-ethano-1H-isoindole-1,3,5(2H,4H)-trione. | 2.71 LCMS | 51 |
| 340 | | (3aα,4α,7α,7aα)-2-(4-Chloro-3-methylphenyl)-tetrahydro-4,7-ethano-1H-isoindole-1,3,5(2H,4H)-trione. | 2.70 LCMS | 51 |
| 341 | | (3aα,4α,7α,7aα)-Tetrahydro-2-[4-(methoxymethyl)-2-oxo-2H-1-benzopyran-7-yl]-4,7-ethano-1H-isoindole-1,3,5(2H,4H)-trione. | 2.16 LCMS | 51 |
| 342 | | (3aα,4α,7α,7aα)-N-Methyl-3-(octahydro-1,3,5-trioxo-4,7-ethano-2H-isoindol-2-yl)benzamide. | 1.54 LCMS | 51 |
| 343 | | (3aα,4α,7α,7aα)-2-(6-Acetyl-1,3-benzodioxol-5-yl)tetrahydro-4,7-ethano-1H-isoindole-1,3,5(2H,4H)-trione. | 1.90 LCMS | 51 |
| 344 | | (3aα,4α,7α,7aα)-Tetrahydro-2-(3,4,5-trifluorophenyl)-4,7-ethano-1H-isoindole-1,3,5(2H,4H)-trione. | 2.59 LCMS | 51 |
| 345 | | (3aα,4α,7α,7aα)-2-Bromo-5-(octahydro-1,3,5-trioxo-4,7-ethano-2H-isoindol-2-yl)benzoic acid, methyl ester. | 2.51 LCMS | 51 |
| 346 | | (3aα,4α,7α,7aα)-2-(3-Chloro-4-nitrophenyl)-tetrahydro-4,7-ethano-1H-isoindole-1,3,5(2H,4H)-trione. | 2.55 LCMS | 51 |

TABLE 3-continued

| Ex. No. | —L—G | Compound Name | Retention Time Min. | Procedure of Example |
|---|---|---|---|---|
| 347 | (difluoromethylsulfonyl-methoxyphenyl with methyl group) | (3aα,4α,7α,7aα)-2-[5-[(Difluoromethyl)sulfonyl]-2-methoxyphenyl]tetrahydro-4,7-ethano-1H-isoindole-1,3,5(2H,4H)-trione. | 2.02 LCMS | 51 |
| 348 | (1-naphthalenyl) | (3aα,4α,7α,7aα)-Tetrahydro-2-(1-naphthalenyl)-4,7-ethano-1H-isoindole-1,3,5(2H,4H)-trione. | 2.45 LCMS | 51 |
| 349 | (4-bromo-1-naphthalenyl) | (3aα,4α,7α,7aα)-2-(4-Bromo-1-naphthalenyl)-tetrahydro-4,7-ethano-1H-isoindole-1,3,5(2H,4H)-trione. | 3.07 LCMS | 13C |
| 350 | (3,5-dichlorophenyl) | (3aα,4α,7α,7aα)-2-(3,5-Dichlorophenyl)tetrahydro-4,7-ethano-1H-isoindole-1,3,5(2H,4H)-trione. | 2.97 LCMS | 13C |
| 351 | (4-bromo-3-trifluoromethylphenyl) | (3aα,4α,7α,7aα)-2-[4-Bromo-3-(trifluoromethyl)-phenyl]tetrahydro-4,7-ethano-1H-isoindole-1,3,5(2H,4H)-trione. | 3.10 LCMS | 13C |
| 352 | (4-bromo-3-methylphenyl) | (3aα,4α,7α,7aα)-2-(4-Bromo-3-methylphenyl)-tetrahydro-4,7-ethano-1H-isoindole-1,3,5(2H,4H)-trione. | 2.85 LCMS | 13C |
| 353 | (4-bromo-1-naphthalenyl) | (3aα,4α,7α,7aα)-2-(4-Bromo-1-naphthalenyl)-tetrahydro-4,7-ethano-1H-isoindole-1,3,5(2H,4H)-trione. | 3.62 LC | 13C |
| 354 | (1-naphthalenyl) | (3aα,4α,7α,7aα)-Tetrahydro-2-(1-naphthalenyl)-4,7-ethano-1H-isoindole-1,3,5(2H,4H)-trione. | 2.97 LC | 13C |
| 355 | (2-methyl-3-trifluoromethylphenyl) | (3aα,4α,7α,7aα)-Tetrahydro-2-[2-methyl-3-(trifluoromethyl)phenyl]-4,7-ethano-1H-isoindole-1,3,5(2H,4H)-trione. | 3.35 LC | 13C |

TABLE 3-continued

| Ex. No. | —L—G | Compound Name | Retention Time Min. | Procedure of Example |
|---|---|---|---|---|
| 356 | | (3aα,4α,7α,7aα)-2-(2,2-Difluoro-1,3-benzodioxol-5-yl)tetrahydro-4,7-ethano-1H-isoindole-1,3,5(2H,4H)-trione. | 3.20 LC | 13C |
| 357 | | (3aα,4α,7α,7aα)-2-[4-(4-Chlorophenoxy)-2-(trifluoromethyl)phenyl]-tetrahydro-4,7-ethano-1H-isoindole-1,3,5(2H,4H)-trione. | 3.97 LC | 13C |
| 358 | | (3aα,4α,7α,7aα)-2-Fluoro-5-(octahydro-1,3,5-trioxo-4,7-ethano-2H-isoindol-2-yl)benzonitrile. | 2.55 LC | 13C |
| 359 | | (3aα,4α,7α,7aα)-2-Chloro-4-(octahydro-1,3,5-trioxo-4,7-ethano-2H-isoindol-2-yl)benzonitrile. | 2.81 LC | 13C |
| 360 | | (3aα,4α,7α,7aα)-N-[4-(Octahydro-1,3,5-trioxo-4,7-ethano-2H-isoindol-2-yl)-2-(trifluoromethyl)-phenyl]acetamide. | 3.68 LC | 13C |
| 361 | | (3aα,4α,7α,7aα)-2-[4-(1,1-Dimethylethyl)-3-nitrophenyl]tetrahydro-4,7-ethano-1H-isoindole-1,3,5(2H,4H)-trione | 3.12 LC | 13C |
| 362 | | (3aα,4α,7α,7aα)-Tetrahydro-2-(3-methyl-4-nitrophenyl)-4,7-ethano-1H-isoindole-1,3,5(2H,4H)-trione. | 2.40 LC | 13C |
| 363 | | (3aα,4α,7α,7aα)-Tetrahydro-2-[3-(1-methylethyl)phenyl]-4,7-ethano-1H-isoindole-1,3,5(2H,4H)-trione. | 2.78 LC | 13C |

TABLE 3-continued

| Ex. No. | —L—G | Compound Name | Retention Time Min. | Procedure of Example |
|---|---|---|---|---|
| 364 | | (3aα,4α,7α,7aα)-N-(1,1-Dimethylethyl)-5-(octahydro-1,3,5-trioxo-4,7-ethano-2H-isoindol-2-yl)-1-naphthalenesulfonamide. | 2.57 & 2.72 LC | 13C |
| 365 | | (3aα,4α,7α,7aα)-2-[3-(1,1-Dimethylethyl)-phenyl]tetrahydro-4,7-ethano-1H-isoindole-1,3,5(2H,4H)-trione. | 2.99 LC | 13C |
| 366 | | (3aα,4α,7α,7aα)-N-Butyl-3-(octahydro-1,3,5-trioxo-4,7-ethano-2H-isoindol-2-yl)benzenesulfonamide. | 2.52 LC | 13C |

EXAMPLES 367 TO 460

Additional compounds of the formula I were prepared by procedures analogous to those described above. The compounds of Examples 367 to 460 have the following structure:

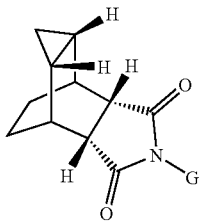

where G, the compound name, retention time, and the procedure employed are set forth in Table 4 (L is a bond for the compounds of Table 4).

The chromatography techniques used to determine the compound retention times of Table 4 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

LCMS*=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 4, where provided, were determined by MS (ES) by the formula m/z.

TABLE 4

| Ex. No. | —L—G | Compound Name | Retention Time Min. | Procedure of Example |
|---|---|---|---|---|
| 367 | | (3aα,4β,4aα,5aα,6β,6aα)-2-(3,4-Dichlorophenyl)-4,4a,5,5a,6,6a-hexahydro-4,6-ethanocycloprop[f]isoindole-1,3(2H,3aH)-dione. | 3.69 LCMS | 51 |

TABLE 4-continued

| Ex. No. | —L—G | Compound Name | Retention Time Min. | Procedure of Example |
|---|---|---|---|---|
| 368 | 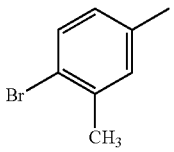 | (3aα,4β,4aα,5aα,6β,6aα)-2-(4-Bromo-3-methylphenyl)-4,4a,5,5a,6,6a-hexahydro-4,6-ethanocycloprop[f]isoindole-1,3(2H,3aH)-dione. | 3.64 LCMS | 51 |
| 369 | 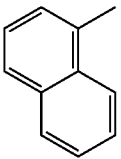 | (3aα,4β,4aα,5aα,6β,6aα)-4,4a,5,5a,6,6a-Hexahydro-2-(1-naphthalenyl)-4,6-ethanocycloprop[f]isoindole-1,3(2H,3aH)-dione. | 3.22 LCMS | 51 |
| 370 | 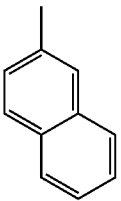 | (3aα,4β,4aα,5aα,6β,6aα)-4,4a,5,5a,6,6a-Hexahydro-2-(2-naphthalenyl)-4,6-ethanocycloprop[f]isoindole-1,3(2H,3aH)-dione. | 3.46 LCMS | 51 |
| 371 | 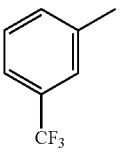 | (3aα,4β,4aα,5aα,6β,6aα)-4,4a,5,5a,6,6a-Hexahydro-2-[3-(trifluoromethyl)phenyl]-4,6-ethanocycloprop[f]isoindole-1,3(2H,3aH)-dione. | 3.45 LCMS | 51 |
| 372 | 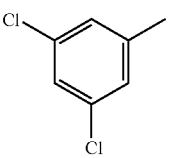 | (3aα,4β,4aα,5aα,6β,6aα)-2-(3,5-Dichlorophenyl)-4,4a,5,5a,6,6a-hexahydro-4,6-ethanocycloprop[f]isoindole-1,3(2H,3aH)-dione. | 3.56 LCMS | 51 |
| 373 | 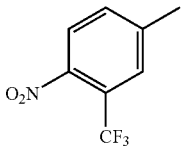 | (3aα,4β,4aα,5aα,6β,6aα)-4,4a,5,5a,6,6a-Hexahydro-2-[4-nitro-3-(trifluoromethyl)phenyl]-4,6-ethanocycloprop[f]isoindole-1,3(2H,3aH)-dione. | 3.55 LCMS | 51 |
| 374 | 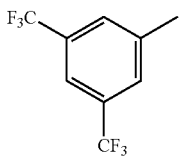 | (3aα,4β,4aα,5aα,6β,6aα)-2-[3,5-Bis(trifluoromethyl)phenyl]-4,4a,5,5a,6,6a-hexahydro-4,6-ethanocycloprop[f]isoindole-1,3(2H,3aH)-dione. | 3.93 LCMS | 51 |
| 375 | 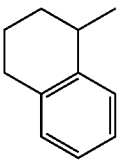 | (3aα,4β,4aα,5aα,6β,6aα)-4,4a,5,5a,6,6a-Hexahydro-2-(1,2,3,4-tetrahydro-1-naphthalenyl)-4,6-ethanocycloprop[f]isoindole-1,3(2H,3aH)-dione. | 3.67 LCMS | 51 |
| 376 | 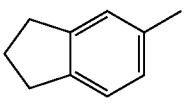 | (3aα,4β,4aα,5aα,6β,6aα)-2-(2,3-Dihydro-1H-inden-5-yl)-4,4a,5,5a,6,6a-hexahydro-4,6-ethanocycloprop[f]isoindole-1,3(2H,3aH)-dione. | 3.48 LCMS | 51 |

TABLE 4-continued

| Ex. No. | —L—G | Compound Name | Retention Time Min. | Procedure of Example |
|---|---|---|---|---|
| 377 | | (3aα,4β,4aα,5aα,6β,6aα)-4-(Octahydro-1,3-dioxo-4,6-ethanocycloprop[f]isoindole-2(1H)-yl)-1-naphthalenecarbonitrile. | 3.15 LCMS | 51 |
| 378 | | (3aα,4β,4aα,5aα,6β,6aα)-2-(4-Bromo-1-naphthalenyl)-4,4a,5,5a,6,6a-hexahydro-4,6-ethanocycloprop[f]isoindole-1,3(2H,3aH)-dione. | 3.65 LCMS | 51 |
| 379 | | (3aα,4β,4aα,5aα,6β,6aα)-2-(4-Chloro-1-naphthalenyl)-4,4a,5,5a,6,6a-hexahydro-4,6-ethanocycloprop[f]isoindole-1,3(2H,3aH)-dione. | 3.62 LCMS | 51 |
| 380 | | (3aα,4β,4aα,5aα,6β,6aα)-4,4a,5,5a,6,6a-Hexahydro-2-(5-quinolinyl)-4,6-ethanocycloprop[f]isoindole-1,3(2H,3aH)-dione. | 2.25 LCMS | 51 |
| 381 | | (3aα,4β,4aα,5aα,6β,6aα)-4,4a,5,5a,6,6a-Hexahydro-2-(6-quinolinyl)-4,6-ethanocycloprop[f]isoindole-1,3(2H,3aH)-dione. | 2.14 LCMS | 51 |
| 382 | | (3aα,4β,4aα,5aα,6β,6aα)-4,4a,5,5a,6,6a-Hexahydro-2-(4-methyl-2-oxo-2H-1-benzopyran-7-yl)-4,6-ethanocycloprop[f]isoindole-1,3(2H,3aH)-dione. | 2.97 LCMS | 51 |
| 383 | | (3aα,4β,4aα,5aα,6β,6aα)-4,4a,5,5a,6,6a-Hexahydro-2-(5-isoquinolinyl)-4,6-ethanocycloprop[f]isoindole-1,3(2H,3aH)-dione. | 1.94 LCMS | 51 |
| 384 | | (3aα,4β,4aα,5aα,6β,6aα)-2-(3,5-Dinitrophenyl)-4,4a,5,5a,6,6a-hexahydro-4,6-ethanocycloprop[f]isoindole-1,3(2H,3aH)-dione. | 3.38 LCMS | 51 |

TABLE 4-continued

| Ex. No. | —L—G | Compound Name | Retention Time Min. | Procedure of Example |
|---|---|---|---|---|
| 385 | 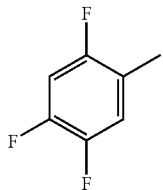 | (3aα,4β,4aα,5aα,6β,6aα)-4,4a,5,5a,6,6a-Hexahydro-2-(2,4,5-trifluorophenyl)-4,6-ethanocycloprop[f]isoindole-1,3(2H,3aH)-dione. | 3.26 LCMS | 51 |
| 386 | 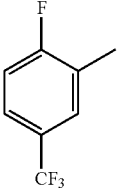 | (3aα,4β,4aα,5aα,6β,6aα)-2-[2-Fluoro-5-(trifluoromethyl)phenyl]-4,4a,5,5a,6,6a-hexahydro-4,6-ethanocycloprop[f]isoindole-1,3(2H,3aH)-dione. | 3.49 LCMS | 51 |
| 387 | 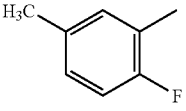 | (3aα,4β,4aα,5aα,6β,6aα)-2-(2-Fluoro-5-methylphenyl)-4,4a,5,5a,6,6a-hexahydro-4,6-ethanocycloprop[f]isoindole-1,3(2H,3aH)-dione. | 3.19 LCMS | 51 |
| 388 | 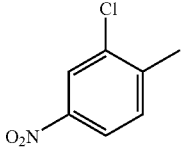 | (3aα,4β,4aα,5aα,6β,6aα)-2-(2-Chloro-4-nitrophenyl)-4,4a,5,5a,6,6a-hexahydro-4,6-ethanocycloprop[f]isoindole-1,3(2H,3aH)-dione. | 2.40 LCMS | 51 |
| 389 | 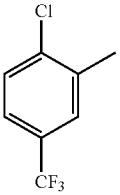 | (3aα,4β,4aα,5aα,6β,6aα)-2-[2-Chloro-5-(trifluoromethyl)phenyl]-4,4a,5,5a,6,6a-hexahydro-4,6-ethanocycloprop[f]isoindole-1,3(2H,3aH)-dione. | 3.48 LCMS | 51 |
| 390 | 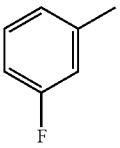 | (3aα,4β,4aα,5aα,6β,6aα)-2-(3-Fluorophenyl)-4,4a,5,5a,6,6a-hexahydro-4,6-ethanocycloprop[f]isoindole-1,3(2H,3aH)-dione. | 3.06 LCMS | 51 |
| 391 | 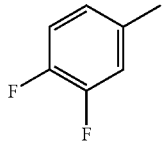 | (3aα,4β,4aα,5aα,6β,6aα)-2-(3,4-Difluorophenyl)-4,4a,5,5a,6,6a-hexahydro-4,6-ethanocycloprop[f]isoindole-1,3(2H,3aH)-dione. | 3.21 LCMS | 51 |
| 392 | 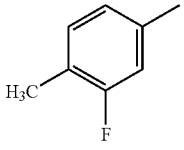 | (3aα,4β,4aα,5aα,6β,6aα)-2-(3-Fluoro-4-methylphenyl)-4,4a,5,5a,6,6a-hexahydro-4,6-ethanocycloprop[f]isoindole-1,3(2H,3aH)-dione. | 3.34 LCMS | 51 |

TABLE 4-continued

| Ex. No. | —L—G | Compound Name | Retention Time Min. | Procedure of Example |
|---|---|---|---|---|
| 393 | 3,5-difluorophenyl | (3aα,4β,4aα,5aα,6β,6aα)-2-(3,5-Difluorophenyl)-4,4a,5,5a,6,6a-hexahydro-4,6-ethanocycloprop[f]isoindole-1,3(2H,3aH)-dione. | 3.30 LCMS | 51 |
| 394 | 3-chlorophenyl | (3aα,4β,4aα,5aα,6β,6aα)-2-(3-Chlorophenyl)-4,4a,5,5a,6,6a-hexahydro-4,6-ethanocycloprop[f]isoindole-1,3(2H,3aH)-dione. | 3.32 LCMS | 51 |
| 395 | 3-chloro-4-fluorophenyl | (3aα,4β,4aα,5aα,6β,6aα)-2-(3-Chloro-4-fluorophenyl)-4,4a,5,5a,6,6a-hexahydro-4,6-ethanocycloprop[f]isoindole-1,3(2H,3aH)-dione. | 3.43 LCMS | 51 |
| 396 | 3,4,5-trichlorophenyl | (3aα,4β,4aα,5aα,6β,6aα)-4,4a,5,5a,6,6a-Hexahydro-2-(3,4,5-trichlorophenyl)-4,6-ethanocycloprop[f]isoindole-1,3(2H,3aH)-dione. | 4.07 LCMS | 51 |
| 397 | 3-chloro-4-methylphenyl | (3aα,4β,4aα,5aα,6β,6aα)-2-(3-Chloro-4-methylphenyl)-4,4a,5,5a,6,6a-hexahydro-4,6-ethanocycloprop[f]isoindole-1,3(2H,3aH)-dione. | 3.78 LCMS | 51 |
| 398 | 3-iodophenyl | (3aα,4β,4aα,5aα,6β,6aα)-4,4a,5,5a,6,6a-Hexahydro-2-(3-iodophenyl)-4,6-ethanocycloprop[f]isoindole-1,3(2H,3aH)-dione. | 3.47 LCMS | 51 |
| 399 | 3-nitrophenyl | (3aα,4β,4aα,5aα,6β,6aα)-4,4a,5,5a,6,6a-Hexahydro-2-(3-nitrophenyl)-4,6-ethanocycloprop[f]isoindole-1,3(2H,3aH)-dione. | 3.0 LCMS | 51 |
| 400 | 3-acetylphenyl | (3aα,4β,4aα,5aα,6β,6aα)-2-(3-Acetylphenyl)-4,4a,5,5a,6,6a-hexahydro-4,6-ethanocycloprop[f]isoindole-1,3(2H,3aH)-dione. | 2.81 LCMS | 51 |
| 401 | 3,4-dimethylphenyl | (3aα,4β,4aα,5aα,6β,6aα)-2-(3,4-Dimethylphenyl)-4,4a,5,5a,6,6a-hexahydro-4,6-ethanocycloprop[f]isoindole-1,3(2H,3aH)-dione. | 3.36 LCMS | 51 |

TABLE 4-continued

| Ex. No. | —L—G | Compound Name | Retention Time Min. | Procedure of Example |
|---|---|---|---|---|
| 402 | 3,5-dimethylphenyl | (3aα,4β,4aα,5aα,6β,6aα)-2-(3,5-Dimethylphenyl)-4,4a,5,5a,6,6a-hexahydro-4,6-ethanocycloprop[f]isoindole-1,3(2H,3aH)-dione. | 3.38 LCMS | 51 |
| 403 | 3-(hydroxymethyl)phenyl | (3aα,4β,4aα,5aα,6β,6aα)-4,4a,5,5a,6,6a-Hexahydro-2-[3-(hydroxymethyl)phenyl]-4,6-ethanocycloprop[f]isoindole-1,3(2H,3aH)-dione. | 2.97 LCMS | 51 |
| 404 | 3-ethylphenyl | (3aα,4β,4aα,5aα,6β,6aα)-2-(3-Ethylphenyl)-4,4a,5,5a,6,6a-Hexahydro-4,6-ethanocycloprop[f]isoindole-1,3(2H,3aH)-dione. | 3.38 LCMS | 51 |
| 405 | 4-cyanophenyl | (3aα,4β,4aα,5aα,6β,6aα)-4-(Octahydro-1,3-dioxo-4,6-ethanocycloprop[f]isoindol-2(1H)-yl)benzonitrile. | 2.89 LCMS | 51 |
| 406 | 4-bromophenyl | (3aα,4β,4aα,5aα,6β,6aα)-2-(4-Bromophenyl)-4,4a,5,5a,6,6a-hexahydro-4,6-ethanocycloprop[f]isoindole-1,3(2H,3aH)-dione. | 3.43 LCMS | 51 |
| 407 | 4-bromo-3-(trifluoromethyl)phenyl | (3aα,4β,4aα,5aα,6β,6aα)-2-[4-Bromo-3-(trifluoromethyl)phenyl]-4,4a,5,5a,6,6a-hexahydro-4,6-ethanocycloprop[f]isoindole-1,3(2H,3aH)-dione. | 3.80 LCMS | 51 |
| 408 | 4-fluoro-3-nitrophenyl | (3aα,4β,4aα,5aα,6β,6aα)-2-(4-Fluoro-3-nitrophenyl)-4,4a,5,5a,6,6a-hexahydro-4,6-ethanocycloprop[f]isoindole-1,3(2H,3aH)-dione. | 3.14 LCMS | 51 |
| 409 | 4-fluoro-3-(trifluoromethyl)phenyl | (3aα,4β,4aα,5aα,6β,6aα)-2-[4-Fluoro-3-(trifluoromethyl)phenyl]-4,4a,5,5a,6,6a-hexahydro-4,6-ethanocycloprop[f]isoindole-1,3(2H,3aH)-dione. | 3.55 LCMS | 51 |
| 410 | 4-chloro-3-nitrophenyl | (3aα,4β,4aα,5aα,6β,6aα)-2-(4-Chloro-3-nitrophenyl)-4,4a,5,5a,6,6a-hexahydro-4,6-ethanocycloprop[f]isoindole-1,3(2H,3aH)-dione. | 3.42 LCMS | 51 |

TABLE 4-continued

| Ex. No. | —L—G | Compound Name | Retention Time Min. | Procedure of Example |
|---|---|---|---|---|
| 411 | 4-iodophenyl group | (3aα,4β,4aα,5aα,6β,6aα)-4,4a,5,5a,6,6a-Hexahydro-2-(4-iodophenyl)-4,6-ethanocycloprop[f]isoindole-1,3(2H,3aH)-dione. | 3.53 LCMS | 51 |
| 412 | 4-nitrophenyl group | (3aα,4β,4aα,5aα,6β,6aα)-4,4a,5,5a,6,6a-Hexahydro-2-(4-nitrophenyl)-4,6-ethanocycloprop[f]isoindole-1,3(2H,3aH)-dione. | 3.12 LCMS | 51 |
| 413 | 4-isopropylphenyl group | (3aα,4β,4aα,5aα,6β,6aα)-4,4a,5,5a,6,6a-Hexahydro-2-[4-(1-methylethyl)phenyl]-4,6-ethanocycloprop[f]isoindole-1,3(2H,3aH)-dione. | 3.64 LCMS | 51 |
| 414 | 4-methyl-3-nitrophenyl group | (3aα,4β,4aα,5aα,6β,6aα)-4,4a,5,5a,6,6a-Hexahydro-2-(4-methyl-3-nitrophenyl)-4,6-ethanocycloprop[f]isoindole-1,3(2H,3aH)-dione. | 3.28 LCMS | 51 |
| 415 | 4-(cyanomethyl)phenyl group | (3aα,4β,4aα,5aα,6β,6aα)-4-(Octahydro-1,3-dioxo-4,6-ethanocycloprop[f]isoindole-2(1H)-yl)benzeneacetonitrile. | 2.67 LCMS | 51 |
| 416 | 4-ethylphenyl group | (3aα,4β,4aα,5aα,6β,6aα)-2-(4-Ethylphenyl)-4,4a,5,5a,6,6a-hexahydro-4,6-ethanocycloprop[f]isoindole-1,3(2H,3aH)-dione. | 3.44 LCMS | 51 |
| 417 | 4-propylphenyl group | (3aα,4β,4aα,5aα,6β,6aα)-4,4a,5,5a,6,6a-Hexahydro-2-(4-propylphenyl)-4,6-ethanocycloprop[f]isoindole-1,3(2H,3aH)-dione. | 3.68 LCMS | 51 |
| 418 | 2,3,4-trifluorophenyl group | (3aα,4β,4aα,5aα,6β,6aα)-4,4a,5,5a,6,6a-Hexahydro-2-(2,3,4-trifluorophenyl)-4,6-ethanocycloprop[f]isoindole-1,3(2H,3aH)-dione. | 3.44 LCMS | 51 |
| 419 | 4-tert-butyl-3-nitrophenyl group | (3aα,4β,4aα,5aα,6β,6aα)-2-[4-(1,1-Dimethylethyl)-3-nitrphenyl]-4,4a,5,5a,6,6a-hexahydro-4,6-ethanocycloprop[f]isoindole-1,3(2H,3aH)-dione. | 3.76 LCMS | 51 |
| 420 | 4-bromo-2,6-difluorophenyl group | (3aα,4β,4aα,5aα,6β,6aα)-2-(4-Bromo-2,6-difluorophenyl)-4,4a,5,5a,6,6a-hexahydro-4,6-ethanocycloprop[f]isoindole-1,3(2H,3aH)-dione. | 3.62 LCMS | 51 |

TABLE 4-continued

| Ex. No. | —L—G | Compound Name | Retention Time Min. | Procedure of Example |
|---|---|---|---|---|
| 421 | 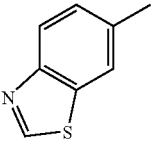 | (3aα,4β,4aα,5aα,6β,6aα)-2-(6-Benzothiazolyl)-4,4a,5,5a,6,6a-hexahydro-4,6-ethanocycloprop[f]isoindole-1,3(2H,3aH)-dione. | 2.95 LCMS | 51 |
| 422 |  | (3aα,4β,4aα,5aα,6β,6aα)-4,4a,5,5a,6,6a-Hexahydro-2-(2-methyl-8-quinolinyl)-4,6-ethanocycloprop[f]isoindole-1,3(2H,3aH)-dione. | 2.95 LCMS | 51 |
| 423 | 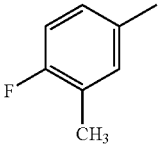 | (3aα,4β,4aα,5aα,6β,6aα)-2-(4-Fluoro-3-methylphenyl)-4,4a,5,5a,6,6a-hexahydro-4,6-ethanocycloprop[f]isoindole-1,3(2H,3aH)-dione. | 2.83 LCMS | 51 |
| 424 | 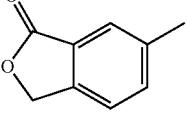 | (3aα,4β,4aα,5aα,6β,6aα)-2-(1,3-Dihydro-3-oxo-5-isobenzofuranyl)-4,4a,5,5a,6,6a-hexahydro-4,6-ethanocycloprop[f]isoindole-1,3(2H,3aH)-dione. | 2.54 LCMS | 51 |
| 425 | 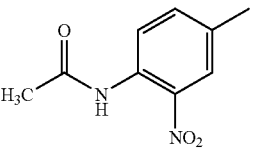 | (3aα,4β,4aα,5aα,6β,6aα)-N-[2-Nitro-4-(octahydro-1,3-dioxo-4,6-ethanocycloprop[f]isoindole-2(1H)-yl)phenyl]acetamide. | 2.85 LCMS | 51 |
| 426 | 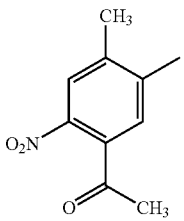 | (3aα,4β,4aα,5aα,6β,6aα)-2-(5-Acetyl-2-methyl-4-nitrophenyl)-4,4a,5,5a,6,6a-hexahydro-4,6-ethanocycloprop[f]isoindole-1,3(2H,3aH)-dione. | 3.05 LCMS | 51 |
| 427 | 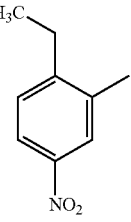 | (3aα,4β,4aα,5aα,6β,6aα)-2-(2-Ethyl-5-nitrophenyl)-4,4a,5,5a,6,6a-hexahydro-4,6-ethanocycloprop[f]isoindole-1,3(2H,3aH)-dione. | 3.28, 3.24 LCMS | 51 |
| 428 | 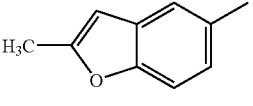 | (3aα,4β,4aα,5aα,6β,6aα)-4,4a,5,5a,6,6a-Hexahydro-2-(2-methyl-5-benzofuranyl)-4,6-ethanocycloprop[f]isoindole-1,3(2H,3aH)-dione. | 3.33 LCMS | 51 |

TABLE 4-continued

| Ex. No. | —L—G | Compound Name | Retention Time Min. | Procedure of Example |
|---|---|---|---|---|
| 429 | | (3aα,4β,4aα,5aα,6β,6aα)-2-(2,3-Dihydro-1-oxo-1H-inden-5-yl)-4,4a,5,5a,6,6a-hexahydro-4,6-ethanocycloprop[f]isoindole-1,3(2H,3aH)-dione. | 2.84 LCMS | 51 |
| 430 | | (3aα,4β,4aα,5aα,6β,6aα)-4,4a,5,5a,6,6a-Hexahydro-2-(1H-indazol-5-yl)-4,6-ethanocycloprop[f]isoindole-1,3(2H,3aH)-dione. | 2.59 LCMS | 51 |
| 431 | | (3aα,4β,4aα,5aα,6β,6aα)-4,4a,5,5a,6,6a-Hexahydro-2-[4-[2,2,2-trifluoro-1-hydroxy-1-(trifluoromethyl)ethyl]phenyl]-4,6-ethanocycloprop[f]isoindole-1,3(2H,3aH)-dione. | 3.53 LCMS | 51 |
| 432 | | (3aα,4β,4aα,5aα,6β,6aα)-2-(4-Bromo-3-chlorophenyl)-4,4a,5,5a,6,6a-hexahydro-4,6-ethanocycloprop[f]isoindole-1,3(2H,3aH)-dione. | 3.75 LCMS | 51 |
| 433 | | (3aα,4β,4aα,5aα,6β,6aα)-4,4a,5,5a,6,6a-Hexahydro-2-[3-(trifluoromethoxy)phenyl]-4,6-ethanocycloprop[f]isoindole-1,3(2H,3aH)-dione. | 3.55 LCMS | 51 |
| 434 | | (3aα,4β,4aα,5aα,6β,6aα)-4-(Octahydro-1,3-dioxo-4,6-ethanocycloprop[f]isoindole-2(1H)-yl)-2-(trifluoromethyl)benzonitrile. | 3.42 LCMS | 51 |
| 435 | | (3aα,4β,4aα,5aα,6β,6aα)-4,4a,5,5a,6,6a-Hexahydro-2-[4-methoxy-3-(trifluoromethyl)phenyl]-4,6-ethanocycloprop[f]isoindole-1,3(2H,3aH)-dione. | 3.19 LCMS | 51 |
| 436 | | (3aα,4β,4aα,5aα,6β,6aα)-2-(3,5-Dibromophenyl)-4,4a,5,5a,6,6a-hexahydro-4,6-ethanocycloprop[f]isoindole-1,3(2H,3aH)-dione. | 3.93 LCMS | 51 |
| 437 | | (3aα,4β,4aα,5aα,6β,6aα)-4,4a,5,5a,6,6a-Hexahydro-2-(3-iodo-4-methylphenyl)-4,6-ethanocycloprop[f]isoindole-1,3(2H,3aH)-dione. | 3.66 LCMS | 51 |

TABLE 4-continued

| Ex. No. | —L—G | Compound Name | Retention Time Min. | Procedure of Example |
|---|---|---|---|---|
| 438 | | (3aα,4β,4aα,5aα,6β,6aα)-2-(3-Chloro-4-iodophenyl)-4,4a,5,5a,6,6a-hexahydro-4,6-ethanocycloprop[f]isoindole-1,3(2H,3aH)-dione. | 3.78 LCMS | 51 |
| 439 | | (3aα,4β,4aα,5aα,6β,6aα)-4,4a,5,5a,6,6a-Hexahydro-2-(2-methyl-6-quinolinyl)-4,6-ethanocycloprop[f]isoindole-1,3(2H,3aH)-dione. | 1.93 LCMS | 51 |
| 440 | | (3aα,4β,4aα,5aα,6β,6aα)-4,4a,5,5a,6,6a-Hexahydro-2-[4-(trifluoromethyl)phenyl]-4,6-ethanocycloprop[f]isoindole-1,3(2H,3aH)-dione. | 3.51 LCMS | 51 |
| 441 | | (3aα,4β,4aα,5aα,6β,6aα)-2-(4-Chloro-3-methylphenyl)-4,4a,5,5a,6,6a-hexahydro-4,6-ethanocycloprop[f]isoindole-1,3(2H,3aH)-dione. | 3.57 LCMS | 51 |
| 442 | | (3aα,4β,4aα,5aα,6β,6aα)-4,4a,5,5a,6,6a-Hexahydro-2-[4-(methoxymethyl)-2-oxo-2H-1-benzopyran-7-yl]-4,6-ethanocycloprop[f]isoindole-1,3(2H,3aH)-dione. | 3.03 LCMS | 51 |
| 443 | | (3aα,4β,4aα,5aα,6β,6aα)-4,4a,5,5a,6,6a-Hexahydro-2-(2-oxo-2H-1-benzopyran-6-yl)-4,6-ethanocycloprop[f]isoindole-1,3(2H,3aH)-dione. | 2.76 LCMS | 51 |
| 444 | | (3aα,4β,4aα,5aα,6β,6aα)-4,4a,5,5a,6,6a-Hexahydro-2-[2-[(1-methylethyl)amino]-5-(trifluoromethyl)phenyl]-4,6-ethanocycloprop[f]isoindole-1,3(2H,3aH)-dione. | 3.67 LCMS | 51 |
| 445 | | (3aα,4β,4aα,5aα,6β,6aα)-2-(3-Chloro-4-nitrophenyl)-4,4a,5,5a,6,6a-hexahydro-4,6-ethanocycloprop[f]isoindole-1,3(2H,3aH)-dione. | 3.46 LCMS | 51 |

TABLE 4-continued

| Ex. No. | —L—G | Compound Name | Retention Time Min. | Procedure of Example |
|---|---|---|---|---|
| 446 | | (3aα,4β,4aα,5aα,6β,6aα)-4,4a,5,5a,6,6a-Hexahydro-2-(3-methyl-4-nitrophenyl)-4,6-ethanocycloprop[f]isoindole-1,3(2H,3aH)-dione. | 3.29 LCMS | 51 |
| 447 | | (3aα,4β,4aα,5aα,6β,6aα)-2-[5-[(Difluoromethyl)sulfonyl]-2-methoxyphenyl]-4,4a,5,5a,6,6a-hexahydro-4,6-ethanocycloprop[f]isoindole-1,3(2H,3aH)-dione. | 2.81 LCMS | 51 |
| 448 | | (3aα,4β,4aα,5aα,6β,6aα)-4,4a,5,5a,6,6a-Hexahydro-2-[3-(1-methylethyl)phenyl]-4,6-ethanocycloprop[f]isoindole-1,3(2H,3aH)-dione. | 3.39 LC | 6B |
| 449 | | (3aα,4β,4aα,5aα,6β,6aα)-N-(1,1-Dimethylethyl)-5-(octahydro-1,3-dioxo-4,6-ethanocycloprop[f]isoindole-2(1H)-yl)-1-naphthalenesulfonamide. | 3.393 LC | 6B |
| 450 | | (3aα,4β,4aα,5aα,6β,6aα)-4,4a,5,5a,6,6a-Hexahydro-2-[4-[(trifluoromethyl)thio]phenyl]-4,6-ethanocycloprop[f]isoindole-1,3(2H,3aH)-dione. | 3.57 LC | 6B |
| 451 | | (3aα,4β,4aα,5aα,6β,6aα)-4,4a,5,5a,6,6a-Hexahydro-2-[2-(2-methoxyphenoxy)-5-(trifluoromethyl)phenyl]-4,6-ethanocycloprop[f]isoindole-1,3(2H,3aH)-dione. | 2.88 LC | 6B |
| 452 | | (3aα,4β,4aα,5aα,6β,6aα)-4,4a,5,5a,6,6a-Hexahydro-2-[4-(1,1,2,2-tetrafluoroethoxy)phenyl]-4,6-ethanocycloprop[f]isoindole-1,3(2H,3aH)-dione. | 3.23 LC | 6B |
| 453 | | (3aα,4β,4aα,5aα,6β,6aα)-N-[4-(Octahydro-1,3-dioxo-4,6-ethanocycloprop[f]isoindole-2(1H)-yl)-2-(trifluoromethyl)phenyl]acetamide. | 3.53 LC | 6B |

TABLE 4-continued

| Ex. No. | —L—G | Compound Name | Retention Time Min. | Procedure of Example |
|---|---|---|---|---|
| 454 | (aryl group with O₂N and C(O)CH₃ substituents) | (3aα,4β,4aα,5aα,6β,6aα)-2-(3-Acetyl-4-nitrophenyl)-4,4a,5,5a,6,6a-hexahydro-4,6-ethanocycloprop[f]isoindole-1,3(2H,3aH)-dione. | 2.91 LC | 6B |
| 455 | (aryl group with C(CH₃)₃ substituent) | (3aα,4β,4aα,5aα,6β,6aα)-2-[3-(1,1-Dimethylethyl)phenyl]-4,4a,5,5a,6,6a-hexahydro-4,6-ethanocycloprop[f]isoindole-1,3(2H,3aH)-dione. | 3.52 LC | 6B |
| 456 | (aryl group with SO₂NHCH₂CH₂CH₂CH₃) | (3aα,4β,4aα,5aα,6β,6aα)-N-Butyl-3-(Octahydro-1,3-dioxo-4,6-ethanocycloprop[f]isoindole-2(1H)-yl)benzenesulfonamide. | 3.05 LC | 6B |
| 457 | (aryl group with CH₃ and CF₃ substituents) | (3aα,4β,4aα,5aα,6β,6aα)-4,4a,5,5a,6,6a-Hexahydro-2-[2-methyl-3-(trifluoromethyl)phenyl]-4,6-ethanocycloprop[f]isoindole-1,3(2H,3aH)-dione. | 3.24 & 3.42 LC | 6B |
| 458 | (aryl group with F and CN substituents) | (3aα,4β,4aα,5aα,6β,6aα)-2-Fluoro-5-(Octahydro-1,3-dioxo-4,6-ethanocycloprop[f]isoindole-2(1H)-yl)benzonitrile. | 2.74 LC | 6B |
| 459 | (aryl group with C(O)NHCH₃ substituent) | (3aα,4β,4aα,5aα,6β,6aα)-N-Methyl-3-(octahydro-1,3-dioxo-4,6-ethanocycloprop[f]isoindole-2(1H)-yl)benzamide. | 2.52 LC | 6B |
| 460 | (naphthalenyl group with O₂N substituent) | (3aα,4β,4aα,5aα,6β,6aα)-4,4a,5,5a,6,6a-Hexahydro-2-(4-nitro-1-naphthalenyl)-4,6-ethanocycloprop[f]isoindole-1,3(2H,3aH)-dione. | 3.30 & 3.40 *LCMS | 6B |

EXAMPLES 461 TO 544

Additional compounds of the formula I were prepared by procedures analogous to those described above. The compounds of Examples 461 to 544 have the following structure:

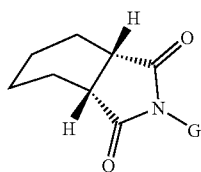

where G, the compound name, retention time, and the procedure employed, are set forth in Table 5 (L is a bond for the compounds of Table 5).

The chromatography techniques used to determine the compound retention times of Table 5 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

LCMS*=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 5, where provided, were determined by MS (ES) by the formula m/z.

TABLE 5

| Ex. No. | —L—G | Compound Name | Retention Time Min. | Procedure of Example |
|---|---|---|---|---|
| 461 | | 2-(2-Fluorenyl)hexahydro-1H-isoindole-1,3(2H)-dione. | 0.98 LCMS | 51 |
| 462 | | 2-[3-Chloro-4-(4-morpholinyl)phenyl]hexahydro-1H-isoindole-1,3(2H)-dione. | 0.23 LCMS | 51 |
| 463 | | 2-(2,3-Dihydro-1H-inden-5-yl)hexahydro-1H-isoindole-1,3(2H)-dione. | 3.17 LCMS | 51 |
| 464 | | 2-(4-Bromo-1-naphthalenyl)hexahydro-1H-isoindole-1,3(2H)-dione. | 3.30 LCMS | 51 |
| 465 | | 2-(4-Chloro-1-naphthalenyl)hexahydro-1H-isoindole-1,3(2H)-dione. | 3.26 LCMS | 51 |
| 466 | | Hexahydro-2-(3-iodo-4-methylphenyl)-1H-isoindole-1,3(2H)-dione. | 3.55 LCMS | 51 |

TABLE 5-continued

| Ex. No. | —L—G | Compound Name | Retention Time Min. | Procedure of Example |
|---|---|---|---|---|
| 467 | | Hexahydro-2-(4-nitro-1-naphthalenyl)-1H-isoindole-1,3(2H)-dione. | 3.09 LCMS | 51 |
| 468 | | Hexahydro-2-(1H-indol-5-yl)-1H-isoindole-1,3(2H)-dione. | 2.66 LCMS | 51 |
| 469 | | Hexahydro-2-(5-quinolinyl)-1H-isoindole-1,3(2H)-dione. | 2.03 LCMS | 51 |
| 470 | | Hexahydro-2-(1H-indazol-6-yl)-1H-isoindole-1,3(2H)-dione. | 2.56 LCMS | 51 |
| 471 | | 2-(1,3-Benzodioxol-5-yl)hexahydro-1H-isoindole-1,3(2H)-dione. | 1.06 LCMS | 51 |
| 472 | | 2-(3-Fluoro-4-methylphenyl)hexahydro-1H-isoindole-1,3(2H)-dione. | 3.06 LCMS | 51 |
| 473 | | Hexahydro-2-[4-nitro-3-(trifluoromethyl)phenyl]-1H-isoindole-1,3(2H)-dione. | 0.29 LCMS | 51 |
| 474 | | Hexahydro-2-(8-quinolinyl)-1H-isoindole-1,3(2H)-dione. | 0.31 LCMS | 51 |
| 475 | | 2-(2,3-Dihydro-1,4-benzodioxin-6-yl)hexahydro-1H-isoindole-1,3(2H)-dione. | 2.76 LCMS | 51 |

TABLE 5-continued

| Ex. No. | —L—G | Compound Name | Retention Time Min. | Procedure of Example |
|---|---|---|---|---|
| 476 | | Hexahydro-2-(4-methyl-2-oxo-2H-1-benzopyran-7-yl)-1H-isoindole-1,3(2H)-dione. | 0.31 LCMS | 51 |
| 477 | | Hexahydro-2-(5-isoquinolinyl)-1H-isoindole-1,3(2H)-dione. | 1.83 LCMS | 51 |
| 478 | | Hexahydro-2-(2,4,5-trifluorophenyl)-1H-isoindole-1,3(2H)-dione. | 0.27 LCMS | 51 |
| 479 | | Hexahydro-2-(2,4,5-trichlorophenyl)-1H-isoindole-1,3(2H)-dione. | 3.11 LCMS | 51 |
| 480 | | Hexahydro-2-(2,3,4,6-tetrafluorophenyl)-1H-isoindole-1,3(2H)-dione. | 3.10 LCMS | 51 |
| 481 | | 2-(3,4-Difluorophenyl)hexahydro-1H-isoindole-1,3(2H)-dione. | 1.08 LCMS | 51 |
| 482 | | 1-Acetyl-2,3-dihydro-6-(octahydro-1,3-dioxo-2H-isoindol-2-yl)-1H-indole. | 2.58 LCMS | 51 |
| 483 | | 2-(3-Chloro-4-fluorophenyl)hexahydro-1H-isoindole-1,3(2H)-dione. | 3.13 LCMS | 51 |

TABLE 5-continued

| Ex. No. | —L—G | Compound Name | Retention Time Min. | Procedure of Example |
|---|---|---|---|---|
| 484 | 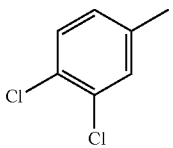 | 2-(3,4-Dichlorophenyl)hexahydro-1H-isoindole-1,3(2H)-dione. | 1.05 LCMS | 51 |
| 485 | 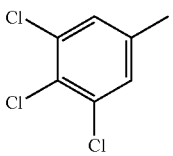 | Hexahydro-2-(3,4,5-trichlorophenyl)-1H-isoindole-1,3(2H)-dione. | 3.63 LCMS | 51 |
| 486 | 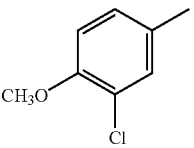 | 2-(3-Chloro-4-methoxyphenyl)hexahydro-1H-isoindole-1,3(2H)-dione. | 2.99 LCMS | 51 |
| 487 | 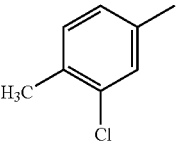 | 2-(3-Chloro-4-methylphenyl)hexahydro-1H-isoindole-1,3(2H)-dione. | 3.25 LCMS | 51 |
| 488 | 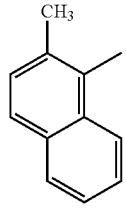 | Hexahydro-2-(2-methyl-1-naphthalenyl)-1H-isoindole-1,3(2H)-dione. | 3.04 LCMS | 51 |
| 489 | 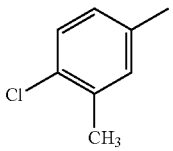 | 2-(4-Chloro-3-methylphenyl)hexahydro-1H-isoindole-1,3(2H)-dione. | 3.23 LCMS | 51 |
| 490 | 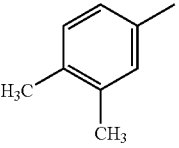 | 2-(3,4-Dimethylphenyl)hexahydro-1H-isoindole-1,3(2H)-dione. | 3.07 LCMS | 51 |
| 491 | 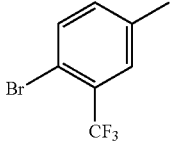 | 2-[4-Bromo-3-(trifluoromethyl)phenyl]hexahydro-1H-isoindole-1,3(2H)-dione. | 1.23 LCMS | 51 |
| 492 | 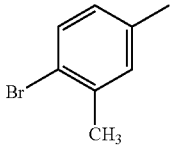 | 2-(4-Bromo-3-methylphenyl)hexahydro-1H-isoindole-1,3(2H)-dione. | 3.30 LCMS | 51 |

TABLE 5-continued

| Ex. No. | —L—G | Compound Name | Retention Time Min. | Procedure of Example |
|---|---|---|---|---|
| 493 | 4-F, 3-NO₂-phenyl | 2-(4-Fluoro-3-nitrophenyl)hexahydro-1H-isoindole-1,3(2H)-dione. | 2.88 LCMS | 51 |
| 494 | 4-F, 3-CF₃-phenyl | 2-[4-Fluoro-3-(trifluoromethyl)phenyl]hexahydro-1H-isoindole-1,3(2H)-dione. | 1.23 LCMS | 51 |
| 495 | 4-Cl, 3-NO₂-phenyl | 2-(4-Chloro-3-nitrophenyl)hexahydro-1H-isoindole-1,3(2H)-dione. | 3.10 LCMS | 51 |
| 496 | 4-Cl, 3-CF₃-phenyl | 2-[4-Chloro-3-(trifluoromethyl)phenyl]hexahydro-1H-isoindole-1,3(2H)-dione. | 1.07 LCMS | 51 |
| 497 | 4-Cl, 2-OCH₃, 5-CH₃-phenyl | 2-(4-Chloro-2-methoxy-5-methylphenyl)hexahydro-1H-isoindole-1,3(2H)-dione. | 2.90 LCMS | 51 |
| 498 | 3-F, 4-OCH₃-phenyl | 2-(3-Fluoro-4-methoxyphenyl)hexahydro-1H-isoindole-1,3(2H)-dione. | 2.80 LCMS | 51 |
| 499 | 2-Br, 5-CO₂CH₃-phenyl | 2-Bromo-5-(octahydro-1,3-dioxo-2H-isoindol-2-yl)benzoic acid, methyl ester. | 3.05 LCMS | 51 |
| 500 | 4-CH₃, 3-NO₂-phenyl | Hexahydro-2-(4-methyl-3-nitrophenyl)-1H-isoindole-1,3(2H)-dione. | 3.01 LCMS | 51 |

TABLE 5-continued

| Ex. No. | —L—G | Compound Name | Retention Time Min. | Procedure of Example |
|---|---|---|---|---|
| 501 | (3,4,5-trimethoxyphenyl) | Hexahydro-2-(3,4,5-trimethoxyphenyl)-1H-isoindole-1,3(2H)-dione. | 2.65 LCMS | 51 |
| 502 | (3,4-dimethoxyphenyl, with OCH3 also at other position as shown) | 2-(3,4-Dimethoxyphenyl)hexahydro-1H-isoindole-1,3(2H)-dione. | 2.58 LCMS | 51 |
| 503 | 2-(2-pyridinyl)-1H-benzimidazol-5-yl | Hexahydro-2-[2-(2-pyridinyl)-1H-benzimidazol-5-yl]-1H-isoindole-1,3(2H)-dione. | 2.41 LCMS | 51 |
| 504 | 9-ethyl-9H-carbazol-3-yl | 2-(9-Ethyl-9H-carbazol-3-yl)hexahydro-1H-isoindole-1,3(2H)-dione. | 3.39 LCMS | 51 |
| 505 | 2-methoxy-3-dibenzofuranyl | Hexahydro-2-(2-methoxy-3-dibenzofuranyl)-1H-isoindole-1,3(2H)-dione. | 3.17 LCMS | 51 |
| 506 | 2,3,4-trifluorophenyl | Hexahydro-2-(2,3,4-trifluorophenyl)-1H-isoindole-1,3(2H)-dione. | 3.09 LCMS | 51 |
| 507 | 2-methyl-5-(octahydro-1,3-dioxo-2H-isoindol-2-yl) | Hexahydro-2-methyl-5-(octahydro-1,3-dioxo-2H-isoindol-2-yl)-1H-isoindole-1,3(2H)-dione. | 2.29 LCMS | 51 |
| 508 | 6-(methylthio)-5-nitro-8-quinolinyl | Hexahydro-2-[6-(methylthio)-5-nitro-8-quinolinyl]-1H-isoindole-1,3(2H)-dione. | 3.14 LCMS | 51 |

TABLE 5-continued

| Ex. No. | —L—G | Compound Name | Retention Time Min. | Procedure of Example |
|---|---|---|---|---|
| 509 | (2,5-dichloro-4-(1H-pyrrol-1-yl)phenyl group) | 2-[2,5-Dichloro-4-(1H-pyrrol-1-yl)phenyl]hexahydro-1H-isoindole-1,3(2H)-dione. | 3.15 LCMS | 51 |
| 510 | (5,6-dimethylquinolin-5-yl group) | Hexahydro-2-(6-methyl-5-quinolinyl)-1H-isoindole-1,3(2H)-dione. | 0.17 LCMS | 51 |
| 511 | (5-methyl-N-tert-butylnaphthalene-1-sulfonamide group) | N-(1,1-Dimethylethyl)-5-(octahydro-1,3-dioxo-2H-isoindol-2-yl)-1-naphthalenesulfonamide. | 0.98 LCMS | 51 |
| 512 | (7-methyl-4-(methoxymethyl)-2H-chromen-2-one group) | Hexahydro-2-[4-(methoxymethyl)-2-oxo-2H-1-benzopyran-7-yl]-1H-isoindole-1,3(2H)-dione. | 2.82 LCMS | 51 |
| 513 | (6-methylbenzothiazol-6-yl group) | 2-(6-Benzothiazolyl)hexahydro-1H-isoindole-1,3(2H)-dione. | 2.65 LCMS | 51 |
| 514 | (2-methoxy-4-methyl benzoic acid methyl ester group) | 2-Methoxy-4-(octahydro-1,3-dioxo-2H-isoindol-2-yl)benzoic acid, methyl ester. | 2.82 LCMS | 51 |
| 515 | (2-methyl-5-methyl-benzonitrile group) | 2-Methyl-5-(octahydro-1,3-dioxo-2H-isoindol-2-yl)benzonitrile. | 2.85 LCMS | 51 |

TABLE 5-continued

| Ex. No. | —L—G | Compound Name | Retention Time Min. | Procedure of Example |
|---|---|---|---|---|
| 516 | | Hexahydro-2-(2-oxo-2H-1-benzopyran-6-yl)-1H-isoindole-1,3(2H)-dione. | 2.64 LCMS | 51 |
| 517 | | Hexahydro-2-(2-methyl-8-quinolinyl)-1H-isoindole-1,3(2H)-dione. | 1.10 LCMS | 51 |
| 518 | | 2-[3,5-Bis(trifluoromethyl)phenyl]hexahydro-1H-isoindole-1,3(2H)-dione. | 3.51 LCMS | 51 |
| 519 | | Hexahydro-2-(2,4,5-trimethylphenyl)-1H-isoindole-1,3(2H)-dione. | 3.16 LCMS | 51 |
| 520 | | 2-(4-Fluoro-3-methylphenyl)hexahydro-1H-isoindole-1,3(2H)-dione. | 3.00 LCMS | 51 |
| 521 | | Hexahydro-2-(3-methoxy-4-methylphenyl)-1H-isoindole-1,3(2H)-dione. | 0.98 LCMS | 51 |
| 522 | | N-Ethyl-2-methyl-5-(octahydro-1,3-dioxo-2H-isoindol-2-yl)-N-phenylbenzenesulfonamide. | 3.01 LCMS | 51 |
| 523 | | 2-(2,3-Dimethyl-1H-indol-5-yl)hexahydro-1H-isoindole-1,3(2H)-dione. | 2.97 LCMS | 51 |

TABLE 5-continued

| Ex. No. | —L—G | Compound Name | Retention Time Min. | Procedure of Example |
|---|---|---|---|---|
| 524 | | 2-(3-Dibenzofuranyl)hexahydro-1H-isoindole-1,3(2H)-dione. | 1.04 LCMS | 51 |
| 525 | | 2-(4-Bromophenyl)hexahydro-1H-isoindole-1,3(2H)-dione. | 3.12 LCMS | 51 |
| 526 | | 2-(3-Chloro-4-nitrophenyl)hexahydro-1H-isoindole-1,3(2H)-dione. | 0.98 LCMS | 51 |
| 527 | | 2-(1,3-Dihydro-2,2-dioxidobenzo[c]thiophen-5-yl)hexahydro-1H-isoindole-1,3(2H)-dione. | 2.30 LCMS | 51 |
| 528 | | Hexahydro-2-(6-nitro-2-naphthalenyl)-1H-isoindole-1,3(2H)-dione. | 3.213 LCMS | 51 |
| 529 | | Hexahydro-2-(1H-indazol-5-yl)-1H-isoindole-1,3(2H)-dione. | 2.45 LCMS | 51 |
| 530 | | 2-(4-Amino-2,3,5,6-tetrafluorophenyl)hexahydro-1H-isoindole-1,3(2H)-dione. | 2.86 LCMS | 51 |
| 531 | | 2-(4-Bromo-3-chlorophenyl)hexahydro-1H-isoindole-1,3(2H)-dione. | 3.37 LCMS | 51 |
| 532 | | 2-(1,2-Dihydro-4-methyl-2-oxo-7-quinolinyl)hexahydro-1H-isoindole-1,3(2H)-dione. | 2.73 LCMS | 51 |

TABLE 5-continued

| Ex. No. | —L—G | Compound Name | Retention Time Min. | Procedure of Example |
|---|---|---|---|---|
| 533 | | 4-(Octahydro-1,3-dioxo-2H-isoindol-2-yl)-2-(trifluoromethyl)benzonitrile. | 3.26 LCMS | 51 |
| 534 | | Hexahydro-2-(9-oxo-9H-fluoren-1-yl)-1H-isoindole-1,3(2H)-dione. | 3.07 LCMS | 51 |
| 535 | | 2-Fluoro-5-(octahydro-1,3-dioxo-2H-isoindol-2-yl)benzonitrile. | 2.22 LCMS | 51 |
| 536 | | Hexahydro-2-(9-oxo-9H-fluoren-2-yl)-1H-isoindole-1,3(2H)-dione. | 0.23 LCMS | 51 |
| 537 | | 2-(3-Chloro-4-iodophenyl)hexahydro-1H-isoindole-1,3(2H)-dione. | 3.40 LCMS | 51 |
| 538 | | 2-(4-Bromo-2,3,5,6-tetrafluorophenyl)hexahydro-1H-isoindole-1,3(2H)-dione. | 3.50 LCMS | 51 |
| 539 | | Hexahydro-2-(2,3,5,6-tetramethyl-4-nitrophenyl)-1H-isoindole-1,3(2H)-dione. | 3.22 LCMS | 51 |
| 540 | | Hexahydro-2-(2,2,3,3-tetrafluoro-2,3-dihydro-1,4-benzodioxin-6-yl)-1H-isoindole-1,3(2H)-dione. | 3.43 LCMS | 51 |

TABLE 5-continued

| Ex. No. | —L—G | Compound Name | Retention Time Min. | Procedure of Example |
|---|---|---|---|---|
| 541 | | 2-(3-Bromo-4-methylphenyl)hexahydro-1H-isoindole-1,3(2H)-dione. | | 51 |
| 542 | | 2-(4-Bromo-2-methylphenyl)hexahydro-1H-isoindole-1,3(2H)-dione. | | 51 |
| 543 | | Hexahydro-2-(1-naphthalenyl)-1H-isoindole-1,3(2H)-dione. | | 51 |
| 544 | | 2-(3-Chloro-2-methylphenyl)hexahydro-1H-isoindole-1,3(2H)-dione. | | 51 |

EXAMPLES 545 TO 580

Additional compounds of the formula I were prepared by procedures analogous to those described above. The compounds of Examples 545 to 580 have the following structure:

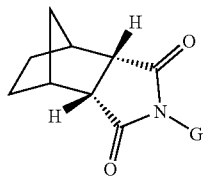

where G, the compound name, retention time, and the procedure employed, are set forth in Table 6 (L is a bond for the compounds of Table 6).

The chromatography techniques used to determine the compound retention times of Table 6 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

LCMS*=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 6, where provided, were determined by MS (ES) by the formula m/z.

TABLE 6

| Ex. No. | —L—G | Compound Name | Retention Time Min. | Procedure of Example |
|---|---|---|---|---|
| 545 | | (3aα,4α,7α,7aα)-Hexahydro-2-(2-naphthalenyl)-4,7-methano-1H-isoindole-1,3(2H)-dione. | 6.85 LCMS | 39B |

TABLE 6-continued

| Ex. No. | —L—G | Compound Name | Retention Time Min. | Procedure of Example |
|---|---|---|---|---|
| 546 | (2-amino-4,5-dichlorophenyl with methyl) | (3aα,4α,7α,7aα)-2-(2-Amino-4,5-dichlorophenyl)hexahydro-4,7-methano-1H-isoindole-1,3(2H)-dione. | 3.62 LC | 39B |
| 547 | (4-nitro-1-naphthalenyl with methyl) | (3aα,4α,7α,7aα)-Hexahydro-2-(4-nitro-1-naphthalenyl)-4,7-methano-1H-isoindole-1,3(2H)-dione. | 3.47 & 3.58 LC | 39B |
| 548 | (8-hydroxy-5-quinolinyl with methyl) | (3aα,4α,7α,7aα)-Hexahydro-2-(8-hydroxy-5-quinolinyl)-4,7-methano-1H-isoindole-1,3(2H)-dione. | 1.92 LC | 39B |
| 549 | (1-naphthalenyl with methyl) | (3aα,4α,7α,7aα)-Hexahydro-2-(1-naphthalenyl)-4,7-methano-1H-isoindole-1,3(2H)-dione. | 3.30 & 3.44 LC | 39B |
| 550 | (1-cyano-naphthalenyl with methyl) | (3aα,4α,7α,7aα)-4-(Octahydro-1,3-dioxo-4,7-methano-2H-isoindol-2-yl)-1-naphthalenecarbonitrile. | 3.29 LC | 39B |
| 551 | (4-nitro-3-trifluoromethylphenyl with methyl) | (3aα,4α,7α,7aα)-Hexahydro-2-[4-nitro-3-(trifluoromethyl)phenyl]-4,7-methano-1H-isoindole-1,3(2H)-dione. | 3.76 LC | 39B |
| 552 | (4-bromo-1-naphthalenyl with methyl) | (3aα,4α,7α,7aα)-2-(4-Bromo-1-naphthalenyl)hexahydro-4,7-methano-1H-isoindole-1,3(2H)-dione. | 3.93 LC | 39B |
| 553 | (2-fluorenyl with methyl) | (3aα,4α,7α,7aα)-2-(2-Fluorenyl)hexahydro-4,7-methano-1H-isoindole-1,3(2H)-dione. | 4.04 LC | 39B |

TABLE 6-continued

| Ex. No. | —L—G | Compound Name | Retention Time Min. | Procedure of Example |
|---|---|---|---|---|
| 554 | 2,1-dimethylnaphthalenyl | (3aα,4α,7α,7aα)-Hexahydro-2-(2-methyl-1-naphthalenyl)-4,7-methano-1H-isoindole-1,3(2H)-dione. | 3.56 LC | 39B |
| 555 | 3,5-dichlorophenyl | (3aα,4α,7α,7aα)-2-(3,5-Dichlorophenyl)hexahydro-4,7-methano-1H-isoindole-1,3(2H)-dione. | 1.70 LCMS | 39B |
| 556 | 3-chlorophenyl | (3aα,4α,7α,7aα)-2-(3-Chlorophenyl)hexahydro-4,7-methano-1H-isoindole-1,3(2H)-dione. | 2.83 LCMS | 39B |
| 557 | 3-chloro-4-fluorophenyl | (3aα,4α,7α,7aα)-2-(3-Chloro-4-fluorophenyl)hexahydro-4,7-methano-1H-isoindole-1,3(2H)-dione. | 3.11 LCMS | 39B |
| 558 | 3-(trifluoromethyl)phenyl | (3aα,4α,7α,7aα)-Hexahydro-2-[3-(trifluoromethyl)phenyl]-4,7-methano-1H-isoindole-1,3(2H)-dione. | 3.12 LCMS | 39B |
| 559 | 4-bromo-3-(trifluoromethyl)phenyl | (3aα,4α,7α,7aα)-2-[4-Bromo-3-(trifluoromethyl)phenyl]hexahydro-4,7-methano-1H-isoindole-1,3(2H)-dione. | 3.57 LCMS | 39B |
| 560 | 4-bromo-3-methylphenyl | (3aα,4α,7α,7aα)-2-(4-Bromo-3-methylphenyl)hexahydro-4,7-methano-1H-isoindole-1,3(2H)-dione. | 3.35 LCMS | 39B |
| 561 | 1,2-dihydro-4-methyl-2-oxo-7-quinolinyl | (3aα,4α,7α,7aα)-2-(1,2-Dihydro-4-methyl-2-oxo-7-quinolinyl)hexahydro-4,7-methano-1H-isoindole-1,3(2H)-dione. | 2.48 LCMS | 39B |
| 562 | 4-pyridinyl | (3aα,4α,7α,7aα)-Hexahydro-2-(4-pyridinyl)-4,7-methano-1H-isoindole-1,3(2H)-dione. | 1.19 LC | 39B |

TABLE 6-continued

| Ex. No. | —L—G | Compound Name | Retention Time Min. | Procedure of Example |
|---|---|---|---|---|
| 563 | | (3aα,4α,7α,7aα)-Hexahydro-2-(1-oxido-4-pyridinyl)-4,7-methano-1H-isoindole-1,3(2H)-dione. | 1.47 LC | 39B |
| 564 | | (3aα,4α,7α,7aα)-Hexahydro-2-(6-quinolinyl)-4,7-methano-1H-isoindole-1,3(2H)-dione. | 1.57 LC | 39B |
| 565 | | (3aα,4α,7α,7aα)-Hexahydro-2-(1-oxido-6-quinolinyl)-4,7-methano-1H-isoindole-1,3(2H)-dione. | 2.08 LCMS | 39B |
| 566 | | (3aα,4α,7α,7aα)-Hexahydro-2-(5-nitro-8-isoquinoliny)-4,7-methano-1H-isoindole-1,3(2H)-dione, trifluoroacetate(1:1). | 2.59 LC | 39B |
| 567 | | (3aα,4α,7α,7aα)-Hexahydro-2-[4-(methylsulfonyl)phenyl]-4,7-methano-1H-isoindole-1,3(2H)-dione. | 2.03 LCMS | 39B |
| 568 | | (3aα,4α,7α,7aα)-Hexahydro-2-[4-(methylthio)phenyl]-4,7-methano-1H-isoindole-1,3(2H)-dione. | 2.79 LCMS | 39B |
| 569 | | (3aα,4α,7α,7aα)-4-(Octahydro-1,3-dioxo-4,7-methano-2H-isoindol-2-yl)benzenesulfonamide. | 1.90 LCMS | 39B |
| 570 | | (3aα,4α,7α,7aα)-Hexahydro-2-[4-(methylsulfinyl)phenyl]-4,7-methano-1H-isoindole-1,3(2H)-dione. | 1.98 LCMS | 39B |
| 571 | | (3aα,4α,7α,7aα)-2-(4-Fluoro-1-naphthalenyl)hexahydro-4,7-methano-1H-isoindole-1,3(2H)-dione. | 2.87 & 2.93 LCMS | 39B |

TABLE 6-continued

| Ex. No. | —L—G | Compound Name | Retention Time Min. | Procedure of Example |
|---|---|---|---|---|
| 572 | | (3aα,4α,7α,7aα)-4-(Octahydro-1,3-dioxo-4,7-methano-2H-isoindol-2-yl)-1-naphthalenecarboxylic acid, methyl ester. | 2.92 & 3.02 LCMS | 39B |
| 573 | | (3aα,4α,7α,7aα)-2-(1,1-Dioxido-2H-naphth[1,8-cd]isothiazol-5-yl)hexahydro-4,7-methano-1H-isoindole-1,3(2H)-dione. | 2.28 & 2.43 LC | 39B |
| 574 | | (3aα,4α,7α,7aα)-Hexahydro-2-(6-hydroxy-3-pyridinyl)-4,7-methano-1H-isoindole-1,3(2H)-dione. | 1.49 LCMS | 39B |
| 575 | | (3aα,4α,7α,7aα)-2-(1,2-Benzisothiazol-3-yl)hexahydro-4,7-methano-1H-isoindole-1,3(2H)-dione. | 2.59 LCMS | 39B |
| 576 | | (3aα,4α,7α,7aα)-2-(3-Benzofuranyl)hexahydro-4,7-methano-1H-isoindole-1,3(2H)-dione. | 3.04 LCMS | 39B |
| 577 | | (3aα,4α,7α,7aα)-3-(Octahydro-1,3-dioxo-4,7-methano-2H-isoindol-2-yl)-2-benzofurancarboxylic acid, methyl ester. | 3.08 LCMS | 39B |
| 578 | | (3aα,4α,7α,7aα)-Hexahydro-2-[4-(4-isothiazolyl)phenyl]-4,7-methano-1H-isoindole-1,3(2H)-dione. | 2.74 LC | 39B |
| 579 | | (3aα,4α,7α,7aα)-2-(3-Chloro-4-hydroxyphenyl)hexahydro-4,7-methano-1H-isoindole-1,3(2H)-dione. | 2.36 LC | 39B |
| 580 | | (3aα,4α,7α,7aα)-Hexahydro-2-[4-(1H-tetrazol-5-yl)phenyl]-4,7-methano-1H-isoindole-1,3(2H)-dione, trifluoroacetate(1:1). | 2.13 LC | 39B |

EXAMPLES 581 TO 588

Additional compounds of the formula I were prepared by procedures analogous to those described above. The compounds of Examples 581 to 588 have the following structure:

A.

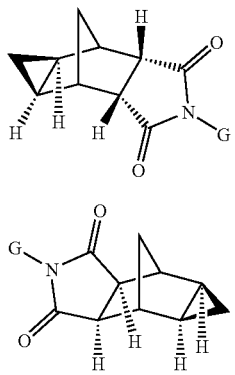

B.

where G, the compound name, retention time, and the procedure employed, are set forth in Table 7 (L is a bond for the compounds of Table 7).

The chromatography techniques used to determine the compound retention times of Table 7 are as follows:

LCMS=YMC S5 ODS column, 4.6×50 mm eluting with 10-90% MeOH/$H_2O$ over 4 minutes containing 0.1% TFA; 4 mL/min, monitoring at 220 nm.

*LCMS=YMC S5 ODS column, 4.6×50 mm eluting with 10-90% MeOH/$H_2O$ over 2 minutes containing 0.1% TFA; 4 mL/min, monitoring at 220 nm.

LC=YMC S5 ODS column 4.6×50 mm eluting with 10-90% MeOH/$H_2O$ over 4 minutes containing 0.2% phosphoric acid, 4 mL/min, monitoring at 220 nm.

The molecular mass of the compounds listed in Table 7, where provided, were determined by MS (ES) by the formula m/z.

TABLE 7

| Ex. No. | —L—G | A/B | Compound Name | Retention Time Min. | Procedure of Example |
|---|---|---|---|---|---|
| 581 | 3-CF₃-phenyl | A | (3aα,4α,4aβ,5aβ,6α,6aα)-4,4a,5,5a,6,6a-Hexahydro-2-[3-(trifluoromethyl)phenyl]-4,6-methanocycloprop[f]isoindole-1,3(2H,3aH)-dione. | 3.21 LC | 10B |
| 582 | 4-nitro-3-CF₃-phenyl | A | (3aα,4α,4aβ,5aβ,6α,6aα)-4,4a,5,5a,6,6a-Hexahydro-2-[4-nitro-3-(trifluoromethyl)phenyl]-4,6-methanocycloprop[f]isoindole-1,3(2H,3aH)-dione. | 3.35 LC | 10B |
| 583 | 4-nitro-1-naphthalenyl | A | (3aα,4α,4aβ,5aβ,6α,6aα)-4,4a,5,5a,6,6a-Hexahydro-2-(4-nitro-1-naphthalenyl)-4,6-methanocycloprop[f]isoindole-1,3(2H,3aH)-dione. | 5.74 & 6.01 LC | 10B |
| 584 | 1,2-dihydro-4-methyl-2-oxo-7-quinolinyl | A | (3aα,4α,4aβ,5aβ,6α,6aα)-2-(1,2-Dihydro-4-methyl-2-oxo-7-quinolinyl)-4,4a,5,5a,6,6a-hexahydro-4,6-methanocycloprop[f]isoindole-1,3(2H,3aH)-dione. | 2.59 LC | 10B |
| 585 | 3-CF₃-phenyl | B | (3aα,4β,4aα,5aα,6β,6aα)-4,4a,5,5a,6,6a-Hexahydro-2-[3-(trifluoromethyl)phenyl]-4,6-methanocycloprop[f]isoindole-1,3(2H,3aH)-dione. | 3.34 LC | 11B |

TABLE 7-continued

| Ex. No. | —L—G | A/B | Compound Name | Retention Time Min. | Procedure of Example |
|---|---|---|---|---|---|
| 586 | 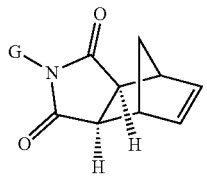 | B | (3aα,4β,4aα,5aα,6β,6aα)-2-(3,5-Dichlorophenyl)-4,4a,5,5a,6,6a-hexahydro-4,6-methanocycloprop[f]isoindole-1,3(2H,3aH)-dione. | 3.68 LC | 11B |
| 587 | 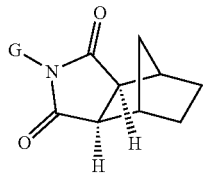 | B | (3aα,4β,4aα,5aα,6β,6aα)-4,4a,5,5a,6,6a-Hexahydro-2-[4-nitro-3-(trifluoromethyl)phenyl]-4,6-methanocycloprop[f]isoindole-1,3(2H,3aH)-dione. | 3.44 LC | 11B |
| 588 | (structure: 1,2-dihydro-4-methyl-2-oxo-7-quinolinyl) | B | (3aα,4β,4aα,5aα,6β,6aα)-2-(1,2-Dihydro-4-methyl-2-oxo-7-quinolinyl)-4,4a,5,5a,6,6a-hexahydro-4,6-methanocycloprop[f]isoindole-1,3(2H,3aH)-dione. | 2.77 LC | 11B |

EXAMPLES 589 TO 601

Additional compounds of the formula I were prepared by procedures analogous to those described above. The compounds of Examples 589 to 601 have the following structure:

A

[structure A]

B

[structure B]

where G, the compound name, retention time, and the procedure employed, are set forth in Table 8 (L is a bond for the compounds of Table 8).

The chromatography techniques used to determine the compound retention times of Table 8 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

*LCMS=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 8, where provided, were determined by MS (ES) by the formula m/z.

TABLE 8

| Ex. No. | —L—G | A/B | Compound Name | Retention Time Min. | Procedure of Example |
|---|---|---|---|---|---|
| 589 | (2-naphthalenyl) | A | (3aα,4β,7β,7aα)-3a,4,7,7a-tetrahydro-2-(2-naphthalenyl)-4,7-methano-1H-isoindole-1,3(2H)-dione. | 1.68 *LCMS | 3B |

TABLE 8-continued

| Ex. No. | —L—G | A/B | Compound Name | Retention Time Min. | Procedure of Example |
|---|---|---|---|---|---|
| 590 | 1-naphthyl | B | (3aα,4β,7β,7aα)-Hexahydro-2-(1-naphthalenyl)-4,7-methano-1H-isoindole-1,3(2H)-dione. | 1.57 *LCMS | 4B |
| 591 | 3,5-dichlorophenyl | A | (3aα,4β,7β,7aα)-2-(3,5-Dichlorophenyl)-3a,4,7,7a-tetrahydro-4,7-methano-1H-isoindole-1,3(2H)-dione. | 3.53 LCMS | 3B |
| 592 | 3-(trifluoromethyl)phenyl | A | (3aα,4β,7β,7aα)-3a,4,7,7a-Tetrahydro-2-[3-(trifluoromethyl)phenyl]-4,7-methano-1H-isoindole-1,3(2H)-dione. | 3.16 LCMS | 3B |
| 593 | 4-methyl-2-oxo-2H-1-benzopyran-7-yl | A | (3aα,4β,7β,7aα)-3a,4,7,7a-Tetrahydro-2-(4-methyl-2-oxo-2H-1-benzopyran-7-yl)-4,7-methano-1H-isoindole-1,3(2H)-dione. | 2.52 LCMS | 3B |
| 594 | 4-nitro-3-(trifluoromethyl)phenyl | A | (3aα,4β,7β,7aα)-3a,4,7,7a-Tetrahydro-2-[4-nitro-3-(trifluoromethyl)phenyl]-4,7-methano-1H-isoindole-1,3(2H)-dione. | 3.27 LCMS | 3B |
| 595 | 4-nitro-1-naphthyl | A | (3aα,4β,7β,7aα)-3a,4,7,7a-Tetrahydro-2-(4-nitro-1-naphthalenyl)-4,7-methano-1H-isoindole-1,3(2H)-dione. | 3.01 LCMS | 3B |
| 596 | 2-naphthyl | B | (3aα,4β,7β,7aα)-Hexahydro-2-(2-naphthalenyl)-4,7-methano-1H-isoindole-1,3(2H)-dione. | 1.45 *LCMS | 4B |
| 597 | 3-(trifluoromethyl)phenyl | B | (3aα,4β,7β,7aα)-Hexahydro-2-[3-(trifluoromethyl)phenyl]-4,7-methano-1H-isoindole-1,3(2H)-dione. | 3.25 LC | 4B |

TABLE 8-continued

| Ex. No. | —L—G | A/B | Compound Name | Retention Time Min. | Procedure of Example |
|---|---|---|---|---|---|
| 598 | 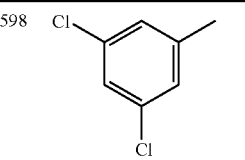 | B | (3aα,4β,7β,7aα)-2-(3,5-Dichlorophenyl)hexahydro-4,7-methano-1H-isoindole-1,3(2H)-dione. | 3.64 LC | 4B |
| 599 | 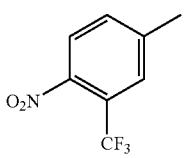 | B | (3aα,4β,7β,7aα)-Hexahydro-2-[4-nitro-3-(trifluoromethyl)phenyl]-4,7-methano-1H-isoindole-1,3(2H)-dione. | 3.41 LC | 4B |
| 600 | 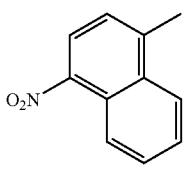 | B | (3aα,4β,7β,7aα)-Hexahydro-2-(4-nitro-1-naphthalenyl)-4,7-methano-1H-isoindole-1,3(2H)-dione. | 3.13 & 3.22 LC | 4B |
| 601 | 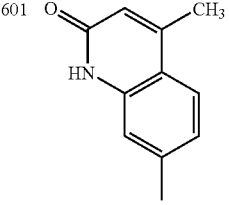 | B | (3aα,4β,7β,7aα)-2-(1,2-Dihydro-4-methyl-2-oxo-7-quinolinyl)hexahydro-4,7-methano-1H-isoindole-1,3(2H)-dione. | 2.68 LC | 4B |

EXAMPLES 602 TO 613

Additional compounds of the formula I were prepared by procedures analogous to those described above. The compounds of Examples 602 to 613 have the following structure:

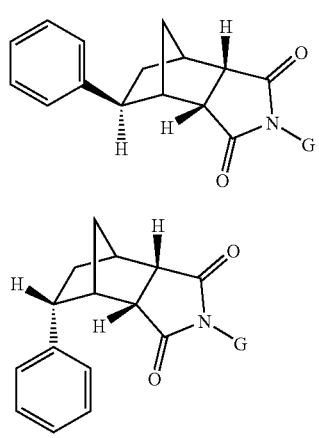

where G, the compound name, retention time, and the procedure employed, are set forth in Table 9 (L is a bond for the compounds of Table 9).

The chromatography techniques used to determine the compound retention times of Table 9 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

*LCMS=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 9, where provided, were determined by MS (ES) by the formula m/z.

TABLE 9

| Ex. No. | —L—G | A/B | Compound Name | Retention Time Min. | Procedure of Example |
|---|---|---|---|---|---|
| 602 | 2-naphthyl | A | (3aα,4α,5α,7α,7aα)-Hexahydro-2-(2-naphthalenyl)-5-phenyl-4,7-methano-1H-isoindole-1,3(2H)-dione. | 1.95 *LCMS | 7C |
| 603 | 3-(CF$_3$)phenyl | A | (3aα,4α,5α,7α,7aα)-Hexahydro-5-phenyl-2-[3-(trifluoromethyl)phenyl]-4,7-methano-1H-isoindole-1,3(2H)-dione. | 1.94 *LCMS | 7C |
| 604 | 1-naphthyl | A | (3aα,4α,5α,7α,7aα)-Hexahydro-2-(1-naphthalenyl)-5-phenyl-4,7-methano-1H-isoindole-1,3(2H)-dione. | 1.83 *LCMS | 7C |
| 605 | 3,4-dichlorophenyl | A | (3aα,4α,5α,7α,7aα)-2-(3,4-Dichlorophenyl)hexahydro-5-phenyl-4,7-methano-1H-isoindole-1,3(2H)-dione. | 1.97 *LCMS | 7C |
| 606 | 3,5-dichlorophenyl | A | (3aα,4α,5α,7α,7aα)-2-(3,5-Dichlorophenyl)hexahydro-5-phenyl-4,7-methano-1H-isoindole-1,3(2H)-dione. | 2.03 *LCMS | 7C |
| 607 | 1,2-dihydro-4-methyl-2-oxo-7-quinolinyl | A | (3aα,4α,5α,7α,7aα)-2-(1,2-Dihydro-4-methyl-2-oxo-7-quinolinyl)hexahydro-5-phenyl-4,7-methano-1H-isoindole-1,3(2H)-dione. | 3.26 LCMS | 7C |
| 608 | 1,2-dihydro-4-methyl-2-oxo-7-quinolinyl | B | (3aα,4α,5β,7α,7aα)-2-(1,2-Dihydro-4-methyl-2-oxo-7-quinolinyl)hexahydro-5-phenyl-4,7-methano-1H-isoindole-1,3(2H)-dione, trifluoroacetate(1:1). | 1.62 *LCMS | 9B |
| 609 | 3-(CF$_3$)phenyl | B | (3aα,4α,5β,7α,7aα)-Hexahydro-5-phenyl-2-[3-(trifluoromethyl)phenyl]-4,7-methano-1H-isoindole-1,3(2H)-dione. | 3.59 LCMS | 9B |

TABLE 9-continued

| Ex. No. | —L—G | A/B | Compound Name | Retention Time Min. | Procedure of Example |
|---|---|---|---|---|---|
| 610 | O₂N—C₆H₃(CF₃)— | A | (3aα,4α,5α,7α,7aα)-Hexahydro-2-[4-nitro-3-(trifluoromethyl)phenyl]-5-phenyl-4,7-methano-1H-isoindole-1,3(2H)-dione. | 3.81 LCMS | 7C |
| 611 | O₂N—naphthyl-CH₃ | A | (3aα,4α,5α,7α,7aα)-Hexahydro-2-(4-nitro-1-naphthalenyl)-5-phenyl-4,7-methano-1H-isoindole-1,3(2H)-dione. | 3.66 LCMS | 7C |
| 612 | O₂N—naphthyl-CH₃ | B | (3aα,4α,5β,7α,7aα)-Hexahydro-2-(4-nitro-1-naphthalenyl)-5-phenyl-4,7-methano-1H-isoindole-1,3(2H)-dione. | 3.49 LCMS | 9B |
| 613 | O₂N—C₆H₃(CF₃)— | B | (3aα,4α,5β,7α,7aα)-Hexahydro-2-[4-nitro-3-(trifluoromethyl)phenyl]-5-phenyl-4,7-methano-1H-isoindole-1,3(2H)-dione. | 3.68 LCMS | 9B |

EXAMPLES 614 TO 621

Additional compounds of the formula I were prepared by procedures analogous to those described above. The compounds of Examples 614 to 621 have the following structure:

A
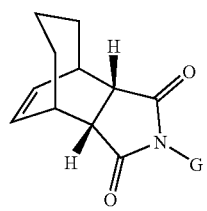

B
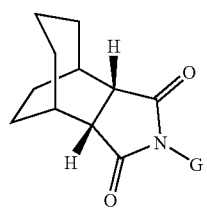

where G, the compound name, retention time, and the procedure employed are set forth in Table 10 (L is a bond for the compounds of Table 10).

The chromatography techniques used to determine the compound retention times of Table 10 are as follows:

LCMS=YMC S5 ODS column, 4.6×50 mm eluting with 10-90% MeOH/H₂O over 4 minutes containing 0.1% TFA; 4 mL/min, monitoring at 220 nm.

*LCMS=YMC S5 ODS column, 4.6×50 mm eluting with 10-90% MeOH/H₂O over 2 minutes containing 0.1% TFA; 4 mL/min, monitoring at 220 nm.

LC=YMC S5 ODS column 4.6×50 mm eluting with 10-90% MeOH/H₂O over 4 minutes containing 0.2% phosphoric acid, 4 mL/min, monitoring at 220 nm.

The molecular mass of the compounds listed in Table 10, where provided, were determined by MS (ES) by the formula m/z.

TABLE 10

| Ex. No. | —L—G | A/B | Compound Name | Retention Time Min. | Procedure of Example |
|---|---|---|---|---|---|
| 614 | (4-nitro-1-naphthalenyl group, O₂N) | A | (3aα,4β,8β,8aα)-4,5,6,7,8,8a-Hexahydro-2-(4-nitro-1-naphthalenyl)-4,8-ethenocyclohepta[c]pyrrole-1,3(2H,3aH)-dione. | 1.81 *LCMS | 1B |
| 615 | (4-nitrophenyl group, O₂N) | A | (3aα,4β,8β,8aα)-4,5,6,7,8,8a-Hexahydro-2-(4-nitrophenyl)-4,8-ethenocyclohepta[c]pyrrole-1,3(2H,3aH)-dione. | 1.72 *LCMS | 1B |
| 616 | (2-naphthalenyl group) | A | (3aα,4β,8β,8aα)-4,5,6,7,8,8a-Hexahydro-2-(2-naphthalenyl)-4,8-ethenocyclohepta[c]pyrrole-1,3(2H,3aH)-dione. | 2.01 *LCMS | 1B |
| 617 | (4-Bromo-3-(trifluoromethyl)phenyl group, Br, CF₃) | A | (3aα,4β,8β,8aα)-2-[4-Bromo-3-(trifluoromethyl)phenyl]-4,5,6,7,8,8a-hexahydro-4,8-ethenocyclohepta[c]pyrrole-1,3(2H,3aH)-dione. | 2.04 *LCMS | 1B |
| 618 | (3,4-dichlorophenyl group, Cl, Cl) | B | (3aα,4β,8β,8aα)-2-(3,4-Dichlorophenyl)-4,5,6,7,8,8a-hexahydro-4,8-ethanocyclohepta[c]pyrrole-1,3(2H,3aH)-dione. | 2.09 *LCMS | 2B |
| 619 | (4-nitro-1-naphthalenyl group, O₂N) | B | (3aα,4β,8β,8aα)-4,5,6,7,8,8a-Hexahydro-2-(4-nitro-1-naphthalenyl)-4,8-ethanocyclohepta[c]pyrrole-1,3(2H,3aH)-dione. | 1.91 *LCMS | 2B |
| 620 | (3,4-dichlorophenyl group, Cl, Cl) | A | (3aα,4β,8β,8aα)-2-(3,4-Dichlorophenyl)-4,5,6,7,8,8a-hexahydro-4,8-ethenocyclohepta[c]pyrrole-1,3(2H,3aH)-dione. | 1.94 *LCMS | 1B |
| 621 | (3,5-dichlorophenyl group, Cl, Cl) | A | (3aα,4β,8β,8aα)-2-(3,5-Dichlorophenyl)-4,5,6,7,8,8a-hexahydro-4,8-ethenocyclohepta[c]pyrrole-1,3(2H,3aH)-dione. | 1.89 *LCMS | 1B |

EXAMPLES 622 TO 635

Additional compounds of the formula I were prepared by procedures analogous to those described above. The compounds of Examples 622 to 635 have the following structure:

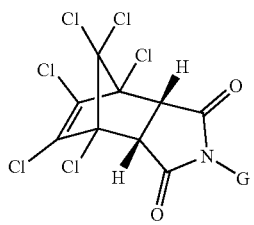

where G, the compound name, retention time, and the procedure employed are set forth in Table 11 (L is a bond for the compounds of Table 11).

The chromatography techniques used to determine the compound retention times of Table 11 are as follows:

LCMS=YMC S5 ODS column, 4.6×50 mm eluting with 10-90% MeOH/$H_2O$ over 4 minutes containing 0.1% TFA; 4 mL/min, monitoring at 220 nm.

*LCMS=YMC S5 ODS column, 4.6×50 mm eluting with 10-90% MeOH/$H_2O$ over 2 minutes containing 0.1% TFA; 4 mL/min, monitoring at 220 nm.

LC=YMC S5 ODS column 4.6×50 mm eluting with 10-90% MeOH/$H_2O$ over 4 minutes containing 0.2% phosphoric acid, 4 mL/min, monitoring at 220 nm.

The molecular mass of the compounds listed in Table 11, where provided, were determined by MS (ES) by the formula m/z.

TABLE 11

| Ex. No. | —L—G | Compound Name | Retention Time Min. | Procedure of Example |
|---|---|---|---|---|
| 622 | 3-nitrophenyl | (3aα,4α,7α,7aα)-4,5,6,7,8,8-Hexachloro-3a,4,7,7a-tetrahydro-2-(3-nitrophenyl)-4,7-methano-1H-isoindole-1,3(2H)-dione. | | 51 |
| 623 | 4-(methylthio)phenyl | (3aα,4α,7α,7aα)-4,5,6,7,8,8-Hexachloro-2-[4-(methylthio)phenyl]-3a,4,7,7a-tetrahydro-4,7-methano-1H-isoindole-1,3(2H)-dione. | | 51 |
| 624 | 5-chloro-2-methoxyphenyl | (3aα,4α,7α,7aα)-4,5,6,7,8,8-Hexachloro-2-(5-chloro-2-methoxyphenyl)-3a,4,7,7a-tetrahydro-4,7-methano-1H-isoindole-1,3(2H)-dione. | | 51 |
| 625 | 3-methoxyphenyl | (3aα,4α,7α,7aα)-4,5,6,7,8,8-Hexachloro-3a,4,7,7a-tetrahydro-2-(3-methoxyphenyl)-4,7-methano-1H-isoindole-1,3(2H)-dione. | | 51 |
| 626 | 1-naphthalenyl | (3aα,4α,7α,7aα)-4,5,6,7,8,8-Hexachloro-3a,4,7,7a-tetrahydro-2-(1-naphthalenyl)-4,7-methano-1H-isoindole-1,3(2H)-dione. | | 51 |
| 627 | 2,3-dimethylphenyl | (3aα,4α,7α,7aα)-4,5,6,7,8,8-Hexachloro-2-(2,3-dimethylphenyl)-3a,4,7,7a-tetrahydro-4,7-methano-1H-isoindole-1,3(2H)-dione. | | 51 |

TABLE 11-continued

| Ex. No. | —L—G | Compound Name | Retention Time Min. | Procedure of Example |
|---|---|---|---|---|
| 628 | 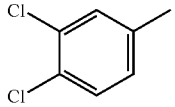 | (3aα,4α,7α,7aα)-4,5,6,7,8,8-Hexachloro-2-(3,4-dichlorophenyl)-3a,4,7,7a-tetrahydro-4,7-methano-1H-isoindole-1,3(2H)-dione. | | 51 |
| 629 | 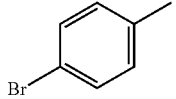 | (3aα,4α,7α,7aα)-2-(4-Bromophenyl)4,5,6,7,8,8-hexachloro-3a,4,7,7a-tetrahydro-4,7-methano-1H-isoindole-1,3(2H)-dione. | | 51 |
| 630 | 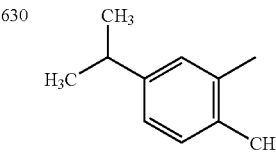 | (3aα,4α,7α,7aα)-4,5,6,7,8,8-Hexachloro-3a,4,7,7a-tetrahydro-2-[2-methyl-5-(1-methylethyl)phenyl]-4,7-methano-1H-isoindole-1,3(2H)-dione. | | 51 |
| 631 | 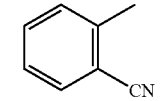 | (3aα,4α,7α,7aα)-N-(2-cyanophenyl)-1,4,5,6,7,7-hexachloro-5-norbornene-2,3-dicarboximide | | 51 |
| 632 | 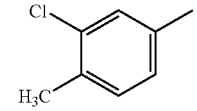 | (3aα,4α,7α,7aα)-4,5,6,7,8,8-Hexachloro-2-(3-chloro-4-methylphenyl)-3a,4,7,7a-tetrahydro-4,7-methano-1H-isoindole-1,3(2H)-dione. | | 51 |
| 633 | 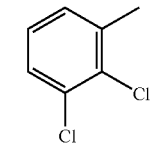 | (3aα,4α,7α,7aα)-4,5,6,7,8,8-Hexachloro-2-(2,3-dichlorophenyl)-3a,4,7,7a-tetrahydro-4,7-methano-1H-isoindole-1,3(2H)-dione. | | 51 |
| 634 | 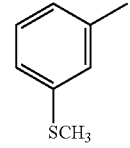 | (3aα,4α,7α,7aα)-4,5,6,7,8,8-Hexachloro-3a,4,7,7a-tetrahydro-2-[3-(methylthio)phenyl]-4,7-methano-1H-isoindole-1,3(2H)-dione. | | 51 |
| 635 | 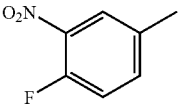 | (3aα,4α,7α,7aα)-4,5,6,7,8,8-Hexachloro-2-(4-fluoro-3-nitrophenyl)-3a,4,7,7a-tetrahydro-4,7-methano-1H-isoindole-1,3(2H)-dione. | | 51 |

EXAMPLES 636 TO 679

Additional compounds of the formula I were prepared by procedures analogous to those described above. The compounds of Examples 636 to 679 have the following structure:

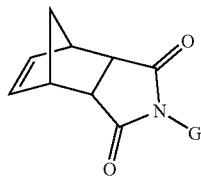

where G, the compound name, retention time and the procedure employed are set forth in Table 12 (L is a bond for the compounds of Table 12).

The chromatography techniques used to determine the compound retention times of Table 12 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

*LCMS=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H₂O over 4 minutes containing 0.2% phosphoric acid, 4 mL/min, monitoring at 220 nm.

The molecular mass of the compounds listed in Table 12, where provided, were determined by MS (ES) by the formula m/z.

TABLE 12

| Ex. No. | G | Compound Name | Retention Time Min. | Procedure of Example |
|---|---|---|---|---|
| 636 | 2,6-dimethylpyridinyl | 3a,4,7,7a-Tetrahydro-2-(6-methyl-2-pyridinyl)-4,7-methano-1H-isoindole-1,3(2H)-dione. | | 25D or 38A |
| 637 | 4-pyridinyl | 3a,4,7,7a-Tetrahydro-2-(4-pyridinyl)-4,7-methano-1H-isoindole-1,3(2H)-dione. | | 25D or 38A |
| 638 | 4-ethoxyphenyl | 2-(4-Ethoxyphenyl)-3a,4,7,7a-tetrahydro-4,7-methano-1H-isoindole-1,3(2H)-dione. | | 25D or 38A |
| 639 | 3-pyridinyl | 3a,4,7,7a-Tetrahydro-2-(3-pyridinyl)-4,7-methano-1H-isoindole-1,3(2H)-dione. | | 25D or 38A |
| 640 | 2-pyridinyl | 3a,4,7,7a-Tetrahydro-2-(2-pyridinyl)-4,7-methano-1H-isoindole-1,3(2H)-dione. | | 25D or 38A |
| 641 | 3-methyl-2-pyridinyl | 3a,4,7,7a-Tetrahydro-2-(3-methyl-2-pyridinyl)-4,7-methano-1H-isoindole-1,3(2H)-dione. | | 25D or 38A |
| 642 | N-(4,6-dimethylpyrimidin-2-yl)-4-methylbenzenesulfonamide | N-(4,6-Dimethyl-2-pyrmidinyl)-4-(1,3,3a,4,7,7a-hexahydro-1,3-dioxo-4,7-methano-2H-isoindol-2-yl)benzenesulfonamide. | | 25D or 38A |
| 643 | 4-(2-hydroxyethyl)phenyl | 3a,4,7,7a-Tetrahydro-2-[4-(2-hydroxyethyl)phenyl]-4,7-methano-1H-isoindole-1,3(2H)-dione. | | 25D or 38A |
| 644 | 2-mercaptophenyl | 3a,4,7,7a-Tetrahydro-2-(2-mercaptophenyl)-4,7-methano-1H-isoindole-1,3(2H)-dione. | | 25D or 38A |
| 645 | 2-carboxyphenyl | 2-(1,3,3a,4,7,7a-Hexahydro-1,3-dioxo-4,7-methano-2H-isoindol-2-yl)benzoic acid. | | 25D or 38A |

TABLE 12-continued

| Ex. No. | G | Compound Name | Retention Time Min. | Procedure of Example |
|---|---|---|---|---|
| 646 | | 2-(1,3,3a,4,7,7a-Hexahydro-1,3-dioxo-4,7-methano-2H-isoindol-2-yl)benzoic acid, methyl ester. | | 25D or 38A |
| 647 | | 4-(1,3,3a,4,7,7a-Hexahydro-1,3-dioxo-4,7-methano-2H-isoindol-2-yl)benzoic acid. | | 25D or 38A |
| 648 | | 3-(1,3,3a,4,7,7a-Hexahydro-1,3-dioxo-4,7-methano-2H-isoindol-2-yl)benzoic acid, methyl ester. | | 25D or 38A |
| 649 | | 4-(1,3,3a,4,7,7a-Hexahydro-1,3-dioxo-4,7-methano-2H-isoindol-2-yl)benzenesulfonamide. | | 25D or 38A |
| 650 | | N-(4,5-Dihydro-5-methyl-3-isoxazolyl)-4-(1,3,3a,4,7,7a-hexahydro-1,3-dioxo-4,7-methano-2H-isoindol-2-yl)benzenesulfonamide. | | 25D or 38A |
| 651 | | 3a,4,7,7a-Tetrahydro-2-(2-hydroxyphenyl)-4,7-methano-1H-isoindole-1,3(2H)-dione. | | 25D or 38A |
| 652 | | 3a,4,7,7a-Tetrahydro-2-[4-(phenylmethoxy)phenyl]-4,7-methano-1H-isoindole-1,3(2H)-dione. | | 25D or 38A |
| 653 | | 3a,4,7,7a-Tetrahydro-2-[2-(phenylmethoxy)phenyl]-4,7-methano-1H-isoindole-1,3(2H)-dione. | | 25D or 38A |
| 654 | | 3a,4,7,7a-Tetrahydro-2-[3-(phenylmethoxy)phenyl]-4,7-methano-1H-isoindole-1,3(2H)-dione. | | 25D or 38A |

TABLE 12-continued

| Ex. No. | G | Compound Name | Retention Time Min. | Procedure of Example |
|---|---|---|---|---|
| 655 | | 3a,4,7,7a-Tetrahydro-2-[4-[(4-nitrophenyl)methoxy]phenyl]-4,7-methano-1H-isoindole-1,3(2H)-dione. | | 25D or 38A |
| 656 | | 3a,4,7,7a-Tetrahydro-2-[2-[(4-nitrophenyl)methoxy]phenyl]-4,7-methano-1H-isoindole-1,3(2H)-dione. | | 25D or 38A |
| 657 | | 3a,4,7,7a-Tetrahydro-2-[3-[(4-nitrophenyl)methoxy]phenyl]-4,7-methano-1H-isoindole-1,3(2H)-dione. | | 25D or 38A |
| 658 | | 3a,4,7,7a-Tetrahydro-2-[4-[(4-methylphenyl)methoxy]phenyl]-4,7-methano-1H-isoindole-1,3(2H)-dione. | | 25D or 38A |
| 659 | | 3a,4,7,7a-Tetrahydro-2-[3-[(4-methylphenyl)methoxy]phenyl]-4,7-methano-1H-isoindole-1,3(2H)-dione. | | 25D or 38A |
| 660 | | 3a,4,7,7a-Tetrahydro-2-[2-[(4-methylphenyl)methoxy]phenyl]-4,7-methano-1H-isoindole-1,3(2H)-dione. | | 25D or 38A |

TABLE 12-continued

| Ex. No. | G | Compound Name | Retention Time Min. | Procedure of Example |
|---|---|---|---|---|
| 661 | | 2-[4-[(4-Butylphenyl)methoxy]phenyl]-3a,4,7,7a-tetrahydro-4,7-methano-1H-isoindole-1,3(2H)-dione. | | 25D or 38A |
| 662 | | 2-[2-[(4-Butylphenyl)methoxy]phenyl]-3a,4,7,7a-tetrahydro-4,7-methano-1H-isoindole-1,3(2H)-dione. | | 25D or 38A |
| 663 | | 2-[3-[(4-Butylphenyl)methoxy]phenyl]-3a,4,7,7a-tetrahydro-4,7-methano-1H-isoindole-1,3(2H)-dione. | | 25D or 38A |
| 664 | | 2-[4-[(2-Chlorophenyl)methoxy]phenyl]-3a,4,7,7a-tetrahydro-4,7-methano-1H-isoindole-1,3(2H)-dione. | | 25D or 38A |
| 665 | | 2-[4-[(4-Chlorophenyl)methoxy]phenyl]-3a,4,7,7a-tetrahydro-4,7-methano-1H-isoindole-1,3(2H)-dione. | | 25D or 38A |
| 666 | | 2-[2-[(4-Chlorophenyl)methoxy]phenyl]-3a,4,7,7a-tetrahydro-4,7-methano-1H-isoindole-1,3(2H)-dione. | | 25D or 38A |
| 667 | | 2-[2-[(2-Chlorophenyl)methoxy]phenyl]-3a,4,7,7a-tetrahydro-4,7-methano-1H-isoindole-1,3(2H)-dione. | | 25D or 38A |
| 668 | | 2-[3-[(2-Chlorophenyl)methoxy]phenyl]-3a,4,7,7a-tetrahydro-4,7-methano-1H-isoindole-1,3(2H)-dione. | | 25D or 38A |

TABLE 12-continued

| Ex. No. | G | Compound Name | Retention Time Min. | Procedure of Example |
|---|---|---|---|---|
| 669 | | 2-[3-[(4-Chlorophenyl)methoxy]phenyl]-3a,4,7,7a-tetrahydro-4,7-methano-1H-isoindole-1,3(2H)-dione. | | 25D or 38A |
| 670 | | 3a,4,7,7a-Tetrahydro-2-phenyl-4,7-methano-1H-isoindole-1,3(2H)-dione. | | 25D or 38A |
| 671 | | 2-[(Benzoyloxy)phenyl]-3a,4,7,7a-tetrahydro-4,7-methano-1H-isoindole-1,3(2H)-dione. | | 25D or 38A |
| 672 | | 2-[3-(3,4-Dimethylbenzoyl)phenyl]-3a,4,7,7a-tetrahydro-4,7-methano-1H-isoindole-1,3(2H)-dione. | | 25D or 38A |
| 673 | | 2-(3,4-Dimethylphenyl)-3a,4,7,7a-tetrahydro-4,7-methano-1H-isoindole-1,3(2H)-dione. | | 25D or 38A |
| 674 | | 4-(1,3,3a,4,7,7a-Hexahydro-1,3-dioxo-4,7-methano-2H-isoindol-2-yl)benzoic acid, ethyl ester. | | 25D or 38A |
| 675 | | 5-(1,3,3a,4,7,7a-Hexahydro-1,3-dioxo-4,7-methano-2H-isoindol-2-yl)-1,3-benzenedioic acid. | | 25D or 38A |
| 676 | | 4-[2-(1,3,3a,4,7,7a-Hexahydro-1,3-dioxo-4,7-methano-2H-isoindol-2-yl)phenoxy]benzonitrile. | | 25D or 38A |

TABLE 12-continued

| Ex. No. | G | Compound Name | Retention Time Min. | Procedure of Example |
|---|---|---|---|---|
| 677 | (H3C-O-phenyl with Cl) | 2-(5-Chloro-2-methoxyphenyl)-3a,4,7,7a-tetrahydro-4,7-methano-1H-isoindole-1,3(2H)-dione. | | 25D or 38A |
| 678 | (H3C-C(=O)-phenyl) | 2-(2-Acetylphenyl)-3a,4,7,7a-tetrahydro-4,7-methano-1H-isoindole-1,3(2H)-dione. | | 25D or 38A |
| 679 | (oxazolyl-phenyl-methyl) | 3a,4,7,7a-Tetrahydro-2-[4-(5-oxazolyl)phenyl]-4,7-methano-1H-isoindole-1,3(2H)-dione. | | 25D or 38A |

EXAMPLES 680 TO 702

Additional compounds of the formula I were prepared by procedures analogous to those described above. The compounds of Examples 680 to 702 have the structures, compound names, retention times, and were prepared by the procedures indicated in Table 13.

The chromatography techniques used to determine the compound retention times of Table 13 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

*LCMS=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 13, where provided, were determined by MS (ES) by the formula m/z.

ND=no data provided; compound was unstable under chromatography conditions employed

TABLE 13

| Ex. No. | Structure | Compound Name | Retention Time Min. | Procedure of Example |
|---|---|---|---|---|
| 680 | (bicyclic structure with H3C, CF3, Br substituents) | (3aα,4α,7α,7aα)-2-[4-Bromo-3-(trifluoromethyl)phenyl]-3a,4,7,7a-tetrahydro-5-methyl-4,7-methano-1H-isoindole-1,3(2H)-dione | 7.72 LCMS | 30 |

TABLE 13-continued

| Ex. No. | Structure | Compound Name | Retention Time Min. | Procedure of Example |
|---|---|---|---|---|
| 681 | 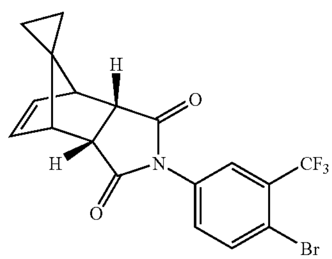 | (3aα,4α,7α,7aα)-2'-[4-Bromo-3-(trifluoromethyl)phenyl]-3'a,4',7',7'a-tetrahydrospiro-[cyclopropane-1,8'-[4,7]methano[1H]-isoindole]-1',3'(2'H)-dione. | 3.45 LC | 12B |
| 682 | 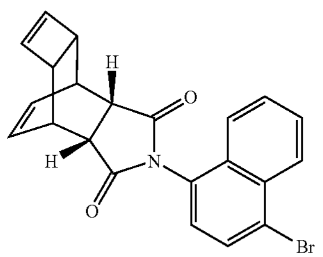 | (3aα,4β,4aα 6aα,7β,7aα)-2-(4-Bromo-1-naphthalenyl)-3a,4,4a,6a,7,7a-hexahydro-4,7-etheno-1H-cyclobut[f]isoindole-1,3(2H)-dione. | 3.597 LC | 29 |
| 683 | 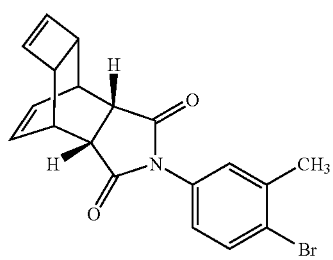 | (3aα,4β,4aα 6aα,7β,7aα)-2-(4-Bromo-3-methylphenyl)-3a,4,4a,6a,7,7a-hexahydro-4,7-etheno-1H-cyclobut[f]isoindole-1,3(2H)-dione | 3.61 LC | 29 |
| 684 | 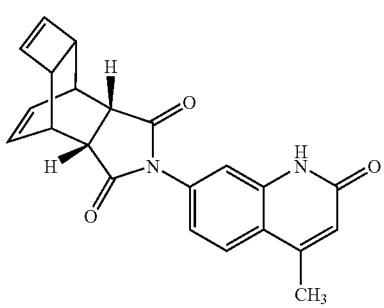 | (3aα,4β,4aα 6aα,7β,7aα)-2-(1,2-Dihydro-4-methyl-2-oxo-7-quinolinyl)-3a,4,4a,6a,7,7a-hexahydro-4,7-etheno-1H-cyclobut[f]isoindole-1,3(2H)-dione. | 2.73 LC | 29 |
| 685 | 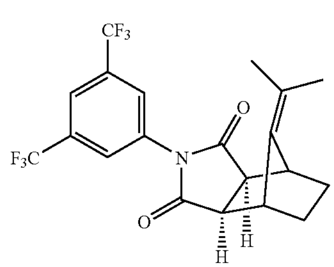 | (3aα,4β,7β,7aα)-2-[3,5-Bis(trifluoromethyl)phenyl]hexahydro-8-(1-methylethylidene)-4,7-methano-1H-isoindole-1,3(2H)-dione. | 450 LC | 31B |

TABLE 13-continued

| Ex. No. | Structure | Compound Name | Retention Time Min. | Procedure of Example |
|---|---|---|---|---|
| 686 | 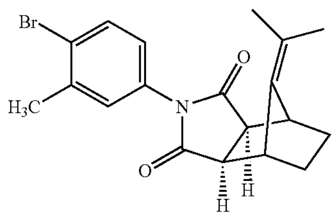 | (3aα,4β,7β,7aα)-2-(4-Bromo-3-methylphenyl)hexa-hydro-8-(1-methylethylidene)-4,7-methano-1H-isoindole-1,3(2H)-dione | 4.27 LC | 31B |
| 687 | 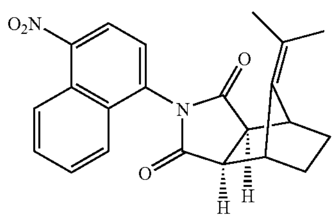 | (3aα,4β,7β,7aα)-Hexahydro-8-(1-methylethylidene)-2-(4-nitro-1-naphthalenyl)-4,7-methano-1H-isoindole-1,3(2H)-dione. | 4.06 LC | 31B |
| 688 | 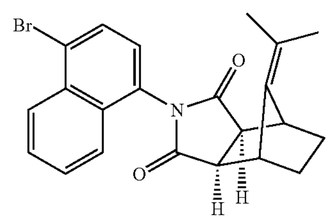 | (3aα,4β,7β,7aα)-2-(4-Bromo-1-naphthalenyl)hexa-hydro-8-(1-methylethylidene)-4,7-methano-1H-isoindole-1,3(2H)-dione. | 4.30 LC | 31B |
| 689 | 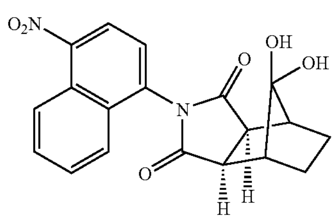 | (3aα,4β,7β,7aα)-Hexahydro-8,8-dihydroxy-2-(4-nitro-1-naphthalenyl)-4,7-methano-1H-isoindole-1,3(2H)-dione. | ND | 32 |
| 690 | 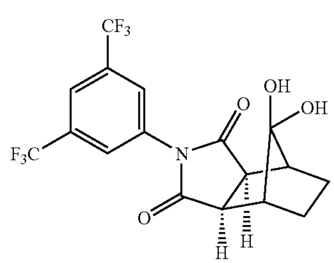 | (3aα,4β,7β,7aα)-2-[3,5-Bis(trifluoromethyl)-phenyl]hexahydro-8,8-dihydroxy-4,7-methano-1H-isoindole-1,3(2H)-dione. | ND HRMS (ESI): m/z 408.0664 [M − H]⁻ | 32 |
| 691 | 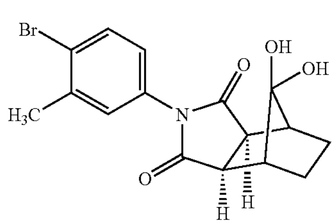 | (3aα,4β,7β,7aα)-2-(4-Bromo-3-methylphenyl)hexa-hydro-8,8-dihydroxy-4,7-methano-1H-isoindole-1,3(2H)-dione. | HRMS (ESI) m/z 364.0199 [M − H]⁻ | 32 |

TABLE 13-continued

| Ex. No. | Structure | Compound Name | Retention Time Min. | Procedure of Example |
|---|---|---|---|---|
| 692 | 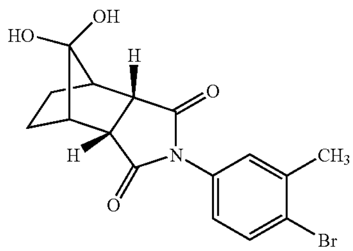 | (3aα,4α,7α,7aα)-2-(4-Bromo-3-methylphenyl)hexahydro-8,8-dihydroxy-4,7-methano-1H-isoindole-1,3(2H)-dione. | ND | 18 |
| 693 | 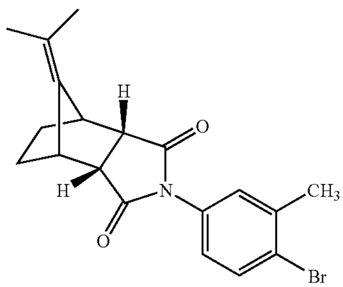 | (3aα,4α,7α,7aα)-2-(4-Bromo-3-methylphenyl)hexahydro-8-(1-methylethylidene)-4,7-methano-1H-isoindole-1,3(2H)-dione. | 4.35 LC | 17B |
| 694 | 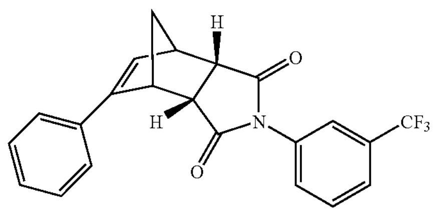 | (3aα,4α,7α,7aα)-3a,4,7,7a-Tetrahydro-5-phenyl-2-[3-(trifluoromethyl)-phenyl]-4,7-methano-1H-isoindole-1,3(2H)-dione. | 3.57 LC | 8C |
| 695 | 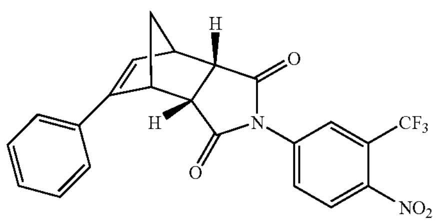 | (3aα,4α,7α,7aα)-3a,4,7,7a-Tetrahydro-2-[4-nitro-3-(trifluoromethyl)-phenyl]-5-phenyl-4,7-methano-1H-isoindole-1,3(2H)-dione. | 3.69 LC | 8C |
| 696 | 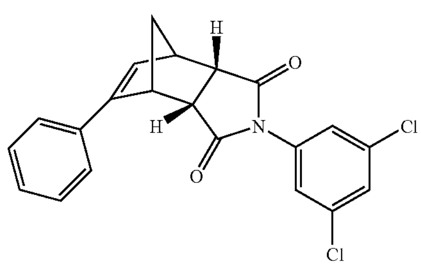 | (3aα,4α,7α,7aα)-2-(3,5-Dichlorophenyl)-3a,4,7,7a-tetrahydro-5-phenyl-4,7-methano-1H-isoindole-1,3(2H)-dione. | 3.86 LC | 8C |
| 697 | 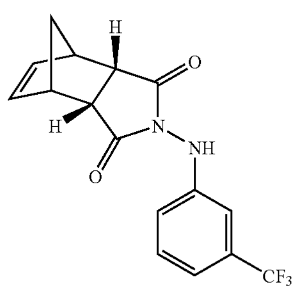 | (3aα,4α,7α,7aα)-Tetrahydro-2-[[3-(trifluoromethyl)phenyl]-amino]-4,7-methano-1H-isoindole-1,3(2H)-dione. | 3.00 LC | 35 |

TABLE 13-continued

| Ex. No. | Structure | Compound Name | Retention Time Min. | Procedure of Example |
|---|---|---|---|---|
| 698 | 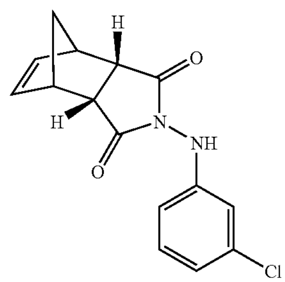 | (3aα,4α,7α,7aα)-2-[(3-Chlorophenyl)amino]-3a,4,7,7a-tetrahydro-4,7-methano-1H-isoindole-1,3(2H)-dione. | 2.78 LC | 35 |
| 699 | 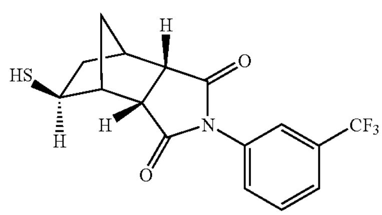 | (3aα,4α,5α,7α,7aα)-Hexahydro-5-mercapto-2-[3-(trifluoromethyl)phenyl]-4,7-methano-1H-isoindole-1,3(2H)-dione. | 3.19 LC | 43B |
| 700 | 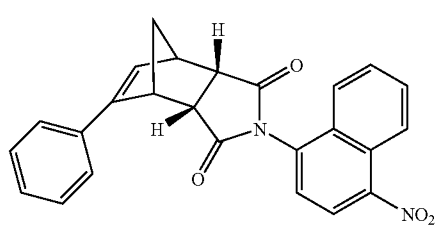 | (3aα,4α,7α,7aα)-3a,4,7,7a-Tetrahydro-2-(4-nitro-1-naphthalenyl)-5-phenyl-4,7-methano-1H-isoindole-1,3(2H)-dione. | 3.51 LC | 8C |
| 701 | 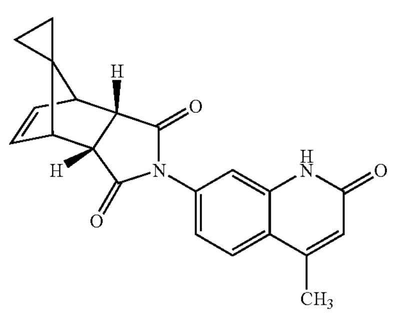 | (3a'α,4'α,7'α,7a'α)-2'-(1,2-Dihydro-4-methyl-2-oxo-7-qiunolinyl)-3a',4',7',7a'-tetrahydrospiro[cyclopropane-1,8'-[4,7]methano[1H]isoindole]-1',3'(2'H)-dione. | 2.66 LC | 12B |
| 702 | 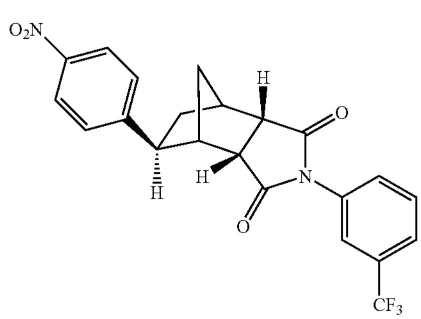 | (3aα,4α,5α,7α,7aα)-Hexahydro-5-(4-nitropheny)-2-[3-(trifluoromethyl)phenyl]-4,7-methano-1H-isoindole-1,3(2H)-dione. | 3.60 LCMS | 7C |

EXAMPLES 703 TO 755

Additional compounds of the formula I can be prepared by procedures analogous to those described above. The compounds of Examples 703 to 755 have the structures, compound names, and retention times, and can be prepared by the procedure indicated in Table 14.

The chromatography techniques used to determine the compound retention times of Table 14 are as follows:

LCMS=YMC S5 ODS column, 4.6×50 mm eluting with 10-90% MeOH/H₂O over 4 minutes containing 0.1% TFA; 4 mL/min, monitoring at 220 nm.

*LCMS=YMC S5 ODS column, 4.6×50 mm eluting with 10-90% MeOH/H₂O over 2 minutes containing 0.1% TFA; 4 mL/min, monitoring at 220 nm.

LC=YMC S5 ODS column 4.6×50 mm eluting with 10-90% MeOH/H₂O over 4 minutes containing 0.2% phosphoric acid, 4 mL/min, monitoring at 220 nm.

The molecular mass of the compounds listed in Table 14, where provided, were determined by MS (ES) by the formula m/z.

TABLE 14

| Ex. No. | Structure | Compound Name | Retention Time Min | Procedure of Example |
|---|---|---|---|---|
| 703 | 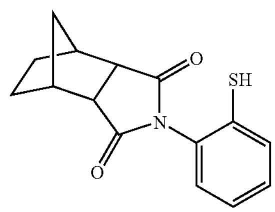 | Hexahydro-2-(2-mercaptophenyl)-4,7-methano-1H-isoindole-1,3(2H)-dione. | | 39B |
| 704 | 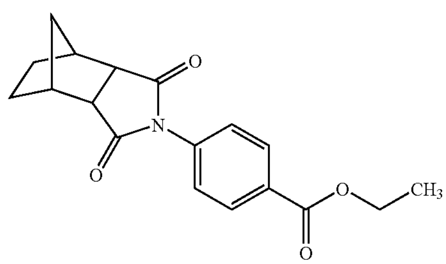 | 4-(Octahydro-1,3-dioxo-4,7-methano-2H-isoindol-2-yl)-benzoic acid, ethyl ester. | | 39B |
| 705 | 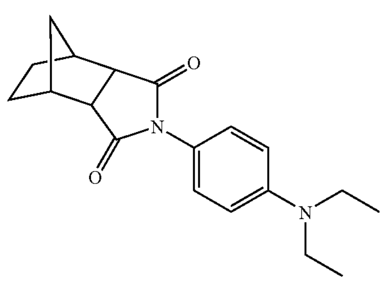 | 2-[4-(Diethylamino)phenyl]-hexahydro-4,7-methano-1H-isoindole-1,3(2H)-dione. | | 39B |
| 706 | 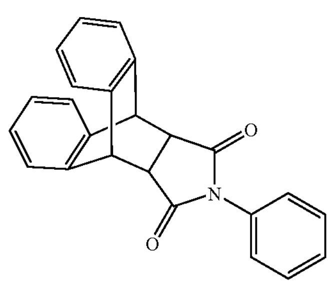 | 3a,4,9,9a-Tetrahydro-2-phenyl-4,9[1',2']-benzeno-1H-benz[f]isoindole-1,3(2H)-dione. | | |

TABLE 14-continued

| Ex. No. | Structure | Compound Name | Retention Time Min | Procedure of Example |
|---|---|---|---|---|
| 707 | 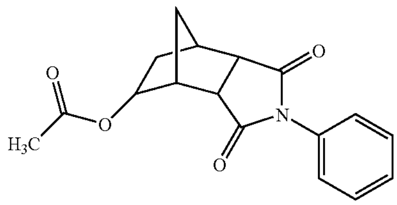 | 5-(Acetyloxy)hexahydro-2-phenyl-4,7-methano-1H-isoindole-1,3(2H)-dione. | | |
| 708 | 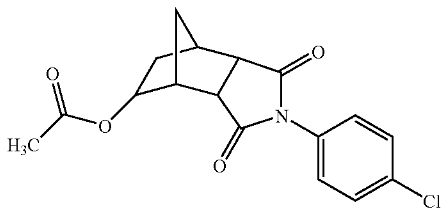 | 5-(Acetyloxy)-2-(4-chlorophenyl)hexahydro-4,7-methano-1H-isoindole-1,3(2H)-dione. | | |
| 709 | 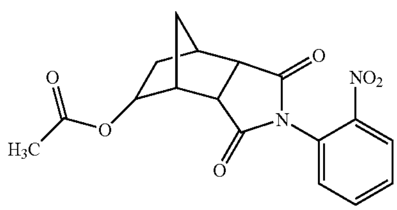 | 5-(Acetyloxy)hexahydro-2-(2-nitrophenyl)-4,7-methano-1H-isoindole-1,3(2H)-dione. | | |
| 710 | 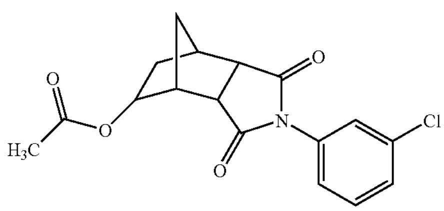 | 5-(Acetyloxy)-2-(3-chlorophenyl)hexahydro-4,7-methano-1H-isoindole-1,3(2H)-dione. | | |
| 711 | 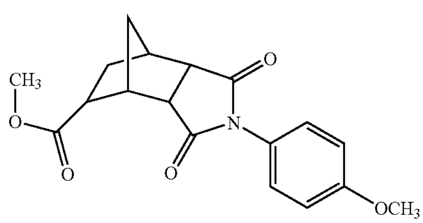 | Octahydro-2-(4-methoxyphenyl)-1,3-dioxo-4,7-methano-1H-isoindole-5-carboxylic acid, methyl ester. | | |
| 712 | 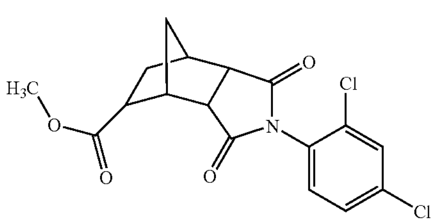 | 2-(2,4-Dichlorophenyl)octahydro-1,3-dioxo-4,7-methano-1H-isoindole-5-carboxylic acid, methyl ester. | | |
| 713 | 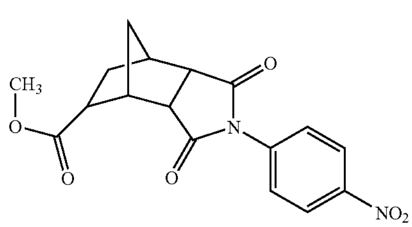 | Octahydro-2-(4-nitrophenyl)-1,3-dioxo-4,7-methano-1H-isoindole-5-carboxylic acid, methyl ester. | | |

TABLE 14-continued

| Ex. No. | Structure | Compound Name | Retention Time Min | Procedure of Example |
|---|---|---|---|---|
| 714 | 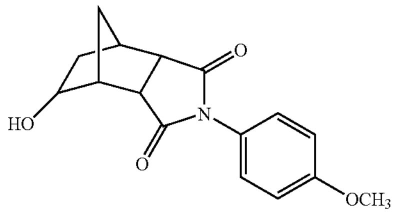 | Hexahydro-5-hydroxy-2-(4-methoxyphenyl)-4,7-methano-1H-isoindole-1,3(2H)-dione. | | |
| 715 | 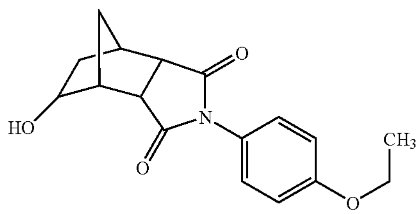 | 2-(4-Ethoxyphenyl)hexahydro-5-hydroxy-4,7-methano-1H-isoindole-1,3(2H)-dione. | | |
| 716 | 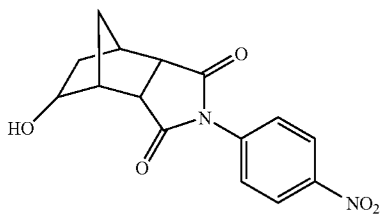 | Hexahydro-5-hydroxy-2-(4-nitrophenyl)-4,7-methano-1H-isoindole-1,3(2H)-dione. | | |
| 717 | 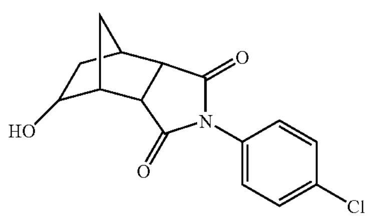 | 2-(4-Chlorophenyl)hexahydro-5-hydroxy-4,7-methano-1H-isoindole-1,3(2H)-dione. | | |
| 718 | 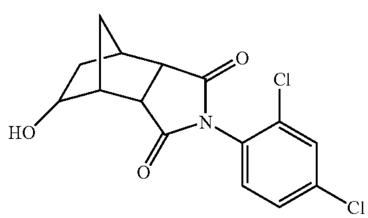 | 2-(2,4-Dichlorophenyl)hexahydro-5-hydroxy-4,7-methano-1H-isoindole-1,3(2H)-dione. | | |
| 719 | 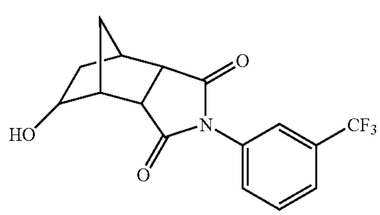 | Hexahydro-5-hydroxy-2-[3-(trifluoromethyl)phenyl]-4,7-methano-1H-isoindole-1,3(2H)-dione. | | |
| 720 | 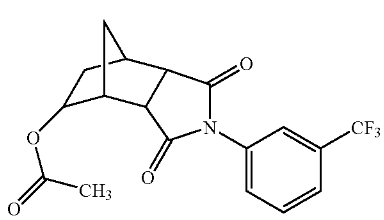 | 5-(Acetyloxy)hexahydro-2-[3-(trifluoromethyl)phenyl]-4,7-methano-1H-isoindole-1,3(2H)-dione. | | |

TABLE 14-continued

| Ex. No. | Structure | Compound Name | Retention Time Min | Procedure of Example |
|---|---|---|---|---|
| 721 | 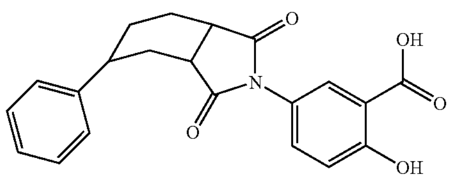 | 2-Hydroxy-5-(octahydro-1,3-dioxo-5-phenyl-1H-isoindol-2-yl)-benzoic acid. | | |
| 722 | 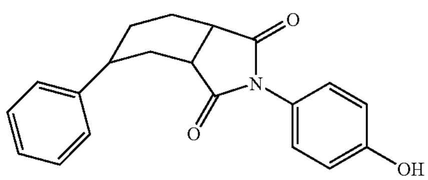 | Hexahydro-2-(4-hydroxyphenyl)-5-phenyl-1H-isoindole-1,3(2H)-dione. | | |
| 723 | 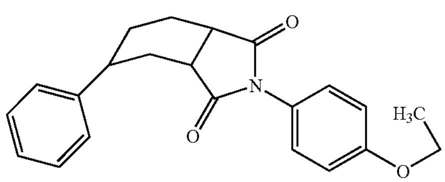 | 2-(4-Ethoxyphenyl)hexahydro-5-phenyl-1H-isoindole-1,3(2H)-dione. | | |
| 724 | 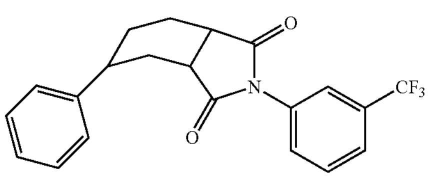 | Hexahydro-5-phenyl-2-[3-(trifluoromethyl)-phenyl]-1H-isoindole-1,3(2H)-dione. | | |
| 725 | 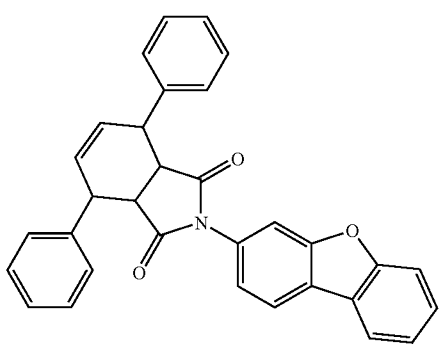 | 2-(3-Dibenzofuranyl)-3a,4,7,7a-tetrahydro-4,7-diphenyl-1H-isoindole-1,3(2H)-dione. | | |
| 726 | 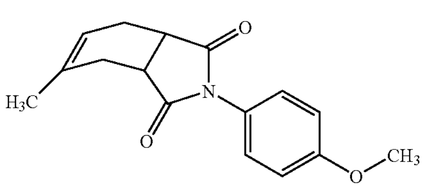 | 3a,4,7,7a-Tetrahydro-2-(4-methoxyphenyl)-5-methyl-1H-isoindole-1,3(2H)-dione. | | |
| 727 | 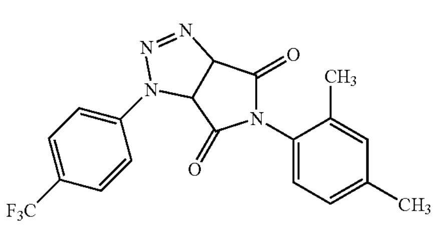 | 5-(2,4-Dimethylphenyl)-1,6a-dihydro-1-[4-(trifluoromethyl)-phenyl]pyrrolo[3,4-d]-1,2,3-triazole-4,6(3aH,5H)-dione. | | |

| Ex. No. | Structure | Compound Name | Retention Time Min | Procedure of Example |
|---|---|---|---|---|
| 728 | 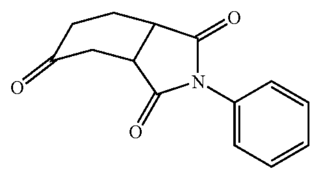 | Tetrahydro-2-phenyl-1H-isoindole-1,3,5(2H,4H)-trione. | | |
| 729 | 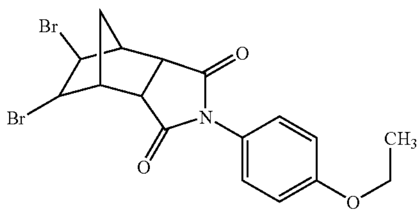 | 5,6-Dibromo-2-(4-ethoxyphenyl)hexahydro-4,7-methano-1H-isoindole-1,3(2H)-dione. | | |
| 730 | 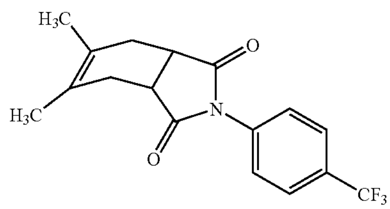 | 3a,4,7,7a-Tetrahydro-5,6-dimethyl-2-[4-(trifluoromethyl)phenyl]-1H-isoindole-1,3(2H)-dione. | | |
| 731 | 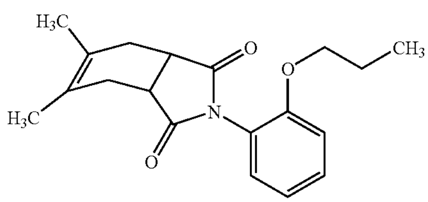 | 3a,4,7,7a-Tetrahydro-5,6-dimethyl-2-(2-propoxyphenyl)-1H-isoindole-1,3(2H)-dione. | | |
| 732 | 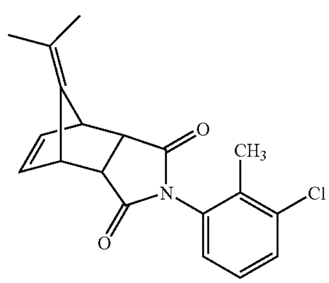 | 2-(3-Chloro-2-methylphenyl)-3a,4,7,7a-tetrahydro-8-(1-methylethylidene)-4,7,-methano-1H-isoindole-1,3(2H)-dione. | | 17A 17B |
| 733 | 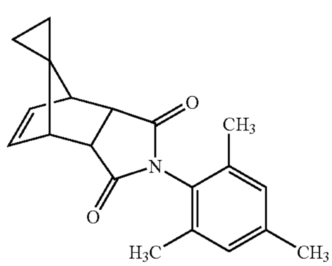 | 3'a,4',7',7'a-Tetrahydro-2'-(2,4,6-trimethylphenyl)spiro-[cyclopropane-1,8'-[4,7]methano[1H]isoindole]-1',3'(2'H)-dione. | | 12B |
| 734 | 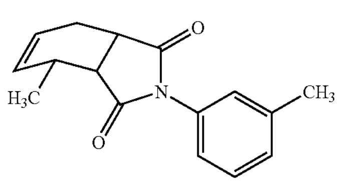 | 3a,4,7,7a-Tetrahydro-4-methyl-2-(3-methylphenyl)-1H-isoindole-1,3(2H)-dione. | | |

TABLE 14-continued

| Ex. No. | Structure | Compound Name | Retention Time Min | Procedure of Example |
|---|---|---|---|---|
| 735 | 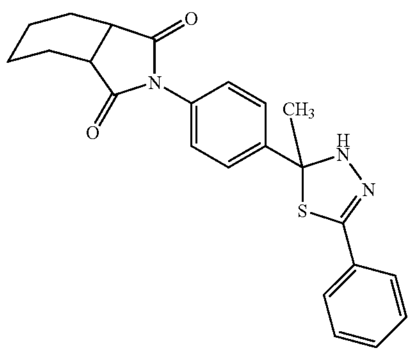 | Hexahydro-2-[4-(2-methyl-5-phenyl-1,3,4-thiadiazol-2-yl)phenyl]-1H-isoindole-1,3(2H)-dione. | | |
| 736 | 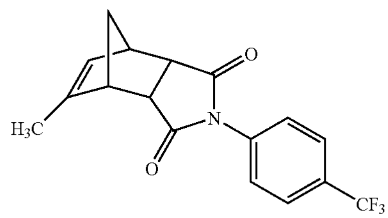 | 3a,4,7,7a-Tetrahydro-5-methyl-2-[4-(trifluoromethyl)-phenyl]-4,7-methano-1H-isoindole-1,3(2H)-dione. | | |
| 737 | 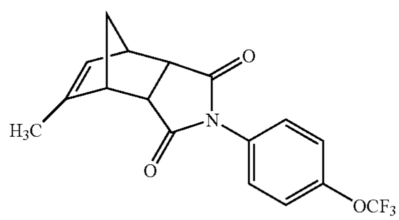 | 3a,4,7,7a-Tetrahydro-5-methyl-2-[4-(trifluoromethoxy)-phenyl]-4,7-methano-1H-isoindole-1,3(2H)-dione. | | |
| 738 | 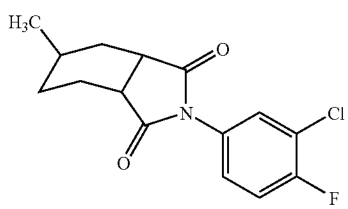 | 2-(3-Chloro-4-fluorophenyl)hexahydro-5-methyl-1H-isoindole-1,3(2H)-dione. | | |
| 739 | 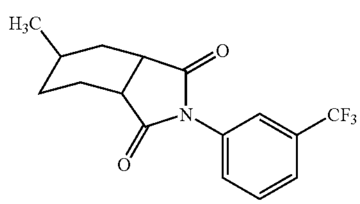 | 3a,4,7,7a-Tetrahydro-5-methyl-2-[3-(trifluoromethyl)-phenyl]-1H-isoindole-1,3(2H)-dione. | | |
| 740 | 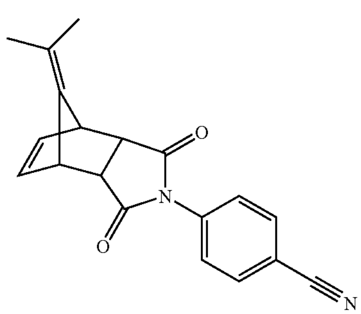 | 4-[1,3,3a,4,7,7a-Hexahydro-8-(1-methylethylidene)-1,3-dioxo-4,7-methano-2H-isoindol-2-yl]-benzonitrile. | | 17A 17B |

TABLE 14-continued

| Ex. No. | Structure | Compound Name | Retention Time Min | Procedure of Example |
|---|---|---|---|---|
| 741 | 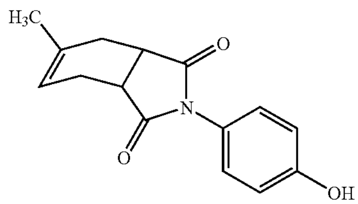 | 3a,4,7,7a-Tetrahydro-2-(4-hydroxyphenyl)-1H-isoindole-1,3(2H)-dione. | | |
| 742 | 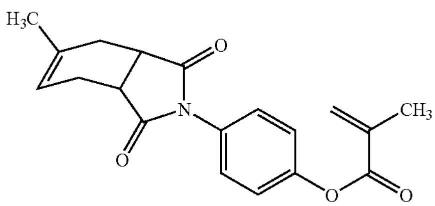 | 2-Methyl-2-propenoic acid, 4-(1,3,3a,4,7,7a-hexahydro-5-methyl-1,3-dioxo-2H-isoindol-2-yl)phenyl ester. | | |
| 743 | 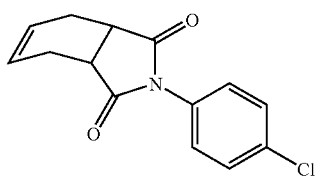 | 2-(4-Chlorophenyl)-3a,4,7,7a-tetrahydro-1H-isoindole-1,3(2H)-dione. | | |
| 744 | 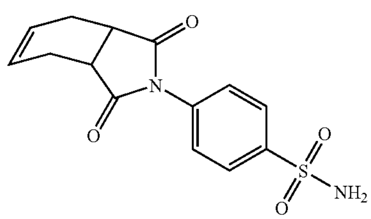 | 4-(1,3,3a,4,7,7a-Hexahydro-1,3-dioxo-2H-isoindol-2-yl)benzenesulfonamide. | | |
| 745 | 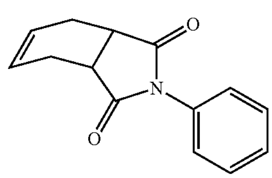 | 3a,4,7,7a-Tetrahydro-2-phenyl-1H-isoindole-1,3(2H)-dione. | | |
| 746 | 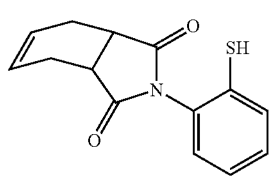 | 3a,4,7,7a-Tetrahydro-2-(2-mercaptophenyl)-1H-isoindole-1,3(2H)-dione. | | |
| 747 | 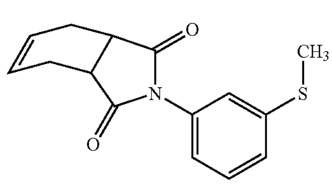 | 3a,4,7,7a-Tetrahydro-2-[3-(methylthio)phenyl]-1H-isoindole-1,3(2H)-dione. | | |

TABLE 14-continued

| Ex. No. | Structure | Compound Name | Retention Time Min | Procedure of Example |
|---|---|---|---|---|
| 748 | 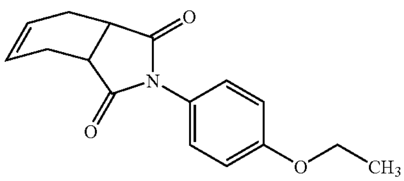 | 2-(4-Ethoxyphenyl)-3a,4,7,7a-tetrahydro-1H-isoindole-1,3(2H)-dione. | | |
| 749 | 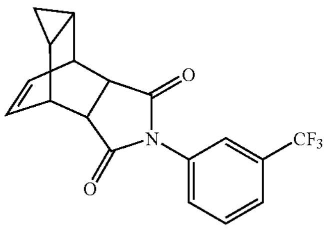 | 4,4a,5,5a,6,6a-Hexahydro-2-[3-(trifluoromethyl)phenyl]-4,6-ethenocycloprop[f]-isoindole-1,3(2H,3aH)-dione. | | 5B |
| 750 | 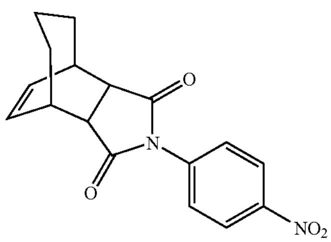 | 3'a,4',7',7'a-Tetrahydro-2'-(4-nitrophenyl)spiro[cyclopropane-1,8'-[4,7]methano[1H]isoindole]-1',3'(2'H)-dione. | | 1B |
| 751 | 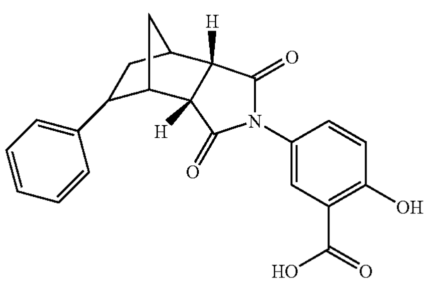 | 2-Hydroxy-5-(octahydro-1,3-dioxo-5-phenyl-4,7-methano-1H-isoindol-2-yl)-benzoic acid. | | 7C 9B |
| 752 | 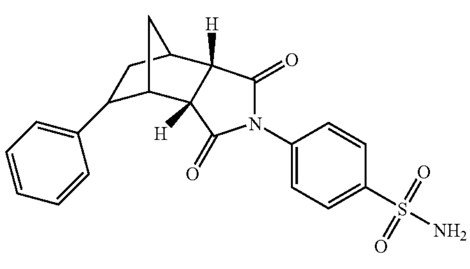 | 4-(Octahydro-1,3-dioxo-5-phenyl-4,7-methano-1H-isoindol-2-yl)-benzenesulfonamide | | 7C 9B |
| 753 | 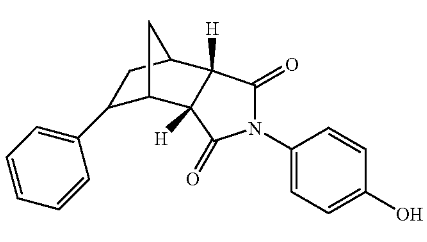 | Hexahydro-2-(4-hydroxyphenyl)-5-phenyl-4,7-methano-1H-isoindole-1,3(2H)-dione. | | 7C 9B |

TABLE 14-continued

| Ex. No. | Structure | Compound Name | Retention Time Min | Procedure of Example |
|---|---|---|---|---|
| 754 | 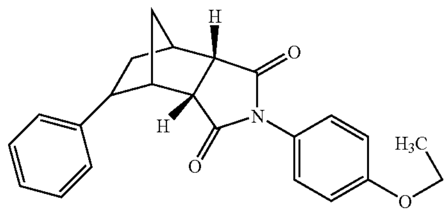 | 2(4-Ethoxyphenyl)-hexahydro-5-phenyl-4,7-methano-1H-isoindole-1,3(2H)-dione. | | 7C 9B |
| 755 | 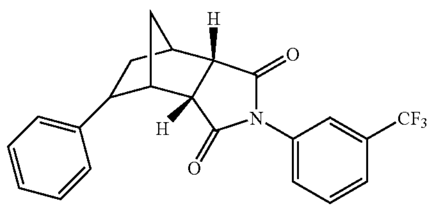 | Hexahydro-5-phenyl-2-[3-(trifluoromethyl)-phenyl]-4,7-methano-1H-isoindole-1,3(2H)-dione. | | 7C 9B |

EXAMPLES 756 TO 763

Additional compounds of the formula I were prepared by procedures analogous to those described above. The compounds of Example 756 to 763 have the following structure:

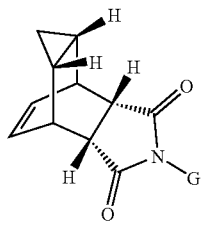

where G, the compound name, retention time, and the procedure employed, are set forth in Table 15 (L is a bond for the compounds of Table 15).

The chromatography techniques used to determine the compound retention times of Table 15 are as follows:

LCMS=YMC S5 ODS column, 4.6×50 mm eluting with 10-90% MeOH/H$_2$O over 4 minutes containing 0.1% TFA; 4 mL/min, monitoring at 220 nm.

*LCMS=YMC S5 ODS column, 4.6×50 mm eluting with 10-90% MeOH/H$_2$O over 2 minutes containing 0.1% TFA; 4 mL/min, monitoring at 220 nm.

LC=YMC S5 ODS column 4.6×50 mm eluting with 10-90% MeOH/H$_2$O over 4 minutes containing 0.2% phosphoric acid, 4 mL/min, monitoring at 220 nm.

The molecular mass of the compounds listed in Table 15, where provided, were determined by MS (ES) by the formula m/z.

TABLE 15

| Ex. No. | G | Compound Name | Retention Time Min | Procedure of Example |
|---|---|---|---|---|
| 756 | | (3aα,4β,4aα,5aα,6β,6aα)-2-(3,4-Dichlorophenyl)-4,4a,5,5a,6,6a-hexahydro-4,6-ethenocycloprop[f]isoindole-1,3(2H,3aH)-dione. | 1.85 LCMS | 5B |
| 757 | | (3aα,4β,4aα,5aα,6β,6aα)-2-(3,5-Dichlorophenyl)-4,4a,5,5a,6,6a-hexahydro-4,6-ethenocycloprop[f]isoindole-1,3(2H,3aH)-dione. | 1.91 LCMS | 5B |

TABLE 15-continued

| Ex. No. | G | Compound Name | Retention Time Min | Procedure of Example |
|---|---|---|---|---|
| 758 | 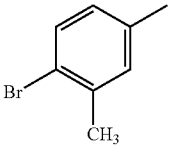 | (3aα,4β,4aα,5aα,6β,6aα)-2-(4-Bromo-3-methylphenyl)-4,4a,5,5a,6,6a-hexahydro-4,6-ethenocycloprop[f]isoindole-1,3(2H,3aH)-dione. | 1.83 LCMS | 5B |
| 759 | 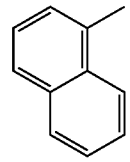 | (3aα,4β,4aα,5aα,6β,6aα)-4,4a,5,5a,6,6a-Hexahydro-2-(1-naphthalenyl)-4,6-ethenocycloprop[f]isoindole-1,3(2H,3aH)-dione. | 1.77 LCMS | 5B |
| 760 | 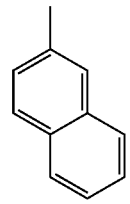 | (3aα,4β,4aα,5aα,6β,6aα)-4,4a,5,5a,6,6a-Hexahydro-2-(2-naphthalenyl)-4,6-ethenocycloprop[f]isoindole-1,3(2H,3aH)-dione. | 1.64 LCMS | 5B |
| 761 | 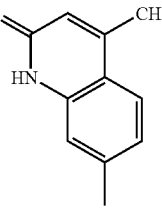 | (3aα,4β,4aα,5aα,6β,6aα)-2-(1,2-Dihydro-4-methyl-2-oxo-7-quinolinyl)-4,4a,5,5a,6,6a-hexahydro-4,6-ethenocycloprop[f]isoindole-1,3(2H,3aH)-dione. | 2.79 LC | 5B |
| 762 | 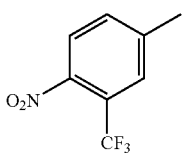 | (3aα,4α,4aα,5aα,6β,6aα)-4,4a,5,5a,6,6a-Hexahydro-2-[4-nitro-3-(trifluoromethyl)phenyl]-4,6-ethenocycloprop[f]isoindole-1,3(2H,3aH)-dione. | 3.49 LC | 5B |
| 763 | 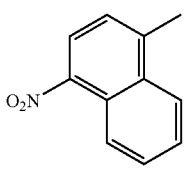 | (3aα,4α,4aα,5aα,6β,6aα)-4,4a,5,5a,6,6a-Hexahydro-2-(4-nitro-1-naphthalenyl)-4,6-ethenocycloprop[f]isoindole-1,3(2H,3aH)-dione. | 3.30 LC | 5B |

EXAMPLE 764

(3aα,4β,7β,7aα)-Hexahydro-8-(1-methyleth-ylidene)-2-(4-nitro-1-naphthalenyl)-4,7-methano-1H-isoindole-1,3(2H)-dione (764)

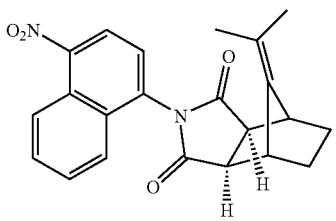

Compound 31A (0.247 g, 1.20 mmol) and 4-nitro-1-naphthalamine (0.188 g, 1.00 mmol) were dissolved in AcOH (2.0 mL) and then heated at 105° C. for 15 h. The reaction was allowed to cool to 25° C. and then the AcOH was removed in vacuo. The resulting slurry was added to cold sat $K_2CO_3$ and stirred vigorously for 15 min. The suspension was then filtered and rinsed with water. The crude product was purified by flash chromatography on $SiO_2$ eluting with 20% hexanes/methylene chloride affording 0.322 g of compound 764 as a yellow solid. HPLC: 92.4% at 4.063 min (retention time) (YMC S5 ODS column 4.6×50 mm, 10-90% aqueous methanol over 4 minutes containing 0.2% phosphoric acid, 4 mL/min, monitoring at 220 nm).

EXAMPLE 765

(3aα,4β,7β,7aα)-Hexahydro-8,8-dihydroxy-2-(4-nitro-1-naphthalenyl)-4,7-methano-1H-isoindole-1,3(2H)-dione (765)

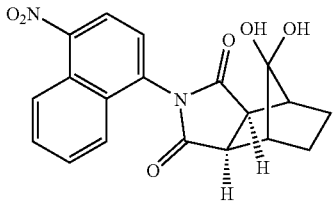

Compound 764 (0.214 g, 0.570 mmol) was dissolved in $CCl_4$ (10.0 mL) and methylene chloride (2.0 mL) and cooled to −25° C. $O_3$ was then bubbled through the reaction until a blue color persisted (~10 min). DMS (0.418 mL, 5.70 mmol) was then added and the reaction warmed to 25° C. After 12 h, a white precipitate formed and was filtered, rinsing with $CCl_4$ and dried to yield 0.171 g of compound 765. The precipitate was shown to be 95% pure by $H^1$ NMR spectroscopy, but was not stable to reverse phase LC conditions. HRMS (ESI): m/z 367.0932 [M−H]−. $^1$H NMR Data: Compound 765 is a mixture of atropisomers at 25° C., signals reported as major, minor or both (overlapping) atropisomers. $^1$H NMR (Joel, 500 MHz, DMSO-d6, 25° C.) δ 1.35 (2H, m, both); 1.94 (2H, m, both); 2.23 (2H, s, major); 2.29 (2H, s, minor); 3.01 (2H, s, minor); 3.12 (2H, s, major); 6.23 (1H, s, major); 6.31 (1H, s, minor); 6.55 (1H, s, major); 6.82 (1H, s, minor); 7.45 (1H, d, J=7.7 Hz, major); 7.60 (1H, d, J=8.3 Hz, minor); 7.73-7.88 (2H, m, both); 8.04 (1H, d, J=8.2 Hz, major); 8.35-8.44 (2H, m, both).

EXAMPLE 766

(3aα,4α,7α,7aα)-2-[4-Nitro-3-(trifluoromethyl)phenyl]-3a,4,7,7a-tetrahydro-4,7-methano-1H-isoindole-1,3(2H)-dione (766)

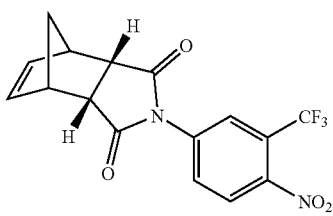

Compound 766 was synthesized as described in Example 38A. HPLC: 96.2% at 3.03 min (retention time) (YMC ODSA S5 C18 column 4.6×50 mm, 10-90% aqueous methanol over 4 minutes containing 0.1% $CF_3COOH$, 4 mL/min, monitoring at 220 nm). MS (ES): m/z 352.1 [M+H]+.

We claim:

1. A method of modulating the function of a nuclear hormone receptor in a mammal for the treatment of cancer, wherein the cancer cells express estrogen receptor, or contain progesterone or androgen receptor, comprising administering to the mammal an effective nuclear receptor modulating amount of a compound of the following formula (I) or a pharmaceutical acceptable salt thereof:

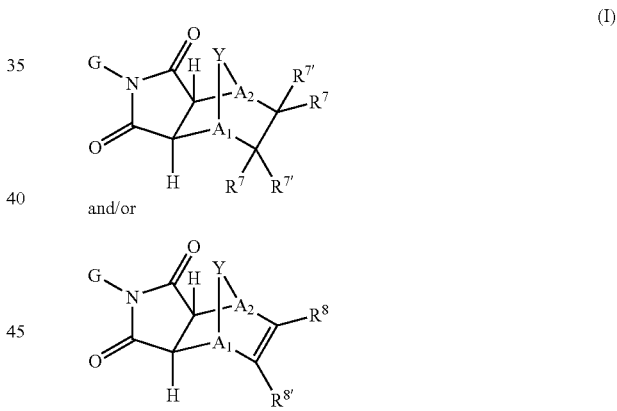

where the symbols have the following meanings, and are, for each occurrence, independently selected:

G is a cycloalkenyl, aryl or heterocyclo group, where said group is mono- or polycyclic and is optionally substituted at one or more positions;

Y is $(CR^7R^{7'})_n$ and n=1-3;

$A_1$ is $CR^7$;

$A_2$ is $CR^7$;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, provided, however, that $R^1$ is not hydrogen when attached to —$SO_2O$— or —$SO_2$—;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)$R^1$, —C(=O)O$R^1$, —C(=O)NH$R^1$, —SO$_2$O$R^1$, —SO$_2$$R^1$ or —SO$_2$N$R^1$$R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)$R^1$, —C(=O)NH$R^1$, —SO$_2$$R^1$, —SO$_2$$R^1$ or —SO$_2$N$R^1$$R^{1'}$;

$R^7$ and $R^{7'}$ are at each occurrence independently selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, O$R^4$, nitro, hydroxylamine, hydroxylamide, NH$R^4$, —N$R^5$$R^5$, —NHO$R^1$, thiol, alkylthio or substituted alkylthio, oxo (=O), —C(=O)$R^1$, —OC(=O)$R^1$, —C(=O)O$R^1$, —PO$_3$$R^1$$R^{1'}$, —C(=O)N$R^1$$R^{1'}$, —C(=O)S$R^1$, —C(=O)NHSO$_2$$R^1$, —SO$R^1$, —SO$_2$$R^1$, —SO$_2$O$R^1$ and —SO$_2$N$R^1$$R^{1'}$;

or two $R^7$ and $R^{7'}$ groups attached to the same carbon atom may be joined to form a spiro ring, or two $R^7$ and $R^{7'}$ groups attached to two different carbon atoms may be joined to form a fused, optionally-substituted monocyclic or bicyclic heterocyclic or carbocyclic ring; and $R^8$ and $R^{8'}$ are at each occurrence independently selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, O$R^4$, amino, NH$R^4$, —N$R^5$$R^5$, —NHO$R^1$, alkylthio or substituted alkylthio, —C(=O)$R^1$, —C(=O)O$R^1$, —PO$_3$$R^1$$R^{1'}$, —C(=O)N$R^1$$R^{1'}$, —C(=O)S$R^1$, —SO$R^1$, —SO$_2$$R^1$, —SO$_2$O$R^1$ and —SO$_2$N$R^1$$R^{1'}$, or $R^8$ and $R^{8'}$ may be joined to form a fused, optionally-substituted monocyclic or bicyclic heterocyclic or carbocyclic ring.

2. The method of claim 1, wherein:

$R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, —C(=O)$R^1$, —SO$_2$$R^1$, or —SO$_2$N$R^1$$R^{1'}$;

$R^7$ and $R^{7'}$ are each independently H, alkyl or substituted alkyl, alkenyl or substituted alkenyl, heterocycloalkyl or substituted heterocycloalkyl, halo, cyano, O$R^4$, —NH$R^4$, —N$R^5$$R^5$, —C(=O)$R^1$, —OC(=O)$R^1$, —C(=O)O$R^1$, —C(=O)N$R^1$$R^{1'}$, —SO$_2$$R^1$, or —SO$_2$N$R^1$$R^{1'}$; or two $R^7$ and $R^{7'}$ groups attached to the same carbon atom may be joined to form a spiro ring, or two $R^7$ and $R^{7'}$ groups attached to two different carbon atoms may be joined to form a fused, optionally-substituted monocyclic heterocyclic or carbocyclic ring.

3. The method of claim 1 wherein,

G is a monocyclic or bicyclic aryl or heterocyclo and is optionally substituted at one or more positions;

$A_1$ is CH, C(alkyl), or C(substituted alkyl);

$A_2$ is CH, C(alkyl), or C(substituted alkyl);

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, —C(=O)$R^1$, —SO$_2$$R^1$, or —SO$_2$N$R^1$$R^{1'}$; and $R^7$ and $R^{7'}$ are each independently H, alkyl or substituted alkyl, alkenyl or substituted alkenyl, heterocycloalkyl or substituted heterocycloalkyl, halo, cyano, O$R^4$, —NH$R^4$, —N$R^5$$R^5$, —C(=O)$R^1$, —OC(=O)$R^1$, —C(=O)O$R^1$, —C(=O)N$R^1$$R^{1'}$, —SO$_2$$R^1$, or —SO$_2$N$R^1$$R^{1'}$; or two $R^7$$R^{7'}$ groups are joined to a spiro cyclopropyl, or said $R^7$ and $R^{7'}$ groups may be joined to form a fused, optionally-substituted monocyclic heterocyclic or carbocyclic ring; and $R^8$ and $R^{8'}$ are each independently H, alkyl or substituted alkyl, alkenyl or substituted alkenyl, heterocycloalkyl or substituted heterocycloalkyl, halo, cyano, O$R^4$, —NH$R^4$, —N$R^5$$R^5$, —C(=O)$R^1$, —OC(=O)$R^1$, —C(=O)O$R^1$, —C(=O)N$R^1$$R^{1'}$, —SO$_2$$R^1$, or —SO$_2$N$R^1$$R^{1'}$.

4. The method of claim 1, wherein said cancer is prostate cancer.

5. The method of claim 1 wherein,

G is a monocyclic or bicyclic aryl or heterocyclo and is optionally substituted at one or more positions;

$A^1$ is CH, C(alkyl), or C(substituted alkyl);

$A^2$ is CH, C(alkyl), or C(substituted alkyl);

$R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, —C(=O)$R^1$, —SO$_2$$R^1$, or —SO$_2$N$R^1$$R^{1'}$, $R^7$ and $R^{7'}$ are each independently H, alkyl or substituted alkyl, alkenyl or substituted alkenyl, heterocycloalkyl or substituted heterocycloalkyl, halo, cyano, O$R^4$, —NH$R^4$, —N$R^5$$R^5$, —C(=O)$R^1$, —OC(=O)$R^1$, —C(=O)O$R^1$, C(=O)N$R^1$$R^{1'}$, —SO$_2$$R^1$, or —SO$_2$N$R^1$$R^{1'}$; or two R⁷ and R⁷' groups are joined to a spiro cyclopropyl, or said R⁷ and R⁷' groups may be joined to form a fused, optionally-substituted monocyclic heterocyclic or carbocyclic ring; and R⁸ and R⁸' are each independently H, alkyl or substituted alkyl, alkenyl or substituted alkenyl, heterocycloalkyl or substituted heterocycloalkyl, halo, cyano, OR⁴, —NHR⁴, —NR⁵R⁵, —C(=O)R¹, —OC(=O)R¹, —C(=O)OR¹, —C(=O)NR¹R¹', —SO₂R¹, or —SO₂NR¹R¹'.

6. The method of claim 5, wherein G is phenyl or napthyl optionally substituted at one to three positions.

7. The method of claim 1 wherein,

G is phenyl or napthyl optionally substituted at one to three positions;

A₁ is CH, C(alkyl), or C(substituted alkyl;

A₂ is CH, C(alkyl), or C(substituted alkyl);

R¹ and R¹' are each independently selected from H, alkyl or substituted alkyl, alkenyl or substituted alkenyl, cycloalkyl or substituted cycloalkyl, heterocyclo or substituted heterocyclo, and aryl or substituted aryl;

R⁴ is H, alkyl or substituted alkyl, alkenyl or substituted alkenyl, cycloalkylalkyl or substituted cycloalkylalkyl, arylalkyl or substituted arylalkyl, C(=O)R¹, —C(=O)OR¹, —C(=O)NHR¹, —SO₂R¹ or —SO₂NR¹R¹';

R⁵ is alkyl or substituted alkyl, —C(=O)R¹, —SO₂R¹, or —SO₂NR¹R¹';

R⁷ and R⁷' are each independently H, alkyl or substituted alkyl, alkenyl or substituted alkenyl, heterocycloalkyl or substituted heterocycloalkyl, halo, cyano, OR⁴, —NHR⁴, —NR⁵R⁵, —C(=O)R¹, —OC(=O)R¹, —C(=O)OR¹, —C(=O)NR¹R¹', —SO₂R¹, or —SO₂NR¹R¹'; or two R⁷ and R⁷' groups are joined to a spiro cyclopropyl, or said R⁷ and R⁷' groups may be joined to form a fused, optionally-substituted monocyclic heterocyclic or carbocyclic ring; and R⁸ and R⁸' are each independently H, alkyl or substituted alkyl, alkenyl or substituted alkenyl, heterocycloalkyl or substituted heterocycloalkyl, halo, cyano, OR⁴, —NHR⁴, —NR⁵R⁵, —C(=O)R¹, —OC(=O)R¹, —C(=O)OR¹, —C(=O)NR¹R¹', —SO₂R¹, or —SO₂NR¹R¹.

8. A method of modulating the function of a nuclear hormone receptor in a mammal for the treatment of cancer, wherein the cancer cells express estrogen receptor, or contain progesterone or androgen receptor, comprising administering to the mammal an effective nuclear receptor modulating amount of a compound selected from:

(3aα,4α,7α,7aα)-2-(3-Chloro-4-hydroxyphenyl)hexahydro-4,7-methano-1H-isoindole-1,3(2H)-dione, (3aα,4α,7α,7aα)-Hexahydro-2-[1H-tetrazol-5-yl)phenyl]-4,7-methano-1H-isoindole-1,3(2H)-dione, trifluoroacetate (1:1), (3aα,4α,7α,7aα)-Hexahydro-2-[3-methoxy-4-(1H-1,2,4-triazol-1-yl)phenyl]-4,7-methano-1H-isoindole-1,3(2H)-dione, (3aα,4α,7α,7aα)-2-(2,3-Dihydro-2-oxo-6-benzothiazolyl)-3a,4,7,7a-tetrahydro-4,7-methano-1H-isoindole-1,3(2H)-dione, (3aα,4α,7α,7aα)-2-(2,3-Dihydro-3-methyl-2-oxo-6-benzothiazolyl)-3a,4,7,7a-tetrahydro-4,7-methanol-1H-isoindole-1,3(2H)-dione, (3aα,4α,7α,7aα)-2-(2,3-Dihydro-1-methyl-2-oxo-1H-indol-5-yl)-3a,4,7,7a-tetrahydro-4,7-methano-1H-isoindole-1,3(2H)-dione, (3aα,4α,7α,7aα)-2-(2-Fluorenyl)-3a,4,7,7a-tetrahydro-4,7-methano-1H-isoindole-1,3(2H)-dione, (3aα,4α,7α,7aα)-2-(1H-Benzotriazol-5-yl)-3a,4,7,7a-tetrahydro-4,7-methano-1H-isoindole-1,3(2H)-dione, (3aα,4α,7α,7aα)-2-[3-Chloro-4-(4-morpholinyl)phenyl]-3a,4,7,7a-tetrahydro-4,7-methano-1H-isoindole-1,3(2H)-dione, (3aα,4α,7α,7aα)-2-(2,3-Dihydro-1H-inden-5-yl)-3a,4,7,7a-tetrahydro-4,7-methano-1H-isoindole-1,3(2H)-dione, (3aα,4α,7α,7aα)-2-(4-Bromo-1-naphthalenyl)-3a,4,7,7a-tetrahydro-4,7-methano-1H-isoindole-1,3(2H)-dione, (3aα,4α,7α,7aα)-2-(4-Chloro-1-naphthalenyl)-3a,4,7,7a-tetrahydro-4,7-methano-1H-isoindole-1,3(2H)-dione, (3aα,4α,7α,7aα)-3a,4,7,7a-Tetrahydro-2-(7-hydroxy-1-naphthalenyl)-4,7-methano-1H-isoindole-1,3(2H)-dione, (3aα,4α,7α,7aα)-3a,4,7,7a-Tetrahydro-2-(4-nitro-1-naphthalenyl)-4,7-methano-1H-isoindole-1,3(2H)-dione, (3aα,4α,7α,7aα)-3a,4,7,7a-Tetrahydro-2-(1H-indol-5-yl)-4,7-methano-1H-isoindole-1,3(2H)-dione, (3aα,4α,7α,7aα)-3a,4,7,7a-Tetrahydro-2-(1H-indazol-6-yl)-4,7-methano-1H-isoindole-1,3(2H)-dione, (3aα,4α,7α,7aα)-2,4,1,3-Benzodioxol-5-yl)-3a,4,7,7a-tetrahydro-4,7-methano-1H-isoindole-1,3(2H)-dione, (3aα,4α,7α,7aα)-2-[4-Amino-3-(trifluoromethyl)phenyl]-3a,4,7,7a-tetrahydro-4,7-methano-1H-isoindole-1,3(2H)-dione, (3aα,4α,7α,7aα)-3a,4,7,7a-Tetrahydro-2-(2-methyl-4-quinolinyl)-4,7-methano-1H isoindole-1,3(2H)-dione, (3aα,4α,7α,7aα)-3a,4,7,7a-Tetrahydro-2-(8-quinolinyl)-4,7-methano-1H-isoindole-1,3(2H)-dione, (3aα,4α,7α,7aα)-2-(2,3-Dihydro-1,4-benzodioxin-6-yl)-3a,4,7,7a-tetrahydro-4,7-methano-1H-isoindole-1,3(2H)dione, (3aα,4α,7α,7aα)-3a,4,7,7a-Tetrahydro-2-(4-methyl-2-oxo-2H-1-benzopyran-7-yl)-4,7-methano-1H-isoindole-1,3(2H)-dione, (3aα,4α,7α,7aα)-3a,4,7,7a-Tetrahydro-2-(5-isoquinolinyl)-4,7-methano-1H-isoindole-1,3(2H)-dione, (3aα,4α,7α,7aα)-2-(2,5-Dimethoxy-4-nitrophenyl)-3a,4,7,7a-tetrahydro-4,7-methano-1,1-isoindole-1,3(2H)-dione, (3aα,4α, 7α,7aα)-2,3,5,6-Tetrafluoro-4-(1,3,3a,4,7,7a-hexahydro-1,3-dioxo-4,7-methano-2H-isoindol-2-yl)benzonitrile, (3aα,4α,7',7aα)-3a,4,7,7a-Tetrahydro-2-(2,4,5-trifluorophenyl)-4,7-methano-1H-isoindole-1,3(2H)-dione, (3aα,4α,7α,7aα)-3a,4,7,7a-Tetrahydro-2-(2,4,5-trichlorophenyl)-4,7-methano-1H-isoindole-1,3(2H)-dione, (3aα,4α,7α,7aα)-2-(3,4-Difluorophenyl)-3a,4,7,7a-tetrahydro-4,7-methano-1H-isoindole-1,3(2H)-dione, (3aα,4α,7α,7aα)-2-(2,3-Dihydro-1H-indol-6-yl)-3a,4,7,7a-tetrahydro-4,7-methano-1H-isoindole-1,3(2H)-dione, (3aα,4α,7α,7aα)-2-(3-Chloro-4-fluorophenyl)-3a,4,7,7a-tetrahydro-4,7-methano-1H-isoindole-1,3(2H)-dione, (3aα,4α,7α,7aα)-2-(3,4-Dichlorophenyl)-3a,4,7,7a-tetrahydro-4,7-methano-1H-isoindole-1,3(2H)-dione, (3aα,4α,7α,7aα)-3a,4,7,7a-Tetrahydro-2-(3,4,5-trichlorophenyl)-4,7-methano-1H-isoindole-1,3(2H)-dione, (3aα,4α,7α,7aα)-2-(3-Chloro-4-methoxyphenyl)-3a,4,7,7a-tetrahydro-4,7-methano-1,1-isoindole-1,3(2H)-dione, (3aα,4α,7α,7aα)-2-(3-Chloro-4-methylphenyl)-3a,4,7,7a-tetrahydro-4,7-methano-1,1-isoindole-1,3(2H)-dione, (3aα,4α,7α,7aα)-3a,4,7,7a-Tetrahydro-2-(2-methyl-1-naphthalenyl)-4,7-methano-1H-isoindole-1,3(2H)-dione, (3aα,4α,7α,7aα)-2-(4-Chloro-3-methylphenyl)-3a,4,7,7a-tetrahydro-4,7-methano-1,11-isoindole-1,3(2H)-dione, (3aα,4α,7α,7aα)-2-(3,4-Dimethylphenyl)-3a,4,7,7a-tetrahydro-4,7-methano-1H-isoindole-1,3(2H)-dione, (3aα,4α,7α,7aα)-2-4-Bromo-[4-trifluoromethyl)phenyl]-3a,4,7,7a-tetrahydro-4,7-methano-1H-isoindole-1,3(2H)-dione, (3aα,4α,7α,7aα)-2-(4-Bromo-3-methylphenyl)-3a,4,7,7a-tetrahydro-4,7-methano-1H-isoindole-1,3(2H)-dione, (3aα,4α,7α,7aα)-2-(4-Fluoro-3-nitrophenyl)-3a,4,7,7a-tetrahydro-4,7-methano-1H-isoindole-1,3(2H)-dione, (3aα,4α,7α,7aα)-2-4-Fluoro-3-(trifluoromethyl)phenyl)-3a,4,7,7a-tetrahydro-4,7-methano-1H-isoindole-1,3(2H)-dione, (3aα,4α,7α,7aα)-2-(4-Chloro-3-nitrophenyl)-3a,4,7,7a-tetrahydro-4,7-methano-1H-isoindole-1,3(2H)-dione, (3aα,4α,7α,7aα)-2-[4-Chloro-3-(trifluoromethyl)phenyl]-3a,4,7,7a-tetrahydro-4,7-methano-1H-isoindole-1,3(2H)-dione, (3aα,4α,7α,7aα)-2-(4-Chloro-C-methoxy-5-methylphenyl)-3a,4,7,7a-tetrahydro-4,7-methano-1H-isoindole-1,3(2H)-dione, (3aα,4α,7α,7aα)-2-(3,5-Dichloro-4-hydroxyphenyl)-3a,4,7,7a-tetrahydro-4,7-methano-1H-isoindole-1,3(2H)-dione, (3aα,4α,7α,7aα)-3a,4,7,7a-Tetrahydro-2-(4-hydroxy-3-nitrophenyl)-4,7-methano-1,1-isoindole-1,3(2H)-dione, (3aα,4α,7α,7aα)-2-(4-Amino-3-nitrophenyl-3a,4,7,7a-tetrahydro-4,7-methano-1,1-isoindole-1,3(2H)-dione, (3aα,4α,7α,7aα)-2,2'-(2,3,5,6-Tetramethyl-1,4-phenylene)bis[3a,4,7,7a-tetrahydro-4,7-methano-1,4-isoindole-1,3(2H)-dione], (3aα,4α,7α,7aα)-3a,4,7,7a-Tetrahydro-2-(4-methyl-3-nitrophenyl)-4,7-methano-1H-isoindole-1,3(2H)-dione, (3aα,4α,7α,7aα)-3a,4,7,7a-Tetrahydro-2-(3,4,5-trimethoxyphenyl)-4,7-methano-1H-isoindole-1,3(2H)-dione, (3aα,4α,7α,7aα)-2-(3,4-Dimethoxyphenyl)-3a,4,7,7a-tetrahydro-4,7-methano-1H-isoindole-1,3(2H)-dione, (3aα,4α,7α,7aα)-3a,4,7,7a-Tetrahydro-2-(3-hydroxy-4-methoxyphenyl)-4,7-methano-1,1-isoindole-1,3(2H)-dione, (3aα,4a,7α, 7aα)-2-(5-Chloro-2-hydroxy-4-nitrophenyl-3a,4,7,7a-tetrahydro-4,7-methano-1H-isoindole-1,3(2H)-dione,(3aα,4α,7α, 4aα)-3a,4,7,7a-Tetrahydro-2-(2-methoxy-3-dibenzofuranyl)-4,7-methano-1H-isoindole-1,3(2H)-dione, (3aα,4α,7α,7aα)-3a,4,7,7a-Tetrahydro-2-(2,3,4-trifluorophenyl)-4,7-Methano-1H-isoindole-1,3(2H)-dione, (3aα,4α,7α,7aα)-2-(2,3-Dihydro-2-methyl-1,3-dioxo-1H-isoindol-5-yl)-3a,4,7,7a-tetrahydro-4,7-methano-1H-isoindole-1,3(2H)-dione, (3aα,4α,7α,7aα)-2-(4-Bromo-2,3,5,6-tetrafluorophenyl)-3a,4,7,7a-tetrahydro-4,7-methano-1H-isoindole-1,3(2H)-dione, (3aα,4α,7α,7aα)-2-[2,5-Dichloro-4-(1H-pyrrol-1-yl)phenyl]-3a,4,7,7a-tetrahydro-4,7-methano-1H-isoindole-1,3(2H)-dione, (3aα,4α,7α,7aα)-2-[3-[(Diethylamino)methyl]-4-hydroxyphenyl]-3a,4,7,7a-tetrahydro-4,7-methano-1H-isoindole-1,3(2H)-dione, (3aα,4α,7α,7aα)-2-(6-Benzothiazolyl)-3a,4,7,7a-tetrahydro-4,7-methano-1H-isoindole-1,3(2H)-dione, (3aα,4α,7α,7aα)-4-(1,3,3a,4,7,7a-Hexahydro-1,3-dioxo-4,7-methano-2H-isoindol-2-yl)-2-methoxybenzenecarboxylic acid,
methyl ester, (3aα,4α,7α,7aα)-3a,4,7,7a-Tetrahydro-2-(2-oxo-2H)-benzopyran-6-yl)-4,7-methano-1H-isoindole-1,3(2H)-dione, (3aα,4α,7α,7aα)-3a,4,7,7a-Tetrahydro-2-(2-methyl-8-quinolinyl)-4,7-methano-1H-isoindole-1,3(2H)-dione, (3aα,4α,7α,7aα)-3a,4,7,7a-Tetrahydro-2-(2,3,5,6-tetramethyl-4-nitrophenyl)-4,7-methano-1H-isoindole-1,3(2H)-dione, (3α, 4α,7α,7aα)-3a,4,7,7a-Tetrahydro-2-(2,4,5-trimethylphenyl)-4,7-Tetrahydro-1H-isoindole-1,3(2H)-dione, (3α, 4α,7α,7aα)-2-(4-Fluoro-3-methylphenyl)-3a,4,7,7a-tetrahydro-4,7-methano-1H-isoindole-1,3(2H)-dione, (3aα,4α,7α,7aα)-3a,4,7,7a-Tetrahydro-2-(3-methoxy-4-methylphenyl-4,7-methano-1H-isoindole-1,3(2H)-dione, (3aα,4α,7α,7aα)-2-(3-Dibenzofuranyl)-3a,4,7,7a-tetrahydro-4,7-methano-1H-isoindole-1,3(2H)-dione, (3aα,4α,7α,7aα)-3a,4,7,7a-Tetrahydro-2-(2'-hydroxy[1,1':3',1"-terphenyl]-5'-yl)-4,7-methano-1H-isoindole-1,3(2H)-dione, (3aα,4α,7α,7aα)-2-(1,3-Dihydro-2,2-dioxidobenzo[c]thiophen-5-yl)-3a,4,7,7a-tetrahydro-4,7-methano-1H-isoindole-1,3(2H)-dione, (3aα,4α7α, 7aα)-3a,4,7,7a-Tetrahydro-2-(2,2,3,3-tetrafluoro-2,3-dihydro-1,4-benzodioxin-6-yl)-4,7-methano-1H-isoindole-1,3(2H)-dione, (3aα,4α,7α,7aα)-2-(4Amino-2,3,5,6-tetrafluorophenyl)-3a,4,7,7a-tetrahydro-4,7-methano-1H-isoindole-1,3(2H)-dione, (3aα,4α,7α,7aα)-N-2-Chloro-6-fluoro-4-(1,3,3a,4,7,7a-hexahydro-1,3-dioxo-4,7-methano-2H-isoindol-2-yl)phenyl)acetamide, (3aα,4α,7α,7aα)-3a,4,7,7a-Tetrahydro-2-[3-trifluoromethyl)phenyl]-4,7-methano-1H-isoindole-1,3(2H)-dione, (3aα,4α,7α,7aα)-2-[2-Ethoxy-8-methyl-4-(trifluoromethyl)-7-quinolinyl]-3a,4,7,7a-tetrahydro-4,7-methano-1H-isoindole-1,3(2H)-dione, (3α, 4α,7α,7aα)-2-[1,2-Dihydro-8-methyl-2-oxo-4-(trifluoromethyl)-7-quinolinyl]-3a,4,7,7a-tetrahydro-4,7-methano-1H-isoindole-1,3(2H)-dione, (3aα,4α,7α,7aα)-2-(9-Ethyl-9H-carbazol-2-yl)-3a,4,7,7a-tetrahydro-4,7-methano-1H-isoindole-1,3(2H)-dione, (3aα,4α,7α,7aα)-3a,4,7,7a-Tetrahydro-2-1,4-(1-piperidinyl)phenyl)-4,7-methano-1H-isoindole-1,3(2H)-dione, (3aα,4α,7α,7aα)-3a,4,7,7a-Tetrahydro-2-[4-(4-morpholinyl)phenyl]A,7-methano-1H-isoindole-1,3(2H)-dione, (3aα,4α,7α,7aα)-3a,4,7,7a-Tetrahydro-2-(7-quinolinyl)-4,7-methano-1H-isoindole-1,3(2H)-dione, (3aα,4α, 7α,7aα)-2-(3-Chlorophenyl)-3a,4,7,7a-tetrahydro-4,7-methano-1H-isoindole-1,3(2H)-dione, (3aα,4α, 7α,7aα)-3a,4,7,7a-Tetrahydro-2-(2-naphthalenyl)-4,7-methano-1H-isoindole-1,3(2H)-dione, (3aα,4α, 7α,7aα)-3a,4,7,7a-Tetrahydro-2-(1,2,3,4-tetrahydro-2-oxo-7-quinolinyl)-4,7-methano-1H-isoindole-1,3(2H)-dione, (3aα,4α, 7α,7aα)-3a,4,7,7a-Tetrahydro-2-[4-(4-methyl-1-piperazinyl)phenyl]-4,7-methano-1H-isoindole-1,3(2H)-dione, (3aα,4α,7α,7aα)-2-[4-(Diethylamino)-1-naphthalenyl]-3a,4,7,7a-tetrahydro-4,7-methano-1H-isoindole-1,3(2H)-dione, (3aα,4α,7α,7aα)-3a,4,7,7a-Tetrahydro-2-(8-hydroxy-5-quinolinyl)-4,7-methano-1H-isoindole-1,3(2H)-dione, (3aα,4α, 7α,7aα)-3a,4,7,7a-Tetrahydro-2-(4-nitrophenyl)-4,7-methano-1H-isoindole-1,3(2H)-dione, (3aα,4α, 7α,7aα)-3a,4,7,7a-Tetrahydro-2-[2-(4-morpholinyl)-5-(trifluoromethyl)phenyl]-4,7-methano-1H-isoindole-1,3(2H)-dione, (3aα,4α,7α,7aα)-2-(3,5-Dichlorophenyl)-3a,4,7,7a-tetrahydro-4,7-methano-1H-isoindole-1,3(2H)-dione, (3aα,4α,7α,7aα)-2-(3-Chloro-4-fluorophenyl)-3a,4,7,7a-tetrahydro-4,7-methano-1H-isoindole-1,3(2H)-dione, (3aα,4α,7α,7aα)-2,4,4-Fluorophenyl)-3a,4,7,7a-tetrahydro-4,7-methano-1H-isoindole-1,3(2H)-dione, (3aα,4α,7α,7aα)-3a,4,7,7a-Tetrahydro-2-[4-(1,2,3-thiadiazol-4-yl)phenyl]-4,7-methano-1H-isoindole-1,3(2H)-dione, (3aα,4α,7α,7aα)-N-[5-(1,3,3a,4,7,7a-Hexahydro-1,3-dioxo-4,7-methano-2H-isoindol-2-yl)-3-(trifluoromethyl)phenyl]acetamide, (3aα,4α,7α,7aα)-2-[3-Amino-5-(trifluoromethyl)phenyl]-3a,4,7,7a-tetrahydro-4,7-methano-1H-isoindole-1,3(2H)-dione, (3aα,4α, 7α,7aα)-2-[1,2-Dihydro-2-oxo-4-(trifluoromethyl)-7-quinolinyl]-3a,4,7,7a-tetrahydro-4,7-methano-1H-1-isoindole-1,3(2H)-dione, (3aα,4α, 7α,7aα)-2-{5-Ethoxy-2-(methoxymethyl)-4-(4-morpholinyl)phenyl}-3a,4,7,7a-tetrahydro-4,7-methano-1H-isoindole-1,3(2H)-dione, (3aα,4α,7α,7aα)-2-[(1R)-1-(1-naphthalenyl)ethyl]-3a,4,7,7a-tetrahydro-4,7-methano-1H-isoindole-1,3(2H)-dione, (3aα,4α,7α,7aα)-2-[(1S)-1-(1-naphthalenyl)ethyl]-3a,4,7,7a-tetrahydro-4,7-methano-1H-isoindole-1,3(2H)-dione, (3aα,4α, 7α,7aα)-3a,4,7,7a-Tetrahydro-2-[7-(trifluoromethyl)-4-quinolinyl]-4,7-methano-1H-isoindole-1,3(2H)-dione, (3aα,4α, 7α,7aα)-3a,4,7,7a-Tetrahydro-2-[8-(trifluoromethyl)-4-quinolinyl]-4,7-methano-1H-isoindole-1,3(2H)-dione, (3aα,4α,7α,7aα)-2-(3,4-Dimethyl-5-isoxazolyl)-3a,4,7,7a-tetrahydro-4,7-methano-1H-isoindole-1,3(2H)-dione, (3aα,4α, 7α,7aα)-3a,4,7,7a-tetrahydro-2-(1-naphthalenyl)-4,7-methano-1H-isoindole-1,3(2H)-dione, (3aα,4α,7α,7aα)-3a,4,7,7a-Tetrahydro-2-(5-nitro-8-isoquinolinyl)-4,7-methano-1H-isoindole-1,3(2H)-dione, trifluoroacetate (1:1), (3α,4α,7α,7aα)-2-(4-Amino-1-naphthalenyl)-3a,4,7,7a-tetrahydro-4,7-methano-1H-isoindole-1,3(2H)-dione, (3aα,4α, 7α,7aα)-3a,4,7,7a-Tetrahydro-2-(4-hydroxy-1-naphthalenyl)-4,7-methano-1H-isoindole-1,3(2H)-dione, (3aα,4α,7α,7aα)-3a,4,7,7a-Tetrahydro-2-(3-methylphenyl)-4,7-methano-1H-isoindole-1,3(2H)-dione, (3aα,4α, 7α,7aα)-2-(4-Bromophenyl)-3a,4,7,7a-tetrahydro-4,7-methano-1H-isoindole-1,3(2H)-dione, (3aα,4α,7α,7aα)-2-(5-Bromo-8-isoquinolinyl)-3a,4,7,7a-tetrahydro-4,7-methano-1H-isoindole-1,3(2H)-dione, (3aα,4α, 7α,7aα)-2-(7,8-Dichloro-5-quinolinyl)-3a,4,7,7a-tetrahydro-4,7-methano-1H-isoindole-1,3(2H)-dione, (3aα,4α, 7α,7aα)-3a,4,7,7a-Tetrahydro-2-(3-methyl-4-nitrophenyl)-4,7-methano-1H-isoindole-1,3(2H)-dione, (3aα,4α, 7α,7aα)-N-[4-(1,3,3a,4,7,7a-Hexahydro-1,3-dioxo-4,7-methano-2H-isoindol-2-yl)-1-naphthalenyl]-N'-methylurea, (3aα,4α,7α,7aα)-2-(6-Bromo-1,2-benzisoxazol-3-yl)-3a,4,7,7a-tetrahydro-4,7-methano-1H-isoindole-1,3(2H)-dione, (3aα,4α,7α,7aα)-2-(5-Bromo-1,2-benzisoxazol-3-yl)-3a,4,7,7a-tetrahydro-4,7-methano-1H-isoindole-1,3(2H)-dione, (3aα,4α,7α,7aα)-2-(4-Fluoro-1H-1-indazole-3-yl)-3a,4,7,7a-tetrahydro-4,7-methano-1H-isoindole-1,3(2H)-dione, (3aα,4α,7α,7aα)-2-(6-Chloro-1H-indazol-3-yl)-3a,4,7,7a-tetrahydro-4,7-methano-1H-isoindole-1,3(2H)-dione, (3aα,4α,7α,7aα)-3a,4,7,7a-Tetrahydro-2-(5-nitro-1,2-benzisoxazol-3-yl)-4,7-methano-1H-isoindole-1,3(21-1)-dione, (3aα,4α, 7α,7aα)-2-(3-Benzofuranyl)-3a,4,7,7a-tetrahydro-4,7-methano-1H-isoindole-1,3(2H)-dione, (3aα,4α, 7α,7aα)-2-(4-Chlorophenyl)-3a,4,7,7a-tetrahydro-4,7-methano-1H-isoindole-1,3(2H)-dione, (3aα,4α,7α,7aα)-2-(2-Fluorenyl)-3a,4,7,7a-tetrahydro-4,7-ethano-1H-isoindole-1,3(2H)-dione, (3aα,4α, 7α,7aα)-2-(1H-Benzotriazol-5-yl)-3a,4,7,7a-tetrahydro-4,7-ethano-1H-isoindole-1,3(2H)-dione, (3aα,4α, 7α,7aα))-2-[3-Chloro-4-(4-morpholinyl)phenyl]-3a,4,7,7a-tetrahydro-4,7-ethano-1H-isoindole-1,3(2H)-dione, (3aα,4α, 7α,7aα)-2-(2,3-Dihydro-1H-inden-5-yl)-3a,4,7,7a-tetrahydro-4,7-ethano-1,1-isoindole-1,3(2H)-dione, (3aα,4α,7α,7aα)-2-(4-Bromo-1-naphthalenyl)-3a,4,7,7a-tetrahydro-4,7-ethano-1H-isoindole-1,3(2H)-dione, (3aα,4α, 7α,7aα)-2-(4-Chloro-1-naphthalenyl)-3a,4,7,7a-tetrahydro-4,7-ethano-1H-isoindole-1,3(2H)-dione, (3aα,4α,7α,7aα)-2-(5-Amino-1-naphthalenyl)-3a,4,7,7a-tetrahydro-4,7-ethano-1H-isoindole-1,3(2H)-dione, (3aα,4α,7α,7aα)-3a,4,7,7a-Tetrahydro-2-(7-hydroxy-1-naphthalenyl)-4,7-ethano-1H-isoindole-1,3(2H)-dione, (3aα,4α, 7α,7aα)-3a,4,7,7a-Tetrahydro-2-(4-nitro-1-naphthalenyl)-4,7-ethano-1H-isoindole-1,3(2H)-dione, (3aα,4α,7α,7aα)-3a,4,7,7a-Tetrahydro-2-(1H-indol-5-yl)-4,7-ethano-1H-isoindole-1,3(2H)-dione, (3aα,4α,7α,7aα)-3a,4,7,7a-Tetrahydro-2-(1H-indazol-6-yl)-4,7-ethano-1H-isoindole-1,3(2H)-dione, (3aα,4α, 7α,7aα)-2-(1,3-Benzodioxol-5-yl)-3a,4,7,7a-tetrahydro-4,7-ethano-1H-isoindole-1,3(2H)-dione, (3aα,4α,7α,7aα)-2-[4-Amino-3-(trifluoromethyl)phenyl]-3a,4,7,7a-tetrahydro-4,7-ethano-1H-isoindole-1,3(2H)-dione, (3aα,4α,7α,7aα)-2-(3-Chloro-4-iodophenyl)-3a,4,7,7a-tetrahydro-4,7-ethano-1H-isoindole-1,3(2H)-dione, (3aα,4α,7α,7aα)-3a,4,7,7a-Tetrahydro-2-(8-quinolinyl)-4,7-ethano-1H-isoindole-1,3(211)-dione, (3aα,4α,7α,7aα)-2-(1,4-Benzodioxin-6-yl)-3a,4,7,7a-tetrahydro-4,7-ethano-1H-isoindole-1,3(2H)-dione, (3aα,4α, 7α,7aα)-3a,4,7,7a-Tetrahydro-2-[2-oxo-4-(trifluoromethyl)-2H-1-benzopyran-7-yl]-4,7-ethano-1H-isoindole-1,3(2H)-dione, (3aα,4α, 7α,7aα)-3a,4,7,7a-Tetrahydro-2-(4-methyl-2-oxo-2H-benzopyran-7-yl)-4,7-ethano-1H-isoindole-1,3(2H)-dione,
(3aα,4α,7α,7aα)-3a,4,7,7a-Tetrahydro-2-(5-isoquinolinyl)-4,7-ethano-1H-isoindole-1,3(2H)-dione,
(3aα,4α, 7α,7aα)-2-(2,5-Dimethoxy-4-iodophenyl)-3a,4,7,7a-tetrahydro-4,7-ethano-1H-isoindole-1,3(2H)-dione,
(3aα,4α,7α,7aα)-3a,4,7,7a-Tetrahydro-2-(2,4,5-trifluorophenyl)-4,7-ethano-1H-isoindole-1,3(2H)-dione,
(3aα,4α,7α,7aα)-3a,4,7,7a-Tetrahydro-2-(2,4,5-trichlorophenyl)-4,7-ethano-1H-isoindole-1,3(2H)-dione,
(3aα,4α,7α,7aα)-2-(2-Amino-4,5-dichlorophenyl)-3a,4,7,7a-tetrahydro-4,7-ethano-1H-isoindole-1,3(2H)-dione,
(3aα,4α, 7α,7aα)-2-(3,4-Difluorophenyl)-3a,4,7,7a-tetrahydro-4,7-ethano-1H-isoindole-1,3(2H)-dione,
(3aα,4α,7α,7aα)-(3-Chloro-4-fluorophenyl-3a,4,7,7a-tetrahydro-4,7-ethano-1H-isoindole-1,3(2H)-dione,
(3aα,4α,7α,7aα)-2-(3,4-Dichlorophenyl)-3a,4,7,7a-tetrahydro-4,7-ethano-1H-isoindole-1,3(2H)-dione,
(3aα,4α,7α,7aα)-3a,4,7,7a-Tetrahydro-2-(3,4,5-trichlorophenyl)-4,7-ethano-1H-isoindole-1,3(2H)-dione,
(3aα,4α,7α,7aα)-2-(3-Chloro-4-methoxyphenyl)-3a,4,7,7a-tetrahydro-4,7-ethano-1H-isoindole-1,3(2H)-dione,
(3α,4α,7α,7aα)-2-(3-Chloro-4-methylphenyl)-3a,4,7,7a-tetrahydro-4,7-ethano-1H-isoindole-1,3(2H)-dione,
(3aα,4α,7α,7aα)-3a,4,7,7a-Tetrahydro-2-(2-methyl-1-naphthalenyl)-4,7-ethano-1H-isoindole-1,3(2H)-dione,
(3aα,4α,7α,7aα)-2-(4-Chloro-3-methylphenyl-3a,4,7,7a-tetrahydro-4,7-ethano-1H-isoindole-1,3(2H)-dione,
(3aα,4α, 7α,7aα)-2-(3,4-Dimethylphenyl)-3a,4,7,7a-tetrahydro-4,7-ethano-1H-isoindole-1,3(2H)-dione,
(3aα,4α,7α,7aα)-2-[4-Bromo-3-(trifluoromethyl)phenyl]-3a,4,7,7a-tetrahydro-4,7-ethano-1H-isoindole-1,3(2H)-dione,
(3aα,4α,7α,7aα)-2-(4-Bromo-3-methylphenyl)-3a,4,7,7a-tetrahydro-4,7-ethano-1H-isoindole-1,3(2H)-dione,
(3aα,4α, 7α,7aα)-2-(4-Fluoro-3-nitrophenyl)-3a,4,7,7a-tetrahydro-4,7-ethano-1H-isoindole-1,3(2H)-dione,
(3aα,4α,7α,7aα)-2-[4-Fluoro-3-(trifluoromethyl)phenyl]-3a,4,7,7a-tetrahydro-4,7-ethano-1H-isoindole-1,3(2H)-dione,
(3aα,4α,7α,7aα)-2-(4-Chloro-3-nitrophenyl)-3a,4,7,7a-tetrahydro-4,7-ethano-1H-isoindole-1,3(2H)-dione,
(3aα,4α, 7α,7aα)-2-[4-Chloro-3-(trifluoromethyl)phenyl]-3a,4,7,7a-tetrahydro-4,7-ethano-1H-isoindole-1,3(2H)-dione,
(3aα,4α,7α,7aα)-2-(4-Chloro-2-methoxy-5-methylphenyl)-3a,4,7,7a-tetrahydro-4,7-ethano-1H-isoindole-1,3(2H)-dione,
(3aα,4α,7α,7aα)-2-(3,5-Dichloro-4-hydroxyphenyl)-3a,4,7,7a-tetrahydro-4,7-ethano-1H-isoindole-1,3(2H)-dione,
(3aα,4α,7α,7aα)-3a,4,7,7a-Tetrahydro-2-(4-hydroxy-3-nitrophenyl)-4,7-ethano-1H-isoindole-1,3(2H)-dione,
(3aα,4α, 7α,7aα)-2-(4-Amino-3-nitrophenyl)-3a,4,7,7a-tetrahydro-4,7-ethano-1H-isoindole-1,3(2H)-dione,
(3aα,4α,7α,7aα)-2-(4-Amino-2,3,5,6-tetramethylphenyl)-3a,4,7,7a-tetrahydro-4,7-ethano-1H-isoindole-1,3(2H)-dione,
(3aα,4α,7α,7aα)-3a,4,7,7a-Tetrahydro-2-(4-methyl-3-nitrophenyl)-4,7-ethano-1H-isoindole-1,3(2H)-dione,
(3aα,4α, 7α,7aα)-3a,4,7,7a-Tetrahydro-2-(3,4,5-trimethoxyphenyl)-4,7-ethano-1H-isoindole-1,3(2H)-dione,
(3aα,4α,7α,7aα)-2-(3,4-Dimethoxyphenyl)-3a,4,7,7a-tetrahydro-4,7-ethano-1H-isoindole-1,3(2H)-dione,
(3aα,4α,7α,7aα)-3a,4,7,7a-Tetrahydro-2-(3-hydroxy-4-methoxyphenyl)-4,7-ethano-1H-isoindole-1,3(2H)-dione,
(3aα,4α,7α,7aα)-3a,4,7,7a-Tetrahydro-2-(4-methyl-5-nitro-2-pyridinyl)-4,7-ethano-1H-isoindole-1,3(2H)-dione,
(3aα,4α,7α,7aα)-3a,4,7,7a-Tetrahydro-2-(2-methoxy-3-dibenzofuranyl)-4,7-ethano-1H-isoindole-1,3(2H)-dione,
(3aα,4α,7α,7aα)-3a,4,7,7a-Tetrahydro-2-(2,3,4-trifluorophenyl)-4,7-ethano-1H-isoindole-1,3(2H)-dione,
(3aα,4α,7α,7aα)-2-(2,3-Dihydro-2-methyl-1,3-dioxo-1H-isoindol-5-yl)-3a,4,7,7a-tetrahydro-4,7-ethano-1H-isoindole-1,3(2H)-dione,
(3aα,4α, 7α,7aα)-2-[2,5-Dichloro-4-(1H-pyrrol-1-yl)phenyl]-3a,4,7,7a-tetrahydro-4,7-ethano-1H-isoindole-1,3(2H)-dione,
(3aα,4α, 7α,7aα)-2-[3-[(Diethylamino)methyl]-4-hydroxyphenyl]-3a,4,7,7a-tetrahydro-4,7-ethano-1H-isoindole-1,3(2H)-dione,
(3aα,4α,7α,7aα)-3a,4,7,7a-Tetrahydro-2-[4-(methoxymethyl)-2-oxo-2H-1-benzopyran-7-yl]-4,7-ethano-1H-isoindole-1,3(2H)-dione,
(3aα,4α,7α,7aα)-2-(6-Benzothiazolyl)-3a,4,7,7a-tetrahydro-4,7-ethano-1H-isoindole-1,3(2H)-dione,
(3aα,4α,7α,7aα)-3a,4,7,7a-Tetrahydro-2-(2-oxo-2H-1-benzopyran-6-yl)-4,7-ethano-1H-isoindole-1,3(2H)-dione,
(3aα,4α, 7α,7aα)-3a,4,7,7a-Tetrahydro-2-(2-methyl-8-quinolinyl-4,7-ethano-1H-isoindole-1,3(2H)-dione,
(3aα,4α,7α,7aα)-3a,4,7,7a-Tetrahydro-2-(2,3,5,6-tetramethyl-4-nitrophenyl)-4,7-ethano-1H-isoindole-1,3(2H)-dione,
(3aα,4α,7α,7aα)-3a,4,7,7a-Tetrahydro-2-(2,4,5-trimethylphenyl)-4,7-ethano-1H-isoindole-1,3(2H)-dione,
(3aα,4α, 7α,7aα)-2-(4-Fluoro-3-methylphenyl)-3a,4,7,7a-tetrahydro-4,7-ethano-1H-isoindole-1,3(2H)-dione,
(3aα,4α,7α,7aα)-3a,4,7,7a-Tetrahydro-2-(3-methoxy-4-methylphenyl)-4,7-ethano-1H-isoindole-1,3(2H)-dione,
(3aα,4α,8α,8aα)-2-(2,3-Dimethyl-1H-indol-5-yl)-3a,4,7,7a-tetrahydro-4,7-ethano-1H-isoindole-1,3(2H)-dione,
(3aα,4α,7α,7aα)-2-(3-Dibenzofuranyl)-3a,4,7,7a-tetrahydro-4,7-ethano-1H-isoindole-1,3(2H)-dione,
(3aα,4α,7α,7aα)-3a,4,7,7a-Tetrahydro-2-(2'-hydroxy[1,1':3',1'-terphenyl]-5-yl)-4,7-ethano-1H-isoindole-1,3(2H)-dione,
(3aα,4α,7α,7aα)-3a,4,7,7a-Tetrahydro-2-(5,6,7,8-tetrahydro-3-hydroxy-2-naphthalenyl)-4,7-ethano-1H-isoindole-1,3(2H)-dione,
(3aα,4α,7α,7aα)-2-(1,3-Dihydro-2,2-dioxidobenzo[c]thiophen-5-yl)hexahydro-4,7-ethano-1H-isoindole-1,3(2H)-dione,
(3aα,4α,7α,7aα)-3a,4,7,7a-Tetrahydro-2-(2-hydroxy-4,5-dimethylphenyl)-4,7-ethano-1H-isoindole-1,3(2H)-dione,
(3aα,4α,7α,7aα)-3a,4,7,7a-Tetrahydro-2-(2,2,3,3-tetrafluoro-2H-dihydro-1,4-benzodioxin-6-yl)-4,7-ethano-1H-isoindole-1,3(2H)-dione,
(3aα,4α,7α,7aα)-3a,4,7,7a-Tetrahydro-2-(1H-indazol-5-yl)-4,7-ethano-1H-isoindole-1,3(2H)-dione,
(3aα,4α,7α,7aα)-2-(4-Amino-2,3,5,6-tetrafluorophenyl)-3a,4,7,7a-tetrahydro-4,7-ethano-1H-isoindole-1,3(2H)-dione, (3aα,4α,7α,7aα)-2-(4-Bromo-3-chlorophenyl)-3a,4,7,7a-tetrahydro-4,7-ethano-1H-isoindole-1,3(2H)-dione, (3aα,4α,7α,7aα)-3a,4,7,7a-Tetrahydro-2-(5-hydroxy-1-naphthenyl)-4,7-ethano-1H-isoindole-1,3(2H)-dione, (3aα,4α,7α,7aα)-2-(4-Bromophenyl)-3a,4,7,7a-tetrahydro-4,7-ethano-1H-isoindole-1,3(2H)-dione, (3aα,4α,7α,7aα)-3a,4,7,7a-Tetrahydro-2-(2-naphthalenyl)-4,7-ethano-1H-isoindole-1,3(2H)-dione, (3aα-4α,7α,7aα)-3a,4,7,7a-Tetrahydro-2-[3-(trifluoromethyl)phenyl]-4,7-ethano-1H-isoindole-1,3(2H)-dione, (3aα,4α,7α,7aα)-3a,4,7,7a-Tetrahydro-2-(4-nitrophenyl)-4,7-ethano-1H-isoindole-1,3(2H)-dione, (3aα,4α,8α,8aα)-2-(9-Ethyl-9H-carbazol-3-yl)-3a,4,7,7a-tetrahydro-4,7-ethano-1H-isoindole-1,3(2H)-dione, (3aα,4α,8α,8aα)-2-[1,2-Dihydro-8-methyl-2-oxo-4-(trifluoromethyl-7-quinolinyl]-3a,4,7-tetrahydro-4,7-ethano-1H-isoindole-1,3(2H)-dione, (3aα,4β,4aα,5aα,6β,6aα)-2-(3,4-Dichlorophenyl)-4,4a,5,5a,6,6a-hexahydro-4,6-ethanocycloprop[f]isoindole-1,3(2H,3aH)-dione, (3aα,4β,4aα,5aα,6β,6aα)-2-(4-Bromo-3-methylphenyl)-4,4-a,5,5a,6,6a-hexahydro-4,6-ethanocycloprop[f]isoindole-1,3(2H,3aH)dione, (3aα,4β,4aα,5aα,6β,6aα)-4,4-a,5,5a,6,6a-Hexahydro-2-(1-naphthalenyl)-4,6-ethanocycloprop[f]isoindole-1,3(2H,3aH)-dione, (3aα,4β,4aα,5aα,6β,6aα)-4,4-a,5,5a,6,6a-Hexahydro-2-(2-naphthalenyl)-4,6-ethanocycloprop[f]isoindole-1,3(2H,3aH)-dione, (3aα,4β,4aα,5aα,6β,6aα)-4,4a,5,5a,6,6a-Hexahydro-2-[3-(trifluoromethyl)phenyl]-4,6-ethanocycloprop[f]isoindole-1,3(2H,3aH)-dione, (3aα,4β,4aα,5aα,6β,6aα)-2-(3,5-Dichlorophenyl)-4,4-a,5,5a,6,6a-hexahydro-4,6-ethanocycloprop[f]isoindole-1,3(2H,3aH)-dione, (3aα,4β,4aα,5aα,6β,6aα)-4,4-a,5,5a,6,6a-Hexahydro-2-1,4-nitro-3,4-trifluoromethyl)phenyl-4,6-ethanocycloprop[f]isoindole-1,3(2H,3aH)-dione, (3aα,4β,4aα,5aα,6β,6aα)-2-[3,5-Bis(trifluoromethyl)phenyl]-4,4a,5,5a,6,6a-hexahydro-4,6-ethanocycloprop[f]isoindole-1,3(2H,3aH)-dione, (3aα,4β,4aα,5α,6β,6aα)-4,4-a,5,5a,6,6a-Hexahydro-2-(1,2,3,4-tetrahydro-1-naphthalenyl)-4,6-ethanocycloprop[f]isoindole-1,3(2H,3aH)-dione, (3aα,4β,4aα,5aα,6β,6aα)-2-(2,3-Dihydro-1H-inden-5-yl-4,4-a,5,5a,6,6a-hexahydro-4,6-ethanocycloprop[f]isoindole-1,3(2H,3aH)-dione, (3aα,4β,4aα,5aα,6β,6aα)-4-(Octahydro-1,3-dioxo-4,6-ethanocycloprop[f]isoindol-2(1H)-yl)-1-naphthalenecarbonitrile, (3aα,4β,4aα,5aα,6β,6aα)-2-(4-Bromo-1-naphthalenyl)-4,4a,5,5a/5,6a-hexahydro-4,6-ethanocycloprop[f]isoindole-1,3(2H,3aH)-dione, (3aα,4β,4aα,5aα,6β,6aα)-4-2-(4-Chloro-1-naphthalenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(5-quinolinyl)-4,6-ethanocycloprop[f]isoindole-1,3(2H,3aH)-dione, (3aα,4β,4aα,5aα,6β,6aα)-4,4a,5,5a,6,6a-Hexahydro-2-(6-quinolinyl)-4,6-ethanocycloprop[f]isoindole-1,3(2H,3aH)-dione, (3aα,4β,4aα,5aα,6β,6aα)-4,4a,5,5a,6,6a-Hexahydro-2-(4-methyl-2-oxo-2H-1-benzopyran-7-yl)-4,6-ethanocycloprop[f]isoindole-1,3(2H,3aH)-dione, (3aα,4β,4aα,5aα,6β,6aα)-4,4-a,5,5a,6,6a-Hexahydro-2-(5-isoquinolinyl)-4,6-ethanocycloprop[f]isoindole-1,3(2H,3aH)-dione, (3aα,4β,4aα,5aα,6β,6aα)-2-(3,5-Dinitrophenyl)-4,4-a,5,5a,6,6a-hexahydro-4,6-ethanocycloprop[f]isoindole-1,3(2H,3aH)dione, (3aα,4β,4aα,5aα,6β,6aα)-4,4a,5,5a,6,6a-Hexahydro-2-(2,4,5-trifluorophenyl)-4,6-ethanocycloprop[f]isoindole-1,3(2H,3aH)-dione, (3aα,4β,4aα,5aα,6β,6aα)-2-[2-Fluoro-5-(trifluoromethyl)phenyl]-4,4a,5,5a,6,6a-hexahydro-4,6-ethanocycloprop[f]isoindole-1,3(2H,3aH)-dione, (3aα,4β,4aα,5aα,6β,6aα)-2-(2-Fluoro-5-methyl-phenyl)-4,4a,5,5a,6,6a-hexahydro-4,6-ethanocycloprop[f]isoindole-1,3(2H,3aH)-dione, (3aα,4β,4aα,5aα,6β,6aα)-2-(2-Chloro-4-nitrophenyl)-4,4a,5,5a,6,6a-hexahydro-4,6-ethanocycloprop[f]isoindole-1,3(2H,3aH)-dione, (3aα,4β,3,4aα,5aα,6β,6aα)-2-[2-Chloro-5-(trifluoromethyl)phenyl]-4,4a,5,5a,6,6a-hexahydro-4,6-ethanocycloprop[f]isoindole-1,3(2H,3aH)-dione, (3aα,4β,4aα,5aα,6β,6aα)-2-(3-Fluorophenyl)-4,4a,5,5a,6,6a-hexahydro-4,6-ethanocycloprop[f]isoindole-1,3(2H,3aH)-dione, (3aα,4β,4aα,5aα,6β,6aα)-2-(3,4-Difluorophenyl)-4,4a,5,5a,6,6a-hexahydro-4,6-ethanocycloprop[f]isoindole-1,3(2H,3aH)-dione, (3aα,4β,4aα,5aα,6β,6aα)-2-(3-Fluoro-4-methylphenyl)-4,4-a,5,5a,6,6a-hexahydro-4,6-ethanocycloprop[f]isoindole-1,3(2H,3aH)-dione, (3aα,4β,4aα,5aα,6β,6aα)-2-(3,5-Difluorophenyl)-4,4a,5,5a,6,6a-hexahydro-4,6-ethanocycloprop[f]isoindole-1,3(2H,3aH)-dione, (3aα,4β,4aα,5aα,6β,6aα)-2-(3-Chlorophenyl)-4,4a,5,5a,6,6a-hexahydro-4,6-ethanocycloprop[f]isoindole-1,3(2H,3aH)-dione, (3aα,4β,4aα,5aα,6β,6aα)-2-(3-Chloro-4-fluorophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(3,4,5-trichlorophenyl)-4,6-ethanocycloprop[f]isoindole-1,3(2H,3aH)-dione, (3aα,4β,4aα,5aα,6β,6aα)-2(3-Chloro-4-methylphenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(3-iodophenyl)-4,6-ethanocycloprop[f]isoindole-1,3(2H,3aH)-dione, (3aα,4β,4aα,5aα,6β,6aα)-4,4a,5,5a,6,6a-Hexahydro-2-(3-nitrophenyl)-4,6-ethanocycloprop[f]isoindole-1,3(2H,3aH)-dione, (3aα,4β,4aα,5aα,6β,6aα)-2-(3-Acetylphenyl)-4,4a,5,5a,6,6a-hexahydro-4,6-ethanocycloprop[f]isoindole-1,3(2H,3aH)-dione, (3aα,4β,4aα,5aα,6β,6aα)-2,4,3,4-Dimethylphenyl)-4,4a,5,5a,6,6a-hexahydro-4,6-ethanocycloprop[f]isoindole-1,3(2H,3aH)-dione, (3aα,4β,4aα,5aα,6β,6aα)-2-(3,5-Dimethylphenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-[3-(hydroxymethyl)phenyl]-4,6-ethanocycloprop[f]isoindole-1,3(2H,3aH)-dione, (3aα,4β,4aα,5aα,6β,6aα)-2-(Ethylphenyl)-4,4a,5,5a,6,6a-hexahydro-4,6-ethanocycloprop[f]isoindole-1,3(2H,3aH)-dione, (3aα,4β,4aα,5aα,6β,6aα)-2-(4-Bromophenyl)-4,4a,5,5a,6,6a-hexahydro-4,6-ethanocycloprop[f]isoindole-1,3(2H,3aH)-dione, (3aα,4β,4aα,5aα,6β,6aα)-2-(4-Bromo-3-(trifluoromethyl)phenyl)-4,4a,5,5a,6,6a-hexahydro-4,6-ethanocycloprop[f]isoindole-1,3(2H,3aH)-dione, (3aα,4β,4aα,5aα,6β,6aα)-2-(4-Fluoro-3-nitrophenyl)-4,4a,5,5a,6,6a-hexahydro-4,6-ethanocycloprop[f]isoindole-1,3(2H,3aH)-dione, (3aα,4β,4aα,5aα,6β,6aα)-2-(4-Fluoro-3-(trifluoromethyl)phenyl-4,4a,5,5a,6,6a-hexahydro-4,6-ethanocycloprop[f]isoindole-1,3(2H,3aH)-dione, (3aα,4β,4aα, 5aα,6β,6aα)-2-(4-Chloro-3-nitrophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(4-iodophenyl)-4,6-ethanocycloprop[f]isoindole-1,3(2H,3aH)-dione, (3aα,4β,4aα,5aα,6β,6aα)-4,4a,5,5a,6,6a-Hexahydro-2-(4-nitrophenyl)-4,6-ethanocycloprop[f]isoindole-1,3(2H,3aH)-dione, (3aα,4β,4aα,5aα,6β,6aα)-4,4a,5,5a,6,6a-Hexahydro-2-(4-(1-methylethyl)phenyl-4,6-ethanocycloprop[f]isoindole-1,3(2H,3aH)-dione, (3aα,4β,4aα,5aα,6β,6aα)-4,4a,5,5a,6,6a-Hexahydro-2-(4-methyl-3-nitrophenyl)-4,6-ethanocycloprop[f]isoindole-1,3(2H,3aH)-dione, (3aα,4β,4aα,5aα,6β,6aα)-2-(4-Ethylphenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(4-propylphenyl)-4,6-ethanocycloprop[f]isoindole-1,3(2H,3aH)-dione, (3aα,4β,4aα,5aα,6β,6aα)-4,4a,5,5a,6,6a-Hexahydro-2-(2,3,4-trifluorophenyl)-4,6-ethanocycloprop[f]isoindole-1,3(2H,3aH)-dione, (3aα,4β,4aα,5aα,6β,6aα)-2-[4-(1,1-Dimethylethyl)-3-nitrophenyl]-4,4a,5,5a,6,6a-hexahydro-4,6-ethanocycloprop[f]isoindole-1,3(2H,3aH)-dione, (3aα,4β,4aα,5aα,6β,6aα-4-2-(4-Bromo-2,6-difluorophenyl)-4,4a,5,5a,6,6a-hexahydro-4,6-ethanocycloprop[f]isoindole-1,3(2H,3aH)dione, (3aα,4β,4aα,5aα,6β,6aα-2-(6-Benzothiazolyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-1-Hexahydro-2-(2-methyl-8-quinolinyl)-4,6-ethanocycloprop[f]isoindole-1,3(2H,3aH)-dione, (3aα, 4β,4aα,5aα,6β,6aα)-2-(4-Fluoro-3-methylphenyl)-4,4a,5,5a,6,6a-hexahydro-4,6-ethanocycloprop[f]isoindole-1,3(2H,3aH)-dione, (3aα,4β,4aα,5aα,6β,6aα)-2-(1,3-Dihydro-3-oxo-5-isobenzofuranyl)-4,4a,5,5a,6,6a-hexahydro-4,6-ethanocycloprop[f]isoindole-1,3(2H,3aH)-dione, (3aα,4β,4aα,5aα,6β,6aα)-2-(5-Acetyl-2-methyl-4-nitrophenyl)-4,4a,5,5a,6,6a-hexahydro-4,6-ethanocycloprop[f]isoindole-1,3(2H,3aH)-dione, (3aα,4β,4aα,5aα,6β,6aα)-2-(2-Ethyl-5-nitrophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(2-methyl-5-benzofuranyl)-4,6-ethanocycloprop[f]isoindole-1,3(2H,3aH)-dione, (3aα,4β,4aα,5aα,6β,6aα)-2-(2,3-Dihydro-1-oxo-1H-inden-5-yl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(1H-indazol-5-yl)-4,6-ethanocycloprop[f]isoindole-1,3(2H,3aH)-dione, (3aα,4β,4aα,5aα,6β,6aα)-4,4a,5,5a,6,6a-Hexahydro-2-[4-[2,2,2-trifluoro-1-hydroxy-1-(trifluoromethyl)ethyl]phenyl]-4,6-ethanocycloprop[f]isoindole-1,3(2H,3aH)-dione, (3aα,4β,4aα,5aα,6β,6aα)-2-(4-Bromo-3-chlorophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-[3-(trifluoromethoxy)phenyl]-4,6-ethanocycloprop[f]isoindole-1,3(2H,3aH)-dione, (3aα,4β,4aα,5aα,6β,6aα)-4,4a,5,5a,6,6a-Hexahydro-2-[4-methoxy-3-(trifluoromethyl)phenyl]-4,6-ethanocycloprop[f]isoindole-1,3(2H,3aH)-dione, (3aα,4β,4aα,5aα,6β,6aα)-2-(3,5-Dibromophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(3-iodo-4-methylphenyl)-4,6-ethanocycloprop[f]isoindole-1,3(2H,3aH)-dione, (3aα,4β,4aα,5aα,6β,6aα-2-(3-Chloro-4-iodophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(2-methyl-6-quinolinyl)-4,6-ethanocycloprop[f]isoindole-1,3(2H,3aH)-dione, (3aα,4β,4aα,5aα,6β,6aα)-4,4a,5,5a,6,6a-Hexahydro-2-[4-(trifluoromethyl)phenyl]-4,6-ethanocycloprop[f]isoindole-1,3(2H,3aH)-dione, (3aα,4β,4aα,5aα,6β,6aα)-2-(4-Chloro-3-methylphenyl-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-[4-(methoxymethyl)-2-oxo-2H-1-benzopyran-7-yl]-4,6-ethanocycloprop[f]isoindole-1,3(2H,3aH)-dione, (3aα,4β,4aα,5aα,6β,6aα)-4,4a, 5,5a, 6,6a-Hexahydro-2-(2-oxo-2H-1-benzopyran-6-yl)-4,6-ethanocycloprop[f]isoindole-1,3(2H,3aH)-dione, (3α,4β,4aα,5aα,6β,6aα)-4,4a,5,5a,6,6a-Hexahydro-2-[2-[(1-methylethyl)amino]-5-(trifluoromethyl)phenyl]-4,6-ethanocycloprop[f]isoindole-1,3(2H,3aH)-dione, (3aα,4β,4aα,5aα,6β,6aα)-2-(3-Chloro-4-fluorophenyl)-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-(3-methyl-4-nitrophenyl)-4,6-ethanocycloprop[f]isoindole-1,3(2H,3aH)-dione, (3aα,4β,4aα,5aα,6β,6aα)-2,4,5-[(Difluoromethyl)sulfonyl)-2-methoxyphenyl]-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-[3-(1-methylethyl)phenyl]-4,6-ethanocycloprop[f]isoindole-1,3(2H,3aH)-dione, (3aα,4β,4aα,5aα,6β,6aα)-4,4a,5,5a,6,6a-Hexahydro-2-[4-L(trifluoromethyl)thio)phenyl]-4,6-ethanocycloprop[f]isoindole-1,3(2H,3aH)-dione, (3aα,4β,4aα,5α,6β,6aα)-4,4a,5,5a,6,6a-Hexahydro-2-[2-(2-methoxyphenoxy)-5-(trifluoromethyl)phenyl]-4,6-ethanocycloprop[f]isoindole-1,3(2H,3aH)-dione, (3aα,4β,4aα,5aα,6β,6aα)-4,4a,5,5a,6,6a-Hexahydro-2-[4-(1,1,2,2-tetrafluoroethoxy)phenyl]-4,6-ethanocycloprop[f]isoindole-1,3(2H,3aH)-dione, (3aα,4β,4aα,5aα,6β,6aα)-2-(3-Acetyl-4-nitrophenyl)-4,4a,5,5a,6,6a-hexahydro-4,6-ethanocycloprop[f]isoindole-1,3(2H,3aH)-dione, (3aα,4β,4aα,5aα,6β,6aα)-2-[3-(1H-Dimethylethyl)phenyl]-4,4a,5,5a,6,6a-hexahydro-4,6-ethanocycloprop[f]isoindole-1,3(2H,3aH)-dione, (3aα,4β,4aα,5aα,6β,6aα)-4,4a,5,5a,6,6a-Hexahydro-2-[2-methyl-3-(trifluoromethyl)phenyl]-4,6-ethanocycloprop[f]isoindole-1,3(2H,3aH)-dione, (3aα,4β,4aα,5aα,6β,6aα)-4,4a,5,5a,6,6a-Hexahydro-2-(4-nitro-1-naphthalenyl)-4,6-ethanocycloprop[f]isoindole-1,3(2H,3aH)-dione, (3aα,4α,7α,7aα)-Hexahydro-2-(2-naphthalenyl)-4,7-methano-1H-isoindole-1,3(2H)-dione, (3aα,4α, 7α,7aα)-2-(2-Amino-4,5-dichlorophenyl)hexahydro-4,7-methano-1H-isoindole-1,3(2H)-dione, (3aα,4α, 7α,7aα)-Hexahydro-2-(4-nitro-1-naphthalenyl)-4,7-methano-1H-isoindole-1,3(2H)-dione, (3aα,4α,7α,7aα)-Hexahydro-2-(8-hydroxy-5-quinolinyl)-4,7-methano-1H-isoindole-1,3(2H)-dione, (3aα,4α,7α,7aα)-Hexahydro-2-(1-naphthalenyl)-4,7-methano-1H-isoindole-1,3(2H)-dione, (3aα,4α,7α,7aα)-Hexahydro-2-[4-nitro-3-(trifluoromethyl)phenyl]-4,7-methano-1H-isoindole-1,3 (2H)-dione, (3aα,4α,7α,7aα)-2-(4-Bromo-1-naphthalenyl)hexahydro-4,7-methano-1H-isoindole-1,3(2H)-dione, (3aα,4α,7α,7aα)-2-(2-Fluorenyl)hexahydro-4,7-methano-1H-isoindole-1,3(2H)-dione, (3aα,4α,7α,7aα)-Hexahydro-2-(2-methyl-1-naphthalenyl)-4,7-methano-1H-isoindole-1,3(2H)-dione, (3aα,4α,7α,7aα)-2-(3,5-Dichlorophenyl)hexahydro-4,7-methano-1H-isoindole-1,3(2H)-dione, (3aα,4α,7α,7aα)-2-(3-Chlorophenyl)hexahydro-4,7-methano-1H-isoindole-1,3(2H)-dione, (3aα,4α,7α,7aα)-2-(3-Chloro-4-fluorophenyl)hexahydro-4,7-methano-1H-isoindole-1,3(2H)-dione, (3aα,4α,7α,7aα)-Hexahydro-2-[3-(trifluoromethyl)phenyl]-4,7-methano-1H-isoindole-1,3(2H)-dione, (3aα,4α,7α,7aα)-2-[4-Bromo-3-(trifluoromethyl)phenyl]-Hexahydro-4,7-methano-1H-isoindole-1,3(2H)-dione, (3aα,4α,7α,7aα)-2-(4-Bromo-3-methylphenyl)hexahydro-4,7-methano-1H-isoindole-1,3(2H)-dione, (3aα,4α,7α,7aα)-2-(1,2-Dihydro-4-methyl-2-oxo-7-quinolinyl)hexahydro-4,7-methano-1H-isoindole-1,3(2H)-dione, (3aα,4α,7α,7aα)-Hexahydro-2-(4-pyridinyl)-4,7-methano-1H-isoindole-1,3(2H)-dione, (3aα,4α,7α,7aα)-Hexahydro-2-(1-oxido-4-pyridinyl)-4,7-methano-1H-isoindole-1,3(2H)-dione, (3aα,4α,7α,7aα)-Hexahydro-2-(6-quinolinyl)-4,7-methano-1H-isoindole-1,3(2H)-dione, (3aα,4α,7α,7aα)-Hexahydro-2-(1-oxido-6-quinolinyl)-4,7-methano-1H-isoindole-1,3(2H)-dione, (3aα,4α,7α,7aα)-Hexahydro-2-(5-nitro-8-isoquinolinyl)-4,7-methano-1,11-isoindole-1,3(2H)-dione, trifluoroacetate (1:1), (3aα,4α,7α,7aα)-Hexahydro-2-[4-(methylsulfanyl)phenyl]-4,7-methano-1H-isoindole-1,3(2H)-dione, (3aα,4α,7α,7aα)-Hexahydro-2-[4-(methylthio)phenyl]-4,7-methano-1H-isoindole-1,3(2H)-dione, (3aα,4α,7α,7aα)-Hexahydro-2-[4-(methylsulfinyl)phenyl]-4,7-methano-1H-isoindole-1,3(2H)-dione, (3aα,4α,7α,7aα)-2-(4-Fluoro-1-naphthalenyl)hexahydro-4,3-methano-1H-isoindole-1,3(2H)-dione, (3aα,4α,7α,7aα)-2-(1,1-Dioxido-2H-naphth[1,8-cd]isothiazol-5-yl)hexahydro-4,7-methano-1H-isoindole-1,3(2H)-dione, (3aα,4α,7α,7aα)-Hexahydro-2-(6-hydroxy-3-pyridinyl)-4,7-methano-1H-isoindole-1,3(2H)-dione, (3aα,4α,7α,7aα)-2-(1,2-Benzisothiazol-3-yl)hexahydro-4,7-methano-1H-isoindole-1,3(2H)-dione, (3aα,4α,7α,7aα)-2-(3-Benzofuranyl)hexahydro-4,7-methano-1H-isoindole-1,3(2H)-dione, (3aα,4α,7α,7aα)-Hexahydro-2-[4-(4-isothiazolyl)phenyl]-4,7-methano-1H-isoindole-1,3(2H)-dione (3aα,4α,4α,5α,6α,6aα)-4,4a,5,5a,6,6a-Hexahydro-2-[3-(trifluoromethyl)phenyl]-4,6-methanocycloprop[f]isoindole-1,3(2H,3aH)-dione, (3aα,4α,4α,5α,6α,6aα)-4,4a,5,5a,6,6a-Hexahydro-2-[4-nitro-3-(trifluoromethyl)phenyl]-4,6-methanocycloprop[f]isoindole-1,3(2H,3aH)-dione, (3aα,4α,4aβ,5aβ,6α,6aα)-4,4a,5,5a,6,6a-Hexahydro-2-(4-nitro-1-naphthalenyl)-4,6-methanocycloprop[f]isoindole-1,3(2H,3aH)-dione, (3aα,4α,4aβ,5aβ,6α,6aα)-2-(1,2-Dihydro-4-methyl-2-oxo-7-quinolinyl)-4,4a,5,5a,6,6a-hexahydro-4,6-methanocycloprop[f]isoindole-1,3(2H,3aH)-dione, (3aα,4β,4aα,5aα,6β,6aα)-4,4-a,5,5a,6,6a-Hexahydro-2-[3-(trifluoromethyl)phenyl]-4,6-methanocycloprop[f]isoindole-1,3(2H,3aH)-dione, (3aα,4β,4aα,5aα,6β,6aα)-2-(3,5-Dichlorphenyl)-4,4a,5,5a,6,6a-hexahydro-4,6-methanocycloprop[f]isoindole-1,3(2H,3aH)-dione, (3aα,4β,4aα,5aα,6β,6aα)-4,4a,5,5a,6,6a-Hexahydro-2-[4-nitro-3-(trifluoromethyl)phenyl]-4,6-methanocycloprop[f]isoindole-1,3(2H,3aH)-dione, (3aα,4β,4aα,5aα,6β,6aα)-2-(1,2-Dihydro-4-methyl-2-oxo-7-quinolinyl)-4,4a,5,5a,6,6a-hexahydro-4,6-methanocycloprop[f]isoindole-1,3(2H,3aH)-dione, (3aα,4β,7β,7aα)-3a,4,7,7a-tetrahydro-2-(2-naphthalenyl)-4,7-methano-1H-isoindole-1,3(2H)-dione, (3aα,4β, 7β,7aα)-Hexahydro-2-(1-naphthalenyl)-4,7-methano-1H-isoindole-1,3(2H)-dione, (3aα,4β,7β,7aα)-2-(3,5-Dichlorophenyl)-3a,4,7,7a-tetrahydro-4,7-methano-1H-isoindole-1,3(2H)-dione, (3aα,4β,7β,7aα)-3a,4,7,7a-Tetrahydro-2-[3-trifluoromethyl)phenyl]-4,7-methano-1H-isoindole-1,3(2H)-dione, (3aα,4β,7β,7aα)-3a,4,7,7a-Tetrahydro-2-(4-methyl-2-oxo-2H-1-benzopyran-7-yl)-4,7-methano-1H-isoindole-1,3(2H)-dione, (3aα,4β,7β,7aα)-3a,4,7,7a-Tetrahydro-2-[4-nitro-3-(trifluoromethyl)phenyl]-4,7-methano-1H-isoindole-1,3 (2H)-dione, (3aα,4β,7β,7aα)-3a,4,7,7a-Tetrahydro-2-(4-nitro-1-naphthalenyl)-4,7-methano-1H-isoindole-1,3(2H)-dione, (3aα,4β,7β,7aα)-Hexahydro-2-(2-naphthalenyl)-4,7-methano-1H-isoindole-1,3(2H)-dione, (3aα,4β,7β,7aα)-Hexahydro-2-[3-(trifluoromethyl)phenyl]-4,7-methano-1H-isoindole-1,3(2H)-dione, (3aα,4β,7β,7aα)-Hexahydro-2-(3,5-Dichlorophenyl)hexahydro-4,7-methano-1H-isoindole-1,3(2H)-dione, (3aα,4β,7β,7aα)-Hexahydro-2-[4-nitro-3-(trifluoromethyl)phenyl]-4,7-methano-1H-isoindole-1,3(2H)-dione, (3aα,4β,7β,7aα)-Hexahydro-2-(4-nitro-1-naphthalenyl)-4,7-methano-1H-isoindole-1,3(2H)-dione, (3aα,4β,7β,7aα)-Hexahydro-2-(1,2-Dihydro-4-methyl-2-oxo-7-quinolinyl)hexahydro-4,7-methano-1H-isoindole-1,3 (2H)-dione, (3aα,4α,5α,7α,7aα)-Hexahydro-2-(2-naphthalenyl)-5-phenyl-4,7-methano-1H-isoindole-1,3(2H)-dione, (3aα,4α, 5α,7α,7aα)-Hexahydro-5-phenyl-2-[3-(trifluoromethyl)phenyl]-4,7-methano-1H-isoindole-1,3(1H)-dione,
(3aα,4α,5α,7α,7aα)-Hexahydro-2-(1-naphthalenyl)-5-phenyl-4,7-methano-1H-isoindole-1,3(2H)-dione,
(3aα,4α,5α,7α,7aα)-2-(3,4-Dichlorophenyl)hexahydro-5-phenyl-4,7-methano-1H-isoindole-1,3(2H)-dione,
(3aα,4α,5α,7α,7aα)-2-(3,5-Dichlorophenyl)hexahydro-5-phenyl-4,7-methano-1H-isoindole-1,3(2H)-dione,
(3aα,4α,5α,7α,7aα)-2-(1,2-Dihydro-4-methyl-2-oxo-7-quinolinyl)hexahydro-5-phenyl-4,7-methano-1H-isoindole-1,3(2H)-dione,
(3aα,4α,5α,7α,7aα)-2-(1,2-Dihydro-4-methyl-2-oxo-7-quinolinyl)hexahydro-5-phenyl-4,7-methano-1H-isoindole-1,3(2H)-dione, trifluoroacetate (1:1),
(3aα,4α,5α,7α,7aα)-Hexahydro-5-phenyl-2-[3-(trifluoromethyl)phenyl]-4,7-methano-1H-isoindole-1,3(2H)-dione,
(3aα,4α,5α,7α,7aα)-Hexahydro-2-[4,4-nitro-3-(trifluoromethyl)phenyl]-5-phenyl-4,7-methano-1H-isoindole-1,3(2H)-dione,
(3aα,4α,5α,7α,7aα)-Hexahydro-2-(4-nitro-1-naphthalenyl)-5-phenyl-4,7-methano-1H-isoindole-1,3(2H)-dione,
(3aα,4α,5α,7α,7aα)-Hexahydro-2-(4-nitro-1-naphthalenyl)-5-phenyl-4,7-methano-1H-isoindole-1,3(2H)-dione,
(3aα,4α,5α,7α,7aα)-Hexahydro-2-[4-nitro-3-(trifluoromethyl)phenyl]-5-phenyl-4,7-methano-1H-isoindole-1,3(2H)-dione,
(3aα,4α,7α,7aα)-4,5,6,7,8,8-Hexachloro-3a,4,7,7a-tetrahydro-2-(3-nitrophenyl)-4,7-methano-1H-isoindole-1,3(2H)-dione,
(3aα,4α,7α,7aα)-4,5,6,7,8,8-Hexachloro-2-[4-(methylthio)phenyl]-3a,4,7,7a-tetrahydro-4,7-methano-1H-isoindole-1,3(2H)-dione,
(3aα,4α,7α,7aα)-4,5,6,7,8,8-Hexachloro-2-(5-chloro-2-methoxyphenyl)-3a,4,7,7a-tetrahydro-4,7-methano-1H-isoindole-1,3(2H)-dione,
(3aα,4α,7α,7α)-4,5,6,7,8,8-Hexachloro-3a,4,7,7a-tetrahydro-2-(3-methoxyphenyl)-4,7-methano-1H-isoindole-1,3(2H)-dione,
(3aα,4α,7α,7aα)-4,5,6,7,8,8-Hexachloro-3a,4,7,7a-tetrahydro-2-(1-naphthalenyl)-4,7-methano-1H-isoindole-1,3(2H)-dione,
(3aα,4α,7α,7aα)-4,5,6,7,8,8-Hexachloro-2-(2,3-dimethylphenyl)-3a,4,7,7a-tetrahydro-4,7-methano-1H-isoindole-1,3(2H)-dione,
(3aα,4α,7α,7aα)-4,5,6,7,8,8-Hexachloro-2-(3,4-dichlorophenyl-3a,4,7,7a-tetrahydro-4,7-methano-1H-isoindole-1,3(2H)-dione,
(3aα,4α,7α,7aα)-2-(4-Bromophenyl-4,5,6,7,8,8-hexachloro-3a,4,7,7a-tetrahydro-4,7-methano-1H-isoindole-1,3(2H)-dione,
(3aα,4α,7α,7aα)-4,5,6,7,8,8-Hexachloro-3a,4,7,7a-tetrahydro-2-[2-methyl-5-(1-methylethyl)phenyl]-4,7-methano-1H-isoindole-1,3(2H)-dione,
(3aα,4α,7α,7aα)-4,5,6,7,8,8-Hexachloro-2-(3-chloro-4-methylphenyl)-3a,4,7,7a-tetrahydro-4,7-methano-1H-isoindole-1,3(2H)-dione,
(3aα,4α,7α,7aα)-4,5,6,7,8,8-Hexachloro-2-(2,3-dichlorophenyl)-3a,4,7,7a-tetrahydro-4,7-methano-1H-isoindole-1,3(2H)-dione,
(3aα,4α,7α,7aα)-4,5,6,7,8,8-Hexachloro-3a,4,7,7a-tetrahydro-2-[3-(methylthio)phenyl]-4,7-methano-1H-isoindole-1,3(2H)-dione,
(3aα,4α,7α,7aα)-4,5,6,7,8,8-Hexachloro-2-(4-fluoro-3-nitrophenyl)-3a,4,7,7a-tetrahydro-4,7-methano-1H-isoindole-1,3(2H)-dione,
3a,4,7,7a-Tetrahydro-2-(6-methyl-2-pyridinyl)-4,7-methano-1H-isoindole-1,3(2H)-dione,
3a,4,7,7a-Tetrahydro-2-(4-pyridinyl)-4,7-methano-1H-isoindole-1,3(2H)-dione,
2-(4-Ethoxyphenyl)-3a,4,7,7a-tetrahydro-4,7-methano-1H-isoindole-1,3(2H)-dione,
3a,4,7,7a-Tetrahydro-2-(3-pyridinyl)-4,7-methano-1H-isoindole-1,3(2H)-dione,
3a,4,7,7a-Tetrahydro-2-(2-pyridinyl)-4,7-methano-1H-isoindole-1,3(2H)-dione,
3a,4,7,7a-Tetrahydro-2-(3-methyl-2-pyridinyl)-4,7-methano-1H-isoindole-1,3(2H)-dione,
3a,4,7,7a-Tetrahydro-2-[4-(2-hydroxyethyl)phenyl]-4,7-methano-1H-isoindole-1,3(2H)-dione,
3a,4,7,7a-Tetrahydro-2-(2-mercaptophenyl)-4,7-methano-1H-isoindole-1,3(2H)-dione,
3a,4,7,7a-Tetrahydro-2-(2-hydroxyphenyl)-4,7-methano-1H-isoindole-1,3(2H)-dione,
3a,4,7,7a-Tetrahydro-2-[4-phenyl-methoxy)phenyl]-4,7-methano-1H-isoindole-1,3(2H)-dione,
3a,4,7,7a-Tetrahydro-2-[2-(phenylmethoxy)phenyl]-4,7-methano-1H-isoindole-1,3(2H)-dione,
3a,4,7,7a-Tetrahydro-2-[3-(phenylmethoxy)phenyl]-4,7-methano-1H-isoindole-1,3(2H)-dione,
3a,4,7,7a-Tetrahydro-2-[4[(4-nitrophenyl)methoxy]phenyl]-4,7-methano-1H-isoindole-1,3(2H)-dione,
3a,4,7,7a-Tetrahydro-2-[2-[(4-nitrophenyl)methoxy]phenyl]-4,7-methano-1H-isoindole-1,3(2H)-dione,
3a,4,7,7a-Tetrahydro-2-[3,4[(4-nitrophenyl)methoxy]phenyl]-4,7-methano-1H-isoindole-1,3(2H)-dione,
3a,4,7,7a-Tetrahydro-2-[4-[(4-methylphenyl)methoxy]phenyl]-4,7-methano-1H-isoindole-1,3(2H)-dione,
3a,4,7,7a-Tetrahydro-2-[3-[(4-methylphenyl)methoxy]phenyl]-4,7-methano-1H-isoindole-1,3(2H)-dione,
3a,4,7,7a-Tetrahydro-2-[2-[(4-methylphenyl)methoxy]phenyl]-4,7-methano-1H-isoindole-1,3(2H)-dione,
2-[4-[(4-Butylphenyl)methoxy]phenyl]-3a,4,7,7a-tetrahydro-4,7-methano-1H-isoindole-1,3(2H)-dione,
2-[2-[(4-Butylphenyl)methoxy]phenyl]-3a,4,7,7a-tetrahydro-4,7-methano-1H-isoindole-1,3(2H)-dione,
2-[3-[(4-Butylphenyl)methoxy]phenyl]-3a,4,7,7a-tetrahydro-4,7-methano-1H-isoindole-1,3(2H)-dione,
2-[4-[(2-Chlorophenyl)methoxy]phenyl]-3a,4,7,7a-tetrahydro-4,7-methano-1H-isoindole-1,3(2H)-dione,
2-[4-[(4-Chlorophenyl)methoxy]phenyl]-3a,4,7,7a-tetrahydro-4,7-methano-1H-isoindole-1,3(2H)-dione,
2-[2-[(4-Chlorophenyl)methoxy]phenyl]-3a,4,7,7a-tetrahydro-4,7-methano-1H-isoindole-1,3(2H)-dione,
2-[2-[(2-Chlorophenyl)methoxy]phenyl]-3a,4,7,7a-tetrahydro-4,7-methano-1H-isoindole-1,3(2H)-dione,
2-[3-[(2-Chlorophenyl)methoxy]phenyl]-3a,4,7,7a-tetrahydro-4,7-methano-1H-isoindole-1,3(2H)-dione,
2-[3-[(4-Chlorophenyl)methoxy]phenyl]-3a,4,7,7a-tetrahydro-4,7-methano-1H-isoindole-1,3(2H)-dione,
3a,4,7,7a-Tetrahydro-2-phenyl-4,7-methano-1H-isoindole-1,3(2H)-dione,
2-[(Benzoyloxy)phenyl]-3a,4,7,7a-tetrahydro-4,7-methano-1H-isoindole-1,3(2H)-dione,
2-[3-(3,4-Dimethylbenzoyl)phenyl]-3a,4,7,7a-tetrahydro-4,7-methano-1H-isoindole-1,3(2H)-dione,
2-(3,4-Dimethylphenyl)-3a,4,7,7a-tetrahydro-4,7-methano-1H-isoindole-1,3(2H)-dione,
2-(5-Chloro-2-methoxyphenyl)-3a,4,7,7a-tetrahydro-4,7-methano-1H-isoindole-1,3(2H)-dione, 2-(2-Acetylphenyl)-3a,4,7,7a-tetrahydro-4,7-methano-1H-isoindole-1,3(2H)-dione,
3a,4,7,7a-Tetrahydro-2-[4-(5-oxazolyl)phenyl]-4,7-methano-1H-isoindole-1,3(2H)-dione,
(3aα,4α,7α,7aα)-2-[4-Bromo-3-(trifluoromethyl)phenyl]-3a,4,7,7a-tetrahydro-5-methyl-4,7-methano-1H-isoindole-1,3(2H)-dione,
(3aα,4α,7α,7aα)-2'-[4-Bromo-3-(trifluoromethyl)phenyl]-3'a,4',7',7'a-tetrahydrospiro[cyclopropane-1,8-[4,7]methano[1H]isoindole]-1',3'(2'H)-dione,
(3aα,4β,7β,7aα)-2-[3,5-Bis(trifluoromethyl)phenyl]hexahydro-8-(1-methylethylidene)-4,7-methano-1H-isoindole-1,3(2H)-dione,
(3aα,4β,7β,7aα)-2-(4-Bromo-3-methylphenyl)hexahydro-8-(1-methylethylidene)-4,7-methano-1H-isoindole-1,3(2H)-dione,
(3aα,4β,7β,7aα)-Hexahydro-8-(1-methylethylidene)-2-(4-nitro-1-naphthalenyl)-4,7-methano-1H-isoindole-1,3(2H)-dione,
(3aα,4β,7β,7aα)-2-(4-Bromo-1-naphthalenyl)hexahydro-8-(1-methylethylidene)-4,7-methano-1H-isoindole-1,3(2H)-dione,
(3aα,4β,7β,7aα)-Hexahydro-8,8-dihydroxy-2-(4-nitro-1-naphthalenyl)-4,7-methano-1H-isoindole-1,3(2H)-dione,
(3aα,4β,7β,7aα)-2-[3,5-Bis(trifluoromethyl)phenyl]hexahydro-8,8-dihydroxy-4,7-methano-1H-isoindole-1,3(2H)-dione,
(3aα,4β,7α,7aα)-2-(4-Bromo-3-methylphenyl)hexahydro-8,8-dihydroxy-4,7-methano-1H-isoindole-1,3(2H)-dione,
(3aα,4α,7α,7aα)-2-(4-Bromo-3-methylphenyl)hexahydro-8,8-dihydroxy-4,7-methano-1H-isoindole-1,3(2H)-dione,
(3aα,4α,7α,7aα)-2-(4-Bromo-3-methylphenyl)hexahydro-8-(1-methylethylidene)-4,7-methano-1H-isoindole-1,3(2H)-dione,
(3aα,4α,7α,7aα)-3a,4,7,7a-Tetrahydro-5-phenyl-2-[3-(trifluoromethyl)phenyl]-4,7-methano-1H-isoindole-1,3(2H)-dione,
(3aα,4α,7α,7aα)-3a,4,7,7a-Tetrahydro-2-[4-nitro-3-(trifluoromethyl)phenyl]5-phenyl-4,7-methano-1H-isoindole-1,3(2H)-dione,
(3aα,4α,7α,7aα)-2-(3,5-Dichlorophenyl)-3a,4,7,7a-tetrahydro-5-phenyl-4,7-methano-1H-isoindole-1,3(2H)-dione,
(3aα,4α, 7α,7aα)-Tetrahydro-2-[[3-(trifluoromethyl)phenyl]amino]-4,7-methano-1H-isoindole-1,3(2H)-dione,
(3aα,4α,7α,7aα)-2-[(3-Chlorophenyl)amino]-3a,4,7,7a-tetrahydro-4,7-methano-1H-isoindole-1,3(2H)-dione,
(3aα,4α, 5α,7α,7aα)-Hexahydro-5-mercapto-2-[3-(trifluoromethyl)phenyl]-4,7-methano-1H-isoindole-1,3(2H)-dione,
(3aα,4α,7α,7aα)-3a,4,7,7a-Tetrahydro-2-(4-nitro-1-naphthalenyl)-5-phenyl-4,7-methano-1H-isoindole-1,3(2H)-dione,
(3a'α,4'α,7'α,7a'α)2'(1,2-Dihydro-4-methyl-2-oxo-7-quinolinyl)-3a',4',7', 7a'-tetrahydrospiro[cyclopropane-1,8'-[4,7]methano[1H]isoindole]1',3'(2'H)-dione,
(3aα,4α, 5α,7α,7aα)-Hexahydro-5-(4-nitrophenyl)-2-[3-(trifluoromethyl)phenyl]-4,7-methano-1H-isoindole-1,3(2H)-dione,
Hexahydro-2-(2-mercaptophenyl)-4,7-methano-[1H]-isoindole-1,3(2H)-dione,
4-(Octahydro-1,3-dioxo-4,7-methano-2H-isoindol-2-yl)benzoic acid, ethyl ester,
2-[4-(Diethylamino)phenyl]hexahydro-4,7-methano-1H-isoindole-1,3(2H)-dione,
5-(Acetyloxy)hexahydro-2-phenyl-4,7-methano-1H-isoindole-1,3(2H)-dione,
5-(Acetyloxy)-2-(4-chlorophenyl)hexahydro-4,7-methano-1H-isoindole-1,3(2H)-dione,
5-(Acetyloxy)hexahydro-2-(2-nitrophenyl)-4,7-methano-1H-isoindole-1,3(2H)-dione,
5-(Acetyloxy)-2-(3-chlorophenyl)hexahydro-4,7-methano-1H-isoindole-1,3(2H)-dione,
Hexahydro-5-hydroxy-2-(4-methoxyphenyl-4,7-methano-1H-isoindole-1,3(2H)-dione,
2-(4-Ethoxyphenyl)hexahydro-5-hydroxy-4,7-methano-1H-isoindole-1,3(2H)-dione,
Hexahydro-5-hydroxy-2-(4-nitrophenyl)-4,7-methano-1H-isoindole-1,3(2H)-dione,
2-(4-Chlorophenyl)hexahydro-5-hydroxy-4,7-methano-1H-isoindole-1,3(2H)-dione,
2-(2,4-Dichlorophenyl)hexahydro-5-hydroxy-4,7-methano-1H-isoindole-1,3(2H)-dione,
Hexahydro-5-hydroxy-2-[3-(trifluoromethyl)phenyl]-4,7-methano-1H-isoindole-1,3(2H)-dione,
5-(Acetyloxy)hexahydro-2-[3-(trifluoromethyl)phenyl]-4,7-methano-1H-isoindole-1,3(2H)-dione,
5,6-Dibromo-2-(4-ethoxyphenyl)hexahydro-4,7-methano-1H-isoindole-1,3(2H)-dione,
2-(3-Chloro-2-methylphenyl)-3a,4,7,7a-tetrahydro-8-(1-methylethylidene)-4,7-methano-1H-isoindole-1,3(2H)-dione,
3'a,4',7',7'a-Tetrahydro-2'-(2,4,6-trimethylphenyl)spiro[cyclopropane-1,8'-[4,7]methano[1H]isoindole]-1',3'(2'H)-dione,
3a,4,7,7a-Tetrahydro-5-methyl-2-[4-(trifluoromethyl)phenyl]-4,7-methano-1H-isoindole-1,3(2H)-dione,
3a,4,7,7a-Tetrahydro-5-methyl-2-[4-(trifluoromethoxy)phenyl]-4,7-methano-1H-isoindole-1,3(2H)-dione,
3'a,4',7'7'a-Tetrahydro-2'-(4-nitrophenyl)spiro[cyclopropane-1,8'-[4,7]methano[1H]isoindole]-1',3'(2'H)-dione,
Hexahydro-2-(4-hydroxyphenyl)-5-phenyl-4,7-methano-1H-isoindole-1,3(2H)-dione,
2-(4-Ethoxyphenyl)hexahydro-5-phenyl-4,7-methano-1H-isoindole-1,3(2H)-dione,
Hexahydro-5-phenyl-2-[3-(trifluoromethyl)phenyl]-4,7-methano-1H-isoindole-1,3(2H)-dione and (3aα,4α,7α,7aα)-2-[4-nitro-3-(trifluoromethyl)phenyl]-3a,4,7,7a-tetrahydro-4,7-methano-1H-isoindole-1,3(2H)-dione,
or a pharmaceutically acceptable salt thereof.

* * * * *

UNITED STATES PATENT AND TRADEMARK OFFICE
CERTIFICATE OF CORRECTION

PATENT NO. : 7,655,688 B2  Page 1 of 1
APPLICATION NO. : 11/311731
DATED : February 2, 2010
INVENTOR(S) : Salvati et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1079 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,655,688 B2 |
| APPLICATION NO. | : 11/311731 |
| DATED | : February 2, 2010 |
| INVENTOR(S) | : Mark E. Salvati et al. |

It is certified that error appears in the above-identified patent and that said Letters Patent is hereby corrected as shown below:

In the Claims:

Claim 1:

Column 267, line 19, change "—$SO_2R^1$" to -- —$SO_2OR^1$ --.

Claim 3:

Column 268, line 19, under "$A_2$ is CH, C(alkyl), or C(substituted alkyl);" insert -- $R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl; --.

Column 268, line 33, change "$R^7R^{7'}$" to -- $R^7$ and $R^{7'}$ --.

Column 268, line 42, change "—$C(—O)NR^1R^{1'}$" to -- —$C(=O)NR^1R^{1'}$ --.

Claim 5:

Column 268, line 46, change "claim 1" to -- claim 4 --.

Column 268, line 49, change "$A^1$" to -- $A_1$ --.

Column 268, line 50, change "$A^2$" to -- $A_2$ --.

Column 268, lines 58 and 59, change "—$C(—O)OR^1$" to -- —$C(=O)OR^1$ --.

Column 268, line 61, change "," to -- ; --.

Column 268, line 66 , change "$C(=O)NR^1R^{1'}$" to -- —$C(=O)NR^1R^{1'}$ --.

Claim 6:

Column 269, line 11, change "napthyl" to -- naphthyl --.

Signed and Sealed this
First Day of March, 2011

David J. Kappos
*Director of the United States Patent and Trademark Office*

In the Claims:

Claim 7:

Column 269, line 14, change "napthyl" to -- naphthyl --.

Column 269, line 16, change "C(substituted alkyl" to -- C(substituted alkyl) --.

Column 269, line 24, change "C(=O)R$^1$" to-- —C(=O)R$^1$ --.

Column 269, lines 24 and 25, change "—C(—O)OR$^1$" to -- —C(=O)OR$^1$ --.

Column 269, line 26, change "—C(—O)R$^1$" to-- —C(=O)R$^1$ --.

Column 269, line 32, change "—C(—O)R$^1$" to-- —C(=O)R$^1$ --.

Column 269, line 44, change "—SO$_2$NR$^1$R$^1$" to -- —SO$_2$NR$^1$R$^{1'}$ --.

Claim 8:

Column 269, line 53, change "-[1H-" to -- -[4-(1H- --.

Column 269, line 63, change "-methanol-" to -- -methano- --.

Column 270, line 25, change "-2,4,1,3-" to -- -2-(1,3- --.

Column 270, line 32, change "-1H isoindole-" to -- -1H-isoindole- --.

Column 270, line 44, change "-1,1-" to -- -1H- --.

Column 270, line 49, change "7'," to -- 7α, --.

Column 270, line 66, change "-1,1-" to -- -1H- --.

Column 271, line 2, change "-1,1-" to -- -1H- --.

Column 271, line 8, change "-1,11-" to -- -1H- --.

Column 271, line 12, change "-4-Bromo-[4-trifluoromethyl)phenyl]-" to -- -[4-Bromo-3-(trifluoromethyl)phenyl]- --.

Column 271, line 20, change "-4-Fluoro-3-(trifluoromethyl)phenyl]-" to -- -[4-Fluoro-3-(trifluoromethyl)phenyl]- --.

Column 271, line 28, change "-C-" to -- -2- --.

Column 271, line 35, change "-1,1-" to -- -1H- --.

Column 271, line 37, change "-nitrophenyl-" to -- -nitrophenyl)- --.

Column 271, line 38, change "-1,1-" to -- -1H- --.

Column 271, line 40, change "-1,4-" to -- -1H- --.

Column 271, line 50, change "-1,1-" to -- -1H- --.

Column 271, line 52, change "-nitrophenyl-" to -- -nitrophenyl)- --.

Column 271, line 54, change "4aα)-" to -- 7aα)- --.

Column 271, line 58, change "-Methano-" to -- -methano- --.

Column 272, line 10, change "-2H)-" to -- -2H- --.

Column 272, line 19, change "-Tetrahydro-" to -- -methano- --.

CERTIFICATE OF CORRECTION (continued)

U.S. Pat. No. 7,655,688 B2

In the Claims:

Claim 8 (continued):

Column 272, line 33, change "4α7α," to -- 4α,7α, --.

Column 272, line 37, change "-(4Amino-" to -- -(4-Amino- --.

Column 272, line 40, change "-2-" to -- -[2- --.

Column 272, line 42, change "phenyl)" to -- phenyl] --.

Column 272, lines 43 and 44, change "-[3-trifluoromethyl)" to -- -[3-(trifluoromethyl) --.

Column 272, line 55, change "-1,4-" to -- -[4- --.

Column 272, line 56, change "phenyl)-" to -- phenyl]- --.

Column 272, line 58, change "phenyl]A," to -- phenyl]-4, --.

Column 273, line 18, change "-2,4,4-" to -- -2-(4- --.

Column 273, line 32, change "-1H-1-" to -- -1H- --.

Column 273, line 33, change "-{5-" to -- -[5- --.

Column 273, line 34, change "phenyl}-" to -- phenyl]- --.

Column 274, line 16, change "-1H-1-indazole-" to -- -1H-indazol- --.

Column 274, lines 23 and 24, change "3(21-1)-" to -- 3(2H)- --.

Column 274, line 34, change "7aα))-" to -- 7aα)- --.

Column 274, line 38, change "-1,1-" to -- -1H- --.

Column 274, line 62, change "3(211)-" to -- 3(2H)- --.

Column 275, line 2, change "-2H-benzopyran-" to -- -2H-1-benzopyran- --.

Column 275, line 6, change "-4-iodophenyl)-" to -- -4-nitrophenyl)- --.

Column 276, line 32, change "quinolinyl-" to -- quinolinyl)- --.

Column276, line 49, change "1'-terphenyl]-5-" to -- 1''-tetraphenyl]-5'- --.

Column 276, line 61, change "-2H-dihydro-" to -- -2,3-dihydro- --.

Column 277, line 9, change "3aα-4α," to -- 3aα,4α, --.

Column 277, lines 15 and 16, change "-(trifluoromethyl-" to -- -(trifluoromethyl)- --.

Column 277, line 22, change "-4,4-a,5," to -- -4,4a,5, --.

Column 277, line 24 , change "-4,4-a," to -- -4,4a, --.

Column 277, line 28, change "-4,4-a," to -- -4,4a, --.

Column 277, line 34, change "-4,4-a," to -- -4,4a, --.

Column 277, line 37, change "-4,4-a," to -- -4,4a, --.

Column 277, line 38, change "1,4-nitro-3,4-trifluoromethyl)phenyl-" to -- [4-nitro-3-(trifluoromethyl)phenyl]- --.

Column 277, line 43, change "5α,6β,6aα)-4,4-a," to -- 5aα,6β,6aα)-4,4a, --.

Column 277, line 47, change "-4,4-a," to -- -4,4a, --.

CERTIFICATE OF CORRECTION (continued)
U.S. Pat. No. 7,655,688 B2

In the Claims:

Claim 8 (continued):

Column 277, line 54, change "5a/5,6a-" to -- 5a,6,6a- --.

Column 277, line 56, change "-4-2-(4-" to -- -2-(4- --.

Column 278, line 1, change "-4,4-a," to -- -4,4a, --.

Column 278, line 4, change "-4,4-a,5," to -- -4,4a,5, --.

Column 278, line 13, change "-methyl-phenyl)-" to -- -methylphenyl)- --.

Column 278, line 19, change "4β,3,4aα," to -- 4β,4aα, --.

Column 278, line 29, change "4,4-a,5," to -- 4,4a,5, --.

Column 278, line 56, change "-2,4,3,4-" to -- -2-(3,4- --.

Column 278, line 65, change "-2-(Ethylphenyl)-" to -- -2-(3-Ethylphenyl)- --.

Column 279, line 4, change "-2-(4-" to -- -2-[4- --.

Column 279, line 5, change "phenyl)-" to -- phenyl]- --.

Column 279, line 10, change "-2-(4-" to -- -2-[4- --.

Column 279, line 11, change "phenyl-" to -- phenyl]- --.

Column 279, line 23, change "(4-(1-methylethyl)phenyl-" to -- [4-(1-methylethyl)phenyl]- --.

Column 279, line 41, change "6aα-4-" to -- 6aα)-2- --.

Column 279, line 44, change "6aα-2-" to -- 6aα)-2- --.

Column 279, line 47, change "6a-1-" to -- 6a- --.

Column 280, line 23, change "6aα-2-" to -- 6aα)-2- --.

Column 280, line 32, change "-methylphenyl-" to -- -methylphenyl)- --.

Column 280, line 44, change "-4-fluorophenyl)-" to -- -4-nitrophenyl)- --.

Column 280, line 50, change "-2,4,5-" to -- -2-[5- --.

Column 280, lines 50 and 51, change "sulfonyl)-" to -- sulfonyl]- --.

Column 280, line 57, change "[4-L(trifluoromethyl)thio)" to -- [4-[(trifluoromethyl)thio] --.

Column 281, line 1, change "-[3-(1H-" to -- -[3-(1,1- --.

Column 281, line 21, change "-1,3 (2H)-" to -- -1,3(2H)- --.

Column 281, line 55, change "-methano-1,11-" to -- -methano-1H- --.

Column 281, line 57, change "-(methylsulfanyl)" to -- -(methylsulfonyl) --.

Column 281, line 64, change "-4,3-" to -- -4,7- --.

Column 282, line 8, after "-dione", insert -- , --.

Column 282, line 9, change "4α,5α," to -- 4aβ,5aβ, --.

Column 282, line 12, change "(3aα,4α,4α,5α,6α,6aα)-" to -- (3aα,4α,4aβ,5aβ,6α,6aα)- --.

Column 282, line 21, change "-4,4-a," to -- -4,4a, --.

In the Claims:

Claim 8 (continued):

Column 283, line 13, change "5α," to -- 5β, --.

Column 283, line 16, change "5α," to -- 5β, --.

Column 283, line 19, change "-2-[4,4-" to -- -2-[4- --.

Column 283, line 25, change "5α," to -- 5β, --.

Column 283, line 28, change "5α," to -- 5β, --.

Column 283, line 41, change "7α)-" to -- 7aα)- --.

Column 283, lines 50 and 51, change "-dichlorophenyl-" to -- -dichlorophenyl)- --.

Column 283, line 53, change "-Bromophenyl-" to -- -Bromophenyl)- --.

Column 284, line 22, change "-[4-phenyl-methoxy)" to -- -[4-(phenylmethoxy) --.

Column 284, line 32, change "-[3,4[(4-" to -- -[3-(4- --.

Column 285, line 9, change "-1,8-" to -- -1,8'- --.

Column 285, line 29, change "7α," to -- 7β, --.

Column 285, line 57, change "2'" to -- -2'- --.

Column 285, line 58, change "7', 7a'-" to -- 7',7a'- --.

Column 285, line 59, change "isoindole]1'" to -- isoindole]-1' --.

Column 286, line 4, change "-[1H]'-" to -- -1H- --.

Column 286, line 18, change "-methoxyphenyl-" to -- -methoxyphenyl)- --.

Column 286, line 38, change "spira" to -- spiro --.

Column 286, line 45, change "7'7'a-" to -- 7',7'a- --.